(12) United States Patent
Yoshida et al.

(10) Patent No.: US 7,217,723 B2
(45) Date of Patent: May 15, 2007

(54) HETEROCYCLIC COMPOUND HAVING OXIME GROUP

(75) Inventors: Ichiro Yoshida, Ibaraki (JP); Shuichi Suzuki, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 26 days.

(21) Appl. No.: 11/047,995

(22) Filed: Feb. 2, 2005

(65) Prior Publication Data
US 2005/0227959 A1    Oct. 13, 2005

(30) Foreign Application Priority Data
Feb. 2, 2004   (JP)  ............................. 2004-025077

(51) Int. Cl.
A61K 31/4436    (2006.01)
A61K 31/381     (2006.01)
C07D 333/66     (2006.01)
C07D 411/12     (2006.01)

(52) U.S. Cl. .................. 514/337; 514/443; 546/281.1; 549/55

(58) Field of Classification Search ..................... None
See application file for complete search history.

(56) References Cited

U.S. PATENT DOCUMENTS 4,108,867 A    8/1978  Baird et al.

FOREIGN PATENT DOCUMENTS

| JP | 10-175964 A | 6/1998 |
| JP | 10-175965 A | 6/1998 |
| JP | 11-106340 A | 4/1999 |
| JP | 11-116481 A | 4/1999 |
| JP | 2003-238565 A | 8/2003 |
| WO | WO-00/50390 A1 | 8/2000 |
| WO | WO-03/011851 A2 | 2/2003 |
| WO | WO 2005/023818 | * 3/2005 |

OTHER PUBLICATIONS

Izuhara et al., J. Biol. Chem., vol. 271, No. 2, pp. 619-622, (1996).
Akimoto et al., J. Exp. Med., vol. 187, No. 9, pp. 1537-1542, (1998).
Kuperman et al., J. Exp. Med., vol. 187, No. 6, pp. 939-948, (1998).

* cited by examiner

Primary Examiner—Golam M. M. Shameem
Assistant Examiner—Andrew B. Freistein
(74) Attorney, Agent, or Firm—Birch, Stewart, Kolasch & Birch, LLP

(57) ABSTRACT

The present invention provides a compound that has an excellent inhibitory activity on STAT6 activation and is effective against allergic diseases, and a medicinal composition thereof. According to the present invention, disclosed is the compound represented by the General Formula (I)

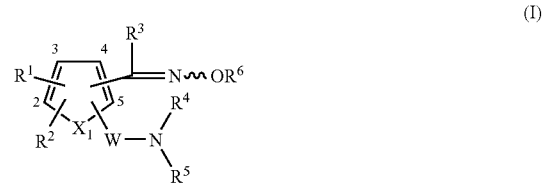

(I)

[where $R^1$ and $R^2$ independently represent a $C_{1-6}$ alkyl group and the like that may have a hydrogen atom or a substituent;
$R^3$ represents a $C_{1-6}$ alkyl group and the like that may have a substituent;
$R^4$ and $R^5$ independent represents a hydrogen atom or a $C_{1-6}$ alkyl group and the like that may have a substituent;
$R^6$ represents a hydrogen atom and the like;
W represents —$SO_2$—and the like; and
X represents a sulphur atom and the like.]
or a salt thereof, or a hydrate thereof.

38 Claims, No Drawings

HETEROCYCLIC COMPOUND HAVING OXIME GROUP

BACKGROUND OF THE INVENTION

1. Field of the Invention

The present invention relates to a novel heterocyclic compound which has an oxime group, and has an Inhibitory activity on STAT6 activation.

2. Description of Related Art

IgE, which is an immunoglobulin, is believed to be involved in generating the symptoms of allergic diseases such as bronchial asthma, atopic dermatitis or pollenosis and the like.

After being produced in a B-cell due to sensitization by an allergen, an antigen-specific IgE binds to an IgE receptor of a mast cell. It is known that when a human body is re-exposed to the allergen, binding of the allergen and the IgE triggers mast cell degranulation, releasing inflammatory mediators such as histamine, thereby giving rise to an allergic inflammation. (Refer to Non-Patent Reference 1)

Here, IL-4 and IL-13, which are cytokines generated by type II helper T-cells (Th2 cells), are said to play a central role in a series of allergic reactions: activation of B-cell that generate IgE, proliferation of mast cells and acceleration of histamine secretion. (Refer to Non-Patent Reference 1)

STAT6 protein is known as an important transcription factor that transmits signals from cytokines such as IL-4 and IL-13, and there are reports that when a signaling pathway involving STAT6 is blocked, the action by IL-4 and IL-13 become ineffective, and that in a STAT6 knock-out mouse, inflammation of the respiratory tract and increase in hypersensitivity of the respiratory tract due to sensitization by an allergen are not observed at all. (Refer to Non-Patent References 2 to 4)

Accordingly, since a compound that possesses an inhibitory action on STAT6 activation, in addition to being considered to be effective for the prevention or the treatment of allergic diseases, can also be thought to have an effect on the balance and adjustment of the immune system, it can also be considered to be effective for the prevention or the treatment of autoimmune disease, various infectious diseases, obesity, hyperphagia, malignant tumor or acquired immune deficiency syndrome (AIDS) and the like.

Currently, for instance, Patent References 1 to 4 and the like describe the compounds having an inhibitory activity on STAT6 activation. However, the compounds described in Patent References 1 to 4 have chemical structures that are totally different from a 5 membered ring compound having an oxime group, which is a compound according to the present application.

On the other hand, 5 membered ring compounds having an oxime group with a similar structure to the compound according to the present application are described in Patent References 5 to 8, Non-Patent References 5 to 6 and the like.

However, the compounds included in the present application are not described in these references, in addition, no description is given at all on the inhibitory activity on STAT6 activation in any of these references, and uses of the references differ entirely from those of the present application.

[Patent Reference 1] Japanese Patent Laid-open Publication No. H10-175964

[Patent Reference 2] Japanese Patent Laid-open Publication No. H10-175965

[Patent Reference 3] Japanese Patent Laid-open Publication No. H11-106340

[Patent Reference 4] Japanese Patent Laid-open Publication No. H11-116481

[Patent Reference 5] WO 03/11851

[Patent Reference 6] WO 00/50390

[Patent Reference 7] U.S. Pat. No. 4,108,867

[Patent Reference 8] Japanese Patent Laid-open Publication No. 2003-238565

[Non-Patent Reference 1] Medical Term library: Allergy, Yodosha, (1996)

[Non-Patent Reference 2] Izuhara K., J. Biol. Chem. 271, 619 (1996) [Non-Patent Reference 3] Akimoto,T et al., J. Exp. Med., 187, 1537, 1998;

[Non-Patent Reference 4] Kuperman D et al, J. Exp. Med., 187, 939, 1998

[Non-Patent Reference 5] Bulletin de la Societe Chimique de France, 479-484, 1963

[Non-Patent Reference 6] Khimiya Geterosiklicheskikh Soedinenii, 9, 1178-1180, 1986

SUMMARY OF THE INVENTION

Although steroid agents are conventionally known in as a therapeutic agent for allergic diseases, in addition to having the problem of adverse events, the problem of little therapeutic effect on patients with resistant against steroid agents exists. In addition, although provision of the aforementioned compound having inhibitory activity on STAT6 activation is much desired, a compound having excellent inhibitory activity on STAT6 activation and having sufficient pharmacological activity, safety and pharmacokinetics as a medicinal drug and whose action is clinically effective has not been found so far.

In view of the above current status, the present inventors thought that a compound having an inhibitory activity on STAT6 activation can be expected to demonstrate a wide array of actions such as inhibition of IgE antibody generation and anti-inflammatory actionbyblocking the signals from IL-4 and IL-13. The present inventors also thought with the compound having an inhibitory activity on STAT6 activation, the prevention or the treatment of a broad range of diseases from a topic to infectious would become possible, and a decrease in the quantity of steroids, which bear the risk of adverse events, would become also possible by the concomitant use of the compound, allowing a novel therapy to be provided to patients with resistance to steroids. As a result of the earnest study undertaken with the objective of providing a compound having excellent inhibitory activity on STAT6 activation and a medicinal composition thereof, they discovered that a "5 membered ring compound having an oxime group", which has a novel structure, had an excellent inhibitory activity on STAT6 activation, and furthermore, that it is effective in the prevention or the treatment of allergic diseases.

That is to say, the present invention relates to:

1) a compound represented by the following general formula (I)

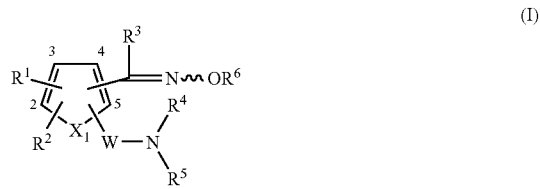

[wherein, $R^1$ and $R^2$ independently represent a hydrogen atom, a $C_{1-6}$ alkyl group that may have a substituent selected from substituent group α, or a substituent selected from substituent group α;

$R^3$ represents a $C_{1-6}$ alkyl group that may have a substituent selected from substituent group α, a $C_{2-6}$ alkenyl group that may have a substituent selected from substituent group α or a $C_{2-6}$ alkynyl group that may have a substituent selected from substituent group α;

or, when $R^1$ and —C(—$R^3$)=N—$OR^6$ are bonded to adjacent carbon atoms, $R^1$ and $R^3$ form a 5–8 membered ring together with the carbon atoms they are bonded to, while the 5–8 membered ring may have 1 to 3 $C_{1-6}$ alkyl groups that may have a substituent selected from substituent group α or substituents selected from substituent group α;

$R^4$ and $R^5$ represent independently a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ or a 5 to 10-membered heteroaryl group that may have a substituent selected from substituent group γ;

or, $R^4$ and $R^5$, together with the nitrogen atom they are bonded to, form a 5–8 membered ring that may have 1 to 2 heteroatoms on the ring in addition to the nitrogen atom; furthermore, the 5–8 membered ring is condensed with a $C_{6-10}$ aryl group or a 5 to 10-membered heteroaryl group, while the 5–8 membered ring may have 1 to 3 $C_{1-6}$ alkyl groups that may have a substituent selected from substituent group α or substituents selected from substituent group α.

$R^6$ represents a hydrogen atom, —$CONR^{7a}R^{7b}$ (wherein, $R^{7a}$ and $R^{7b}$ represent independently a hydrogen atom, a $C_{1-6}$ alkyl group that may have a substituent selected from substituent group α, a $C_{3-8}$ cycloalkyl group that may have a substituent selected from substituent group α or a $C_{6-10}$ aryl group that may have a substituent selected from substituent group γ) or —$COR^{7c}$ (wherein, $R^{7c}$ represents a $C_{1-6}$ alkyl group that may have a substituent selected from substituent group α);

W represents —$SO_2$— or —CO—;

X represents a sulfur atom or an oxygen atom;

with the proviso that when $R^1$ is located at position 3, —C(—$R^3$)=N—$OR^6$ is located at position 4 and —W—N($R^4$)$R^5$ is located at position 5, or when $R^1$ is located at position 4, —C(—$R^3$)=N—$OR^6$ is located at position 3 and —W—N($R^4$)$R^5$ is located at position 2, $R^1$ and $R^3$ do not constitute a 5–8 membered ring together with the carbon atoms they are bonded to;

the substituent group α: halogen atoms, hydroxyl groups, mercapto groups, amino groups that may have a substituent selected from substituent group β, nitro groups, cyano groups, formyl groups, carboxyl groups, carbamoyl groups that may have a substituent selected from substituent group β, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substitutent selected from substituent group γ, $C_{6-10}$ aryl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino groups, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups, $C_{3-8}$ cycloalkyloxy groups, $C_{3-8}$ cycloalkythio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryl $C_{1-6}$ alkyl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups] or a salt thereof, or a hydrate thereof;

2) a compound represented by the following general formula (I-a)

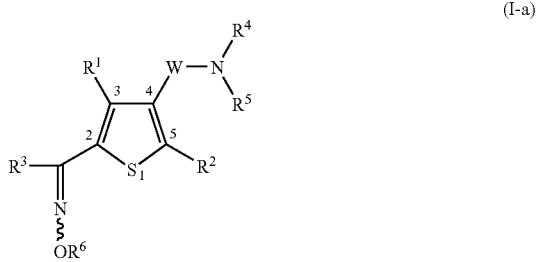

[wherein, $R^1$ and $R^2$ independently represent a hydrogen atom, a $C_{1-6}$ alkyl group that may have a substituent selected from substituent group α, or a substituent selected from substituent group α;

$R^3$ represents a $C_{1-6}$ alkyl group that may have a substituent selected from substituent group α, a $C_{2-6}$ alkenyl group that may have a substituent selected from substituent group α or a $C_{2-6}$ alkynyl group that may have a substituent selected from substituent group α;

or, when $R^1$ and —C(—$R^3$)=N—$OR^6$ are bonded to adjacent carbon atoms, $R^1$ and $R^3$ form a 5–8 membered ring together with the carbon atoms they are bonded to, while the 5–8 membered ring may have 1 to 3 $C_{1-6}$ alkyl groups that may have a substituent selected from substituent group α or substituents selected from substituent group α; $R^4$ and $R^5$ represent independently a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ or a 5 to 10-membered heteroaryl group that may have a substituent selected from substituent group γ;

or, $R^4$ and $R^5$, together with the nitrogen atom they are bonded to, form a 5–8 membered ring that may have 1 to 2 heteroatoms on the ring in addition to the nitrogen atom; furthermore, the 5–8 membered ring is condensed with a $C_{6-10}$ aryl group or a 5 to 10-membered heteroaryl group, while the 5–8 membered ring may have 1 to 3 $C_{1-6}$ alkyl groups that may have a substituent selected from substituent group α or substituents selected from substituent group α.

$R^6$ represents a hydrogen atom, —$CONR^{7a}R^{7b}$ (wherein, $R^{7a}$ and $R^{7b}$ represent independently a hydrogen atom, a $C_{1-6}$ alkyl group that may have a substituent selected from substituent group α, a $C_{3-8}$ cycloalkyl group that may have a substituent selected from substituent group α or a $C_{6-10}$ aryl group that may have a substituent selected from substituent group γ) or —$COR^{7c}$ (wherein, $R^{7c}$ represents a $C_{1-6}$ alkyl group that may have a substituent selected from substituent group α);

W represents —$SO_2$— or —CO—;

the substituent group α: halogen atoms, hydroxyl groups, mercapto groups, amino groups that may have a substituent selected from substituent group β, nitro groups, cyano groups, formyl groups, carboxyl groups, carbamoyl groups that may have a substituent selected from substituent group β, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_6$-10 arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino groups, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups, $C_{3-8}$ cycloalkyloxy groups, $C_{3-8}$ cycloalkythio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryl $C_{1-6}$ alkyl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups] or a salt thereof, or a hydrate thereof;

3) a compound represented by the following general formula (I-a')

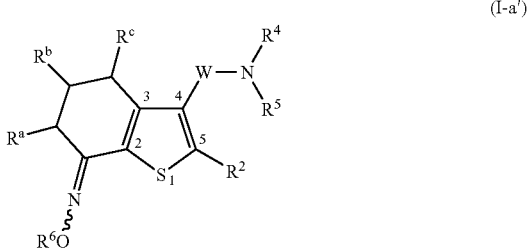

(I-a')

[wherein, $R^2$ represents a hydrogen atom, a $C_{1-6}$ alkyl group that may have a substituent selected from substituent group α or a substituent selected from substituent group α;

$R^4$ and $R^5$ independently represent a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ or a 5 to 10-membered heteroaryl group that may have a substituent selected from substituent group γ;

or, $R^4$ and $R^5$, together with the nitrogen atom they are bonded to, form a 5–8 membered ring that may have 1 to 2 heteroatoms on the ring in addition to the nitrogen atom; furthermore, the 5–8 membered ring is condensed with a $C_{6-10}$ aryl group or a 5 to 10-membered heteroaryl group, while the 5–8 membered ring may have 1 to 3 $C_{1-6}$ alkyl groups that may have a substituent selected from substituent group α or substituents selected from substituent group α.

$R^6$ represents a hydrogen atom, —$CONR^{7a}R^{7b}$ (wherein, $R^{7a}$ and $R^{7b}$ represent independently a hydrogen atom, a $C_{1-6}$ alkyl group that may have a substituent selected from substituent group α, a $C_{3-8}$ cycloalkyl group that may have a substituent selected from substituent group α or a $C_{6-10}$ aryl group that may have a substituent selected from substituent group γ) or —$COR^{7c}$ (wherein, $R^{7c}$ represents a hydrogen atom or a $C_{1-6}$ alkyl group that may have a substituent selected from substituent group α);

$R^a$, $R^b$ and $R^c$ independently represent a hydrogen atom, a $C_{1-6}$ alkyl group that may have a substituent selected from substituent group α or a substituent selected from substituent group α;

W represents —$SO_2$— or —CO—;

the substituent group α: halogen atoms, hydroxyl groups, mercapto groups, amino groups that may have a substituent selected from substituent group β, nitro groups, cyano groups, formyl groups, carboxyl groups, carbamoyl groups that may have a substituent selected from substituent group β, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino groups, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups, $C_{3-8}$ cycloalkyloxy groups, $C_{3-8}$ cycloalkylthio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryl $C_{1-6}$ alkyl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups] or a salt thereof, or a hydrate thereof;

4) the compound or the salt thereof, or the hydrate thereof according to 1) to 2), wherein $R^1$ and $R^2$ independently represent a hydrogen atom, a halogen atom, a hydroxyl group, a mercapto group, an amino group that may have 1 or 2 substituents selected from substituent group β, a nitro group, a cyano group, a formyl group, a carboxyl group, a carbamoyl group, a $C_{1-6}$ alkyl group that may have 1 to 3 substituents selected from substituent group α, a $C_{1-6}$ alkoxy group or a 3 to 8-membered heterocyclyl group that may have 1 to 3 substituents selected from substituent group γ;

5) the compound or the salt thereof, or the hydrate thereof according to any one of 1), 2) or 4), wherein $R^1$ represents a hydrogen atom, a halogen atom, a hydroxyl group, a mercapto group, an amino group, a nitro group, a cyano group, a formyl group, a carboxyl group, a carbamoyl group or a $C_{1-6}$ alkyl group;

6) the compound or the salt thereof, or the hydrate thereof according to any one of 1), 2) or 4), wherein $R^1$ represents a hydrogen atom, a halogen atom, a hydroxyl group, an amino group or a $C_{1-6}$ alkyl group;

7) the compound or the salt thereof, or the hydrate thereof according to any one of 1), 2) or 4), wherein $R^1$ represents a hydrogen atom;

8) the compound or the salt thereof, or the hydrate thereof according to any one of 1) to 7), wherein $R^2$ represents a hydrogen atom, an amino group that may have 1 or 2 substituents selected from substituent group β, a $C_{1-6}$ alkyl group that may have 1 to 3 substituents selected from substituent group α, a $C_{1-6}$ alkoxy group, a 3 to 8-membered heterocyclyl group that may have 1 to 3 substituents selected from substituent group γ;

9) the compound or the salt thereof, or the hydrate thereof according to any one of 1) to 7), wherein $R^2$ represents a hydrogen atom, an amino group that may have 1 or 2 substituents selected from substituent group β or a $C_{1-6}$ alkoxy group;

10) the compound or the salt thereof, or the hydrate thereof according to any one of 1) to 7), wherein $R^2$ represents a hydrogen atom, an amino group or a methoxy group;

11) the compound or the salt thereof, or the hydrate thereof according to any one of 1) to 2) and 4) to 10), wherein $R^3$ represents a $C_{1-6}$ alkyl group that may have 1 to 3 substituents selected from substituent group α;

12) the compound or the salt thereof, or the hydrate thereof according to any one of 1) to 2) and 4) to 10), wherein $R^3$ represents a $C_{1-6}$ alkyl group that may have 1 to 3 substituents selected from the group consisting of a hydroxyl group, an amino group that may have a substituent selected from substituent group p, a $C_{2-7}$ alkylcarbonyloxy group and a $C_{6-10}$ aryl group that may have a substituent selected from substituent group γ (hereinafter referred to as "substituent group α1");

13) the compound or the salt thereof, or the hydrate thereof according to any one of 1) to 2) and 4) to 10), wherein $R^3$ represents a methyl group that may have 1 to 3 substituents selected from substituent group α1;

14) the compound or the salt thereof, or the hydrate thereof according to any one of 1) to 13), wherein $R^4$ and $R^5$ independently represent a hydrogen atom, a $C_{1-6}$ alkyl group that may have 1 to 3 substituents selected from substituent group α, a $C_{2-6}$ alkynyl group that may have 1 to 3 substituents selected from substituent group α or a $C_{3-8}$ cycloalkyl group that may have 1 to 3 substituents selected from substituent group γ;

15) the compound or the salt thereof, or the hydrate thereof according to any one of 1) to 14), wherein $R^4$ represents a $C_{1-6}$ alkyl group that may have 1 or 2 substituents selected from substituent group α;

16) the compound or the salt thereof, or the hydrate thereof according to any one of 1) to 14), wherein $R^4$ is represented by a formula of $-(CH_2)_m-CH(R^{4a})R^{4b}$ [wherein, $R^{4a}$ represents a $C_{6-10}$ aryl group that may have a substituent selected from substituent group γ or a 5 to 10-membered heteroaryl group that may have a substituent selected from substituent group γ, $R^{4b}$ represents a hydrogen atom or a substituent selected from substituent group α, and m stands for 0, 1, 2, 3, 4 or 5];

17) the compound or the salt thereof, or the hydrate thereof according to 16), wherein $R^{4a}$ represents a phenyl group that may have 1 to 3 substituents selected from substituent group γ, a pyridyl group that may have 1 to 3 substituents selected from substituent group γ or a thienyl group that may have 1 to 3 substituents selected from substituent group γ;

18) the compound or the salt thereof, or the hydrate thereof according to 16), wherein $R^{4a}$ represents a phenyl group that may have 1 to 3 substituents selected from the group consisting of a halogen atom, a hydroxyl group, a mercapto group, an amino group, a nitro group, a cyano group, a formyl group, a carboxyl group, a carbamoyl group, a $C_{1-6}$ alkyl group, a $C_{1-6}$ alkoxy group and a $C_{1-6}$ alkylthio group (hereinafter referred to as "substituent group γ1"), a pyridyl group that may have 1 to 3 substituents selected from substituent group γ1 or a thienyl group that may have 1 to 3 substituents selected from substituent group γ1;

19) the compound or the salt thereof, or the hydrate thereof according to 16), wherein $R^{4a}$ represents a phenyl group that may have 1 to 3 substituents selected from substituent group γ1;

20) the compound or the salt thereof, or the hydrate thereof according to 16), wherein $R^{4a}$ represents a phenyl group that may have 1 to 3 halogen atoms, nitro groups or $C_{1-6}$ alkoxy groups;

21) the compound or the salt thereof, or the hydrate thereof according to 16), wherein $R^{4a}$ represents a phenyl group that may have 1 to 3 fluorine atoms, nitro groups or methoxy groups.

22) the compound or the salt thereof, or the hydrate thereof according to 16), wherein $R^{4a}$ represents a 4-fluorophenyl group;

23) the compound or the salt thereof, or the hydrate thereof according to any one of 16) to 22), wherein $R^{4b}$ represents a hydrogen atom, a halogen atom, a hydroxyl group, an amino group that may have 1 or 2 substituents selected from substituent group β, a carboxyl group, a carbamoyl group that may have 1 or 2 substituents selected from substituent group β, a $C_{1-6}$ alkoxy group or a $C_{2-7}$ alkylcarbonyloxy group;

24) the compound or the salt thereof, or the hydrate thereof according to any one of 16) to 22), wherein $R^{4b}$ represents a hydrogen atom, a fluorine atom, a hydroxyl group, a methylcarbonylamino group, a methylsulfonylamino group, a carbamoylamino group, a carboxyl group, a carbamoyl group, a methoxy group or an ethylcarbonyloxy group;

25) the compound or the salt thereof, or the hydrate thereof according to any one of 16) to 22), wherein $R^{4b}$ represents a hydrogen atom or a hydroxyl group;

26) the compound or the salt thereof, or the hydrate thereof according to any one of 16) to 25), wherein m stands for 0, 1 or 2.

27) the compound or the salt thereof, or the hydrate thereof according to any one of 16) to 25), wherein m stands for 1.

28) the compound or the salt thereof, or the hydrate thereof according to any one of 1) to 27), wherein $R^5$ represents a hydrogen atom, a $C_{1-6}$ alkyl group that may have 1 to 3 substituents selected from substituent group α, a $C_{2-6}$ alkynyl group that may have 1 to 3 substituents selected from substituent group α or a $C_{3-8}$ cycloalkyl group that may have 1 to 3 substituents selected from substituent group γ;

29) the compound or the salt thereof, or the hydrate thereof according to any one of 1) to 28), wherein $R^5$ represents a hydrogen atom, a cyanomethyl group, a carbamoylmethyl group, an isopropyl group, a propyn-1-yl group, a cyclopropyl group;

30) the compound or the salt thereof, or the hydrate thereof according to any one of 1) to 28), wherein $R^5$ represents a hydrogen atom or a methyl group;

31) the compound or the salt thereof, or the hydrate thereof according to any one of 1) to 30), wherein $R^6$ represents a hydrogen atom, —$CONR^{7a}R^{7b}$ (wherein, $R^{7a}$ and $R^{7b}$ independently represent a hydrogen atom, a $C_{1-6}$ alkyl group, a $C_{3-8}$ cycloalkyl group or a $C_{6-10}$ aryl group that may have a substituent selected from a halogen atom, a cyano group, a $C_{1-6}$ alkyl group or a $C_{1-6}$ alkoxy group) or —$COR^{7c}$ (wherein, $R^{7c}$ represents a hydrogen atom or a $C_{1-6}$ alkyl group);

32) the compound or the salt thereof, or the hydrate thereof according to any one of 1) to 30), wherein $R^6$ represents a hydrogen atom, a pivaloyl group, a carbamoyl group, a dimethylaminocarbonyl group, an ethylaminocarbonyl group, a propylaminocarbonyl group, an isopropylaminocarbonyl group, a t-butylaminocarbonyl group, a cyclohexylaminocarbonyl group, a benzyl aminocarbonyl group, a fluorophenylaminocarbonyl group, an ethylphenylaminocarbonyl group, a methoxyphenylaminocarbonyl group, an ethoxyphenylaminocarbonyl group, a cyanophenylaminocarbonyl group, a tolylaminocarbonyl group or a methylenedioxyphenylaminocarbonyl group;

33) the compound or the salt thereof, or the hydrate thereof according to any one of 1) to 30), wherein $R^6$ represents a hydrogen atom, a pivaloyl group, a carbamoyl group, a dimethylaminocarbonyl group, an ethylaminocarbonyl group, an isopropylaminocarbonyl group, a cyclohexylaminocarbonyl group, an ethylphenylaminocarbonyl group or a methoxyphenylaminocarbonyl group;

34) the compound or the salt thereof, or the hydrate thereof according to any one of 3), 8) to 10), 14) to 33), wherein $R^a$, $R^b$ and $R^c$ independently represent a hydrogen atom, a halogen atom, a hydroxyl group, a mercapto group, an amino group that may have 1 or 2 substituents selected from substituent group β, a nitro group, a cyano group, a carboxyl group, a carbamoyl group, a $C_{1-6}$ alkyl group that may have 1 to 3 substituents selected from substituent group α or a $C_{1-6}$ alkoxy group;

35) the compound or the salt thereof, or the hydrate thereof according to any one of 3), 8) to 10), 14) to 33), wherein $R^a$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group;

36) the compound or the salt thereof, or the hydrate thereof according to any one of 3), 8) to 10), 14) to 33), wherein $R^a$ represents a hydrogen atom, a hydroxyl group, a cyano group or a methyl group;

37) the compound or the salt thereof, or the hydrate thereof according to any one of 3), 8) to 10), 14) to 33), wherein $R^a$ represents a hydrogen atom;

38) the compound or the salt thereof, or the hydrate thereof according to any one of 3), 8) to 10), 14) to 37), wherein $R^b$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group;

39) the compound or the salt thereof, or the hydrate thereof according to any one of 3), 8) to 10), 14) to 33), wherein $R^b$ represents a hydrogen atom, a hydroxyl group, a cyano group or a methyl group;

40) the compound or the salt thereof, or the hydrate thereof according to any one of 3), 8) to 10), 14) to 37), wherein $R^b$ represents a hydrogen atom;

41) the compound or the salt thereof, or the hydrate thereof according to any one of 3), 8) to 10), 14) to 40), wherein $R^c$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group;

42) the compound or the salt thereof, or the hydrate thereof according to any one of 3), 8) to 10), 14) to 40), wherein R$^c$ represents a hydrogen atom, a hydroxyl group, a cyano group or a methyl group;

43) the compound or the salt thereof, or the hydrate thereof according to any one of 3), 8) to 10), 14) to 40), wherein R$^c$ represents a hydrogen atom;

44) the compound or the salt thereof, or the hydrate thereof according to any one of 1) to 43), wherein W represents —SO$_2$—;

45) the compound or the salt thereof, or the hydrate thereof according to 1), wherein X represents a sulfur atom;

46) a compound or a salt thereof, or a hydrate thereof, the compound selected from (7Z)-7-hydroxyimino-4,5,6,7-tetrahydro-benzo[b]thiophene-3-sulfonic acid [2-(4-fluorophenyl)-2-hydroxyethyl]-methyl-amide, (7Z)-7-hydroxyimino-4,5,6,7-tetrahydro-benzo[b]thiophene-3-sulfonic acid[2-(4-fluorophenyl)-ethyl]-methyl-amide, (7Z)-N-[(2S)-2-(4-fluorophenyl)-2-hydroxyethyl]-7-(hydroxyimino)-N-methyl-4,5,6,7-tetrahydro-1-benzothiophene-3-sulfonamide, (7Z)-7-hydroxyimino-4,5,6,7-tetrahydro-benzo[b]thiophene-3-sulfonic acid(2-hydroxy-2-pyridine-4-yl-ethyl)-methyl-amide, (7Z)-7-({[(ethylamino)carbonyl]oxo}imino)-3-{[[2-(4-fluorophenyl)-2-hydroxyethyl](methyl)amino]sulfonyl}-4,5,6,7-tetrahydro-1-benzothiophene, (7Z)-3-{[[2-(4-fluorophenyl)-2-hydroxyethyl](methyl)amino]sulfonyl}-7-({[(isopropylamino)carbonyl]oxy}imino)-4,5,6,7-tetrahydro-1-benzothiophene, (7Z)-7-({[(dimethylamino)carbonyl]oxy}imino)-3-{[[2-(4-fluorophenyl)-2-hydroxyethyl](methyl)amino]sulfonyl}-4,5,6,7-tetrahydro-1-benzothiophene, (7Z)-7-{[(aminocarbonyl)oxy]imino}-3-{[[2-(4-fluorophenyl)-2-hydroxyethyl](methyl)amino]sulfonyl}-4,5,6,7-tetrahydro-1-benzothiophene or (7Z)-7-{[(2,2-dimethylpropanoyl)oxy]imino}-N-[2-(4-fluorophenyl)-2-hydroxyethyl]-N-methyl-4,5,6,7-tetrahydro-1-benzothiophene-3-sulfonamide;

47) a pharmaceutical composition comprising a compound represented by the general formula (I')

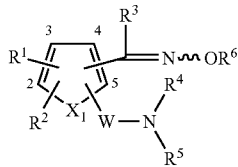

(I')

[wherein, R$^1$ and R$^2$ independently represent a hydrogen atom, a C$_{1-6}$ alkyl group that may have a substituent selected from substituent group α or a substituent selected from substituent group α;

R$^3$ represents a C$_{1-6}$ alkyl group that may have a substituent selected from substituent group α, a C$_{2-6}$ alkenyl group that may have a substituent selected from substituent group α or a C$_{2-6}$ alkynyl group that may have a substituent selected from substituent group α;

or, when R$^1$ and —C(—R$^3$)=N—OR$^6$ are bonded to adjacent carbon atoms, R$^1$ and R$^3$ form a 5–8 membered ring together with the carbon atoms they are bonded to, while the 5–8 membered ring may have 1 to 3 C$_{1-6}$ alkyl groups that may have a substituent selected from substituent group α or substitution groups selected from substituent group α;

R$^4$ and R$^5$ independently represent a hydrogen atom, a C$_{1-6}$ alkyl group that may have a substituent selected from substituent group α, a C$_{2-6}$ alkenyl group that may have a substituent selected from substituent group α, a C$_{2-6}$ alkynyl group that may have a substituent selected from substituent group α, a C$_{3-8}$ cycloalkyl group that may have a substituent selected from substituent group γ, a 3 to 8-membered heterocyclyl group that may have a substituent selected from substituent group γ, a C$_{6-10}$ aryl group that may have a substituent selected from substituent group γ or a 5 to 10-membered heteroaryl group that may have a substituent selected from substituent group γ;

or, R$^4$ and R$^5$, together with the nitrogen atom they are bonded to, form a 5–8 membered ring that may have 1 to 2 heteroatoms on the ring in addition to the nitrogen atom; furthermore, the 5–8 membered ring is condensed with a C$_{6-10}$ aryl group or a 5 to 10-membered heteroaryl group, while the 5–8 membered ring may have 1 to 3 C$_{1-6}$ alkyl groups that may have a substituent selected from substituent group α or substitutents selected from substituent group α.

R$^6$ represents a hydrogen atom, —CONR$^{7a}$R$^{7b}$ (wherein, R$^{7a}$ and R$^{7b}$ represent independently a hydrogen atom, a C$_{1-6}$ alkyl group that may have a substituent selected from substituent group α, a C$_{3-8}$ cycloalkyl group that may have a substituent selected from substituent group α or a C$_{6-10}$ aryl group that may have a substituent selected from substituent group γ) or —COR$^{7c}$ (wherein, R$^{7c}$ represents a C$_{1-6}$ alkyl group that may have a substituent selected from substituent group α);

W represents —SO$_2$ or —CO—;

X represents a sulfur atom or an oxygen atom;

the substituent group α: halogen atoms, hydroxyl groups, mercapto groups, amino groups that may have a substituent selected from substituent group β, nitro groups, cyano groups, formyl groups, carboxyl groups, carbamoyl groups that may have a substituent selected from substituent group β, C$_{1-6}$ alkoxy groups, C$_{1-6}$ alkylthio groups, C$_{2-7}$ alkylcarbonyl groups, C$_{2-7}$ alkylcarbonyloxy groups, C$_{2-7}$ alkoxycarbonyl groups, C$_{1-6}$ alkylsulfinyl groups, C$_{1-6}$ alkylsulfonyl groups, C$_{3-8}$ cycloalkyl groups that may have a substituent selected from substituent group γ, C$_{3-8}$ cycloalkyloxy groups that may have a substituent selected from substituent group γ, C$_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, C$_{6-10}$ aryl groups that may have a substituent selected from substituent group γ, C$_{6-10}$ aryloxy groups that may have a substituent selected from substituent group γ, C$_{6-10}$ arylthio groups that may have a substituent selected from substituent group γ, C$_{6-10}$ arylcarbonyl groups that may have a substituent selected from substituent group γ, C$_{6-10}$ arylcarbonyloxy groups that may have a substituent selected from substituent group γ, C$_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substitution group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino group, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups, $C_{3-8}$ cycloalkyloxy groups, $C_{3-8}$ cycloalkythio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups] or a salt thereof, or a hydrate thereof;

48) an inhibitor for STAT6 activation comprising the compound represented by the general formula (I') or the salt thereof, or the hydrate thereof according to 47);

49) an inhibitor for IL-4 and/or IL-13 signal transduction comprising the compound represented by the general formula (I') or the salt thereof, or the hydrate thereof according to 47);

50) a preventive or therapeutic agent for allergic disease, autoimmune disease, infectious disease, obesity, hyperphagia, malignant tumor or acquired immune deficiency syndrome comprising the compound or the salt thereof, or the hydrate thereof according to any one of 1) to 47);

51) a preventive or therapeutic agent for allergic disease comprising the compound or a salt thereof, or a hydrate thereof according to any one of 1) to 47);

52) the preventive or therapeutic agent for allergic disease according to 51), wherein the allergic disease is atopic dermatitis, allergic coryza, bronchial asthma, hypersensitive pneumoniae or pulmonary aspergillosis;

53) a method for preventing or treating a disease in which an inhibitory action on STAT6 activation and/or inhibitory action on IL-4 and/or IL-13 signal transduction is effective, the method comprising administrating a pharmacologically effective amount of the compound or the salt thereof, or the hydrate thereof according to any one of 1) to 51);

54) use of the compound or the salt thereof, the hydrate thereof according to any one of 1) to 51), for manufacture of a preventive or a therapeutic agent against a disease in which an inhibitory action on STAT6 activation and/or inhibitory action on IL-4 and/or IL-13 signal transduction is effective.

The definitions of the terms used in the specification of the present application are as follows:

The term "halogen atom" used herein means fluorine atom, chlorine atom, bromine atom or iodine atom.

The term "$C_{1-6}$ alkyl group" used herein means an alkyl group that is a straight or branched chain with 1 to 6 carbons. Specifically, examples of "$C_{1-6}$ alkyl group" include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

The term "$C_{2-6}$ alkenyl group" used herein means an alkenyl group that is a straight or branched chain with 2 to 6 carbons. Specifically, examples of "$C_{2-6}$ alkenyl group" include vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group and the like.

The term "$C_{2-6}$ alkynyl group" used herein means an alkynyl group that is a straight or branched chain with 2 to 6 carbons. Specifically, examples of "$C_{2-6}$ alkynyl group" include ethynyl group, 1-propynyl group, 2-propynyl group, 1-butynyl group, 2-butynyl group, 3-butynyl group, 3-methyl-1-propynyl group, 1-ethynyl-2propynyl group, 2-methyl-3-propynyl group, 1-pentynyl group, 1-hexynyl group, 1,3-hexadiynyl group, 1,6-hexadiynyl group, and the like.

The term "$C_{1-6}$ alkoxy group" used herein means an oxy group that is bonded to the previously defined "$C_{1-6}$ alkyl group". Specifically, examples of "$C_{1-6}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

The term "$C_{2-7}$ alkoxycarbonyl group" used herein means a carbonyl group bound to the the previously defined "$C_{1-6}$ alkoxy group".

The term "$C_{2-7}$ alkylcarbonyl group" used herein means a carbonyl group that is bonded to the previously defined "$C_{1-6}$ alkyl group". Specifically, examples of "$C_{2-7}$ alkylcarbonyl group" include acetyl group, propionyl group, butyryl group, isobutyryl group, valeryl group, isovaleryl group, pivaloyl group and the like.

The term "$C_{2-7}$ alkylcarbonyloxy group" used herein means an oxy group that is bonded to the previously defined "$C_{1-6}$ alkylcarbonyl group". Specifically, examples of "$C_{2-7}$ alkylcarbonyloxy group" include acetoxy group, propionyloxy group, butyryloxy group, isobutyryloxy group, valeryloxy group, isovaleryloxy group, pivaloyloxy group and the like.

The term "$C_{1-6}$ alkylthio group" used herein means a thio group that is bonded to the previously defined "$C_{1-6}$ alkyl group". Specifically, examples of "$C_{1-6}$ alkylthio group" include methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, n-hexylthio group, 1-ethyl-2-methylpropylthio group, 1,1,2-trimethylpropylthio group, 1-ethylbutylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group and the like.

The term "$C_{1-6}$ alkylsulfonyl group" used herein means a sulfonyl group that is bonded to the previously defined "$C_{1-6}$ alkyl group". Specifically, examples of "$C_{1-6}$ alkylsulfonyl group" include methylsulfonyl group, ethylsulfonyl group, n-propylsulfonyl group, iso-propylsulfonyl group, n-butylsulfonyl group, iso-butylsulfonyl group, sec-butylsulfonyl group, tert-butylsulfonyl group, n-pentylsulfonyl group, 1,1-dimethylpropylsulfonyl group, 1,2-dimethylpropylsulfonyl group, 2,2-dimethylpropylsulfonyl group, 1-ethylpropylsulfonyl group, n-hexylsulfonyl group, 1-ethyl-2-methylpropylsulfonyl group, 1,1,2-trimethylpropylsulfonyl group, 1-ethylbutylsulfonyl group, 1-methylbutylsulfonyl group, 2-methylbutylsulfonyl group, 1,1-dimethylbutylsulfonyl group, 1,2-dimethylbutylsulfonyl group, 2,2-dimethylbutylsulfonyl group, 1,3-dimethylbutylsulfonyl group, 2,3-dimethylbutylsulfonyl group, 2-ethylbutylsulfonyl group, 2-methylpentylsulfonyl group, 3-methylpentylsulfonyl group and the like.

The term "$C_{1-6}$ alkylsulfinyl group" used herein means a sulfinyl group that is bonded to the previously defined "$C_{1-6}$ alkyl group". Specifically, examples of "$C_{1-6}$ alkylsulfinyl group" include methylsulfinyl group, ethylsulfinyl group, n-propylsulfinyl group, iso-propylsulfinyl group, n-butylsulfinyl group, iso-butylsulfinyl group, sec-butylsulfinyl group, tert-butylsulfinyl group, n-pentylsulfinyl group, 1,1-dimethylpropylsulfinyl group, 1,2-dimethylpropylsulfinyl group, 2,2-dimethylpropylsulfinyl group, 1-ethylpropylsulfinyl group, n-hexylsulfinyl group, 1-ethyl-2-methylpropylsulfinyl group, 1,1,2-trimethylpropylsulfinyl group, 1-ethylbutylsulfinyl group, 1-methylbutylsulfinyl group, 2-methylbutylsulfinyl group, 1,1-dimethylbutylsulfinyl group, 1,2-dimethylbutylsulfinyl group, 2,2-dimethylbutylsulfinyl group, 1,3-dimethylbutylsulfinyl group, 2,3-dimethylbutylsulfinyl group, 2-ethylbutylsulfinyl group, 2-methylpentylsulfinyl group, 3-methylpentylsulfinyl group and the like.

The term "$C_{3-8}$ cycloalkyl group" used herein means a cyclic aliphatic hydrocarbon group with 3 to 8 carbons. Specifically, examples of "$C_{3-8}$ cycloalkyl group" include cyclopropyl group, cyclobutyl group, cyclopentyl group, cyclohexyl group, cycloheptyl group, cyclooctyl group and the like.

The term "$C_{3-8}$ cycloalkyloxy group" used herein means an oxy group that is bonded to the previously described "$C_{3-8}$ cycloalkyl group". Specifically, examples of "$C_{3-8}$ cycloalkyloxy group" include cyclopropyloxy group, cyclobutyloxy group, cyclopentyloxy group, cyclohexyloxy group, cycloheptyloxy group, cyclooctyloxy group and the like.

The term "$C_{3-8}$ cycloalkylthio group" used herein means a thio group that is bonded to the previously described "$C_{3-8}$ cycloalkyl group". Specifically, examples of "$C_{3-8}$ cycloalkylthio group" include cyclopropylthio group, cyclobutylthio group, cyclopentylthio group, cyclohexylthio group, cycloheptylthio group, cyclooctylthio group and the like.

The term "3 to 8-membered heterocyclyl group" used herein means:
1) 3 to 8 atoms forming the ring of the cyclic group,
2) the atom forming the ring contains one or more species of heteroatom selected from the group consisting of a nitrogen atom, a sulphur atom and an oxygen atom,
3) 1 to 3 carbonyl groups within the ring,
4) monovalent or bivalent, and
5) a monocyclic, non-aromatic heterocyclic group. Specifically, examples of "3 to 8-membered heterocyclyl group" include pyrrolidinyl group, piperidyl group, piperidino group, piperadinyl group, morpholinyl group, morpholino group, tetrahydrofuryl group, tetrahydropyranyl group, aziridinyl group, oxiranyl group or oxathiolanyl group and the like, and also include groups derived from a pyridone ring group and non-aromatic condensed ring group (for instance, groups that are derived from phthalimide ring, succinimide ring and the like).

The term "3 to 8-membered heterocyclyloxy group" used herein means an oxy group that is bonded to the previously described "3 to 8-membered heterocyclyl group". Specifically, examples of "3 to 8-membered heterocyclyloxy group" include pyrrolidinyloxy group, piperidyloxy group, piperidinooxy group, piperadinyloxy group, morpholinyloxy group, morpholinooxy group, tetrahydrofuryloxy group, tetrahydropyranyloxy group, aziridinyloxy group, oxiranyloxy group or oxathiolanyloxy group and the like.

The term "3 to 8-membered heterocyclylthio group" used herein means a thio group that is bonded to the previously described "3 to 8-membered heterocyclyl group". Specifically, examples of "3 to 8-membered heterocyclylthio group" include pyrrolidinylthio group, piperidylthio group, piperidinothio group, piperadinylthio group, morpholinylthio group, morpholinothio group, tetrahydrofurylthio group, tetrahydropyranylthio group, aziridinylthio group, oxiranylthio group or oxathiolanylthio group and the like.

The term "$C_{6-10}$ aryl group" used herein means an aryl group constituted by 6 to 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The term "$C_{6-10}$ aryl $C_{1-6}$ alkyl group" used herein means the previously described $C_{1-6}$ alkyl group that is bonded to the previously described "$C_{6-10}$ aryl group". Specifically, examples of "$C_{6-10}$ aryl $C_{1-6}$ alkyl group" include benzylic group, phenylethyl group or naphthylmethyl group and the like.

The term "$C_{6-10}$ aryloxy group" used herein means an oxy group that is bonded to the previously described "$C_{6-10}$ aryl group". Specifically, examples of "$C_{6-10}$ aryloxy group" include phenoxy group, indenyloxy group, naphthyloxy group or azulenyloxy group and the like.

The term "$C_{6-10}$ arylthio group" used herein means a thio group that is bonded to the previously described "$C_{6-10}$ aryl group". Specifically, examples of "$C_{6-10}$ arylthio group" include phenylthio group, indenylthio group, naphthylthio group, or azulenylthio group and the like.

The term "$C_{6-10}$ arylcarbonyl group" used herein means a carbonyl group that is bonded to the previously described "$C_{6-10}$ aryl group". Specifically, examples of "$C_{6-10}$ arylcarbonyl group" include benzoyl group, indenylcarbonyl group, naphthylcarbonyl group or azulenylcarbonyl group and the like.

The term "$C_{6-10}$ arylcarbonyloxy group" used herein means an oxy group that is bonded to the previously described "$C_{6-10}$ arylcarbonyl group". Specifically, examples of "$C_{6-10}$ arylcarbonyloxy group" include benzoyloxy group, indenylcarbonyloxy group, naphthylcarbonyloxy group or azulenylcarbonyloxy group and the like.

The term "$C_{6-10}$ aryloxycarbonyl group" used herein means a carbonyl group that is bonded to the previously described "$C_{6-10}$ aryloxy group". Specifically, examples of "$C_{6-10}$ aryloxycarbonyl group" include phenoxycarbonyl group, indenyloxycarbonyl group, naphthyloxycarbonyl group or azulenyloxycarbonyl group and the like.

The term "5 to 10-membered heteroaryl group" used herein means a monocyclic or bicyclic heteroaryl group, in which the number of atoms forming the ring is 5 to 10, containing one or more species of heteroatom selected from the group consisting of a nitrogen atom, a sulphur atom and an oxygen atom. Specifically, examples of "5 to 10-membered heteroaryl group" include 1) pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group and the like as a nitrogen-containing heteroaryl group; 2) thienyl group, benzothienyl group and the like as a sulphur-containing heteroaryl group; 3) furyl group, pyranyl group, benzofuryl group, isobenzofuryl group and the like as an oxygen-containing heteroaryl group; and 4) thiazolyl group, isothiazolyl group, benzothiazolyl group, benzothiadiazolyl group, phenothiazinyl group, isoxazolyl group, furazanyl group, phenoxazinyl group, oxazolyl group, benzooxazolyl group, oxadiazolyl group, pyrazolooxazolyl group, imidazothiazolyl group, thienofuranyl group, furopyrrolyl group or pyridooxazinyl group and the like as a heteroaryl group containing two or more different species of heteroatoms.

The term "5 to 10-membered heteroaryloxy group" used herein means an oxy group that is bonded to the previously described "5 to 10-membered heteroaryl group". Specifically, examples of "5 to 10-membered heteroaryloxy group" include pyrrolyloxy group, pyridyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolyloxy group, isoquinolyloxy group, quinolizinyloxy group, phthalazyloxy group, naphthylidinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, thienyloxy group, benzothienyloxy group, furyloxy group, pyranyloxy group, benzofuryloxy group, isobenzofuryloxy group, thiazolyloxy group, isothiazolyloxy group, benzothiazolyloxy group, benzothiadiazolyloxy group, phenothiazinyloxy group, isoxazolyloxy group, furazanyloxy group, phenoxazinyloxy group, oxazolyloxy group, benzooxazolyloxy group, oxadiazolyloxy group, pyrazolooxazolyloxy group, imidazothiazolyloxy group, thienofuranyloxy group, furopyrrolyloxy group or pyridooxazinyloxy group and the like.

The term "5 to 10-membered heteroarylthio group" used herein means a thio group that is bonded to the previously described "5 to 10-membered heteroaryl group". Specifically, examples of "5 to 10-membered heteroarylthio group" include pyrrolylthio group, pyridylthio group, pyridazinylthio group, pyrimidinylthio group, pyrazinylthio group, triazolylthio group, tetrazolylthio group, benzotriazolylthio group, pyrazolylthio group, imidazolylthio group, benzimidazolylthio group, indolylthio group, isoindolylthio group, indolizinylthio group, purinylthio group, indazolylthio group, quinolylthio group, isoquinolylthio group, quinolizinylthio group, phthalazylthio group, naphthylidinylthio group, quinoxalinylthio group, quinazolinylthio group, cinnolinylthio group, pteridinylthio group, imidazotriazinylthio group, pyrazinopyridazinylthio group, acridinylthio group, phenanthridinylthio group, thienylthio group, benzothienylthio group, furylthio group, pyranylthio group, benzofurylthio group, isobenzofurylthio group, thiazolylthio group, isothiazolylthio group, benzothiazolylthio group, benzothiadiazolylthio group, phenothiazinylthio group, isoxazolylthio group, furazanylthio group, phenoxazinylthio group, oxazolylthio group, benzooxazolylthio group, oxadiazolylthio group, pyrazolooxazolylthio group, imidazothiazolylthio group, thienofuranylthio group, furopyrrolylthio group or pyridooxazinylthio group and the like.

The term "5 to 10-membered heteroarylcarbonyl group" used herein means a carbonyl group that is bonded to the previously described "5 to 10-membered heteroaryl group". Specifically, examples of "5 to 10-membered heteroarylcarbonyl group" include pyrrolylcarbonyl group, pyridylcarbonyl group, pyridazinylcarbonyl group, pyrimidinylcarbonyl group, pyrazinylcarbonyl group, triazolylcarbonyl group, tetrazolylcarbonyl group, benzotriazolylcarbonyl group, pyrazolylcarbonyl group, imidazolylcarbonyl group, benzimidazolylcarbonyl group, indolylcarbonyl group, isoindolylcarbonyl group, indolizinylcarbonyl group, purinylcarbonyl group, indazolylcarbonyl group, quinolylcarbonyl group, isoquinolylcarbonyl group, quinolizinylcarbonyl group, phthalazylcarbonyl group, naphthylidinylcarbonyl group, quinoxalinylcarbonyl group, quinazolinylcarbonyl group, cinnolinylcarbonyl group, pteridinylcarbonyl group, imidazotriazinylcarbonyl group, pyrazinopyridazinylcarbonyl group, acridinylcarbonyl group, phenanthridinylcarbonyl group, thienylcarbonyl group, benzothienylcarbonyl group, furylcarbonyl group, pyranylcarbonyl group, benzofurylcarbonyl group, isobenzofurylcarbonyl group, thiazolylcarbonyl group, isothiazolylcarbonyl group, benzothiazolylcarbonyl group, benzothiadiazolylcarbonyl group, phenothiazinylcarbonyl group, isoxazolylcarbonyl group, furazanylcarbonyl group, phenoxazinylcarbonyl group, oxazolylcarbonyl group, benzooxazolylcarbonyl group, oxadiazolylcarbonyl group, pyrazolooxazolylcarbonyl group, imidazothiazolylcarbonyl group, thienofuranylcarbonyl group, furopyrrolylcarbonyl group or pyridooxazinylcarbonyl group and the like.

The term "5 to 10-membered heteroarylcarbonyloxy group" used herein means an oxy group that is bonded to the previously described "5 to 10-membered heteroarylcarbonyl group". Specifically, examples of "5 to 10-membered heteroarylcarbonyloxy group" include pyrrolylcarbonyloxy group, pyridylcarbonyloxy group, pyridazinylcarbonyloxy group, pyrimidinylcarbonyloxy group, pyrazinylcarbonyloxy group, triazolylcarbonyloxy group, tetrazolylcarbonyloxy group, benzotriazolylcarbonyloxy group, pyrazolylcarbonyloxy group, imidazolylcarbonyloxy group, benzimidazolylcarbonyloxy group, indolylcarbonyloxy group, isoindolylcarbonyloxy group, indolizinylcarbonyloxy group, purinylcarbonyloxy group, indazolylcarbonyloxy group, quinolylcarbonyloxy group, isoquinolylcarbonyloxy group, quinolizinylcarbonyloxy group, phthalazylcarbonyloxy group, naphthylidinylcarbonyloxy group, quinoxalinylcarbonyloxy group, quinazolinylcarbonyloxy group, cinnolinylcarbonyloxy group, pteridinylcarbonyloxy group, imidazotriazinylcarbonyloxy group, pyrazinopyridazinylcarbonyloxy group, acridinylcarbonyloxy group, phenanthridinylcarbonyloxy group, thienylcarbonyloxy group, benzothienylcarbonyloxy group, furylcarbonyloxy group, pyranylcarbonyloxy group, benzofurylcarbonyloxy group, isobenzofurylcarbonyloxy group, thiazolylcarbonyloxy group, isothiazolylcarbonyloxy group, benzothiazolylcarbonyloxy group, benzothiadiazolylcarbonyloxy group, phenothiazinylcarbonyloxy group, isoxazolylcarbonyloxy group, furazanylcarbonyloxy group, phenoxazinylcarbonyloxy group, oxazolylcarbonyloxy group, benzooxazolylcarbonyloxy group, oxadiazolylcarbonyloxy group, pyrazolooxazolylcarbonyloxy group, imidazothiazolylcarbonyloxy group, thienofuranylcarbonyloxy group, furopyrrolylcarbonyloxy group or pyridooxazinylcarbonyloxy group and the like.

The term "5 to 10-membered heteroaryloxycarbonyl group" used herein means a carbonyl group that is bonded to the previously described "5 to 10-membered heteroaryloxy group". Specifically, examples of "5 to 10-membered heteroaryloxycarbonyl group" include pyrrolyloxycarbonyl group, pyridyloxycarbonyl group, pyridazinyloxycarbonyl group, pyrimidinyloxycarbonyl group, pyrazinyloxycarbonyl group, triazolyloxycarbonyl group, tetrazolyloxycarbonyl group, benzotriazolyloxycarbonyl group, pyrazolyloxycarbonyl group, imidazolyloxycarbonyl group, benzimidazolyloxycarbonyl group, indolyloxycarbonyl group, isoindolyloxycarbonyl group, indolizinyloxycarbonyl group, purinyloxycarbonyl group, indazolyloxycarbonyl group, quinolyloxycarbonyl group, isoquinolyloxycarbonyl group, quinolizinyloxycarbonyl group, phthalazyloxycarbonyl group, naphthylidinyloxycarbonyl group, quinoxalinyloxycarbonyl group, quinazolinyloxycarbonyl group, cinnolinyloxycarbonyl group, pteridinyloxycarbonyl group, imidazotriazinyloxycarbonyl group, pyrazinopyridazinyloxycarbonyl group, acridinyloxycarbonyl group, phenanthridinyloxycarbonyl group, thienyloxycarbonyl group, benzothienyloxycarbonyl group, furyloxycarbonyl group, pyranyloxycarbonyl group, benzofuryloxycarbonyl group, isobenzofuryloxycarbonyl group, thiazolyloxycarbonyl group, isothiazolyloxycarbonyl group, benzothiazolyloxycarbonyl group, benzothiadiazolyloxycarbonyl group, phenothiazinyloxycarbonyl group, isoxazolyloxycarbonyl group, furazanyloxycarbonyl group, phenoxazinyloxycarbonyl group, oxazolyloxycarbonyl group, benzooxazolyloxycarbonyl group, oxadiazolyloxycarbonyl group, pyrazolooxazolyloxycarbonyl group, imidazothiazolyloxycarbonyl group, thienofuranyloxycarbonyl group, furopyrrolyloxycarbonyl group or pyridooxazinyloxycarbonyl group and the like.

The scopes of the compound indicated by the General Formula (I) and the scope of the compound indicated by the General Formula (I') according to the present invention differ on the point of the presence/absence of the compound described in Patent Reference 9. In other words, the scope of the compound indicated by the General Formula (I) is a novel scope as a compound, while the scope of the compound indicated by the General Formula (I') is novel use scope based on STAT6 inhibition activity.

The term "when $R^1$ and $—C(—R^3)=N—OR^6$ are bonded to adjacent carbon atoms, $R^1$ and $R^3$ form a 5–8 membered ring together with the carbon atoms they are bonded to" used herein means that $R^1$ and $R^3$ are bonded to each other, and together with the carbon atoms that $R^1$ and $R^3$ are respectively bonded to, so as to form a 5–8 membered ring. Specifically, examples of the above term include the following structural formulae:

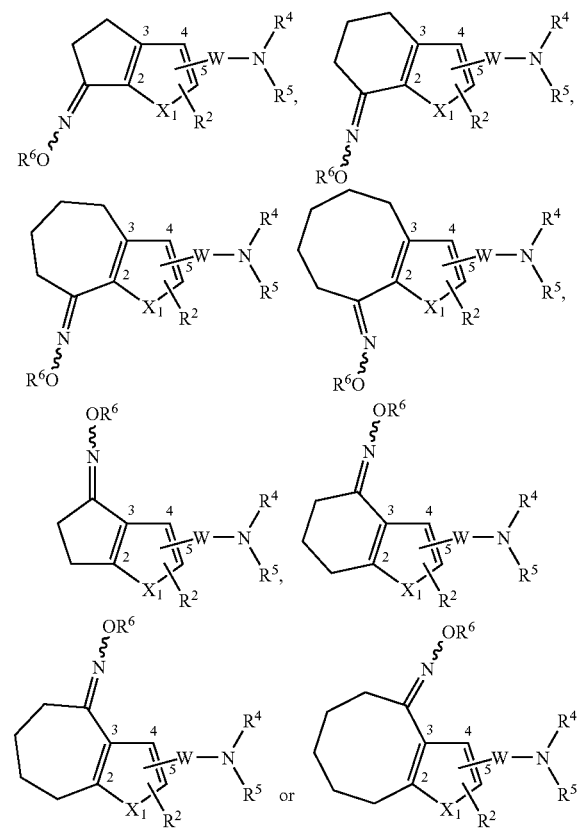

and preferably include the following structural formulae:

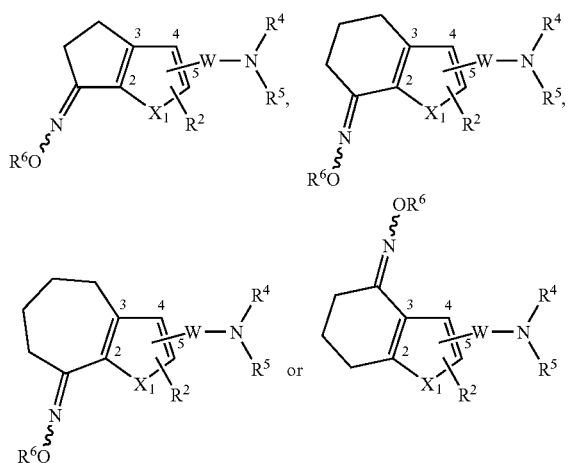

The term "may have a substituent selected from substituent group α" used herein refers to having 1 to 3 homogeneous or heterogenous substituents from a substituent listed in substituent group α, unless specifically specified.

As described above, the terms "may have a substituent selected from substituent group β" and "may have substituent selected from substituent group γ" also refer to having 1 to 3 homogeneous or heterogenous substituents from a substituent listed in each substituent group.

In the following, a substituent or a partial structure thereof in the compounds according to the present invention indicated by the General Formula (I) to (I-d') will be explained.

$R^1$ is a hydrogen atom, a $C_{1-6}$ alkyl group that may have a substitutient selected from substituent group α or a substituent selected from substituent group α, preferably, $R^1$ is a hydrogen atom, a halogen atom, a hydroxyl group, a mercapto group, an amino group, a nitro group, a cyano group, a formyl group, a carboxyl group, a carbamoyl group or a $C_{1-6}$ alkyl group, more preferably a hydrogen atom, a halogen atom, a hydroxyl group, an amino group or a $C_{1-6}$ alkyl group. Most preferably, $R^1$ is a hydrogen atom.

$R^2$ is a hydrogen atom, a $C_{1-6}$ alkyl group that may have a substituent selected from substituent group α or a substituent selected from substituent group α, preferably, $R^2$ is a hydrogen atom, $C_{1-6}$ alkyl group that may have a substituent selected from substituent group α, an amino group that may have a substituent selected from substituent group β or an $C_{1-6}$ alkoxy group, more preferably $R^2$ is a hydrogen atom, an amino group that may have a substituent selected from substituent group β or a $C_{1-6}$ alkoxy group, and most preferably $R^2$ is a hydrogen atom, an amino group or a methoxy group.

$R^3$ is a $C_{1-6}$ alkyl group that may have a substituent selected from substituent group α, a $C_{2-6}$ alkenyl group that may have a substituent selected from substituent group α or a $C_{2-6}$ alkynyl group that may have a substituent selected from substituent group α, preferably $R^3$ is a $C_{1-6}$ alkyl group that may have a substituent selected from substituent group α, more preferably $R^3$ is a $C_{1-3}$ alkyl group that may have a substitutient selected from substituent group α, and most preferably $R^3$ is a methyl group that may have a substituent selected from substituent group α.

$R^4$ is a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ, a 5 to 10-membered heteroaryl group that may have a substituent selected from substituent group γ, preferably, $R^4$ is a $C_{1-6}$ alkyl group that may have a substituent selected from substituent group α, more preferably, $R^4$ is a partial structure represented by the following formula:

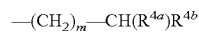

$$-(CH_2)_m-CH(R^{4a})R^{4b}$$

[wherein, $R^{4a}$ is a $C_{6-10}$ aryl group that may have a substituent selected from substituent group γ or a 5 to 10-membered heteroaryl group that may have a substituent selected from substituent group γ, $R^{4b}$ is a hydrogen atom or a substituent selected from substituent group α, and m is 0, 1, 2, 3, 4 or 5].

$R^{4a}$ is a $C_{6-10}$ aryl group that may have a substituent selected from substituent group γ or a 5 to 10-membered heteroaryl group that may have a substituent selected from substituent group γ, preferably, $R^{4a}$ is a phenyl group that may have a substituent selected from substituent group γ, a pyridyl group that may have a substituent selected from substituent group γ, a thienyl group that may have a substituent selected from substituent group γ, more preferably $R^{4a}$ is a phenyl group that may have 1 to 3 substituents selected from the group consisting of a halogen atom, a hydroxyl group, a mercapto group, an amino group, a nitro group, a cyano group, a formyl group, a carboxyl group, carbamoyl groups, $C_{1-6}$ alkyl groups, $C_{1-6}$ alkoxy groups and $C_{1-6}$ alkylthio groups (hereinafter referred to as "substituent group γ1"), a pyridyl group that may have 1 to 3 substituents selected from substituent group γ1 or a thienyl group that may have 1 to 3 substituents selected from substituent group γ1, more preferably $R^{4a}$ is a phenyl group that may have 1 to 3 substituents selected from substituent group γ1, most preferably $R^{4a}$ is a phenyl group that may have 1 to 3 substituents selected from a halogen atom, a nitro group and $C_{1-6}$ alkoxy groups, more desirably $R^{4a}$ is a phenyl group that may have 1 to 3 of a fluorine atom, a nitro group or a methoxy group, and most desirably $R^{4a}$ is a 4-fluoro-phenyl group.

$R^{4b}$ is a hydrogen atom or substituent selected from substituent group α, preferably $R^{4b}$ is a hydrogen atom, a halogen atom, a hydroxyl group, an amino group that may have 1 or 2 substituents selected from substituent group ε, a carboxyl group, a carbamoyl group that may have 1 or 2 substituents selected from substituent group β, a $C_{1-6}$ alkoxy group or a $C_{2-7}$ alkylcarbonyloxy group, more preferably, $R^{4b}$ is a hydrogen atom, a fluorine atom, a hydroxyl group, a methylcarbonylamino group, a methylsulfonylamino group, a carbamoylamino group, a carboxyl group, a carbamoyl group, a methoxy group or an ethylcarbonyloxy group, and most preferably, $R^{4b}$ is a hydrogen atom or a hydroxyl group.

The subfix "m" stands for 0, 1, 2, 3, 4 or 5, preferably m stands for 0, 1 or 2, and most preferably 1.

$R^5$ is a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ, a 5 to 10-membered heteroaryl group that may have a substituent selected from substituent group γ, preferably, $R^5$ is a hydrogen atom, a $C_{1-6}$ alkyl group that may have 1 to 3 substituents selected from substituent group α, a $C_{2-6}$ alkynyl group that may have 1 to 3 substituents selected from substituent group α or a $C_{3-8}$ cycloalkyl group that may have 1 to 3 substituents selected from substituent group γ, more preferably, $R^5$ is a hydrogen atom, a cyanomethyl group, a carbamoylmethyl group, an isopropyl group, a propin-1-yl group, a cyclopropyl group, and most preferably, $R^5$ is a hydrogen atom or a methyl group.

$R^6$ is a hydrogen atom, $—CONR^{7a}R^{7b}$ (wherein, $R^{7a}$ and $R^{7b}$ independently represent a hydrogen atom, a $C_{1-6}$ alkyl group that may have a substituent selected from substituent group α, a $C_{3-8}$ cycloalkyl group that may have a substituent selected from substituent group α or a $C_{6-10}$ aryl group that may have a substituent selected from substituent group γ) or $—COR^{7c}$ (wherein, $R^{7c}$ is a hydrogen atom or a $C_{1-6}$ alkyl group that may have a substituent selected from substituent group α), preferably, $R^6$ is a hydrogen atom, $—CONR^{7a}R^{7b}$ (wherein, $R^{7a}$ and $R^{7b}$ independent represent a hydrogen atom, a $C_{1-6}$ alkyl group, a $C_{3-8}$ cycloalkyl group or a $C_{6-10}$ aryl group having a substitution group selected from a halogen atom, a cyano group, a $C_{1-6}$ alkyl group or a $C_{1-6}$ alkoxy group) or $—COR^{7c}$ (wherein, $R^{7c}$ represents a $C_{1-6}$ alkyl group), more preferably, $R^6$ is a hydrogen atom, a pivaloyl group, a carbamoyl group, a dimethylaminocarbonyl group, an ethylaminocarbonyl group, a propylaminocarbonyl group, an isopropylaminocarbonyl group, a t-butylaminocarbonyl group, a cyclohexylaminocarbonyl group, a benzylaminocarbonyl group, a fluorophenylaminocarbonyl group, an ethylphenylaminocarbonyl group, a methoxyphenylaminocarbonyl group, an ethoxy phenylaminocarbonyl group, a cyano phenylaminocarbonyl group, a tolylaminocarbonyl group or a methylenedioxyphenylaminocarbonyl group, and most preferably, $R^6$ is a hydrogen atom, a pivaloyl group, a carbamoyl group, dimethylaminocarbonyl group, an ethylaminocarbonyl group, a isopropylaminocarbonyl group, a cyclohexylaminocarbonyl group, an ethylphenylaminocarbonyl group or a methoxyphenylaminocarbonyl group.

$R^a$, $R^b$ and $R^c$ independently represent a hydrogen atom, a $C_{1-6}$ alkyl group that may have a substituent selected from substituent group α or a substituent selected from substituent group α, preferably, $R^a$, $R^b$ and $R^c$ represent a hydrogen atom, a halogen atom, a hydroxyl group, a mercapto group, an amino group that may have 1 or 2 substituents selected from substituent group β, a nitro group, a cyano group, a carboxyl group, a carbamoyl group, a $C_{1-6}$ alkyl group that may have 1 to 3 substituents selected from substituent group α or a $C_{1-6}$ alkoxy group.

Preferably $R^a$ is a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group, more preferably $R^a$ is a hydrogen atom, a hydroxyl group, a cyano group or a methyl group, and most preferably $R^a$ is a hydrogen atom.

Preferably $R^b$ is a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group, more preferably $R^b$ is a hydrogen atom, a hydroxyl group, a cyano group or a methyl group, and most preferably $R^b$ is a hydrogen atom.

Preferably $R^c$ is a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group, more preferably $R^c$ is a hydrogen atom, a hydroxyl group, a cyano group or a methyl group, and most preferably $R^c$ is a hydrogen atom.

W represents $—CO_2—$ or $—SO_2—$, preferably $—SO_2—$.

X represents an oxygen atom or a sulphur atom, preferably a sulphur atom.

Among the compounds according to the present invention, examples of the preferrred compounds include (7Z)-7-hydroxyimino-4,5,6,7-tetrahydro-benzo[b] thiophene-3-sulfonic acid[2-(4-fluorophenyl)-2-hydroxyethyl]-methyl-amide, (7Z)-7-hydroxyimino-4,5,6,7-tetrahydro-benzo[b] thiophene-3-sulfonic acid[2-(4-fluorophenyl)-ethyl]-methyl-amide, (7Z)-N-[(2S)-2-(4-fluorophenyl)-2-hydroxyethyl]-7-(hydroxyimino)-N-met hyl-4,5,6,7-tetrahydro-1-benzothiophene-3-sulfonamide, (7Z)-7-hydroxyimino-4,5,6,7-tetrahydro-benzo[b] thiophene-3-sulfonic acid (2-hydroxy-2-pyridine-4-ylethyl)-methyl-amide, (7Z)-7-({[(ethylamino)carbonyl]oxo}imino)-3-{[[2-(4-fluorophenyl)-2-hydroxyethyl](methyl)amino]sulfonyl}-4,5,6,7-tetrahydro-1-benzothiophene, (7Z)-3-{[[2-(4-fluorophenyl)-2-hydroxyethyl](methyl) amino]sulfonyl}-7-({[(isopropylamino)carbonyl] oxy}imino)-4,5,6,7-tetrahydro-1-benzothiophene, (7Z)-7-({[(dimethylamino)carbonyl]oxy}imino)-3-{[[2-(4-fluorophenyl)-2-hydroxyethyl](methyl)amino]sulfonyl}-4,5,6,7-tetrahydro-1-benzothiophene, (7Z)-7-{[(aminocarbonyl)oxy]imino}-3-{[[2-(4-fluorophenyl)-2-hydroxyethyl](methyl)amino]sulfonyl}-4,5,6,7-tetrahydro-1-benzothiophene or (7Z)-7-{[(2,2-dimethylpropanoyl)oxy]imino}-N-[2-(4-fluorophenyl)-2-hydroxyethyl]-N-methyl-4,5,6,7-tetrahydro-1-benzothiophene-3-sulfonamide.

In the General Formulae of the present application, although the wavy lines indicates that both the syn (Z) isomer/anti (E) isomer structures may be adopted, the syn (Z) isomer is preferred.

The structural formula of the compound may be described to represent a given isomer for the sake of convenience; however, all isomers of the compound that may occur structurally such as an geometric isomer, an optical isomer, a stereoisomer and a tautomer are included in the present invention, and there is no limitation to the formula described for the sake of convenience, regardless of whether it is an isolated isomer (for instance, an enantiomer), or a mixture of isomers (for instance, a racemic mixture).

When the compound according to the present invention is obtained in free form, it can be converted into a salt or a hydrate thereof by a conventional method.

Herein, there is no limitation on the "salt" according to the present invention as long as it forms a salt with the compound according to the present invention, and is pharmacologically acceptable. The preferred examples of the salt include hydrohalogenates (for instance, hydrochloride salt, hydrobromide salt, hydroiodide salt and the like), inorganic acid salts (for instance, sulphate salt, nitrate salt, perchlorate salt, phosphate salt, carbonate salt, bicarbonate salt and the like), organic carboxylic acid salts (for instance, acetate salt, maleate salt, tartrate salt, fumarate salt, citrate salt and the like), organic sulfonic acid salts (for instance, methanesulfonate salt, ethane sulfonate salt, benzenesulfonate salt, toluenesulfonate salt, camphorsulfonate salt and the like), amino acid salt (for instance, aspartate salt, glutamate salt and the like), quaternary ammonium salts, alkaline metal salts (for instance, sodium salt, potassium salt and the like), alkaline earth metal salts (magnesium salt, calcium salt and the like) and the like. In addition, hydrochloride salt, sulphate salt, methanesulfonate salt, acetate salt and the like are preferable as a "pharmacologically acceptable salt" of compounds according to the present invention.

Futher, when the compound according to the present invention may comprise various isomers (for instance, the geometric isomer, the optical isomer, the rotational isomer, the tautomer and the like), it can also be purified into a single isomer by means of a conventional separation method, for instance, recrystallization, optical resolution such as diastereomeric salt method, enzyme fractionation method, various chromatographic methods (for instance, thin layer chromatography, column chromatography, glass chromatography and the like). However, a single isomer herein includes not only the isomer having 100% purity, but also the isomer containing non-target isomers still remaining after undergoing conventional purification operation. In addition, when using the compound according to the present invention as a raw material for medicinal drug, the single isomer mentioned above may be used, in addition, a mixture of isomers in any proportions may be used.

Crystal polymorphism may exist for the compound according to the present invention, salts thereof, or hydrates thereof; however, all the polymorphic crystals thereof are included in the present invention. Crystal polymorphism may exist for a single isomer or a mixture, and both are included in the present invention.

In addition, a compound still demonstrating the desired pharmacological activity after the compound according to the present invention has been subjected to metabolism such as oxidation and hydrolysis in vivo is also included in the present invention.

Furthermore, a compound in which when subjected to metabolism such as oxidation, reduction and hydrolysis in vivo, generates the compound according to the present invention, a so-called prodrug, is also included in the present invention.

The compound according to the present invention, a salt thereof or a hydrate thereof can be formulated by a conventional method. Examples of the preferred dosage forms include a tablet, a powder, a subtle granule, a granule, a coated tablet, a capsule, a syrup, a troche, a inhalant, a suppository, a injectable, an ointment, an ophthalmic ointment, an eye drop, a nasal drop, an ear drop, a cataplasm, a lotion and the like. For formulation, a diluent, a binder, a disintegration agent, a lubricant, a colorant and a flavoring agent used in general, and as necessary, additives such as a stabilizer, an emulsifyer, an absorption enhancer, a surfactant, a pH adjuster, an antiseptic agent, and an antioxidant can be used. In addition, formulation is also possible by combining ingredients that are used in general as raw materials of pharmaceutical formulation, by the conventional method. Examples of these ingredients include (1) soybean oil, animal oil such as beef tallow and synthethic glyceride; (2) hydrocarbon such as liquid paraffin, squalane and solid paraffin; (3) an ester oil such as octyldodecylmyristate and isopropylmyristate; (4) higher alcohol such as cetostearylalcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, polyoxyethylene hardened castor oil and polyoxyethylene polyoxypropylene block co-polymer; (8) a water-soluble polymer such as hydroxyethyl cellulose, polyacrylic acid, carboxyvinyl polymer, polyethyleneglycol, polyvinylpyrrolidone and methyl cellulose; (9) lower alcohol such as ethanol and isopropanol; (10) multivalent alcohol such as glycerin, propylene glucol, dipropylene glycol and sorbitol; (11) a sugar such as glucose and cane sugar; (12) an inorganic powder such as anhydrous silicic acid, magnesium aluminium silicate and aluminium silicate; and (13) purified water and the like.

Among the aforementioned additives, use can be made of 1) lactose, corn starch, sucrose, glucose, mannitol, sorbit, crystalline cellulose, silicon dioxide and the like as a diluting agent; 2) polyvinyl alcohol, polyvinyl ether, methyl cellulose, ethyl cellulose, gum arabic, traganth, gelatine, shellac, hydroxypropyl cellulose, hydroxypropylmethyl cellulose, polyvinylpyrrolidone, polypropyleneglycol polyoxyethylene block co-polymer, meglumine, calcium citrate, dextrin, pectin and the like as a binder; 3) a starch, agar, gelatine powder, crystalline cellulose, calcium carbonate, sodium bicarbonate, calcium citrate, dextrin, pectin, calcium carboxymethylcellulose and the like as a disintegration agent; 4) magnesium stearate, talc, polyethyleneglycol, silica, hardened plant oil and the like as a lubricant; 5) a colorant, as long as addition thereof to a pharmaceutical drug is authorized, as a colorant; 6) a cocoa powder, menthol, fragrance, a peppermint oil, a cinnamon powder as a flavoring agent; and 7) an antioxidants whose addition to a pharmaceutical drug is authorized such as ascorbic acid and α-tocophenol as an antioxidant.

The doses of the medicinal drug according to the present invention differ depending on the severity of the symptoms, age, sex, body weight, mode of administration and type of salt, difference in susceptibility to the drug, actual type of disease and the like. Administration may be in general, for an adult, approximately 30 μg to 1000 mg per day, preferably 100 μg to 500 mg and more preferably 100 μg to 100 mg by oral administration, approximately 1 to 3000 μg/kg and preferably 3 to 1000 μg/kg by injection administration, respectively at once or divided over several times.

In the following, the general synthesizing methods for the compounds according to the invention of the present application will be explained; however, they are not limited thereto.

[General Synthesis Methods]

The compound represented by the General Formula (I) of the present invention or salts thereof can be synthesized by the following methods A to G an.

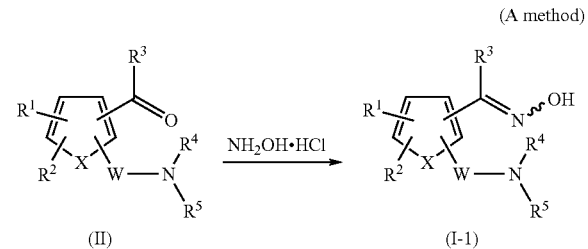

(A method)

(II) → (I-1)

The A method is a preparation method whereby the compound (I-1) according to the present invention is obtained by reacting hydroxylamine hydrochloride with the compound (II) in a polar solvent, in the presence or in the absence of an acid or a base.

In the above-mentioned scheme, $R^1$ and $R^2$ independent represent a hydrogen atom, a $C_{1-6}$ alkyl group that may have a substituent selected from substituent group α or a substituent selected from substituent group α;

$R^3$ represents a $C_{1-6}$ alkyl group that may have a substituent selected from substituent group α, a $C_{2-6}$ alkenyl group that may have a substituent selected from substituent group α or a $C_{2-6}$ alkynyl group that may have a substituent selected from substituent group α;

or, when $R^1$ and —C(—$R^3$)=N—$OR^6$ are bonded to adjacent carbon atoms, $R^1$ and $R^3$ form a 5–8 membered ring together with the carbon atoms they are bonded to, while the 5–8 membered ring may have, as a substituent, 1 to 3 $C_{1-6}$ alkyl groups that may have a substituent selected from substituent group α or substituents selected from substituent group α;

$R^4$ and $R^5$ independent represent a hydrogen atom, a $C_{1-6}$ alkyl group that may have a substituent selected from substituent group α, a $C_{2-6}$ alkenyl group that may have a substituent selected from substituent group α, a $C_{2-6}$ alkynyl group that may have a substituent selected from substituent group α, a $C_{3-8}$ cycloalkyl group that may have a substituent selected from substituent group γ, a 3 to 8-membered heterocyclyl group that may have a substituent selected from substituent group γ, a $C_{6-10}$ aryl group that may have a substituent selected from substituent group γ or a 5 to 10-membered heteroaryl group that may have a substituent selected from substituent group γ;

or, $R^4$ and $R^5$, together with the nitrogen atom they are bonded to, form a 5–8 membered ring that may have 1 to 2 heteroatoms on the ring in addition to the nitrogen atom; furthermore, the 5–8 membered ring is condensed with a $C_{6-10}$ aryl group or a 5 to 10-membered heteroaryl group, while the 5–8 membered ring may have, as a substituent, 1 to 3 $C_{1-6}$ alkyl groups that may have a substituent selected from substituent group α or substituents selected from substituent group α.

W represents —$SO_2$— or —CO—;

X represents a sulphur atom or an oxygen atom;

the substituent group α: halogen atoms, hydroxyl groups, mercapto groups, amino groups that may have a substituent selected from substituent group β, nitro groups, cyano groups, formyl groups, carboxyl groups, carbamoyl groups that may have a substituent selected from substituent group β, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered heterocyclyl groups that may have a substituent selected from substituent group γ, 3 to 8-membered heterocyclyloxy groups that may have a substituent selected from substituent group γ, 3 to 8-membered heterocyclylthio groups that may have a substituent selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-0}$ arylcarbonyloxy groups that may have a substituent selected from substituent group γ, $C_{6-10}$ aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino groups, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alkylsulfonyl groups, $C_{3-8}$ cycloalkyl groups, $C_{3-8}$ cycloalkyloxy groups, $C_{3-8}$ cycloalkythio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryl $C_{1-6}$ alkyl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups.

The quantity of hydroxylamine hydrochloride used is in the range of 1.05 to 2.5 molar equivalents with respect to 1 mole of compound (II), preferably in the range of 1.05 to 2.0 molar equivalents.

There is no particular limitation on the solvent used as long as it dissolves the starting substance to some extent, and does not inhibit the reaction. Specifically, examples of the above solvent include alcohol such as methanol, ethanol and isopropanol, a polar solvent such as tetrahydrofuran, N,N-dimethylformamide, dimethylsulfoxide, acetonitrile, acetic acid, pyridine and water, or solvents that are mixtures of these solvent. Preferably, the solvent is ethanol, tetrahydrofuran, N,N-dimethylformamide, dimethylsulfoxide, pyridine or water.

There is no particular restriction on the acid used as long as the target compound can be obtained, and it does not generate any unseparatable by-products. Specifically, examples of the acid include an organic acid such as acetic acid or trifluoroacetic acid, or an inorganic acid such as hydrochloric acid or phosphoric acid; preferably, it is acetic acid.

There is no particular restriction on the base used as long as the target compound can be obtained, and it does not generate any unseparatable by-products. Specifically, examples of the base include an organic base such as sodium acetate, triethylamine or pyridine, or an inorganic base such as sodium carbonate, sodium bicarbonate or sodium hydride; preferably, sodium acetate or pyridine and the like may be desired There is no particular limitation on the quantity of acid or basic used as long as the reaction is promoted; however, it is in general 0.1 to 2.0 molar equivalents with respect to 1 mole of compound (II), and preferably 0.1 to 1.1 molar equivalent.

The reaction temperature varies depending on the starting materials, the solvent, the reagents and the like; however, it is in general 20 to 200° C., and preferably 60 to 160° C.

The reaction time varies depending on the starting materials, the solvent, reagents and the like; however, it is in general 0.5 to 72 hours, and preferably 0.5 to 24 hours.

In the above-mentioned scheme, $R^1$, $R^2$, $R^3$, $R^4$, $R^5$, W and X have the same meaning as previously defined, and $R^{7a}$ represents a hydrogen atom, the $C_{1-6}$ alkyl group that may have a substituent selected from substituent group α, the $C_{3-8}$ cycloalkyl group that may have a substituent selected from substituent group α or the $C_{6-10}$ aryl group that may have a substituent selected from substituent group γ.

The quantity of compound (b) used is 1.05 to 3.0 molar equivalents with respect to 1 mole of compound (I-1), and preferably 1.05 to 2.0 molar equivalents.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrofuran or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine, or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general 0 to 150° C., and preferably 10 to 120° C.

The reaction time varies depending on the starting materials, the solvent, the reagents and the like; however, it is in general 0.5 to 72 hours, and preferably 0.5 to 24 hours.

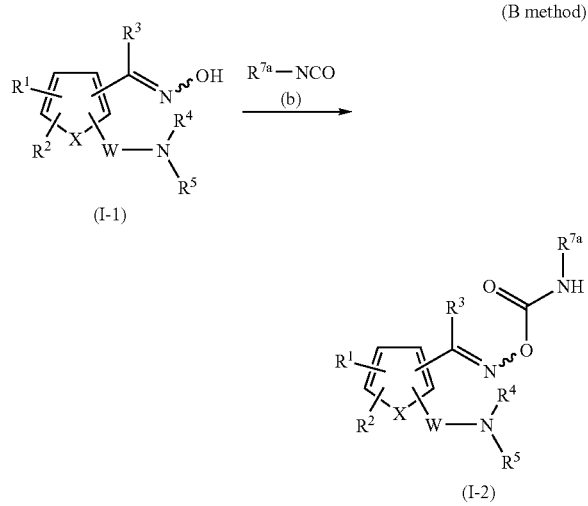

(B method)

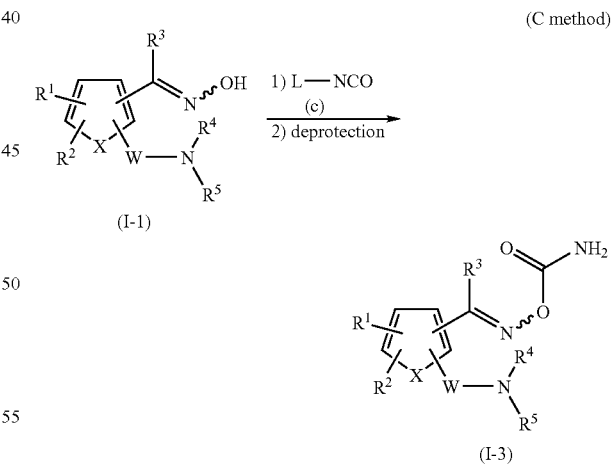

(C method)

The B method is a preparation method whereby the compound (I-2) according to the present invention is obtained by reacting the isocyanate (b) with the compound (I-1) in an inert solvent, in the presence or in the absence of a base.

The C method is a preparation method whereby the compound (I-3) according to the present invention is obtained by reacting the isocyanate (c) with the compound (I-1) and removing the protection group of the compound obtained in an inert solvent, in the presence or in the absence of a base.

In the above-mentioned scheme, $R^1$, $R^2$, $R^3$, $R^4$, $R^5$, W and X have the same meaning as previously defined, and L indicates a so-called protective group; specifically, a trihalomethyl group such as a trichloromethyl group and the like, a trialkylsilyl group such as t-butyldimethylsilyl group, trimethylsilyl group and the like, and preferably a trimethylsilyl group.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine, or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general 0 to 200° C., and preferably 10 to 120° C.

The reaction time varies depending on the starting materials, the solvent, the reagent and the like; however, it is in general 0.5 to 72 hours, and preferably 0.5 to 24 hours.

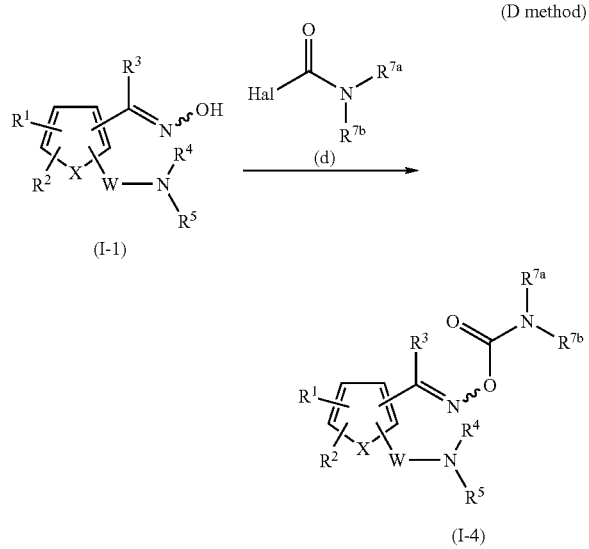

(D method)

The D method is a preparation method whereby the compound (I-4) according to the present invention is obtained by reacting the N-substituted carbamoyl halide (d) with the compound (I-1) in an inert solvent, in the presence or in the absence of a base.

In the above-mentioned scheme, $R^1$, $R^2$, $R^3$, $R^4$, $R^5$, $R^{7a}$, $R^{7b}$, W and X have the same meaning as previously defined, an Hal means a chlorine atom, a bromine atom or an iodine atom, preferably a chlorine atom.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general 10 to 200° C., and preferably 10 to 120° C.

The reaction time varies depending on the starting materials, the solvent, the reagent and the like; however, it is in general 0.5 to 72 hours, and preferably 0.5 to 24 hours.

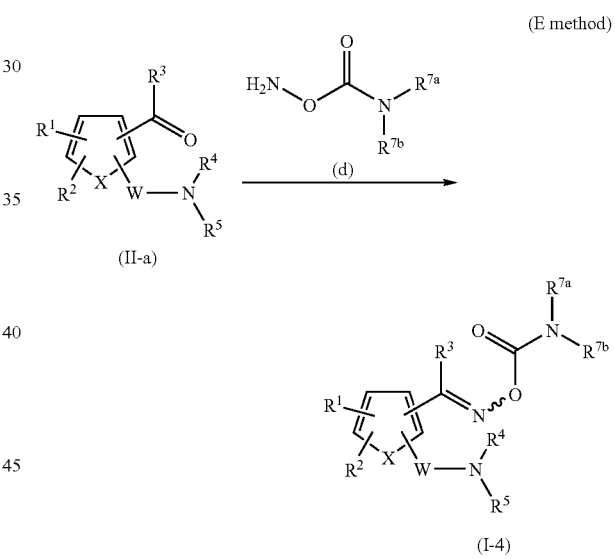

(E method)

The E method is a preparation method whereby the compound (I-4) according to the present invention is obtained by reacting the compound (e) with the compound (II) in an inert solvent, in the presence or in the absence of a base.

In the above-mentioned scheme, $R^1$, $R^2$, $R^3$, $R^4$, $R^5$, $R^{7a}$, $R^{7b}$, W and X have the same meaning as previously defined.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general 10 to 200° C., and preferably 20 to 110° C.

The reaction time varies depending on the starting materials, the solvent, the reagent and the like; however, it is in general 0.5 to 72 hours, and preferably 0.5 to 24 hours.

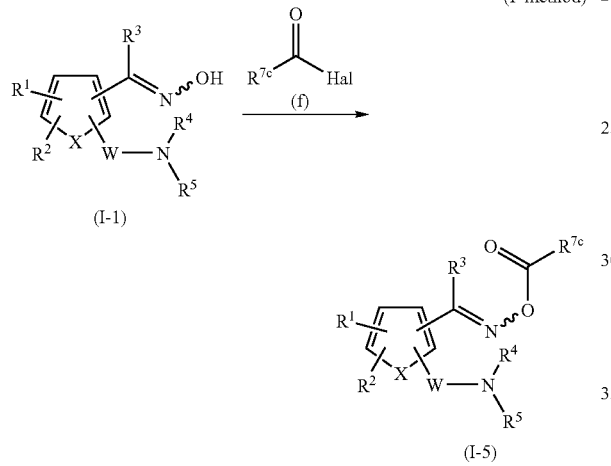

(I-1)

(I-5)

The F method is a preparation method whereby the compound (I-5) according to the present invention is obtained by reacting the compound (f) with the compound (I-1) in an inert solvent, in the presence or in the absence of a base In the above-mentioned scheme, $R^1$, $R^2$, $R^3$, $R^4$, $R^5$, W and X have the same meaning as previously defined, $R^{7c}$ represents a $C_{1-6}$ alkyl group that may have a substituent selected from substituent group α, and Hal means a chlorine atom, a bromine atom, an iodine atom, preferably a chlorine atom.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general −72 to 100° C., and preferably 0 to 60° C.

The reaction time varies depending on the starting materials, the solvent, the reagent and the like; however, it is in general 0.5 to 72 hours, and preferably 0.5 to 24 hours.

The intermediate compound used in the general preparation method of the present invention can be synthesized by preparation methods described in the following Scheme 1 to 15, and the like.

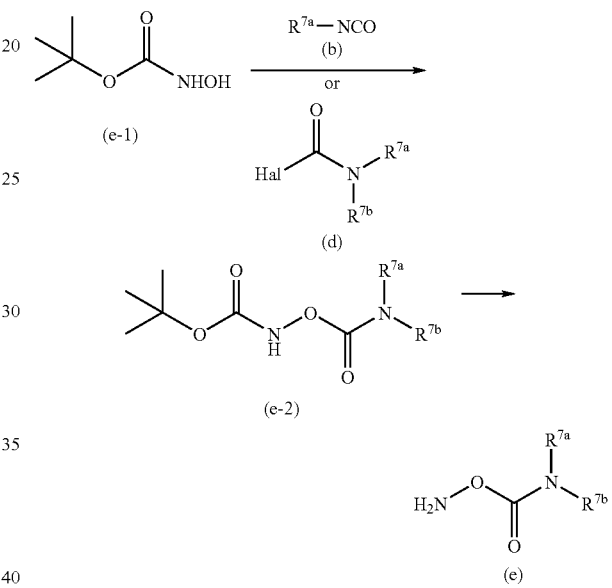

In the above-mentioned scheme, $R^{7a}$ and $R^{7b}$ have the same meaning as defined previously, and Hal means a chlorine atom, a bromine atom or an iodine atom, preferably a chlorine atom.

The compound (e) used in the F method can be synthesized with N-t-butyloxycarbonyl-hydroxylamine (e-1) as the starting materials. That is to say, after synthesizing compound (e-2) by reacting the isocyanate derivative represented by the compound (b) with the compound (f-1) in an inert solvent, in the presence or in the absence of a base, followed by acid treatment of the compound (e-2), compound (e) is obtained.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or the solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine, or an inorganic base such as sodium hydride, potassium carbonate, sodium carbonate or sodium bicarbonate; preferably, the base is triethylamine, pyridine or sodium hydride.

There is no particular restriction on the acid used as long as the target compound can be obtained, and it does not generate any unseparatable by-products. Specifically, examples of the acid include an organic acid such as acetic acid or trifluoroacetic acid, or an inorganic acid such as hydrochloric acid or phosphoric acid, preferably hydrochloric acid.

The reaction temperature varies depending on the starting materials, the solvent, the reagents and the like; however, it is in general 10 to 120° C., and preferably 20 to 80° C.

The reaction time varies depending on the starting materials, the solvent, the reagent and the like; however, it is in general 0.5 to 72 hours, and preferably 0.5 to 24 hours.

As anotehr method, compound (f) can also be synthesized by reacting the compound (f-1) with the N-substituted carbamoyl halide (d) in an inert solvent, in the presence of a base.

There is no particular limitation on the solvent used as long as it dissolves the starting substance to some extent, and does not inhibit the reaction. Specifically, examples of the solvent include halogenated hydrocarbon such as chloroform, dichloromethane or carbon tetrachloride, aromatic hydrocarbon such as benzene, toluene or xylene, ether such as diethyl ether, dioxane, dimethoxy ethane, diethylene glycol, dimethyl ether or tetrahydrafuran, or amide such as formamide, N,N-dimethylformamide, dimethylacetamide, hexamethylphosphoric acid triamide or N-methylpyrrolidone, or solvents that are mixtures of these solvents; preferably, the solvent is benzene, toluene, tetrahydrofuran or N,N-dimethylformamide.

There is no particular restriction on the base used as long as the target compound can be obtained, and it does not generate any unseparatable by-products. Specifically, examples of the base include an organic base such as triethylamine or pyridine, or an inorganic base such as sodium hydride, potassium carbonate, sodium carbonate or sodium bicarbonate; preferably, the base is triethylamine, pyridine or sodium hydride.

The reaction temperature varies depending on the starting materials, the solvent, the reagents and the like; however, it is in general 10 to 200° C., and preferably 20 to 110° C.

The reaction time varies depending on the starting materials, the solvent, the reagent and the like; however, it is in general 0.5 to 72 hours, and preferably 0.5 to 24 hours.

Scheme 2

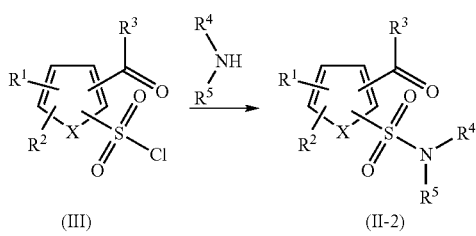

In Scheme 2, $R^1$, $R^2$, $R^3$, $R^4$ and $R^5$ have the same meanings as defined previously.

The compound (II-2), which has —$SO_2$— for W in formlula (II), can be synthesized by the following method: that is to say, compound (II-2) is obtained by reacting 1 molar equivalent of compound (III) and 1.05 to 3.0 molar equivalents of the amine $R^4R^5NH$, preferably 1.05 to 2.0 molar equivalents, in the presence of a base such as triethylamine, diisopropylethylamine, N-methyl morpholin, sodium carbonate or potassium carbonate in catalytic amounts, in an inert solvent such as tetrahydrofuran, N,N-dimethylformamide, dichloromethane and acetonitrile, at below ice-cold temperature to 50° C., for 0.5 to 72 hours.

Scheme 3

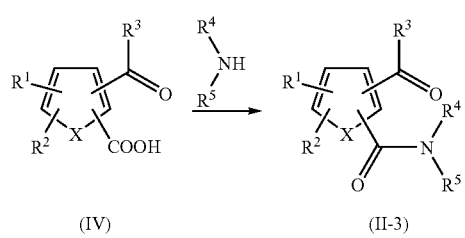

In Scheme 3, $R^1$, $R^2$, $R^3$, $R^4$ and $R^5$ have the same meanings as defined previously.

The compound (II-3), which has —CO— for W in equation (II), can be obtained by a well-known amide bond formation reaction between the compound (IV) and the amine $R^4R^5NH$.

Scheme 4

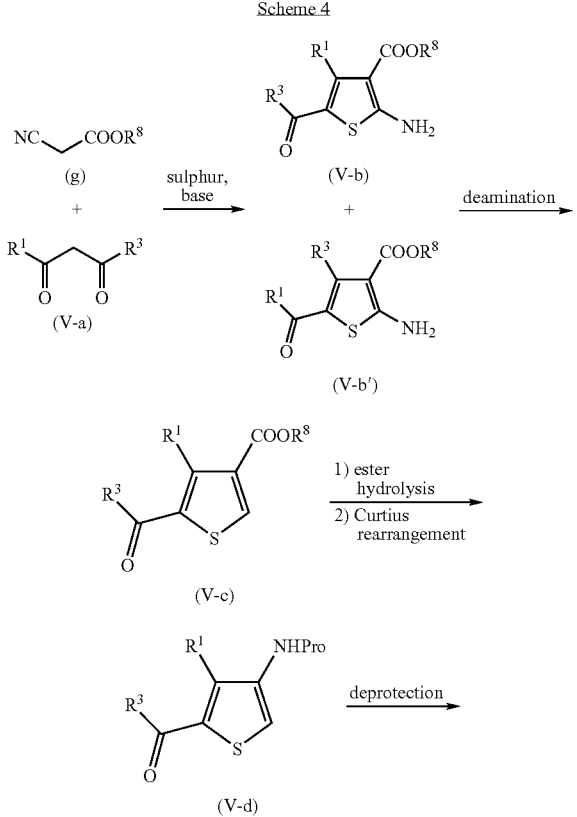

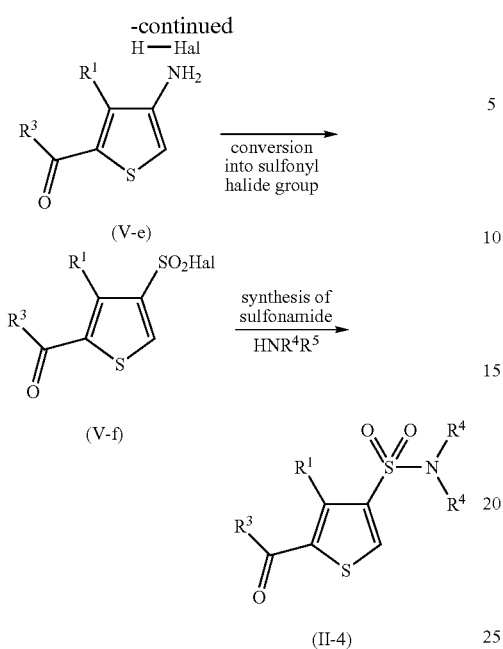

Each symbol of the compounds described in Scheme 4 has the same meaning as defined previously, and $R^8$ represents a $C_{1-4}$ alkyl group, preferably a methyl group or an ethyl group, Hal means a chlorine atom, a bromine atom or an iodine atom, preferably a chlorine atom, and Pro means a protection group such as an acetyl group, a benzoyl group, a t-butyldimethylsilyl group, a trimethylsilyl group, a t-butoxycarbonyl group, fluorenylmethoxycarbonyl group, preferably a t-butoxycarbonyl group.

The compound (II-4), which has S for X, —$SO_2$— for W and H for $R^2$ in General Formula (II), can be synthesized by the following method: that is to say, the compound (V-b) can be synthesized from the diketone (V-a), cyano acetate alkylester (g) and powder sulphur in an inert solvent, in the presence of a base, according to the method described in K. Gewald et. al., Chem. Ber. 99, 94 (1966). The by-product (V-b') can be separated by the conventional separation means such as column chromatography or recrystallization and the like. The compound (V-c) can be obtained by treating the diazonium salt of the compound (V-b) with $Cu_2O$, which diazonium salt can be formed by treating the compound (V-b) with sodium nitrite in an acidic aqueous solution such as sulfuric acid and/or hydrochloric acid and/or acetic acid and the like, below ice-cold temperature (method a), or, through deamination by reacting 1.05 to 3.0 molar equivalents, preferably 1.05 to 2.0 molar equivalents, of isoamyl nitrite and 1.05 to 3.0 molar equivalents, preferably 1.05 to 2.0 molar equivalents, of $Cu_2O$ with catalytic amounts of N,N-dimethylformamide in an inert solvent such as tetrahydrofuran (method b). Then, the compound (V-d) can be obtained by hydrolysis of the compound (V-c) to a carboxylic acid under the well-known ester hydrolysis conditions, then followed by Curtius rearrangement reaction of the carboxylic acid. The Curtius rearrangement can be carried out by heating a solution of 1.05 to 3.0 molar equivalents, preferably 1.05 to 2.0 molar equivalents of $(PhO)_2P(O)$—$N_3$ (diphenylphosphoryl azide), and 1.05 to 3.0 molar equivalents, preferably 1.05 to 2.0 molar equivalents of a base such as triethylamine, and 1 molar equivalent of the carboxylic acid in an alchohol such as t-butanol. The deprotected compound (V-e) is obtained by reacting the compound (V-d) with an acid such as hydrochloric acid/ethyl acetate, hydrochloric acid/1,4-dioxane or trifluoroacetic acid. The compound (V-e) can be used in the subsequent reaction even if it is a salt such as hydrochloride salt. The compound (V-f) can be obtained by adding an aqueous solution of sodium nitrite to the compound (V-e) in sulfuric acid or concentrated hydrochloric acid/acetic acid or a mixture of concentrated hydrochloric acid/acetic acid/sulfuric acid to form a diazonium salt, and reacting with an acetic acid solution saturated with sulfur dioxide gas containing $CuCl_2$ under the conditions of below ice-cold temperature to room temperature. The sulfonamide (II-4) can be synthesized from the compound (V-f) and the amine ($HNR^4R^5$), under the same conditions as the synthesis of the compound (II-2) described in the above Scheme 2.

Scheme 5

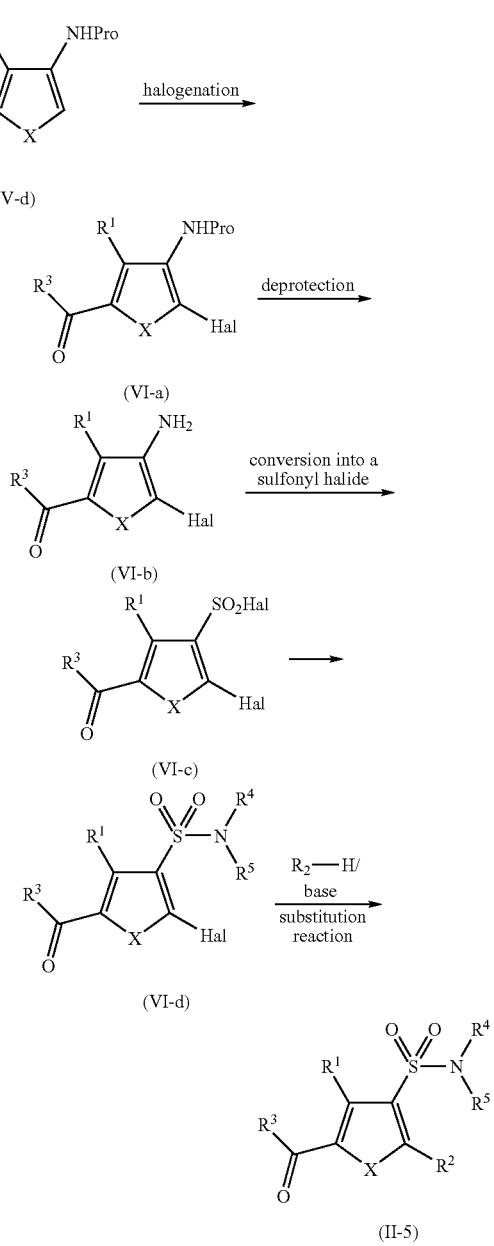

Each symbol of the compounds described in Scheme 5 has the same meaning as defined previously, Hal means a chlorine atom, a bromine atom or an iodine atom, preferably a chlorine atom or a bromine atom, and Pro means a protective group such as an acetyl group, a benzoyl group, a t-butyldimethylsilyl group, a trimethylsilyl group, a t-butoxycarbonyl group and a fluorenylmethoxycarbonyl group, preferably a t-butoxycarbonyl group. It should be noted that a $C_{1-6}$ alkoxy group, a $C_{1-6}$ alkylthio group, a primary amine or a secondary amine are preferred for $R^2$ in the present scheme, and a sulphur atom is preferred for X.

The compound (II-5), which has —$SO_2$— for W in General Formula (II), can be synthesized by the following method: that is to say, the compound (V-d) described in Scheme 4 statement can be reacted with 1.05 to 3.0 molar equivalents, preferably 1.05 to 2.0 molar equivalents, of N-halosuccinimide in a solvent such as N,N-dimethylformamide or an alcohol such as methanol or ethanol, under the conditions of ice-cold to room temperature, to obtain the halogenated compound (VI-a). Synthesis of the amine (VI-b) by deprotection of the amino group, synthesis of the sulfonyl halide (VI-c) via the diazonium salt of the amino group and synthesis of the sulfonamide (VI-d), can be respectively obtained by the same reaction as the synthesis of (V-e) and (V-f) in Scheme 3 and (II-2) in Scheme 2, described above. The compound (II-5), in which Hal has been sibstituted by $R^2$, can be obtained by reacting (VI-d) with $R^2$—H, which is an alcohol, a thiol or a primary or a secondary amine and the like. Examples of the solvent include N,N-dimethylformamide and N-methylpyrrolidone. Examples of the base include sodium hydride, potassium carbonate, triethylamine and the like. Reaction can be carried out at room temperature to 160° C. It should be noted that when $R^2H$ is an amine, the base is not necessary.

Scheme 6

Method 6-1

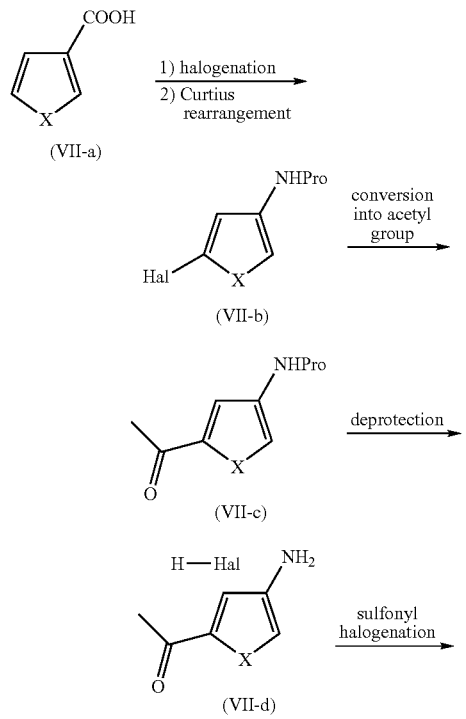

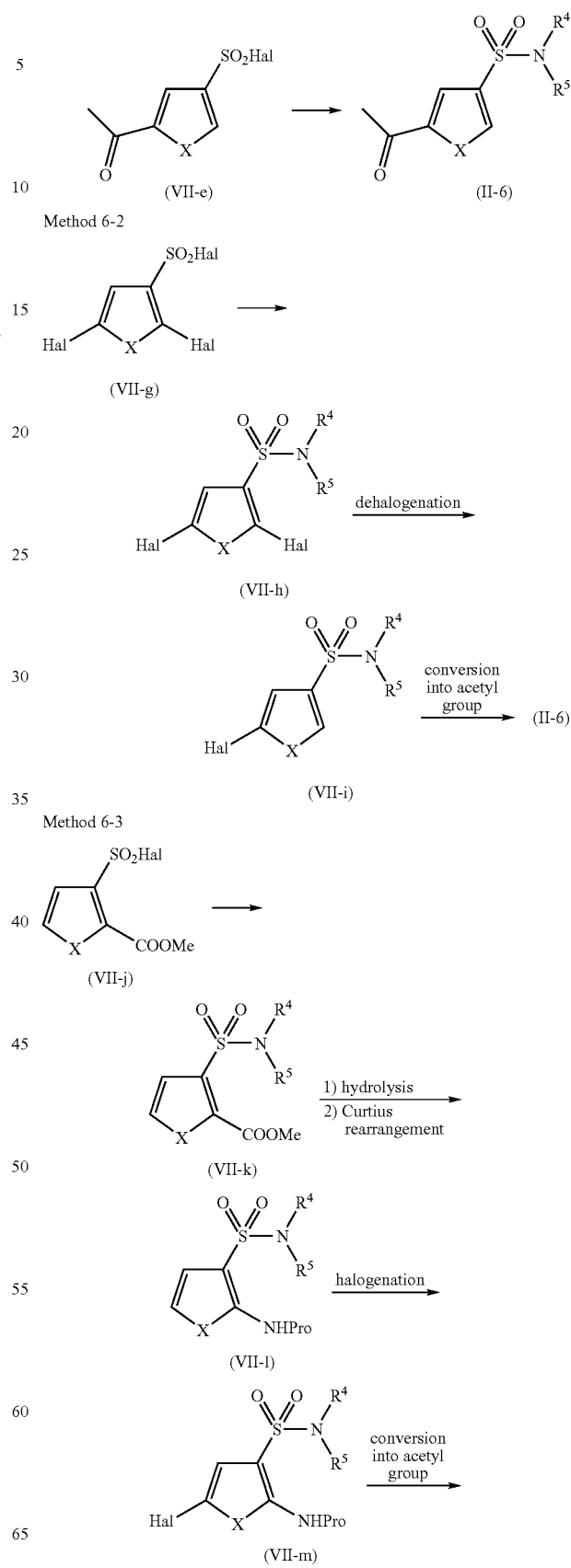

-continued

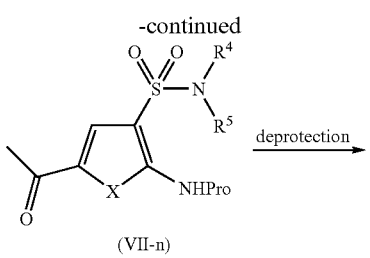

(VII-n)

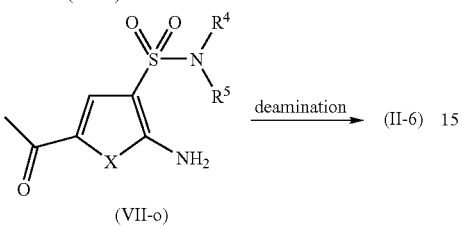

(VII-o)

Each symbol of the compounds described in Scheme 6 has the same meaning as defined previously, Hal means a chlorine atom, a bromine atom or an iodine atom, preferably a chlorine atom or a bromine atom, and Pro means a protective group such as an acetyl group, a benzoyl group, a t-butyldimethylsilyl group, a trimethylsilyl group, a t-butoxycarbonyl group and a fluorenylmethoxycarbonyl group, preferably a t-butoxycarbonyl group. It should be noted that a sulphur atom is preferred for X in the present scheme.

The compound (II-6), which has —$SO_2$— for W, H for $R^1$ and $R^2$, and a methyl group for $R^3$ in General Formula (II), can be synthesized by the method 6-1. That is to say, a 5-halo-3-carboxylic acid compound can be obrtained by reacting a 3-carboxylic acid compound (VII-a) with an N-halosuccinimide in a solvent such as, an alcohol such as methanol or ethanol, water or N,N-dimethylformamide. The by-product, the 2-substituted halogen compound, can be separated by purification in the next step. The compound (VII-b) can be obtained from the 5-halo-3-carboxylic acid compound by carrying out the same Curtius rearrangement reaction as described for the synthesis of the compound (V-d) in Scheme 4. The compound (VII-c) can be obtained by carrying out a Stille reaction with 1.05 to 3.0 molar equivalents, preferably 1.05 to 2.0 molar equivalents, of (1-ethoxyvinyl)tributyltin with respect to 1 molar equivalent of the compound (VII-b), in the presence of a palladium catalyst such as tetrakis(triphenylphosphine)palladium, $Pd(PPh_3)_4$, or tris-hydroxymethyl-aminomethanedibenzylidene acetone dipalladium-tri t-butylphosphine, $Pd_2(dba)_3$—$PBu^t_3$, in a solvent such as, aromatic hydrocarbon such as toluene or xylene, or 1,4-dioxane, at 60 to 110° C., followed by acidic hydrolysis with 1 to 10N hydrochloric acid or sulfuric acid and the like. If desired, a fluoride such as cesium fluoride can also be added as an additive in the Stille reaction. Synthesie of (VII-d), (VII-e) and (II-6) are carried out in the same manner as for the synthesis of the compound (V-e), the compound (V-f) and the compound (II-2) mentioned above, respectively.

(II-6) can also be synthesized by method 6-2 or method 6-3. Method 6-2 is a method wherein the sulfonamide (VII-h) is synthesized from the compound (VII-g) under the same conditions as for the synthesis of the compound (II-2), followed by a reaction with n-butyllithium in a solvent such as tetrahydrofuran, at −70° C. to room temperature to selectively lithiate position 2 of the 5 membered ring, water is added for treatment to obtain (VII-i), and the same Stille reaction as for the synthesis of (VII-c) is carried out for conversion into (II-6). Method 6-3 is a method to obtain the compound (II-6), with compound (VII-j) as the starting substance, via the same sulfonamide synthesis method as for the synthesis of (II-2) in Scheme 2, the same ester hydrolysis and Curtius rearrangement reaction as for the synthesis of (V-d) in Scheme 4, the same halogenation as for the synthesis of (VII-b) in method 6-1, the same acetylation as for the synthesis of (VII-c), the same deprotection as for the synthesis of (V-e) in Scheme 4, and the same deamination reaction as for the synthesis of (V-c) in Scheme 4.

Scheme 7

Method 7-1

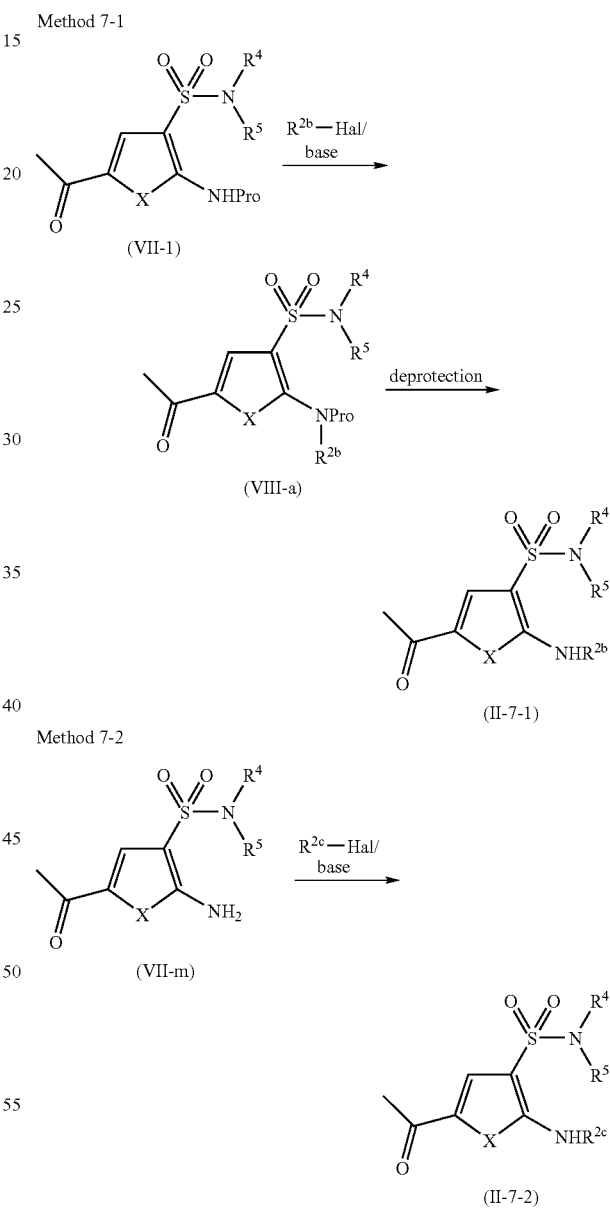

Each symbol of the compounds described in Scheme 7 has the same meaning as defined previously, Hal means a chlorine atom, a bromine atom or an iodine atom, preferably a chlorine atom or a bromine atom, and Pro means a protection group such as an acetyl group, a benzoyl group, a t-butyldimethylsilyl group, a trimethylsilyl group, a t-butoxycarbonyl group and a fluorenylmethoxycarbonyl group, and preferably a t-butoxycarbonyl group. It should be noted that a sulphur atom is preferred for X in the present scheme, a $C_{1-6}$ alkyl group that may have a substituent selected from substituent group γ or a $C_{6-10}$ aryl $C_{1-6}$ alkyl group that may have a substituent selected from substituent group γ are preferred for $R^{2b}$, a $C_{2-6}$ alkylcarbonyl group that may have a substituent selected from substituent group γ, a $C_{2-6}$ alkoxycarbonyl group, a $C_{6-10}$ arylcarbonyl group that may have a substituent selected from substituent group γ or a $C_{6-10}$ aryloxycarbonyl group that may have a substituent selected from substituent group γ are preferred for $R^{2c}$.

The compound that can be represented by General Formula (II-7-1) or (II-7-2), which has —SO$_2$— for W, H for $R^1$, an amino group that may have a substituent selected from substituent group β for $R^2$, a methyl group for $R^3$ in General Formula (II), can be synthesized according to method 7-1 or method 7-2, respectively. (II-7-1) can be obtained by carrying out a reaction with 1 molar equivalent of the compound (VII-1) described in Scheme 6 and 1.05 to 3.0 molar equivalents, preferably 1.05 to 2.0 molar equivalents of $R^{2b}$-Hal, in a solvent such as N,N-dimethylformamide, tetrahydrofuran or dichloromethane, in the presence of a base such as triethylamine, potassium carbonate or sodium hydride, and at a temperature of below ice-cold temperature to 60° C. (method 7-1).

The compound (II-7-2) can be synthesized either by carrying out a reaction with 1 molar equivalent of the compound (VII-m) described in Scheme 6 and 1.05 to 3.0 molar equivalents, preferably 1.05 to 2.0 molar equivalents, of $R^{2c}$-Hal in a solvent such as N,N-dimethylformamide, tetrahydrofuran or dichloromethane, in the presence of a base such as triethylamine, potassium carbonate or sodium hydride, at a temperature of below ice-cold temperature to 60° C., or by reaction in an aqueous solution of dichloromethane/1 to 5N sodium hydroxide (method 7-2).

Scheme 8

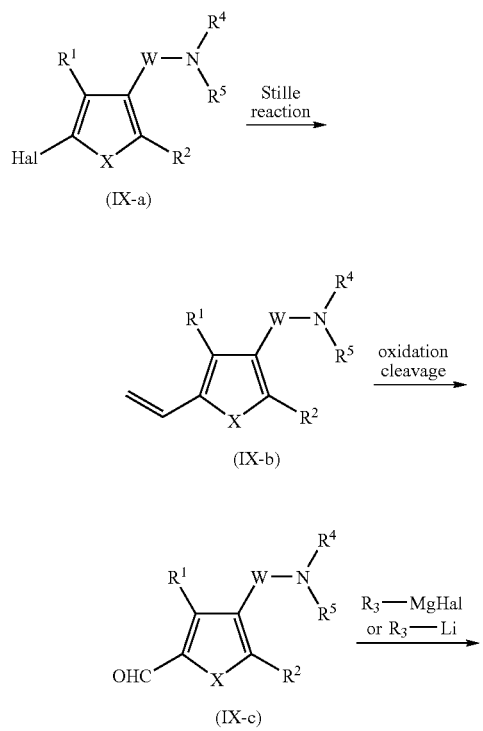

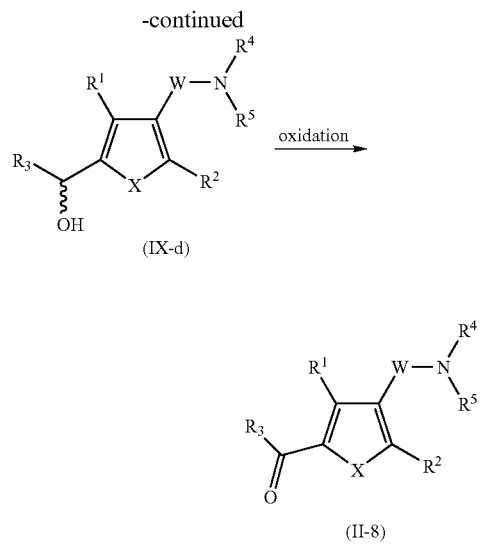

Each symbol of the compounds described in Scheme 8 has the same meaning as defined previously, Hal means a chlorine atom, a bromine atom or an iodine atom, preferably chlorine atom or bromine atom. It should be noted that a sulphur atom is preferred for X in the present scheme.

The compound (IX-a) can be synthesized by the same method as for the synthesis of the compound (VII-i) and the like in Scheme 6.

The compound (IX-b) can be obtained by reacting 1 molar equivalent of compound (IX-a) and 1.05 to 3.0 molar equivalents, preferably 1.05 to 2.0 molar equivalents of vinyltributyltin together with catalytic amounts of a palladium catalyst such as tetrakis(triphenylphosphine)palladium or bis(tri-t-butylphosphine)palladium and cesium fluoride with 1,4-dioxane or toluene as the solvent under the condition of 80 to 120° C. The aldehyde (IX-c) can be obtained by reacting the compound (IX-b) with osmium tetroxide or ruthenium trichloride and sodium periodate, in a mixed solution of an organic solvent such as diethyl ether, dichloromethane or tetrahydrofuran and water, to oxidatively cleave the double bond in the compound (IX-b). Then, after the well-known method of reacting with the Grignard reagent ($R^3$—MgHal) or organolithium ($R^3$—Li) to obtain the alcohol (IX-d), this is subjected to the well-known ketone synthesis reaction by alcohol oxidation to allow (IX-e) to be synthesized.

Scheme 9

Method 9-1

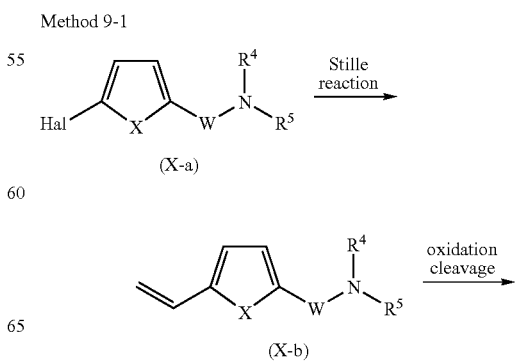

-continued

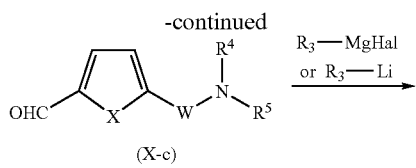

(X-c)

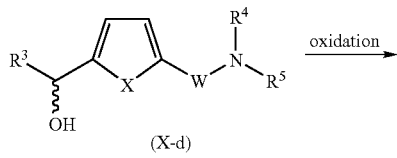

(X-d)

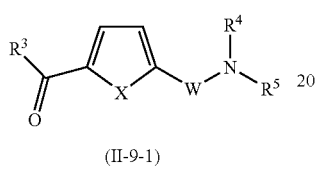

(II-9-1)

Method 9-2

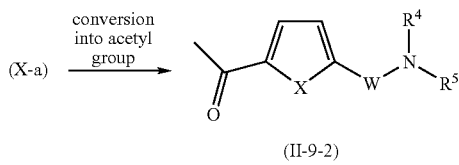

(II-9-2)

Each symbol of the compounds described in Scheme 9 indicates the same meaning as defined previously. It should be notde that a sulphur atom is preferred for X in the present scheme.

The compound (II-9-1), which has H for $R^1$ and $R^2$ in General Formula (II), can be synthesized according to method 9-1. On the other hand, the compound (II-9-2), which has H for $R^1$ and $R^2$, and a methyl group for $R^3$ in General Formula (II), can be synthesized according to method 9-2.

When W is a group represented by —CO—, the compound (X-a) can be synthesized by the same method as for the synthesis of the compound (II-3) described in Scheme 3. In addition, W is a group represented by —SO$_2$—, it can be synthesized by the same method as for the synthesis of the compound (II-2) in Scheme 2. (II-9-1) can be synthesized by the same method as the synthesis method described in Scheme 8, with the compound (X-a) as the starting material.

Further, (II-9-2), which has a methyl group for R3, can be synthesized by converting the compound (X-a) into an acetyl group by the same method as for the synthesis of compound (VII-c) described in Scheme 6.

Scheme 10

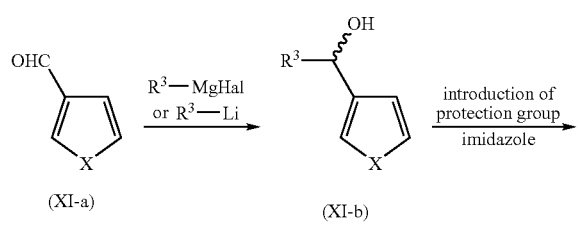

-continued

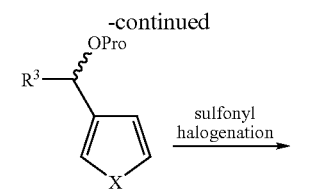

(XI-c)

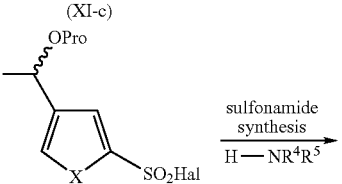

(XI-d)

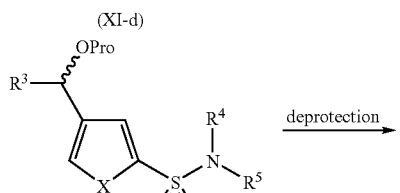

(XI-e)

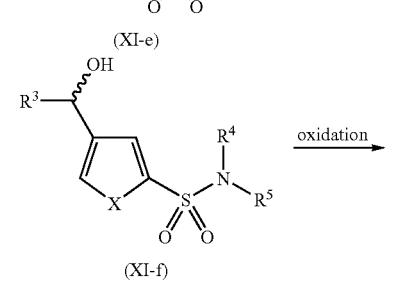

(XI-f)

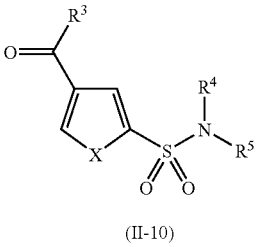

(II-10)

Each symbol of the compounds described in Scheme 10 has the same meaning as defined previously, Hal means a chlorine atom, a bromine atom or an iodine atom, preferably a chlorine atom or a bromine atom, and Pro means a protecting group such as an acetyl group, a benzoyl group, a t-butyldimethylsilyl group, a trimethylsilyl group, a t-butoxycarbonyl group and a fluorenylmethoxycarbonyl group, preferably a t-butyldimethylsilyl group. It should be noted that a sulphur atom is preferred for X in the present scheme.

The compound (II-10), which has H for $R^1$ and $R^2$ in General Formula (II), can be synthesized by the following method. The sulfonyl halide (XI-d) can be synthesized from the 3-carboxyaldehyde (XI-a) according to the method described in J. M. Holmes et. al., J. Med. Chem. 37, 1646. That is to say, the alcohol (XI-b) is synthesized from (XI-a) by the same method as for the synthesis of (IX-d) in Scheme 8, (XI-c) obtained by protecting the hydroxyl group with t-butyldimethyldimethylsilyl group is lithiated by s-butyl-lithium in an inert solvent such as tetrahydrofuran, at −70 to 100° C., then sulfur dioxide gas is bubbled for 30 minute to 3 hours, then, the sulfonylhalide (XI-d) can be synthesized by reaction with N-halosuccinimide. Thereafter, the compound (XI-f) is obtained by synthesizing the compound (XI-e) by the same method as for the synthesis of the compound (II-2) of Scheme 2, and deprotecting the protection group with tetra n-butylammoniumfluoride and the like. The compound (II-10) can be obtained via oxidation by the same method as for the synthesis of the compound (II-8) of Scheme 8.

50° C., or reacted with acetylchloride in an inert solvent such as dichloromethane and in the presence of a base such as triethylamine, to obtain the N-acetyl compound (XII-c). The compound (XI-d) can be obtained by oxidizing the compound (XII-c) in a mixed solution of acetic acid-water, which may contain tetrahydrofuran or 1,4-dioxane, with cerium (IV) sulfate as the oxidizing agent. Alternatively, it may be oxidized in an inert solvent such as chloroform, with

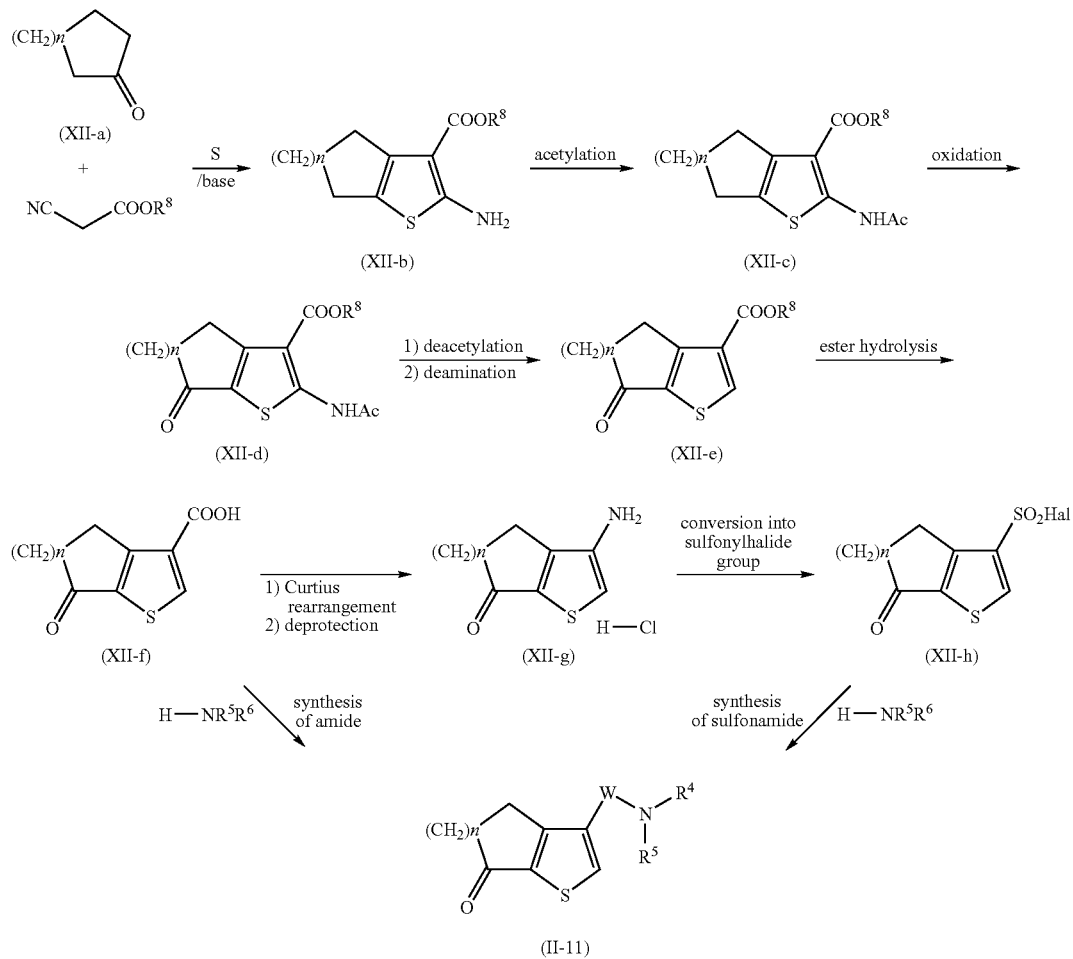

Each symbol of the compounds described in Scheme 11 indicates the same meaning as defined previously. Hal means a chlorine atom, a bromine atom or an iodine atom, preferably a chlorine atom or a bromine atom, n represents 1, 2, 3 or 4, preferably 1 or 2, $R^8$ represents a $C_{1-4}$ alkyl group, preferably a methyl group or an ethyl group.

The compound (II-11), which has S for X, H for $R^2$, and $R^1$ and $R^3$ forming a 5–8 membered ring together with the carbons they are bonded to, in General Formula (II), can be synthesized via the synthesis routes of Scheme 11. The thiophene derivative (XII-b) is synthesized from the cycloalkyl ketone (XII-a) by the same method as for the synthesis of (V-b) of Scheme 4, the amino group of the (XII-b) is either reacted with 1.05 mole to 3.0 molar equivalents of acetyl chloride or 1.05 mole to 3.0 molar equivalents acetic anhydride, in an inert solvent such as pyridine, at 0 to chromate as the oxidizing agent. The carboxylic acid (XII-f) can be synthesized by hydrolyzing the acetyl group of (XII-d) with an aqueous alkali solution such as potassium hydroxide and deaminating the amino group by the same method as for the synthesis of (V-c) of Scheme 4 to obtain (XII-e), and then performing ester hydrolysis. (XII-f) can be converted into the sulfonyl halide (XII-h) through the same methods as for the synthesis of the compound (V-d), the compound (V-e) and the compound (V-f) of Scheme 4. The compound (II-11), which has —CO— for W, can be synthesized by reacting the compound (XII-f) with the amine $HNR^4R^5$ by the same method as the synthesis of (II-3) of Scheme 3. The compound (II-11), which has —$SO_2$— for W, can be synthesized by reacting the compound (XII-h) with the amine $HNR^4R^5$ by the same method as for the synthesis of the compound (II-2) of Scheme 2.

Scheme 12

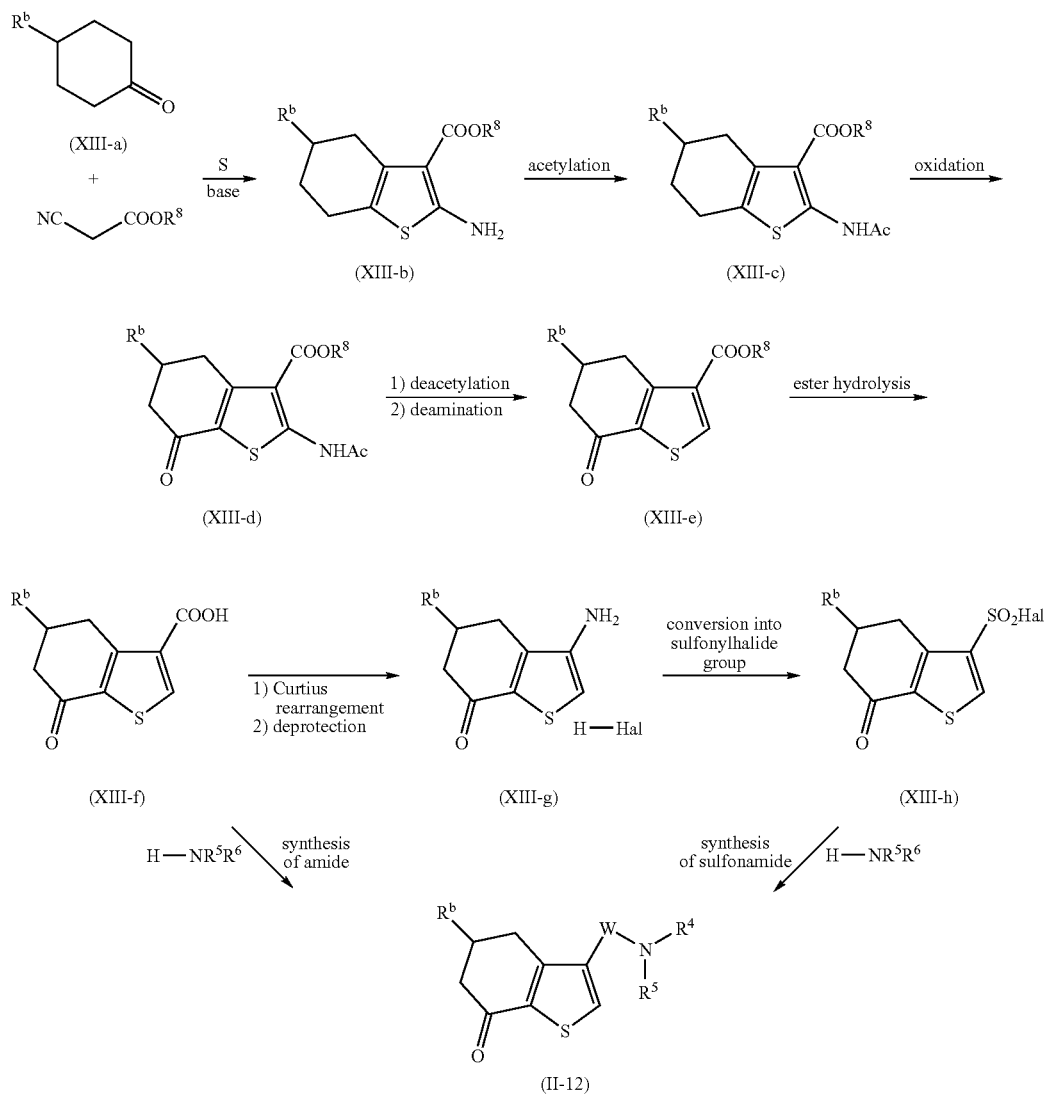

Each symbol of the compounds described in Scheme 12 has the same meaning as defined previously, $R^b$ represents a hydrogen atom, the $C_{1-6}$ alkyl group that may have a substituent selected from substituent group α or the substituent selected from substituent group α, Hal means a chlorine atom, a bromine atom or an iodine atom, preferably a chlorine atom or a bromine atom, n stands for 1, 2, 3 or 4, preferably 1 or 2, and $R^8$ represents a $C_{1-4}$ alkyl group, preferably a methyl group or an ethyl group.

The compound (II-12), which has S for X, H for $R^2$, and $R^1$ and $R^3$ forming a 6 membered ring together with the carbons they are bonded to, in General Formula (II), can be synthesized according to the synthesis routes of Scheme 12. That is to say, the compound (II-12) can be synthesized by synthesizing the thiophene derivative (XIII-b) from the cyclohexanone (XIII-a), which has $R^b$ substituted at position 4, by the same method as for the synthesis of the compound (V-b) of Scheme 4, and by the same synthesis routes as Scheme 11 thereafter.

Scheme 13

Method 13-1

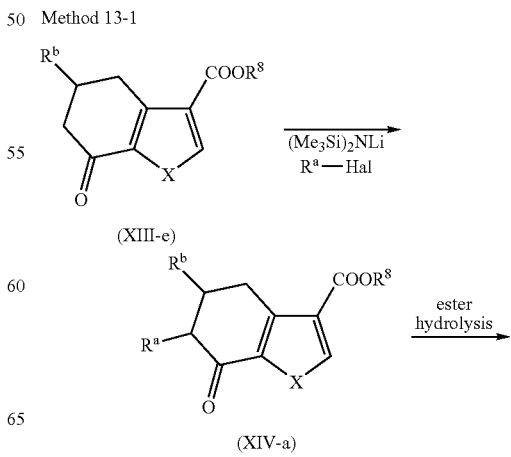

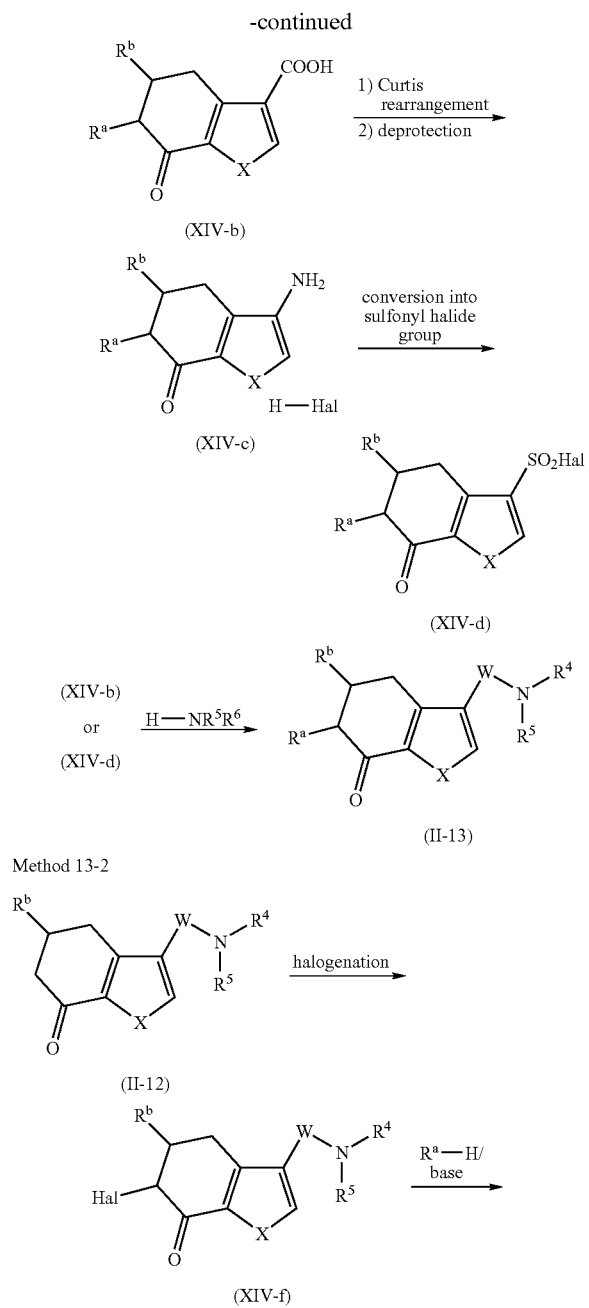

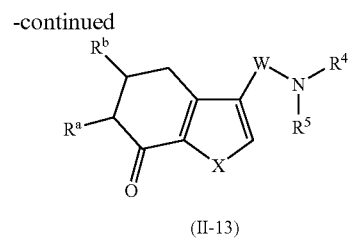

Each symbol of the compounds described in Scheme 13 indicates the same meaning as defined previously. $R^a$ represents a hydrogen atom, the $C_{1-6}$ alkyl group that may have a substituent selected from substituent group α or the substituent selected from substituent group α. In the present scheme, a $C_{1-6}$ alkyl group, an alkylcarbonyloxy group, an arylcarbonyloxy group, a thioalkyl group and an amino group that may be substituted are preferred for $R^a$. A sulphur atom is preferred for X in the present scheme.

The compound (II-13), which has S for X, H for $R^2$, and $R^1$ and $R^3$ forming a 6 membered ring together with the carbons they are bonded to, in General Formula (II), can be synthesized according to method 13-1 or method 13-2 of Scheme 13. The compound (XIV-a), which has an $R^a$ group introduced at the α-position of the ketone, can be synthesized by reacting 1 molar equivalent of the above compound (XIII-e) of Scheme 12 and 1.05 to 3.0 molar equivalents, preferably 1.05 to 2.0 molar equivalents, of $R^a$-Hal in the presence of a strong base such as lithium hexamethyldisilazide or lithium diisopropylamine (method 13-1). Thereafter, the synthesis of the compound (XIV-b), the compound (XIV-c), the compound (XIV-d) and the compound (II-13), is the same synthesis methods as for the above-mentioned compound (XII-f), compound (XII-g), compound (XII-h) and compound (II-2) of Scheme 2, respectively.

In addition, the compound (II-13) can also be synthesized according to method 13-2. That is to say, the compound (XIV-f) can be obtained either by reacting the compound (II-12) of Scheme 12 with a halogen such as $Br_2$ in an inert solvent such as carbon tetrachloride, or by forming a silylenolether with a base such as triethylamine and t-butyldimethylsilyltrifluoromethane sulfonate (t-BuMe$_2$Si—OSO$_2$CF$_3$) in an inert solvent such as dichloromethane, followed by a reaction with N-halosuccinimide. The compound (II-13) is obtained by reacting 1 molar equivalent of the compound (XIV-f) and 1.05 to 3.0 molar equivalents, preferably 1.05 to 2.0 molar equivalents, of $R^a$—H, in the presence of a base such as potassium carbonate, sodium hydride or potassium hydride.

Scheme 14

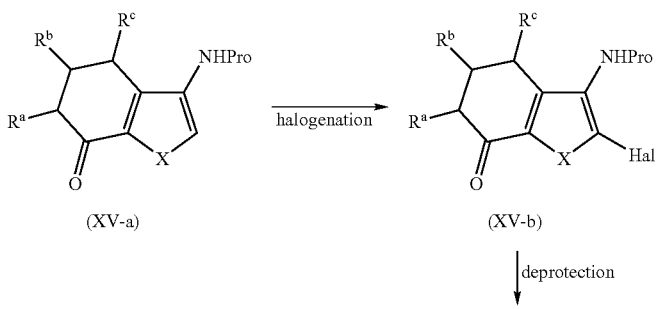

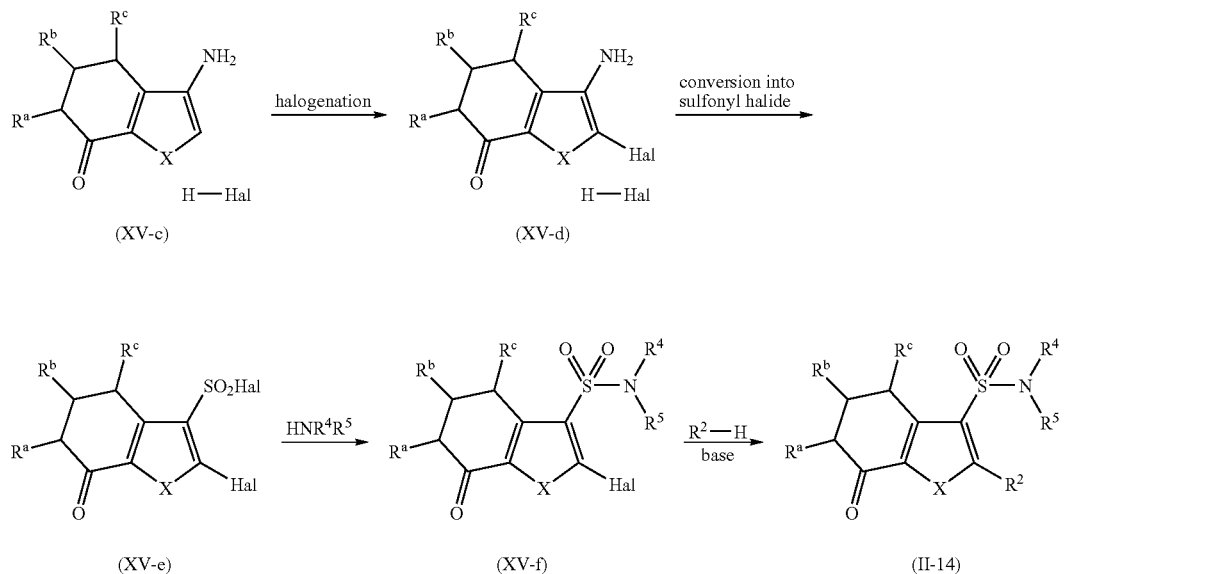

Each symbol of the compounds described in Scheme 14 has the same meaning as defined previously, $R^c$ represents a hydrogen atom, the $C_{1-6}$ alkyl group that may have a substituent selected from substituent group α or the substituent selected from substituent group α, Hal means a chlorine atom, a bromine atom or an iodine atom, preferably a chlorine atom or a bromine atom, and Pro means a protection group such as an acetyl group, a benzoyl group, a t-butyldimethylsilyl group, a trimethylsilyl group, a t-butoxycarbonyl group and a fluorenylmethoxycarbonyl group, preferably a t-butoxycarbonyl group. In the present scheme, an alkoxy group, a thio alkyl group or an amino group that may be substituted are preferred for $R^2$, and a sulphur atom is preferred for X.

The compound (II-14), which has S for X, —$SO_2$— for W, and $R^1$ and $R^3$ forming a 5–8 membered ring together with the carbons they are bonded to, in General Formula (II), can be synthesized according to the synthesis route of Scheme 14. (XV-b) can be obtained by halogenating (XV-a), which is synthesized as an intermediate compound for the synthesis of (XIII-g) of Scheme 12 or (XIV-c) of Scheme 13 by the same method as for the synthesis of (VI-a) of Scheme 5, then, (XV-d) can be obtained by deprotecting the protection group by the same method as for the synthesis of (V-e) of Scheme 4. In addition, (XV-d) can also be obtained by halogenating (XV-c) by the same method as mentioned above. The sulfonamide (XV-f) is obtained by converting the amino group of (XV-d) into the sulfonyl halide (XV-e) by the same method as for the synthesis of the compound (V-f) described in Scheme 4, then, reacting with the amine $HNR^4R^5$ by the same method as for the synthesis of the compound (II-2) described in Scheme 2. The compound (II-14) can be obtained by reacting the compound (XV-f) with $R^2$—H in the presence of base, by the same method as for the synthesis of the compound (II-5) described in Scheme 5.

Scheme 15

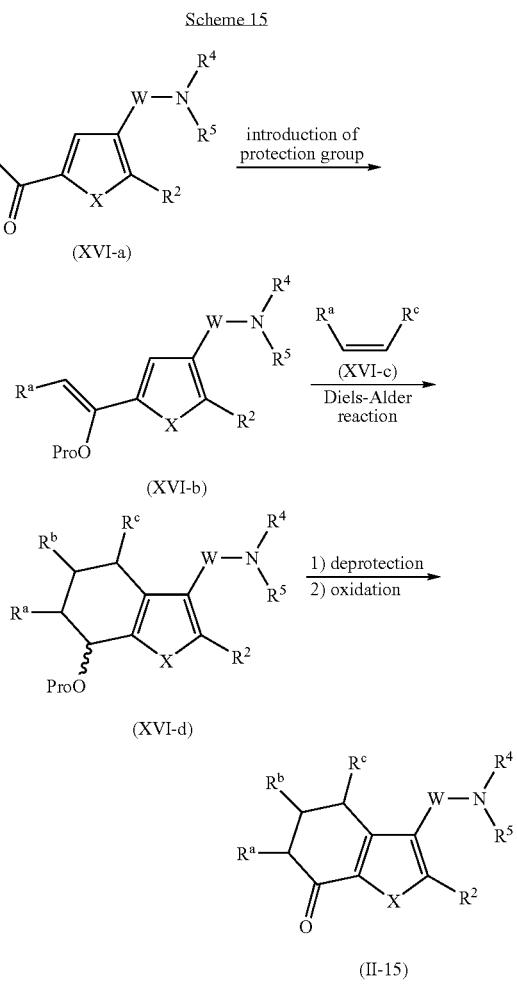

Each symbol of the compounds described in Scheme 15 has the same meaning as defined previously, Pro means a protective group such as an acetyl group, a benzoyl group, a t-butyldimethylsilyl group, a trimethylsilyl group, a t-butoxycarbonyl group and a fluorenylmethoxycarbonyl group, preferably a t-butyldimethylsilyl group, and $R^8$ represents a $C_{1-4}$ alkyl group, preferably a methyl group or an ethyl group. In the present scheme, a sulphur atom is preferred for X, and it is preferred that $R^c$ is an electron acceptor group such as —$COOR^8$, —CN, —$COR^8$, —COPh and —$SO_2$Ph.

The compound (II-15), $R^1$ and $R^3$ forming a 5–8 membered ring together with the carbons they are bonded to, in the General Formula (II), can be synthesized according to the synthesis route of Scheme 15. The compound (XVI-a) can be synthesized by the same method described in Schemes 5, 6, 7 and 8. The compound (XVI-d) is obtained by introducing a protection group such as t-butyldimethylsilyltrifluoromethane sulfonate or t-butyldimethylsilyl chloride to the compound (XVI-a) in the presence of a base such as triethylamine or diisopropylethylamine, to synthesize the compound (XVI-b), followed by carrying out a Diels-Alder reaction with 1.05 to 3.0 molar equivalents, preferably 1.05 to 2.0 molar equivalents, of the dienophile (XVI-c) with respect to 1 molar equivalent of the compound (XVI-b). For the Diels-Alder reaction, the reaction can be accelerated either by using a Lewis acid such as Tin(IV) chloride as catalyst, or by irradiating with a 200 W microwave, to bring the reaction temperature to 100 to 150° C.

The compound (II-15) can be obtained by deprotecting the compound (XVI-d) in a solvent such as tetrahydrofuran and tetra n-butylammonium fluoride, and oxidizing the obtained alcohol by the same method as for the compound (II-8) described in Scheme 8.

BEST MODE FOR CARRYING OUT THE INVENTION

In the following, Preparation Examples and Examples according to the present invention will be indicated; however, the present invention is not limited to these.

PREPARATION EXAMPLE 1

2-Acetylamino-4,5,6,7-tetrahydro-benzo[b]thiophene-3-carboxylic acid ethyl ester Acetyl chloride (62 mL) was added dropwise to a stirred solution of 2-Amino-4,5,6,7-tetrahydro-benzo[b]thiophene-3-carboxylic acid ethyl ester (125 g) in pyridine (750 mL) on an ice bath. After stirring at room temperature for 30 minutes, the solution was poured into water (2.2 L). The resulting solid was collected by filtration and washed with water, and then was dried overnight at 55° C. to provide the title compound (140 g) as a colorless solid.

$^1$H-NMR (CDCl$_3$) δ: 1.38 (t, J=7.2 Hz, 3H), 1.73–1.83 (m, 4H), 2.25 (s, 3H), 2.61–2.66 (m, 2H), 2.74–2.79 (m, 2H), 4.31 (q, J=7.2 Hz, 2H), 11.2 (brs, 1H)

PREPARATION EXAMPLE 2

2-Acetylamino-7-oxo-4,5,6,7-tetrahydro-benzo[b]thiophene-3-carboxylic acid ethyl ester To a suspension of 2-Acetylamino-4,5,6,7-tetrahydrobenzo[b]thiophene-3-carboxylic acid ethyl ester (140 g) in acetic acid (1.5 L) and water (1.5 L) was added gradually cerium (IV) sulfate 4 hydrate (900 g) with vigorously stirring. After the solution was stirred overnight, the solid was removed by filtration and the filtrate was concentrated. The solution was then neutralized with aqueous ammonia and extracted 3 times with ethyl acetate-tetrahydrofuran (=4:1). The organic layers were combined and evaporated in vacuo. The resulting solid was washed with tetrahydrofuran to provide the title compound (44 g) as a pale yellow solid.

$^1$H-NMR (CDCl$_3$) δ: 1.43 (t, J=7.2 Hz, 3H), 2.12–2.20 (m, 2H), 2.31 (s, 3H), 2.54–2.60 (m, 2H), 3.04–3.10 (m, 2H), 2.74–2.79 (m, 2H), 4.38 (q, J=7.2 Hz, 2H), 11.5 (brs, 1H)

PREPARATION EXAMPLE 3

7-Oxo-4,5,6,7-tetrahydro-benzo[b]thiophene-3-carboxylic acid ethyl ester

To a suspension of 2-Acetylamino-7-oxo-4,5,6,7-tetrahydro-benzo[b]thiophene-3-carboxylic acid ethyl ester (55 g) in ethanol (1 L) was added a solution of 13.3 g potassium hydroxide (13.3 g) in water (30 mL). After the suspension was stirred for 1.5 hours, one liter of water was added. The resulting solid was collected by filtration, and washed with tetrahydrofuran to provide a colorless solid (31.1 g). To a solution of the solid in tetrahydrofuran (650 mL) and N,N-dimethylformamide (8 mL) were added isoamyl nitrite (26.2 mL) and powder copper (I) oxide (18.6 g), and the mixture was refluxed for 1 hour. Isoamyl nitrite (7 mL), powder copper (I) oxide (5 g) and N,N-dimethylformamide (5 mL) were added to the solution, and the solution was heated further to reflux for 2.5 hours. The solution was filtered and the filtrate was evaporated in vacuo. The residue was purified by NH silica gel column chromatography (hexane/ethyl acetate), and the title compound (21.6 g) was obtained as a light brown solid.

$^1$H-NMR (CDCl$_3$) δ: 1.43 (t, J=7.2 Hz, 3H), 2.16–2.24 (m, 2H), 2.60–2.66 (m, 2H), 3.16–3.22 (m, 2H), 4.34 (q, J=7.2 Hz, 2H), 8.37 (s, 1H)

PREPARATION EXAMPLE 4

7-Oxo-4,5,6,7-tetrahydro-benzo[b]thiophene-3-carboxylic acid

To a mixture solution of 7-Oxo-4,5,6,7-tetrahydro-benzo[b]thiophene-3-carboxylic acid ethyl ester (21.6 g) in methanol (50 mL) and tetrahydrofuran (50 mL) was added in several portions an aqueous solution of 2N sodium hydroxide (77 mL) on an ice bath. After the solution was stirred for 45 minutes and the pH of solution was adjusted to 2 with 2N hydrochloric acid water, the organic solvent was removed by evaporation. Water was added to the residue to suspend, the solid was collected by filtration, and washed with water and then with ethanol, and then was dried to provide the title compound (18.1 g).

$^1$H-NMR (CDCl$_3$-CD$_3$OD) δ: 2.15–2.25 (m, 2H), 2.60–2.66 (m, 2H), 3.16–3.22 (m, 2H), 8.43 (s, 1H)

PREPARATION EXAMPLE 5

(7-Oxo-4,5,6,7-tetrahydro-benzo[b]thiophene-3-yl)-carbamic acid t-butyl ester

7-Oxo-4,5,6,7-tetrahydro-benzo[b]thiophene-3-carboxylic acid (18 g), 15.3 mL of triethylamine (15.3 mL) and 30.3 g of diphenylphosphoryl azide (30.3 g) in t-butyl alcohol (360 mL) were heat refluxed for 1 hour. After the organic solvent was removed by evaporation at reduced pressure, purification by NH silica gel column chromatography was carried out. Recrystallization from dichloromethane-hexane was carried out to provide the title compound (19.1 g) as a colorless crystal.

$^1$H-NMR (CDCl$_3$) δ: 1.52 (s, 9H), 2.16–2.25 (m, 2H), 2.59–2.69 (m, 4H), 6.36 (brs, 1H), 7.77 (brs, 1H)

PREPARATION EXAMPLE 6

3-Amino-5,6-dihydro-4H-benzo[b]thiophene-7-one hydrochloride (7-Oxo-4,5,6,7-tetrahydro-benzo[b]thiophene-3-yl)-carbamic acid t-butyl ester (18.9 g) in 4N hydrochloric acid/ethyl acetate (200 mL) was stirred for 1 hour. The resulting solid was collected by filtration, washed with ethyl acetate to provide the title compound (13.9 g) as an off-white solid.

$^1$H-NMR (DMSO-d$_6$) δ: 2.05–2.12 (m, 2H), 2.53–2.58 (m, 2H), 2.73–2.78 (m, 2H), 7.57 (s, 1H)

PREPARATION EXAMPLE 7

7-Oxo-4,5,6,7-tetrahydro-benzo[b]thiophene-3-sulfonyl chloride

3-Amino-5,6-dihydro-4H-benzo[b]thiophene-7-one hydrochloride (13.8 g) was suspended in a mixture solution of concentrated hydrochloric acid (43 mL), acid acetic (50 mL) and concentrated sulfuric acid (7 mL). An aqueous solution (8.4 mL) of sodium nitrite (5 g) was added dropwise on an ice bath while stirring vigorously so as to maintain the internal temperature at 5° C. or lower. After stirring for 30 minutes, to this reaction solution was added a solution of acetic acid (56 mL) containing copper (II) chloride dihydrate (1.35 g) saturated with sulfurous acid gas. The solution was warmed to room temperature and stirred at room temperature for 3 hours. The reaction solution was poured into ice water and extracted twice with ethyl acetate. After washing the organic layer twice with water and once with saturated sodium chloride water, and then dried with anhydrous magnesium sulfate. The solvent was evaporated at reduced pressure to provide the title compound (14.8 g) as a tango candy-like substance.

$^1$H-NMR (CDCl$_3$) δ: 2.27–2.35 (m, 2H), 2.67–2.73 (m, 2H), 3.17–3.22 (m, 2H), 8.48 (s, 1H)

PREPARATION EXAMPLE 8

3-Amino-2-bromo-5,6-dihydro-4H-benzo[b]thiophene-7-one hydrochloride

To a suspension of 3-Amino-5,6-dihydro-4H-benzo[b]thiophene-7-one hydrochloride (the compound of Preparation Example 6) (1.2 g) in N,N-dimethylformamide (33 mL) was added 1.05 g of N-bromosuccinimide (1.05 g) on an ice bath. After stirring for 30 minutes, the solvent was evaporated at reduced pressure, the pH was adjusted to 10 with an aqueous solution of sodium bicarbonate. After extracting with ethyl acetate, and washing the organic layer with water, drying with anhydrous magnesium sulfate was carried out and the solvent was evaporated at reduced pressure. The residue was dissolved in ethyl acetate, and the pH was brought to 1 by adding 4N hydrochloric acid/ethyl acetate. The resulting solid was collected by filtration, washed with ethyl acetate to provide the title compound (1.55 g) as an ocher solid.

$^1$H-NMR (DMSO-d$_6$) δ: 2.01–2.09 (m, 2H), 2.47–2.52 (m, 2H), 2.61–2.66 (m, 2H)

PREPARATION EXAMPLE 9

2-Bromo-7-oxo-4,5,6,7-tetrahydro-benzo[b]thiophene-3-sulfonyl chloride

From 3-amino-2-bromo-5,6-dihydro-4H-benzo[b]thiophene-7-one hydrochloride (1.48 g), the title compound (0.63 g) was obtained as a reddish brown oily substance (solidified after ice-cold treatment) in the same way as Preparation Example 7.

$^1$H-NMR (CDCl$_3$) δ: 2.23–2.31 (m, 2H), 2.64–2.69 (m, 2H), 3.14–3.19 (m, 2H)

PREPARATION EXAMPLE 10

6-Methyl-7-oxo-4,5,6,7-tetrahydrobenzo[b]thiophene-3-carboxylic acid ethyl ester To a solution of 7-oxo-4,5,6,7-tetrahydro-benzo[b]thiophene-3-carboxylic acid ethyl ester (the compound of Preparation Example 3) (1.0 g) in tetrahydrofuran (9 mL) was added dropwise 1.0M lithium hexamethyldisilazide-tetrahydrofuran solution (4.9 mL). After stirring at −70° C. for 15 minutes, methyl iodide (0.34 mL) was added and the solution was warmed to room temperature and was stirred for 30 minutes. After an aqueous solution of saturated ammonium chloride was added and a further dilution with water, extraction was carried out with ethyl acetate. After the organic layer was washed with saturated sodium chloride water and dried with anhydrous sodium sulfate, the residue that was obtained upon removing the solvent by evaporation was purified by silica gel column chromatography (hexane/ethyl acetate), and the title compound (426 mg) was obtained as a colorless solid.

$^1$H-NMR (CDCl$_3$) δ: 1.27 (d, J=6.4 Hz, 3H), 1.38 (t, J=7.2 Hz, 3H), 1.86–2.00 (m, 1H), 2.19–2.32 (m, 1H), 2.56–2.70 (m, 1H), 2.94–3.07 (m, 1H), 3.31–3.48 (m, 1H), 4.34 (q, J=7.2 Hz, 2H), 8.36 (s, 1H)

PREPARATION EXAMPLE 11

6-Methyl-7-oxo-4,5,6,7-tetrahydrobenzo[b]thiophene-3-carboxylic acid

From 6-methyl-7-oxo-4,5,6,7-tetrahydrobenzo[b]thiophene-3-carboxylic acid ethyl ester (426 mg), the title compound (367 mg) was obtained as a colorless solid, in the same way as Preparation Example 4.

$^1$H-NMR (CDCl$_3$) δ: 1.28 (d, J=6.8 Hz, 3H), 1.87–2.09 (m, 1H), 2.20–2.36 (m, 1H), 2.58–2.72 (m, 1H), 2.95–3.10 (m, 1H), 3.33–3.48 (m, 1H), 8.47 (s, 1H)

PREPARATION EXAMPLE 12

3-Amino-6-methyl-5,6-dihydro-4H-benzo[b]thiophene-7-one hydrochloride

From 6-methyl-7-oxo-4,5,6,7-tetrahydrobenzo[b]thiophene-3-carboxylic acid (367 mg), the title compound (273 mg) was obtained as a pale yellow solid, in the same way as Preparation Example 5 and Preparation Example 6

$^1$H-NMR (DMSO-d$_6$) δ: 1.10 (d, J=7.2 Hz, 3H), 1.72–1.91 (m, 1H), 2.08–2.26 (m, 1H), 2.40–2.92 (m, 3H), 7.53 (s, 1H)

PREPARATION EXAMPLE 13

6-Methyl-7-oxo-4,5,6,7-tetrahydrobenzo[b]thiophene-3-sulfonyl chloride

From 3-amino-6-methyl7-5,6-dihydro-4H-benzo[b]thiophene-7-one hydrochloride (273 mg), the title compound (280 mg) was obtained as a brown oily substance, in the same way as Preparation Example 7.

$^1$H-NMR (CDCl$_3$) δ: 1.30 (d, J=6.8 Hz, 3H), 1.99–2.14 (m, 1H), 2.26–2.41 (m, 1H), 2.61–2.78 (m, 1H), 3.00–3.14 (m, 1H), 3.30–3.41 (m, $_1$H), 8.47 (s, $_1$H)

PREPARATION EXAMPLE 14

[2-(4-Fluorophenyl)ethyl]-methylamine

To a mixture solution of N-methyl benzylamine (11 g) in dichloromethane and an aqueous solution containing sodium bicarbonate (16 g) was added dropwise 4-fluorophenyl acetyl chloride (12 g) at room temperature with vigorously stirring. After stirring for 1 hour, the organic layer was separated and washed with 2N hydrochloric acid water, water, an aqueous solution of 2N sodium hydroxide and water, in this order. The organic layer was dried with anhydrous magnesium sulfate, and the colorless oily matter (18 g) was obtained. To a suspension of 4 lithium aluminum hydride (4.5 g) in tetrahydrofuran (250 mL) was added dropwise the oily substance (18 g) obtained above in tetrahydrofuran (250 mL) After stirring for 1 hour, water (4.5 mL), an aqueous solution of 15% sodium hydroxide (4.5 mL), and water (13.5 mL) were added in this order, and the resulting precipitate was removed by filtration. The residue that was obtained by evaporated the filtrate in vacuo was purified with NH silica gel (hexane/ethyl acetate), and the colorless oily matter (13.6 g) was obtained. This oily substance was dissolved in methanol (200 mL), a catalytic reduction by 5% palladium-carbon (1 g) was carried out at 50° C. under hydrogen atmosphere, and the title compound (8.55 g) was obtained as a light brown oily substance.

$^1$H-NMR (CDCl$_3$) δ: 1.57 (br, 1H), 2.43 (s, 3H), 2.72–2.86 (m, 4H), 6.93–7.00 (m, 2H), 7.12–7.18 (m, 2H).

PREPARATION EXAMPLE 15

Methyl-(2-pyridine-3-yl-ethyl)-amine a) Benzyl-methyl-(2-pyridine-3-yl-ethyl-)amine

To a solution of pyridine-3-yl-acetic acid hydrochloride (5 g), benzyl-methyl-amine (3.5 g), and benzotriazole-1-yloxy-tris-hydroxymethyl-aminomethane(dimethylamino) phosphonium hexafluorophosphate (14 g) in dichlorometan (50 mL) was added triethylamine (8.8 mL). After this solution was stirred for 15 minutes, the residue from the evaporation of the solvent at reduced pressure was purified by silica gel column chromatography (hexane/ethyl acetate), and a colorless oily matter was obtained. This oily substance was dissolved in a tetrahydrofuran solution (60 mL), added dropwise into an anhydrous tetrahydrofuran (300 mL) in which lithium aluminum hydride (2.1 g) was suspended, and stirred for 1 hour. To the reaction solution was added diethyl ether (60 mL), water (2.1 mL), an aqueous solution (2.1 mL) of 15% sodium hydroxide and water (6.3 mL). After stirring for 30 minutes, the resulting solid was removed by filtration, the residue from the removal of the solvent by evaporation was purified by NH silica gel column chromatography (hexane/ethyl acetate), and the oily residue (4.35 g) was obtained.

$^1$H-NMR (CDCl$_3$) δ: 2.29 (s, 3H), 2.61–2.68 (m, 2H), 2.76–2.84 (m, 2H), 3.55 (s, 2H), 7.15–7.35 (m, 6H), 7.46–7.51 (m, 1H), 8.43–8.47 (m, 2H)

b) Title Compound

To a solution of benzyl-methyl-(2-pyridine-3-yl-ethyl-)amine (4.3 g) in methanol was added 10% palladium-carbon, and was stirred at 50° C. under hydrogen atmosphere for 1 hour. After filtrating with Celite, the filtrate was concentrated, and the title compound (2.39 g) was obtained as a colorless oily matter.

$^1$H-NMR (CDCl$_3$) δ: 2.46 (s, 3H), 2.78–2.90 (m, 4H), 7.15–7.35 (m, 1H), 7.46–7.56 (m, 1H), 8.43–8.51 (m, 2H)

PREPARATION EXAMPLE 16

Methyl-(2-pyridine-4-yl-ethyl)-amine

From pyridine-4-yl-acetic acid hydrochloride (2.6 g), the title compound (810 mg) was obtained as a colorless amorphous substance, in the same way as Preparation Example 15.

$^1$H-NMR (CDCl$_3$) δ: 2.44 (s, 3H), 2.80–2.92 (m, 4H), 7.18–7.22 (m, 2H), 8.44–8.52 (m, 2H)

PREPARATION EXAMPLE 17

1-(4-Fluorophenyl)-2-methylamino-ethanol a) 2-(Benzyl-methyl-amino)-1-(4-fluorophenyl)-ethanone

To a solution of benzyl-methyl-amine (28.9 g) and triethylamine (33.8 mL) in dimethylformamide (600 mL) was added in 5 portions 2-chloro-1-(4-fluorophenyl)-ethanone (40 g) on an ice bath. After stirring at room temperature for 2 hours, ethyl acetate was added, and the salt that precipitated was removed by filtration, and the filtrate was concentrated. A crude purification was carried out by silica gel column chromatography (hexane/ethyl acetate), and the title compound (56.9 g) was obtained as a colorless oily matter.

$^1$H-NMR (CDCl$_3$) δ: 2.36 (s, 3H), 3.66 (s, 2H), 3.73 (s, 2H), 7.06–7.13 (m, 2H), 7.25–7.35 (m, 5H), 7.97–8.30 (m, 2H)

b) 2-(Benzyl-methyl-amino)-1-(4-fluorophenyl)-ethanol 2-(Benzyl-methyl-amino)-1-(4-fluorophenyl)-ethanone (56.9 g) was dissolved in methanol (550 mL), and sodium borohydride was gradually added on an ice bath. After stirring at room temperature for 1 hour, the residue after evaporating methanol at reduced pressure was purified by NH silica gel column chromatography (hexane/ethyl acetate), and a yellow oily substance (54.6 g) was obtained.

$^1$H-NMR (CDCl$_3$) δ: 2.31 (s, 3H), 2.46–2.59 (m, 2H), 3.52 (d, J=13.2 Hz, 1H), 3.74 (d, J=13.2 Hz, 1H), 4.00–4.20 (brd, 1H), 4.71 (dd, J=10.2, 3.8 Hz, 1H), 6.97–7.04 (m, 2H), 7.25–7.37 (m, 7H)

c) Title Compound 2-(Benzyl-methyl-amino)-1-(4-fluorophenyl)-ethanol (54.6 g) and 10% palladium-carbon (5.8 g) was stirred in ethyl acetate-methanol (3:1) (800 mL) at 50° C. under hydrogen atmosphere for three hours. The catalyst was removed by filtration, and the filtrate was concentrated. After solidifying with an ether-hexane solvent, and the title compound (25.8 g) was obtained as a colorless solid.

$^1$H-NMR (CDCl$_3$) δ: 2.44 (s, 3H), 2.68 (dd, J=12.4, 8.8 Hz, 1H), 2.77 (dd, J=12.4, 3.6 Hz, 1H), 4.74 (dd, J=8.8, 3.6 Hz, 1H), 6.97–7.04 (m, 2H), 7.28–7.35 (m, 2H)

PREPARATION EXAMPLE 18

2-Methylamino-1-pyridine-4-yl-ethanol

From 2-bromo-1-pyridine-4-yl-ethanone.bromide (5.62 g), the title compound (711 mg) was obtained as a colorless solid, in the same way as Preparation Example 17.

$^1$H-NMR (CDCl$_3$) δ: 2.47 (s, 3H), 2.66 (dd, J=12.4, 8.8 Hz, 1H), 2.87 (dd, J=12.4, 3.6 Hz, 1H), 4.70 (dd, J=8.8, 3.6 Hz, 1H), 7.29 (ddd, J=4.4, 1.6, 0.8 Hz, 2H), 8.54 (dd, J=4.4, 1.6 Hz, 1H)

PREPARATION EXAMPLE 19

2-Methylamino-1-(4-pyrrolidine-1-yl-phenyl)-ethanol

From 2-bromo-1-(4-pyrrolidine-1-yl-phenyl)-ethanone (3 g), the title compound (85 mg) was obtained as a colorless solid, in the same way as Preparation Example 17.

$^1$H-NMR (CDCl$_3$) δ: 1.95–2.06 (m, 4H), 2.56 (s, 3H), 2.87–2.93 (m, 2H), 3.23–3.30 (m, 2H), 3.32–3.39 (m, 2H), 4.82–4.88 (m, 1H), 6.49–6.56 (m, 2H), 7.20–7.25 (m, 2H)

PREPARATION EXAMPLE 20

2-Amino-1-(2,4-difluorophenyl)-ethanol-hydrochloride a) N-[2-(2,4-difluorophenyl)-2-oxo-ethyl]-diformamide

To a solution of 2-chloro-1-(2,4-difluorophenyl)-ethanone (9.5 g) in N,N-dimethylformamide (150 mL) was added diformylamide sodium salt (4.9 g)/After stirring at room temperature for 3 hours, ethyl acetate was added, the insoluble matter was removed by filtration, and the filtrate was evaporated in vacuo. After purified by silica gel column chromatography (hexane/ethyl acetate), a pale yellow solid (3 g) were obtained.

$^1$H-NMR (CDCl$_3$) δ: 4.99 (d, J=4.0 Hz, 2H), 6.91–6.98 (m, 1H), 6.99–7.05 (m, 1H), 8.00–8.07 (m, 1H), 9.02 (brs, 2H)

b) N-[2-(2,4-difluorophenyl)-2-hydroxy-ethyl]-formamide

N-[2-(2,4-difluorophenyl)-2-oxo-ethyl]-diformamide (1.5 g) was dissolved in a solution of tetrahydrofuraN-methanol (1:1) (50 mL), and sodium borohydride (0.25 g) was gradually added at room temperature. After stirring at room temperature for 30 minutes, the solvent was evaporated at reduced pressure, the residue was purified by NH-silica gel column chromatography (ethyl acetate), and a colorless solid (10 g) was obtained.

$^1$H-NMR (CDCl$_3$) δ: 3.46–3.54 (m, 1H), 3.63 (d, J=4.4 Hz, 1H), 3.72–3.79 (m, 1H), 5.11–5.16 (m, 1H), 5.97 (br, 1H), 6.77–6.83 (m, 1H), 6.88–6.94 (m, 1H), 7.48–7.55 (m, 1H), 8.21 (d, J=1.2 Hz, $_1$H)

c) Title Compound

N-[2-(2,4-difluorophenyl)-2-hydroxy-ethyl]-formamide (1.0 g) was dissolved in methanol (2 mL), 4N hydrochloric acid/ethyl acetate (60 mL) was added. After stirring at 60° C. for 3 hours, the solution was allowed to cooled down to room temperature, and the solid that were generated by adding ethyl acetate (50 mL) was collected by filtration, washed with ethyl acetate, and the title compound (770 mg) was obtained as a colorless solid.

$^1$H-NMR (DMSO-d$_6$) δ: 2.88 (dd, J=12.8, 9.6 Hz, 1H), 3.01 (dd, J=12.8, 3.6 Hz, 1H), 5.06 (ddd, J=9.6, 4.0, 3.6 Hz, 1H), 6.23 (d, J=4.0 Hz, 1H), 7.12–7.18 (m, 1H), 7.22–7.29 (m, 1H), 7.55–7.62 (m, 1H), 8.09 (brs, 3H)

PREPARATION EXAMPLE 21

[2-(4-Fluorophenyl)ethylamino]acetonitrile

To a solution of 4-fluorophenethylamine (1.4 g) in acetonitrile (20 mL) was added dropwise N,N-diisopropylethylamine (2.6 mL) and bromoacetonitrile (0.84 mL). After stirring at room temperature for 50 minutes, the solution was diluted with ethyl acetate, the solution was washed with water, then with saturated sodium chloride water. After drying with anhydrous sodium sulfate, the solvent was removed by evaporation to provide the title compound (2.12 g) as a yellow oily substance.

$^1$H-NMR (CDCl$_3$) δ: 2.77 (t, J=7.2 Hz, 2H), 3.00 (t, J=7.2 Hz, 2H), 3.60 (s, 2H), 6.94–7.06 (m, 2H), 7.11–7.22 (m, 2H)

PREPARATION EXAMPLE 22

[2-(4-Fluorophenyl)ethyl]isopropylamine

To a solution of 4-fluorophenethylamine (1.4 g) in acetic acid (10 mL) was added dropwise acetone (0.82 mL) and methanol (20 mL). After sodium cyano-borohydride (0.64 g) was added, and the solution was stirred at room temperature for 2.5 hours. After adding water and diluting with ethyl acetate, the solution was washed with water and saturated sodium chloride water. After drying with anhydrous sodium sulfate, the residue that was obtained upon removing the solvent by evaporation was purified by NAM silica gel column chromatography (hexane/ethyl acetate), and the title compound (0.62 g) was obtained as colorless solids.

$^1$H-NMR (CDCl$_3$) δ: 1.41 (d, J=6.8 Hz, 6H), 3.02–3.21 (m, 4H), 3.35–3.46 (m, 1H), 6.96–7.05 (m, 2H), 7.16–7.23 (m, 2H)

PREPARATION EXAMPLE 23

N-Cyclopropyl-2-(4-fluorophenyl)acetamide

To a solution of 4-fluorophenylacetic acid (4.5 g) and cyclopropylamine (1.7 g) in N,N-dimethylformamide (60 mL) was added 1-Hydroxybenzotriazole (4.4 g), followed by 1-[3-(dimethylamino)propyl]-3-ethylcarbodiimide (WSC) hydrochloride (6.2 g) on an ice bath. This solution was stirred for 4.5 hours while gradually warming to room temperature. The reaction solution was poured into water (120 mL) on an ice bath, and the resulting solid was collected by filtration, washed with water, then dried, and the title compound (4.19 g) was obtained as a colorless solid.

$^1$H-NMR (CDCl$_3$) δ: 0.35–0.48 (m, 2H), 0.60–0.90 (m, 2H), 2.61–2.73 (m, 1H), 3.49 (s, 2H), 5.36–5.60 (m, 1H), 6.96–7.11 (m, 2H), 7.16–7.24 (m, 2H)

PREPARATION EXAMPLE 24

[2-(4-Fluoro-3-methoxyphenyl)ethyl]carbamic acid t-butyl ester a) 3-(4-Fluoro-3-methoxyphenyl) acrylic acid ethyl ester 4-Fluoro-3-methoxybenzaldehyde (3.08 g) and ethyl(t-riphenylphosphopholanylidene)acetate (7.7 g) was stirred in acetonitrile (40 mL) at room temperature for 20 hours and further heated for 1 hour at 80° C. After cooling the reaction solution, the residue that was obtained upon removing the solvent by evaporation was purified by silica gel column chromatography (hexane/ethyl acetate), and a colorless solid (4.54 g) was obtained.

$^1$H-NMR (CDCl$_3$) δ: 1.34 (t, J=6.8 Hz, 3H), 3.92 (s, 3H), 4.27 (q, J=6.8 Hz, 2H), 6.34 (d, J=15.6 Hz, 1H), 7.00–7.17 (m, 3H), 7.61 (d, J=15.6 Hz, 1H)

b) 3-(4-Fluoro-3-methoxyphenyl)propionic acid

To a solution of 3-(4-fluoro-3-methoxyphenyl)acrylic acid ethyl ester (4.54 g) in ethyl acetate (20 mL)-ethanol (20 mL) was added 10% percent palladium-carbon (450 mg). After stirring under hydrogen gas atmosphere for 2.5 hours, the metal catalyst was removed by filtration, the solvent was removed by evaporation, and an oily substance (4.64 g) was obtained. This was dissolved in a solution of ethanol (40 mL), an aqueous solution of 5N sodium hydroxide was added, and the solution was stirred at room temperature for 30 minutes. After the solution was acidified by adding 5N hydrochloric acid (21 mL), the solid precipitated. After diluting with water, the solid was collected by filtration, dried by aeration, and a colorless solid (3.4 g) was obtained.

$^1$H-NMR (CDCl$_3$) δ: 2.67 (t, J=7.2 Hz, 2H), 2.92 (t, J=7.2 Hz, 2H), 3.88 (s, 3H), 6.62–7.13 (m, 3H)

c) Title Compound 3-(4-Fluoro-3-methoxyphenyl)propionic acid (1.98 g), triethylamine (1.67 mL) and diphenylphosphoryl azide (2.59 mL) in t-butanol (20 mL) were heated at 95 to 100° C. for 5 hours. After cooling the reaction solution, the residue that was obtained upon removing the solvent by evaporation was purified by silica gel column chromatography (hexane/ethyl acetate), and the title compound (1.59 g) was obtained as a colorless oily matter.

$^1$H-NMR (CDCl$_3$) δ: 1.43 (s, 9H), 2.66–2.83 (m, 2H), 3.23–3.43 (m, 2H), 3.88 (s, 3H), 4.43–4.64 (m, 1H), 6.65–6.86 (m, 2H), 6.89 (dd, J=11.6 and 8.0 Hz, 1H)

PREPARATION EXAMPLE 25

2-(4-Fluoro-3-methoxyphenyl)ethylamine-hydrochloride

To a solution of [2-(4-fluoro-3-methoxyphenyl)ethyl]carbamic acid t-butyl ester (90 mg) in ethyl acetate (3 mL) was added a solution of 4N hydrochloric acid-ethyl acetate (3 mL) at room temperature and allowed to stand for 2.5 hours. The resulting solid was diluted with diethyl ether, then filtered, and washed with diethyl ether. After drying by aeration, and the title compound (416 mg) was obtained as a colorless solid.

$^1$H-NMR (DMSO-d$_6$) δ: 2.71–3.12 (m, 4H), 3.85 (s, 3H), 6.72–6.88 (m, 1H), 7.06 (dd, J=6.4 and 2.0 Hz, 1H), 7.12 (dd, J=11.6 and 8.0 Hz, 1H), 7.94 (br)

PREPARATION EXAMPLE 26

[2-(4-Fluoro-3-methoxyphenyl)ethyl]methylcarbamic acid t-butyl ester

To a solution of [2-(4-fluoro-3-methoxyphenyl)ethyl]carbamic acid t-butyl ester (795 mg) in N,N-dimethylformamide (6 mL) was added 60% sodium hydride (154 mg) at room temperature. After stirring for 1 hour, methyl iodide (0.55 mL) was added dropwise and the solution was stirred for 14 hours. Water was added cautiously by small amounts, and after extraction with ethyl acetate, the solution was washed with water and saturated sodium chloride water. The residue that was obtained upon removing the solvent by evaporation was purified by silica gel column chromatography (hexane/ethyl acetate), and the title compound (506 mg) was obtained as a colorless oily matter.

$^1$H-NMR (CDCl$_3$) δ: 1.33–1.53 (m, 9H), 2.69–2.90 (m, 5H), 3.30–3.49 (m, 2H), 3.88 (s, 3H), 6.60–7.05 (m, 3H)

PREPARATION EXAMPLE 27

[2-(4-Fluoro-3-methoxyphenyl)ethyl]methylamine hydrochloride

To a solution of [2-(4-fluoro-3-methoxyphenyl)ethyl]methylcarbamic acid t-butyl ester (506 mg) in ethyl acetate (2 mL) was added a solution of 4N hydrochloric acid-ethyl acetate (2 mL) at room temperature and allowed to stand for 2.5 hours. The resulting solid was diluted with diethyl ether, then filtered, and washed with diethyl ether. After drying by aeration, the title compound (338 mg) was obtained as a colorless solid.

$^1$H-NMR (DMSO-d$_6$) δ: 2.47 (s, 3H), 2.75–2.94 (m, 2H), 3.00–3.18 (m, 2H), 3.82 (s, 3H), 6.71–6.84 (m, 1H), 6.95–7.22 (m, 2H)

PREPARATION EXAMPLE 28

[2-(3-Phenoxyphenyl)ethyl]carbamic acid t-butyl ester

From 3-phenoxy benzaldehyde (3.97 g), the title compound (2.0 g) was obtained as a colorless oily matter, in the same way as Preparation Example 24.

$^1$H-NMR (CDCl$_3$) δ: 1.43 (s, 9H), 2.69–2.83 (m, 2H), 3.23–3.43 (m, 2H), 4.44–4.62 (m, 1H), 6.81–6.96 (m, 3H), 6.98–7.04 (m, 2H), 7.06–7.15 (m, 1H), 7.21–7.43 (m, 3H)

PREPARATION EXAMPLE 29

2-(3-Phenoxyphenyl)ethylamine-hydrochloride

From [2-(3-phenoxyphenyl)ethyl]carbamic acid t-butyl ester (1.06 g), the title compound (615 mg) was obtained as a colorless solid, in the same way as Preparation Example 25.

$^1$H-NMR (DMSO-d$_6$) δ: 2.72–2.89 (m, 2H), 2.93–3.07 (m, 2H), 6.79–7.21 (m, 6H), 7.27–7.49 (m, 3H), 7.73–8.05 (m, 3H)

PREPARATION EXAMPLE 30

[2-(3-Phenoxyphenyl)ethyl]methylamine.hydrochloride

From [2-(3-phenoxyphenyl)ethyl]carbamic acid t-butyl ester (936 mg), the title compound (394 mg) was obtained as a colorless solid by carrying out the same reactions as in Preparation Example 26 and 27.

$^1$H-NMR (DMSO-d$_6$) δ: 2.52 (s, 3H), 2.81–2.97 (m, 2H), 3.03–3.17 (m, 2H), 6.85 (dd, J=8.0 and 2.0 Hz, 1H), 6.92 (s, 1H), 6.95–7.16 (m, 3H), 7.08–7.16 (m, 1H), 7.27–7.45 (m, 3H), 8.46–8.95 (m, 2H)

PREPARATION EXAMPLE 31

1-(4-Fluoro benzyl)cyclopropylamine

To a solution of 4-fluorophenyl acetonitrile (2.7 g) in tetrahydrofuran (40 mL) was added tetraisopropoxy titanium (6.5 mL), whereafter a solution of 1.0M magnesium ethylbromide-tetrahydrofuran (40 mL) was added dropwise over 30 minutes, and stirred for 1 hour. After adding a trifluoroborane-diethyl ether complex (50.1 mL) over 20 minutes, the solution was further stirred for 1 hour. The reaction solution was cooled with ice water, an aqueous solution of 5N sodium hydroxide (20 mL) was added, and stirred at room temperature for 20 minutes. After diluting with water and diethyl ether, and filtration using Celite was carried out. The organic layer was separated, washed with saturated sodium chloride water, and then dried with anhydrous sodium sulfate. After the solvent was evaporated at reduced pressure, filtration was carried out using a small amount of NH-silica gel, and washing was carried out with ethyl acetate. The residue that was obtained upon removing the solvent by evaporation was purified by NAM silica gel column chromatography (dichloromethane/methanol), and the title compound (0.75 g) was obtained as a yellow oily substance.

$^1$H-NMR (CDCl$_3$) δ: 0.48–0.75 (m, H), 2.70 (s, 2H), 7.01 (dd, J=8.4 and 7.2 Hz, 2H), 7.23 (dd, J=8.4 and 5.6 Hz, 2H)

PREPARATION EXAMPLE 32

[2-(4-Fluorophenyl)-2-hydroxyethyl]methylcarbamic acid t-butyl ester

A solution of 1-(4-fluorophenyl)-2-methylamino ethanol (the compound of Preparation Example 17) (9.7 g) and t-butylbicarbonate (10.0 g) in a mixed solvent of tetrahydrofuran solution (100 mL) and an aqueous solution of saturated sodium bicarbonate (50 mL) was stirred at room temperature for 1.5 hours. The solution was diluted with ethyl acetate, and washed with water and saturated sodium chloride water. After drying the organic layer with anhydrous sodium sulfate, the residue that was obtained by evaporating the solvent at reduced pressure was purified by silica gel column chromatography (hexane/ethyl acetate), and the title compound (9.5 g) was obtained as a colorless solid.

$^1$H-NMR (CDCl$_3$) δ: 1.47 (br s, 9H), 2.65–2.95 (m, 4H), 3.30–4.33 (m, 2H), 4.84–5.00 (m, 1H), 7.04 (t, J=8.8 Hz, 2H), 7.27–7.43 (m, 2H)

PREPARATION EXAMPLE 33

[2-Azide-(4-fluorophenyl)ethyl]methylcarbamic acid t-butyl ester

A solution of [2-(4-fluorophenyl)-2-hydroxyethyl]methylcarbamic acid t-butyl ester (1.89 g), diphenylphosphoryl azide (1.7 mL) and 1,8-diazabicyclo[5.4.0]undeca-7-ene (DBU) (1.2 mL) in toluene (15 mL) was stirred at room temperature for 15 hours. After the solution was diluted with ethyl acetate, the solution was washed with water and saturated sodium chloride water. After drying the organic layer with anhydrous sodium sulfate, the residue that was obtained upon removal of the solvent by evaporation was purified by silica gel column chromatography (hexane/ethyl acetate), and phosphate ester (2.94 g) was obtained.

A solution of the above-mentioned phosphate ester (2.7 g) and sodium azide (0.91 g) in N,N-dimethylformamide (14 mL) was stirred at room temperature for 1 hour, then heated at 50° C. for 45 minutes and further at 70° C. for 5 hours. After diluting with water, extraction was carried out with ethyl acetate, and the solution was washed with water and saturated sodium chloride. After drying the organic layer with anhydrous sodium sulfate, the residue that was obtained upon removal of the solvent by evaporation was purified by silica gel column chromatography (hexane/ethyl acetate), and the title compound (0.35 g) was obtained as a colorless oily matter.

$^1$H-NMR (CDCl$_3$) δ: 1.45 (br s, 9H), 2.85 (s, 3H), 3.21–3.56 (m, 2H), 4.62–4.97 (m, 1H), 6.94–7.45 (m, 4H)

PREPARATION EXAMPLE 34

[2-Azide-2-(4-fluorophenyl)ethyl]methylamine-hydrochloride

From [2-azide-(4-fluorophenyl)ethyl]methylcarbamic acid t-butyl ester, the title compound (197 mg) was obtained as a colorless solid, in the same way as Preparation Example 27.

$^1$H-NMR (DMSO-d$_6$) δ: 2.58 (s, 3H), 3.10–3.43 (m, 2H), 5.04–5.19 (m, 1H), 7.31 (t, J=8.8 Hz, 2H), 7.51 (dd, J=8.8 and 5.2 Hz, 2H), 8.60–8.95 (m, 1H)

PREPARATION EXAMPLE 35

(2 S)-Methoxyphenyl acetic acid (1 S)-2-(t-butoxycarbonyl-methylamino)-1-(4-fluorophenyl)ethyl ester To a solution of [2-(4-fluorophenyl)-2-hydroxyethyl]methyl-carbamic acid t-butyl ester (the compound of Preparation Example 32) (8.46 g) and (S)-(+)-α-methoxyphenyl acetic acid (5.74 g) in dichloromethane (60 mL) was added 4-dimethylaminopyridine (0.19 g) and N,N-dicyclohexylcarbodiimide (7.7 g) on an ice bath. The solution was stirred for 3.5 hours while being slowly warmed to room temperature. When the reaction solution was developed with silica gel TLC (hexane/ethyl acetate=4:1), two products could be identified. After diluting with diethyl ether, the insoluble matter was removed by Celite filtration. The residue that was obtained upon removing the solvent by evaporation was purified by silica gel column chromatography (hexane/ethyl acetate), the (S, S) isomer (the compound that demonstrates a high Rf value in TLC) (3.60g) was obtained from the low polarity elution portion. The NMR suggested that it was a mixture of rotamers. The three-dimensional structure was determined from the NMR data by applying the Mosher method.

$^1$H-NMR (CDCl$_3$) δ: 1.37 (s, 9H), 2.45 and 2.50[each br s, 3H (1:1)], 3.27 (dd, J=14.4 and 8.0 Hz, 1H), 3.37 (s 3H), 3.39–3.59 (m, 1H), 4.77 (s, 1H), 5.86–6.06 (m, 1H), 6.90–7.07 (m, 2H), 7.11–7.53 (m, 7H)

PREPARATION EXAMPLE 36

(2S)-Methoxyphenyl acetic acid (1R)-2-(t-butoxy-carbonyl-methylamino)-1-(4-fluorophenyl)ethyl ester The high polarity elution portion (the fraction that demonstrates a low Rf value in TLC) in Preparation Example 35 was isolated by silica gel column chromatography, and the (S, R) isomer, which is the title compound (3.40 g), was obtained. The NMR suggested that is was a mixture of rotamers. The three-dimensional structure was determined from the NMR data by applying the Mosher method.

$^1$H-NMR (CDCl$_3$) δ: 1.40 and 1.43[each br s, 9H (1:1)], 2.77 and 2.81[each br s, 3H (1:1)], 3.39 (s, 3H), 3.40–3.54 (m, 2H), 4.79 (s, 1H), 5.84–6.01 (m, 1H), 6.80–7.02 (m, 4H), 7.28–7.42 (m, 5H)

PREPARATION EXAMPLE 37

(2S)-[2-(4-Fluorophenyl)-2-hydroxyethyl]methylcarbamic acid t-butyl ester

To a solution of (2S)-methoxyphenyl acetic acid (1S)-2-(t-butoxycarbonyl-methylamino)-1-(4-fluorophenyl)ethyl ester (the compound of Preparation Example 35) (3.6 g) in methanol (17 mL) was added potassium carbonate (1.8 g) on an ice bath. After stirring at room temperature for 30 minutes, the colorless solid that was generated by diluting with water was collected by filtration. After washing with water, and then drying by aeration, the title compound (2.35 g) was obtained as a colorless solid. The NMR data matched the racemic mixture described in Preparation Example 32.

PREPARATION EXAMPLE 38

(1S)-1-(4-Fluorophenyl)-2-(methylamino)ethanol

To a solution of (2S)-[2-(4-fluorophenyl)-2-hydroxyethyl]methylcarbamic acid t-butyl ester (1.25 g) in ethyl acetate was added dropwise a solution of 4N hydrochloric acid-ethyl acetate (40 mL). The solution was allowed to stand at room temperature for 1 hour. After removing the solvent by evaporation, the solution was alkalinized by addition of an aqueous solution of 5N sodium hydroxide, and saturated with sodium chloride. The solution was extracted with dichloromethane, then washed with saturated sodium chloride water. After drying with anhydrous sodium sulfate, the solvent was removed by evaporation. The resulting solid in a mixed solvent of diethyl ether-hexane was collected by filtration, and the title compound (480 mg) was obtained as a colorless solid. The NMR data matched the racemic mixture described in Preparation Example 17.

PREPARATION EXAMPLE 39

(2R)-[2-(4-Fluorophenyl)-2-hydroxyethyl]methyl-carbamic acid t-butyl ester

From (2S)-methoxyphenyl acetic acid (1R)-2-(t-butoxycarbonyl-methylamino)-1-(4-fluorophenyl)ethyl ester (the compound of Preparation Example 36) (3.4 g), the title compound (1.4 g) was obtained as a colorless solid, in the same way as Preparation Example 37. The NMR data matched the racemic mixture described in Preparation Example 32.

PREPARATION EXAMPLE 40

(1R)-1-(4-Fluorophenyl)-2-(methylamino)ethanol

From (2R)-[2-(4-fluorophenyl)-2-hydroxyethyl]methylcarbamic acid t-butyl ester (950 mg), the title compound (447 mg) was obtained as a colorless solid, in the same way as Preparation Example 38. The NMR data matched the racemic mixture described in Preparation Example 17.

PREPARATION EXAMPLE 41

7-Oxo-4,5,6,7-tetrahydro-benzo[b]thiophene-3-sulfonic acid [2-(4-fluorophenyl)-ethyl]-methyl-amide To a solution of [2-(4-fluorophenyl)-ethyl]-methyl-amine (the compound of Preparation Example 14) (520 mg) and triethylamine (474 μL) in tetrahydrofuran was added a solution of 7-oxo-4,5,6,7-tetrahydro-benzo[b]thiophene-3-sulfonyl chloride (the compound of Preparation Example 7) (800 mg) in tetrahydrofuran. The solution was stirred on an ice bath for 30 minutes, and at room temperature for 30 minutes. The residue resulting from the removal of the solvent by evaporation was purified by NH silica gel column chromatography (hexane/ethyl acetate), and the title compound (834 mg) was obtained as a colorless candy-like substance.

$^1$H-NMR (CDCl$_3$) δ: 2.16–2.24 (m, 2H), 2.59–2.65 (m, 2H), 2.92 (s, 3H), 3.00–3.06 (m, 2H), 3.24 (dd, J=14.4, 4.0 Hz, 1H), 3.36 (dd, J=14.2, 8.6 Hz, 1H), 4.92–4.99 (m, 1H), 7.00–7.08 (m, 2H), 7.31–7.37 (m, 2H), 8.19 (s, 1H)

PREPARATION EXAMPLE 42

7-Oxo-4,5,6,7-tetrahydro-benzo[b]thiophene-3-sulfonic acid [2-(4-fluoro-2-nitro-phenyl)-ethyl]-methyl-amide 7-Oxo-4,5,6,7-tetrahydro-benzo[b]thiophene-3-sulfonic acid [2-(4-fluorophenyl)-ethyl]-methyl-amide (the compound of Preparation Example 41) (222 mg) was dissolved in a concentrated sulfuric acid (1.5 mL), potassium nitrate (74 mg) was added in small amounts on an ice bath. After stirring for 45 minutes, the reaction solution was poured into ice water, and extracted with ethyl acetate. The organic layer was washed with water, an aqueous solution of sodium bicarbonate and saturated sodium chloride water, and dried with anhydrous magnesium sulfate. Spots for two products were identified by silica gel TLC (hexane/ethyl acetate=1:1). The residue resulting from the removal of the solvent by evaporation was purified by silica gel column chromatography (hexane/ethyl acetate), fractions with a high RF value were collected, and the title compound (78 mg) was obtained as a colorless solid.

$^1$H-NMR (CDCl$_3$) δ: 2.15–2.24 (m, 2H), 2.60–2.65 (m, 2H), 2.89 (s, 3H), 2.99–3.04 (m, 2H), 3.18–3.23 (m, 2H), 3.44–3.49 (m, 2H), 7.32 (ddd, J=8.4, 7.2, 2.4 Hz, 1H), 7.43 (dd, J=8.4, 5.6 Hz, 1H), 7.72 (dd, J=8.4, 2.4 Hz, 1H), 8.17 (s, 1H)

PREPARATION EXAMPLE 43

7-Oxo-4,5,6,7-tetrahydro-benzo[b]thiophene-3-sulfonic acid [2-(4-fluoro-3-nitro-Phenyl)-ethyl]-methyl-amide Fraction showing a low Rf value by TLC in Preparation Example 42 was collected, and the title compound (118 mg) was obtained as a colorless oily matter.
$^1$H-NMR (CDCl$_3$) δ: 2.16–2.24 (m, 2H), 2.60–2.65 (m, 2H), 2.85 (s, 3H), 3.97–3.03 (m, 4H), 3.39–3.45 (m, 2H), 7.24 (dd, J=10.4, 8.4 Hz, 1H), 7.49 (ddd, J=8.4, 4.0, 2.0 Hz, 1H), 7.89 (dd, J=6.8, 2.0 Hz, 1H), 8.17 (s, 1H)

PREPARATION EXAMPLE 44

7-Oxo-4,5,6,7-tetrahydro-benzo[b]thiophene-3-sulfonic acid methyl-(2-pyridine-3-vi-ethyl)-amide From methyl-(2-pyridine-3-yl-ethyl)-amine (the compound of Preparation Example 15) (82 mg) and 7-oxo-4,5,6,7-tetrahydro-benzo-[b]thiophene-3-sulfonyl chloride (the compound of Preparation Example 7) (150 mg), the title compound (138 mg) was obtained as a colorless oily matter, in the same way as Preparation Example 41.
$^1$H-NMR (CDCl$_3$) δ: 2.13–2.22 (m, 2H), 2.58–2.65 (m, 2H), 2.87 (s, 3H), 2.90–2.97 (m, 4H), 3.39–3.45 (m, 2H), 7.22–7.27 (m, 1H), 7.52–7.56 (m, 1H), 8.17 (s, 1H), 8.45–8.51 (m, 2H)

PREPARATION EXAMPLE 45

7-Oxo-4,5,6,7-tetrahydro-benzo[b]thiophene-3-sulfonic acid methyl-(2-pyridine-4-yl-ethyl)-amide From methyl-(2-pyridine-4-yl-ethyl)-amine (the compound of Preparation Example 16) (82 mg) and 7-oxo-4,5,6,7-tetrahydro-benzo[b]thiophene-3-sulfonyl chloride (the compound of Preparation Example 7) (150 mg), the title compound (100 mg) was obtained as a colorless oily matter, in the same way as Preparation Example 41.
$^1$H-NMR (CDCl$_3$) δ: 2.13–2.21 (m, 2H), 2.59–2.65 (m, 2H), 2.84 (s, 3H), 2.90–2.98 (m, 4H), 3.40–3.47 (m, 2H), 7.14–7.17 (m, 2H), 8.19 (s, 1H), 8.52–8.55 (m, 2H)

PREPARATION EXAMPLE 46

3-[4-(4-Fluorophenyl)-piperazine-1-sulfonyl]5,6-dihydro-4H-benzo[b]thiophene-7-one From 1-(4-fluorophenyl)-piperazine (91 mg) and 7-oxo-4,5,6,7-tetrahydro-benzo[b]thiophene-3-sulfonyl chloride (the compound of Preparation Example 7) (120 mg), the title compound (148 mg) was obtained as a colorless solid, in the same way as Preparation Example 41.
$^1$H-NMR (CDCl$_3$) δ: 2.19–2.27 (m, 2H), 2.63–2.69 (m, 2H), 3.08–3.13 (m, 2H), 3.15–3.21 (m, 4H), 3.29–3.35 (m, 4H), 6.84–6.91 (m, 2H), 6.94–7.01 (m, 2H), 8.24 (s, 1H)

PREPARATION EXAMPLE 47

3-(4-Hydroxy-4-phenyl-piperidine-1-sulfonyl) 5,6-dihydro-4H-benzo[b]thiophene-7-one From 4-phenyl-piperidine-4-ol (36 mg) and 7-oxo-4,5,6,7-tetrahydro-benzo[b]thiophene-3-sulfonyl chloride (the compound of Preparation Example 7) (50 mg), the title compound (72 mg) was obtained as a colorless amorphous substance, in the same way as Preparation Example 41.
$^1$H-NMR (CDCl$_3$) δ: 1.82–1.90 (m, 2H), 2.15–2.28 (m, 4H), 2.63–2.79 (m, 2H), 3.00–3.09 (m, 2H), 3.10–3.15 (m, 2H), 3.74–3.81 (m, 2H), 7.27–7.32 (m, 1H), 7.35–7.40 (m, 2H), 7.42–7.46 (m, 2H), 8.21 (s, 1H)

PREPARATION EXAMPLE 48

7-Oxo-4,5,6,7-tetrahydro-benzo[b]thiophene-3-sulfonic acid [2-(4-fluorophenyl)-2-hydroxyethyl]-methyl-amide From 1-(4-fluorophenyl)-2-methylamino-ethanol (the compound of Preparation Example 17) (433 mg) and 7-oxo-4,5,6,7-tetrahydro-benzo[b]thiophene-3-sulfonyl chloride (the compound of Preparation Example 7), the title compound (769 mg) was obtained as a colorless amorphous substance, in the same way as Preparation Example 41.
$^1$H-NMR (CDCl$_3$) δ: 2.16–2.24 (m, 2H), 2.59–2.65 (m, 2H), 2.92 (s, 3H), 3.00–3.06 (m, 2H), 3.24 (dd, J=14.4, 4.0 Hz, 1H), 3.36 (dd, J=14.2, 8.6 Hz, 1H), 4.92–4.99 (m, 1H), 7.00–7.08 (m, 2H), 7.31–7.37 (m, 2H), 8.19 (s, 1H)

PREPARATION EXAMPLE 49

N-[(2S)-2-(4-Fluorophenyl)-2-hydroxyethyl]-N-methyl-7-oxo-4,5,6,7-tetrahydro-1-benzothiophene-3-sulfonamide From 7-oxo-4,5,6,7-tetrahydrobenzo[b]thiophene-3-sulfonyl chloride (the compound of Preparation Example 7) (285 mg) and (1S)-1-(4-fluorophenyl)-2-(methylamino) ethanol (the compound of Preparation Example 38) (230 mg), the title compound (370 mg) was obtained as a light brown solid, in the same way as Preparation Example 41. The NMR data matched the racemic mixture described in Preparation Example 48. The optical purity as measured by high performance liquid chromatography (ChiralPak AD-H, hexane:2-propanol=8:2) was >99% e.e.

PREPARATION EXAMPLE 50

N-[(2R)-2-(4-fluorophenyl)-2-hydroxyethyl]-N-methyl-7-oxo-4,5,6,7-tetrahydro-1-benzothiophene-3-sulfonamide From 7-oxo-4,5,6,7-tetrahydrobenzo[b]thiophene-3-sulfonyl chloride (the compound of Preparation Example 7) (286 mg) and (1R)-1-(4-fluorophenyl)-2-(methylamino) ethanol (the compound of Preparation Example 40) (212 mg), the title compound (356 mg) was obtained as a colorless solid, in the same way as Preparation Example 41. The NMR data matched the racemic mixture described in Preparation Example 48. The optical purity as measured by high performance liquid chromatography (ChiralPak AD-H, hexane:2-propanol=8:2) was >99% e.e.

PREPARATION EXAMPLE 51

7-Oxo-4,5,6,7-tetrahydro-benzo[b]thiophene-3-sulfonic acid [2-(2,4-difluorophenyl)-2-hydroxy-ethyl]-amide From 7-oxo-4,5,6,7-tetrahydro-benzo[b]thiophene-3-sulfonyl chloride (the compound of Preparation Example 7) (280 mg) and 2-amino-1-(2,4-difluorophenyl)-ethanol hydrochloride (the compound of Preparation Example 20) (281 mg), the title compound (290 mg) was obtained as a colorless solid, in the same way as Preparation Example 41.

$^1$H-NMR (CDCl$_3$) δ: 2.18–2.27 (m, 2H), 2.61–2.67 (m, 2H), 2.93–3.10 (m, 2H), 3.16 (dd, J=13.6, 8 Hz, 1H), 3.39 (dd, J=13.6, 3.6 Hz, 1H), 4.90–5.15 (br, 1H), 5.08 (dd, J=8.0, 3.6 Hz, 1H), 6.74–6.81 (m, 1H), 6.89–6.93 (m, 1H), 7.40–7.48 (m, 1H), 8.25 (s, 1H)

PREPARATION EXAMPLE 52

7-Oxo-4,5,6,7-tetrahydro-benzo[b]thiophene-3-sulfonic acid [2-(2,4-difluorophenyl)-2-hydroxy-ethyl]-methyl-amide To a solution of 7-oxo-4,5,6,7-tetrahydro-benzo[b]thiophene-3-sulfonic acid[2-(2,4-difluorophenyl)-2-hydroxy-ethyl]-amide (the compound of Preparation Example 51) (197 mg) in N,N-dimethylformamide (3 mL) was added potassium carbonate (140 mg) and methyl iodide (0.1 mL). After stirring at room temperature for 1 hour, ethyl acetate was added, and the precipitate was removed by filtration. The solvent was evaporated at reduced pressure. Purification was carried out by silica gel column chromatography (hexane/ethyl acetate), and the title compound (190 mg) was obtained as a colorless candy-like substance.

$^1$H-NMR (CDCl$_3$) δ: 2.17–2.25 (m, 2H), 2.61–2.67 (m, 2H), 2.92 (d, J=3.2 Hz, 1H), 2.97 (s, 3H), 3.03–3.08 (m, 2H), 3.28 (dd, J=14.4, 3.2 Hz, 1H), 3.40 (dd, J=14.4, 8.4 Hz, 1H), 4.90–5.15 (br, 1H), 5.08 (dd, J=8.0, 3.6 Hz, 1H), 5.22 (ddd, J=8.4, 3.2, 3.2 Hz, $_1$H), 6.76–6.82 (m, $_1$H), 6.90–6.96 (m, 1H), 7.55–7.61 (m, 1H), 8.21 (s, 1H)

PREPARATION EXAMPLE 53

7-Oxo-4,5,6,7-tetrahydro-benzo[b]thiophene-3-sulfonic acid [2-hydroxy-2-(4-pyrrolidine-1-yl-phenyl)-ethyl]-methyl-amide From 2-methylamino-1-(4-pyrrolidine-1-yl-phenyl)-ethanol (the compound of Preparation Example 19) (63 mg) and 7-oxo-4,5,6,7-tetrahydro-benzo[b]thiophene-3-sulfonyl chloride (the compound of Preparation Example 7) (70 mg), the title compound (35 mg) was obtained as a colorless amorphous substance, in the same way as Preparation Example 41.

$^1$H-NMR (CDCl$_3$) δ: 1.97–2.04 (m, 4H), 2.12–2.23 (m, 2H), 2.55–2.62 (m, 2H), 2.90–3.04 (m, 2H), 2.94 (s, 3H), 3.22–3.31 (m, 5H), 3.36–3.45 (m, 1H), 4.78–4.84 (m, 1H), 6.47–6.55 (m, 2H), 7.12–7.18 (m, 2H), 8.17 (s, 1H)

PREPARATION EXAMPLE 54

7-Oxo-4,5,6,7-tetrahydro-benzo[b]thiophene-3-sulfonic acid [3-(4-chloro-phenoxy)-2-hydroxy-propyl]-methyl-amide a) 7-Oxo-4,5,6,7-tetrahydro-benzo[b]thiophene-3-sulfonic acid [3-(4-chloro-phenoxy)-2-hydroxy-propyl]-amide From 1-amino-3-(4-chloro-phenoxy)-propane-2-ol (58 mg) and 7-oxo-4,5,6,7-tetrahydro-benzo[b]thiophene-3-sulfonyl chloride (the compound of Preparation Example 7) (70 mg), a yield (45 mg) was obtained as a colorless amorphous substance, in the same way as Preparation Example 41

$^1$H-NMR (CDCl$_3$) δ: 2.18–2.27 (m, 2H), 2.60–2.66 (m, 2H), 3.03–3.09 (m, 2H), 3.12–3.20 (m, 1H), 3.27–3.34 (m, 1H), 3.89–3.98 (m, 2H), 4.09–4.18 (br, 1H), 5.02–5.08 (m, 1H), 6.75–6.81 (m, 2H), 7.21–7.26 (m, 2H), 8.26 (s, 1H)

b) Title Compound

From 7-oxo-4,5,6,7-tetrahydro-benzo[b]thiophene-3-sulfonic acid[3-(4-chloro-phenoxy)-2-hydroxy-propyl]-amide (44 mg) and methyl iodide (20 μL), the title compound (41 mg) was obtained as a colorless amorphous substance, in the same way as Preparation Example 52.

$^1$H-NMR (CDCl$_3$) δ: 2.18–2.26 (m, 2H), 2.61–2.67 (m, 2H), 2.98 (s, 3H), 3.09 (t, J=6.0 Hz, 2H), 3.35–3.39 (m, 2H), 3.95–4.06 (m, 2H), 4.19–4.27 (br, 1H), 6.80–6.86 (m, 2H), 7.21–7.26 (m, 2H), 8.21 (s, 1H)

PREPARATION EXAMPLE 55

7-Oxo-4,5,6,7-tetrahydro-benzo[b]thiophene-3-sulfonic acid (2-hydroxy-2-pyridine-4-yl-ethyl)-methyl-amide From 2-methylamino-1-pyridine-4-yl-ethyl-ethanol (the compound of Preparation Example 18) (117 mg) and 7-oxo-4,5,6,7-tetrahydro-benzo[b]thiophene-3-sulfonyl chloride (the compound of Preparation Example 7) (192 mg), the title compound (202 mg) was obtained as a colorless solid, in the same way as Preparation Example 41.

$^1$H-NMR (CDCl$_3$) δ: 2.18–2.26 (m, 2H), 2.61–2.66 (m, 2H), 2.95 (s, 3H), 3.00 (d, J=3.2 Hz, 1H), 3.02–3.07 (m, 2H), 3.30–3.36 (m, 2H), 4.98–5.03 (m, 1H), 7.32–7.36 (m, 2H), 8.21 (s, 1H), 8.60–8.64 (m, 2H),

PREPARATION EXAMPLE 56

7-Oxo-4,5,6,7-tetrahydrobenzo[b]thiophene-3-sulfonic acid [2-azide-2-(4-fluorophenyl)ethyl]-methyl-amide From [2-azide-2-(4-fluorophenyl)ethyl]methylamine hydrochloride (the compound of Preparation Example 34) (197 mg) and 7-oxo-4,5,6,7-tetrahydrobenzo[b]thiophene-3-sulfonyl chloride (the compound of Preparation Example 7) (140 mg), the title compound (223 mg) was obtained as a brown oily substance, in the same way as Preparation Example 41.

$^1$H-NMR (CDCl$_3$) δ: 2.10–2.30 (m, 1H), 2.63 (t, J=6.0 Hz, 2H), 2.87 (s, 3H), 3.01 (t, J=6.0 Hz, 2H), 3.22–3.40 (m, 2H), 4.82 (dd, J=8.0 and 5.6 Hz, 1H), 7.10 (t, J=8.4 Hz, 2H), 7.32 (dd, J=8.4 and 5.6 Hz, 2H), 8.19 (s, 1H)

PREPARATION EXAMPLE 57

7-Oxo-4,5,6,7-tetrahydrobenzo[b]thiophene-3-sulfonic acid [2-amino-2-(4-fluorophenyl)ethyl]-methyl-amide To a mixture solution of 7-oxo-4,5,6,7-tetrahydrobenzo[b]thiophene-3-sulfonic acid [2-azide-2-(4-fluorophenyl)ethyl]-methyl-amide (the compound of Preparation Example 56) (100 mg) in tetrahydrofuran (2 mL)-water (0.2 mL) was added dropwise a solution of 20% triethylphosphine-tetrahydrofuran (175 μL) at room temperature. After stirring for 3 hours, the solution was diluted with ethyl acetate, and then washed with water and saturated sodium chloride water. After drying the organic layer with anhydrous sodium sulfate, purification by column chromatography (dichloromethane/methanol) with a small amount of silica gel, and the title compound (70 mg) was obtained as a brown oily substance.

$^1$H-NMR (CDCl$_3$) δ: 2.10–2.28 (m, 1H), 2.62 (t, J=6.4 Hz, 2H), 2.82 (s, 3H), 2.90–3.11 (m, 2H), 3.37 (dd, J=13.6 and 8.8 Hz, 1H), 4.23 (dd, J=8.8 and 4.8 Hz, 1H), 7.04 (t, J=8.4 Hz, 2H), 7.34 (dd, J=8.4 and 5.6 Hz, 2H), 8.19 (s, 1H)

PREPARATION EXAMPLE 58

2-Bromo-7-oxo-4,5,6,7-tetrahydro-benzo[b]thiophene-3-sulfonic acid[2-(4-fluorophenyl)-2-hydroxy-ethyl]-methyl-amide From 1-(4-fluorophenyl)-2-methylamino-ethanol (the compound of Preparation Example 17) (186 mg) and 2-bromo-7-oxo-4,5,6,7-tetrahydro-benzo[b]thiophene-3-sulfonyl chloride (the compound of Preparation Example 9) (330 mg), the title compound (373 mg) was obtained as a light brown candy-like substance, in the same way as Preparation Example 41.

$^1$H-NMR (CDCl$_3$) δ: 2.15–2.24 (m, 2H), 2.59–2.64 (m, 3H), 2.98 (s, 3H), 3.06–3.11 (m, 2H 3.37 (dd, J=14.7, 4.0 Hz, 1H), 3.46 (dd, J=14.7, 8.4 Hz, 1H), 4.96–5.02 (m, 1H), 7.03–7.10 (m, 2H), 8.34–8.40 (m, 2H),

PREPARATION EXAMPLE 59

2-Amino-7-oxo-4,5,6,7-tetrahydro-benzo[b]thiophene-3-sulfonic acid[2-(4-fluorophenyl)-2-hydroxy-ethyl]-methyl-amide A concentrated aqueous ammonia (24 mL) was added to 2-bromo-7-oxo-4,5,6,7-tetrahydro-benzo[b]thiophene-3-sulfonic acid[2-(4-fluorophenyl)-2-hydroxy-ethyl]-methyl-amide (210 mg). After heating at 110° C. for 4 hours, the reaction solution was poured into water, brought to pH 9 with 5N hydrochloric acid, and extracted with ethyl acetate. The organic layer was dried with anhydrous magnesium sulfate, the residue resulting from the removal of the solvent by evaporation was purified by silica gel column chromatography (hexane/ethyl acetate), and the title compound (145 mg) was obtained as a colorless film.

$^1$H-NMR (CDCl$_3$) δ: 2.05–2.14 (m, 2H), 2.48–2.54 (m, 2H), 2.62 (br, 1H), 2.78–2.86 (m, 2H), 2.88 (s, 3H), 3.26 (dd, J=14.4, 4.0 Hz, 1H), 3.37 (dd, J=14.4, 8.8 Hz, 1H), 4.92 (dd, J=8.8, 4.0 Hz, 1H), 6.23 (br, 2H), 7.01–7.08 (m, 2H), 7.30–7.36 (m, 2H),

PREPARATION EXAMPLE 60

2-Methoxy-7-oxo-4,5,6,7-tetrahydro-benzo[b]thiophene-3-sulfonic acid[2-(4-fluorophenyl)-2-hydroxy-ethyl]-methyl-amide To a solution of 2-bromo-7-oxo-4,5,6,7-tetrahydro-benzo[b]thiophene-3-sulfonic acid [2-(4-fluorophenyl)-2-hydroxy-ethyl]-methyl-amide (the compound of Preparation Example 58) (80 mg) in methanol (3 mL) was added a solution of 28% sodium methoxide/methanol (0.8 mL). After stirring at room temperature for 3 hours, the reaction solution was poured into water, extracted with ethyl acetate and dried with anhydrous magnesium sulfate. The residue resulting from the removal of the solvent by evaporation was purified by silica gel column chromatography (hexane/ethyl acetate), and the title compound (58 mg) was obtained as a light brown candy-like substance.

$^1$H-NMR (CDCl$_3$) δ: 2.13–2.20 (m, 2H), 2.56–2.60 (m, 2H), 2.89 (s, 3H), 2.91 (br, 1H), 3.04–3.09 (m, 2H), 3.36 (dd, J=14.8, 3.6 Hz, 1H), 3.40 (dd, J=14.8, 8.8 Hz, 1H), 4.09 (s, 3H), 4.92–4.96 (m, 1H), 7.03–7.10 (m, 2H), 8.34–8.40 (m, 2H)

PREPARATION EXAMPLE 61

2-Morpholin-4-yl-7-oxo-4,5,6,7-tetrahydro-benzo[b]thiophene-3-sulfonic acid[2-(4-fluorophenyl)-2-hydroxy-ethyl]-methyl-amide 2-Bromo-7-oxo-4,5,6,7-tetrahydro-benzo[b]thiophene-3-sulfonic acid[2-(4-fluorophenyl)-2-hydroxy-ethyl]-methyl-amide (the compound of Preparation Example 58) (80 mg), triethylamine (29 mL) and morpholin (24 μL) were stirred at 60° C. for 3 hours. The residue resulting from the evaporation of the solvent at reduced pressure was purified by silica gel column chromatography (hexane/ethyl acetate), and the title compound (82 mg) was obtained as a colorless candy-like substance.

$^1$H-NMR (CDCl$_3$) δ: 2.11–2.19 (m, 2H), 2.56–2.61 (m, 2H), 2.88 (s, 3H), 2.90 (d, J=2.8 Hz, 1H), 2.99–3.04 (m, 2H), 3.14–3.26 (m, 5H), 3.42 (dd, J=14.8, 9.2 Hz, 1H), 3.77–3.82 (m, 4H), 4.90–4.95 (m, 1H), 7.03–7.10 (m, 2H), 8.34–8.37 (m, 2H),

PREPARATION EXAMPLE 62

6-Methyl-7-oxo-4,5,6,7-tetrahydrobenzo[b]thiophene-3-sulfonic acid[2-(4-fluorophenyl)ethyl]-methyl-amide From 6-methyl-7-oxo-4,5,6,7-tetrahydrobenzo[b]thiophene-3-sulfonyl chloride (the compound of Preparation Example 13) (140 mg) and [2-(4-fluorophenyl)ethyl]methyl-amine (the compound of Preparation Example 14) (98 mg), the title compound (152 mg) was obtained as an orange oily substance, in the same way as Preparation Example 41.

$^1$H-NMR (CDCl$_3$) δ: 1.26 (d, J=6.8 Hz, 3H), 1.80–2.01 (m, 1H), 2.13–2.32 (m, 1H), 2.52–3.02 (m, 4H), 2.83 (s, 3H), 3.09–3.52 (m, 3H), 6.80–7.40 (m, 4H), 8.13 (s, 1H)

PREPARATION EXAMPLE 63

6-Methyl-7-oxo-4,5,6,7-tetrahydrobenzo[b]thiophene-3-sulfonic acid[2-(4-fluorophenyl)2-hydroxyethyl]-methyl-amide From 6-methyl-7-oxo-4,5,6,7-tetrahydrobenzo[b]thiophene-3-sulfonyl chloride (the compound of Preparation Example 13) (140 mg) and 1-(4-fluorophenyl)-2-methylamino ethanol (the compound of Preparation Example 17) (108 mg), the title compound (orange oily substance) (155 mg) was obtained as a mixture of diastereomers, in the same way as Preparation Example 41.

$^1$H-NMR (CDCl$_3$) δ: 1.26 (d, J=6.4 Hz, 3H), 1.83–2.02 (m, 1H), 2.18–2.37 (m, 1H), 2.52–2.78 (m, 2H), 2.80–3.01 (m, 1H), 2.92 (s, 3H), 3.15–3.46 (m, 3H), 4.90–5.03 (m, 1H), 6.95–7.14 (m, 2H), 7.21–7.47 (m, 2H), 8.18 (s, 1H)

PREPARATION EXAMPLE 64

6-Bromo-7-oxo-4,5,6,7-tetrahydrobenzo[b]
thiophene-3-sulfonic acid[2-(4-fluorophenyl)ethyl]-
methyl-amide To a solution of 6-methyl-7-oxo-4,5,6,7-tetrahydro-benzo[b]thiophene-3-sulfonic acid [2-(4-fluorophenyl)ethyl]-methyl-amide (the compound of Preparation Example 41) (203 mg) in dichloromethane (2 mL) was added dropwise triethylamine (0.12 mL) and t-butyldimethylsilyltrifluoromethane sulfonate (0.16 mL) at room temperature. After stirring for 15 minutes, an aqueous solution of saturated sodium bicarbonate was added, and the solution was extracted with ethyl acetate. After drying the organic layer with anhydrous sodium sulfate, the solvent was removed by evaporation and crude silyl enol ether was obtained.

To a solution of the above-mentioned crude silyl enol ether in tetrahydrofuran (2 mL) was added sodium bicarbonate powder (93 mg) and N-bromosucciimide (120 mg) on an ice bath. After stirring for 30 minutes, an aqueous solution of saturated sodium bicarbonate was added and was extracted with ethyl acetate. The organic layer was washed with saturated sodium chloride water. After drying with anhydrous sodium sulfate, the residue that was obtained upon removal of the solvent by evaporation was purified by silica gel column chromatography (hexane/ethyl acetate), and the title compound (246 mg) was obtained as a yellow oily substance.

$^1$H-NMR (CDCl$_3$) δ: 2.42–2.53 (m, 2H), 2.84 (s, 3H), 2.86–3.46 (m, 6H), 4.61–4.69 (m, 1H), 6.91–7.04 (m, 2H), 7.08–7.20 (m, 2H), 8.21 (s, 1H)

PREPARATION EXAMPLE 65

6-Acetoxy-7-oxo-4,5,6,7-tetrahydrobenzo[b]
thiophene-3-sulfonic acid[2-(4-fluorophenyl)ethyl]-
methyl-amide To a solution of 6-bromo-7-oxo-4,5,6,7-tetrahydrobenzo[b]thiophene-3-sulfonic acid [2-(4-fluorophenyl)ethyl]-methyl-amide (246 mg) in dimethylsulfoxide (2 mL) was added potassium acetate (108 mg). After stirring for 30 minutes, the solution was diluted with, and extracted with ethyl acetate. After drying the organic layer with anhydrous sodium sulfate, the solvent was removed by evaporation to provide the title compound (200 mg) as a yellow oily substance.

$^1$H-NMR (CDCl$_3$) δ: 2.21 (s, 3H), 2.72–3.50 (m, 8H), 2.84 (s, 3H), 5.55 (dd, J=12.8 and 5.2 Hz, 1H), 6.79–7.12 (m, 4H), 8.10 (s, 1H)

PREPARATION EXAMPLE 66

5-Bromothiophene-2-sulfonic
acid[2-(4-fluorophenyl)ethyl]amide

To a solution of 5-bromothiophene-2-sulfonyl chloride (600 mg) in tetrahydrofuran (5 mL) was added dropwise triethylamine (0.64 mL) and 4-fluorophenethylamine (0.36 mL) on an ice bath. After stirring for 15 minutes on an ice bath, the solution was further stirred at room temperature for 2 hours. After dilution with ethyl acetate and washing with 5N hydrochloric acid, water, an aqueous solution of saturated sodium bicarbonate and saturated sodium chloride water, the solution was dried with anhydrous sodium sulfate. Silica gel filtration was carried out, and the solvent was removed by evaporation to provide the title compound (860 mg) as a colorless oily matter.

$^1$H-NMR (CDCl$_3$) δ: 2.72–2.88 (m, 2H), 3.20–3.38 (m, 2H), 4.35–4.54 (m, 1H), 6.90–7.40 (m, 6H)

PREPARATION EXAMPLE 67

5-Acetylthiophene-2-sulfonic
acid[2-(4-fluorophenyl)ethyl]amide

5-Bromothiophene-2-sulfonic acid[2-(4-fluorophenyl)ethyl]amide (860 mg), (1-ethoxyvinyl)tributyltin (940 mg) and tetrakis(triphenylphosphine)palladium (273 mg) was heated in toluene (10 mL) at 100° C. for 1.5 hours and further at 120° C. for one hour. After cooling the reaction solution to room temperature, dilution with tetrahydrofuran (10 mL) was carried out, and an aqueous solution (5 mL) of 10% potassium fluoride was added. After stirring for 20 minutes, the insoluble matter that was generated was filtered over Celite, and Celite was washed with ethyl acetate. After washing the filtrate with water and saturated sodium chloride water, drying with anhydrous sodium sulfate was carried out, and crude enol ether was obtained by removing the solvent by evaporation.

Thereafter, the above-mentioned crude enol ether was dissolved in tetrahydrofuran (5 mL)-1N hydrochloric acid (5 mL). After stirring at room temperature for 14 hours, the solution was diluted with water, and extracted with ethyl acetate, and washed with saturated sodium chloride water. After drying with anhydrous sodium sulfate, the residue that was obtained upon removing the solvent by evaporation was purified by silica gel column chromatography (hexane/ethyl acetate), and the title compound (726 mg) was obtained as a colorless oily matter.

$^1$H-NMR (CDCl$_3$) δ: 2.60 (s, 3H), 2.83 (t, J=7.2 Hz, 2H), 3.28–3.40 (m, 2H), 4.48–4.60 (m, 1H), 6.98 (t, J=8.4 Hz, 2H), 7.09 (dd, J=8.4 and 5.6 Hz, 2H), 7.52 (d, J=4.0 Hz, 1H), 7.58 (d, J=4.0 Hz, 1H)

PREPARATION EXAMPLE 68

5-Acetylthiophene-2-sulfonic
acid[2-(4-fluorophenyl)ethyl]-methyl-amide

5-Bromothiophene-2-sulfonic acid [2-(4-fluorophenyl)ethyl]-methyl-amide was synthesized from 5-bromothiophene-2-sulfonyl chloride (523 mg) and [2-(4-fluorophenyl)ethyl]methylamine (the compound of Preparation Example 14) (1.14 g), in the same way as Preparation Example 41, thereafter, an acetyl group was introduced in the same way as Preparation Example 67, and the title compound (257 mg) was obtained as a colorless oily matter.

$^1$H-NMR (CDCl$_3$) δ: 2.59 (s, 3H), 2.81 (s, 3H), 2.83–2.93 (m, 2H), 3.21–3.37 (m, 2H), 6.93–7.04 (m, 2H), 7.10–7.20 (m, 2H), 7.45–7.53 (m, 1H), 7.58–7.64 (m, 1H)

PREPARATION EXAMPLE 69

5-Bromothiophene-2-sulfonic acid methyl-amide

To a solution of 5-bromothiophene-2-sulfonyl chloride (602 mg) in tetrahydrofuran (5 mL) was added dropwise a solution of 2.0M methylamine-tetrahydrofuran (3.5 mL) on an ice bath. After stirring for 15 minutes on an ice bath, the solution was diluted with water and extracted with ethyl acetate. After washing with an aqueous solution of saturated sodium bicarbonate and saturated sodium chloride water, the solution was dried with anhydrous sodium sulfate. After filtration through silica gel, the solvent was removed by evaporation to provide the title compound (608 mg) as a colorless oily matter.

$^1$H-NMR (CDCl$_3$) δ: 2.76 (d, J=5.6 Hz, 3H), 4.30–4.50 (m, 1H), 7.08 (d, J=4.0 Hz, 1H), 7.36 (d, J=4.0 Hz, 1H)

PREPARATION EXAMPLE 70

5-Bromothiophene-2-sulfonic acid[2-(4-fluorophenyl)-2-oxoethyl]-methyl-amide

To a solution of 5-bromothiophene-2-sulfonic acid methyl-amide (608 mg) in tetrahydrofuran (5 mL) was added 60% sodium hydride (115 mg). After stirring for 20 minutes, 2-bromo-1-(4-fluorophenyl)ethanone (630 mg) was added. After adding water and ethyl acetate, and washing the organic layer with saturated sodium chloride water, this solution was dried with anhydrous sodium sulfate. The residue that was obtained upon removing the solvent by evaporation was purified by silica gel column chromatography (hexane/ethyl acetate) and the title compound (464 mg) was obtained as a yellow oily substance.

$^1$H-NMR (CDCl$_3$) δ: 2.91 (s, 3H), 4.56 (s, 2H), 7.12 (d, J=4.0 Hz, 1H), 7.17 (t, J=8.4 Hz, 2H), 7.36 (d, J=4.0 Hz, 1H), 7.87–8.07 (m, 2H)

PREPARATION EXAMPLE 71

5-Bromothiophene-2-sulfonic acid[2-(4-fluorophenyl)-2-hydroxyethyl]-methyl-amide 5-bromothiophene-2-sulfonic acid [2-(4-fluorophenyl)-2-oxoethyl]-methyl-amide (270 mg) was reduced with sodium borohydride (26 mg) on an ice-bath and the title compound (255 mg) was obtained as a yellow oily substance.

$^1$H-NMR (CDCl$_3$) δ: 2.67 (d, J=2.8 Hz, 1H), 2.85 (s, 3H), 3.10 (dd, J=14.0 and 3.6 Hz, 1H), 3.23 (dd, J=14.0 and 8.4 Hz, 1H), 4.90–5.02 (m, 1H), 6.96–7.17 (m, 3H), 7.31 (d, J=4.0 Hz, 1H), 7.31–7.45 (m, 2H)

PREPARATION EXAMPLE 72

5-Acetylthiophene-2-sulfonic acid[2-(4-fluorophenyl)-2-hydroxyethyl]-methyl-amide From 5-bromothiophene-2-sulfonic acid [2-(4-fluorophenyl)-2-hydroxyethyl]-methyl-amide (the compound of Preparation Example 71) (255 mg), the title compound (210 mg) was obtained as a reddish-brown oily substance, in the same way as Preparation Example 67.

$^1$H-NMR (CDCl$_3$) δ: 2.58 (s, 3H), 2.63 (d, J=3.2 Hz, 1H), 2.89 (s, 3H), 3.15 (dd, J=14.4 and 4.4 Hz, 1H), 3.25 (dd, J=14.4 and 8.4 Hz, 1H), 4.86–5.01 (m, 1H), 7.06 (t, J=8.4 Hz, 2H), 7.36 (dd, J=8.4 and 5.2 Hz, 2H), 7.53 (d, J=4.0 Hz, 1H), 7.62 (d, J=4.0 Hz, 1H)

PREPARATION EXAMPLE 73

5-Bromothiophene-2-sulfonic acid[2-(4-fluorophenyl)-2-methoxyethyl]-methyl-amide To a solution of 5-bromothiophene-2-sulfonic acid [2-(4-fluorophenyl)-2-hydroxyethyl]-methyl-amide (the compound of Preparation Example 71) (210 mg) in N,N-dimethylformamide (2 mL) was added 60% sodium hydride (32 mg). After stirring for 45 minutes, methyl iodide (100 µL) was added. Water was added, the solution was extracted with ethyl acetate. After washing the organic layer with saturated sodium chloride water, and then was dried with anhydrous sodium sulfate, the residue that was obtained upon removal of the solvent by evaporation was purified by silica gel column chromatography (hexane/ethyl acetate), and the title compound (110 mg) was obtained as a colorless oily matter.

$^1$H-NMR (CDCl$_3$) δ: 2.84 (s, 3H), 3.12 (dd, J=14.4 and 8.0 Hz, 1H), 3.21 (dd, J=14.4 and 4.4 Hz, 1H), 3.22 (s, 3H), 4.43 (dd, J=8.0 and 4.4 Hz, 1H), 7.00–7.38 (m, 6H)

PREPARATION EXAMPLE 74

5-Acetylthiophene-2-sulfonic acid[2-(4-fluorophenyl)-2-methoxyethyl]-methyl-amide From 5-bromothiophene-2-sulfonic acid [2-(4-fluorophenyl)-2-methoxyethyl]-methyl-amide (the compound of Preparation Example 73) (110 mg), the title compound (86 mg) was obtained as a reddish-brown oily substance, in the same way as Preparation Example 67.

$^1$H-NMR (CDCl$_3$) δ: 2.57 (s, 3H), 2.88 (s, 3H), 3.14 (dd, J=14.8 and 8.0 Hz, 1H), 3.21 (s, 3H), 3.25 (dd, J=14.8 and 4.4 Hz, 1H), 4.43 (dd, J=8.0 and 4.4 Hz, 1H), 6.99–7.12 (m, 2H), 7.21–7.44 (m, 2H), 7.49 (d, J=4.0 Hz, 1H), 7.60 (d, J=4.0 Hz, 1H)

PREPARATION EXAMPLE 75

5-Bromothiophene-2-sulfonic acid [2-fluoro-2-(4-fluorophenyl)ethyl]-methyl-amide To a solution of 5-bromothiophene-2-sulfonic acid [2-(4-fluorophenyl)-2-hydroxyethyl]-methyl-amide (the compound of Preparation Example 71) (210 mg) in dichloromethane (2 mL) was added dropwise (diethylamino)sulfur trifluoride (DAST) (0.1 mL) at −70° C., After gradually warming slowly to 0° C. over 1.5 hours, an aqueous solution of saturated sodium bicarbonate was added, and the solution was extracted with ethyl acetate. After the organic layer was washed with saturated sodium chloride water and was dried with anhydrous sodium sulfate, the residue that was obtained upon removing the solvent by evaporation was purified by silica gel column chromatography (hexane/ethyl acetate), and the title compound (169 mg) was obtained as a pale yellow oily substance.

$^1$H-NMR (CDCl$_3$) δ: 2.92 (s, 3H), 3.30 (ddd, J=14.8, 14.8 and 8.4 Hz, 1H), 3.59 (ddd, J=34.4, 14.8 and 3.6 Hz, 1H), 5.68 (ddd, J=48.0, 8.4 and 3.6 Hz, 1H), 7.00–7.42 (m, 6H)

PREPARATION EXAMPLE 76

5-Acetylthiophene-2-sulfonic acid [2-fluoro-2-(4-fluorophenyl)ethyl]-methyl-amide From 5-bromothiophene-2-sulfonic acid [2-fluoro-2-(4-fluorophenyl)ethyl]-methyl-amide (the compound of Preparation Example 75) (168 mg), the title compound (116 mg) was obtained as a yellow oily substance, in the same way as Preparation Example 67.

$^1$H-NMR (CDCl$_3$) δ: 2.58 (s, 3H), 2.95 (s, 3H), 3.33 (ddd, J=14.8, 14.8 and 8.4 Hz, 1H), 3.53 (ddd, J=30.0, 14.8 and 4.8 Hz, 1H), 5.68 (ddd, J=48.0, 8.4 and 4.8 Hz, 1H), 7.10 (t, J=8.4 Hz, 2H), 7.33 (dd, J=8.4 and 5.2 Hz, 2H), 7.21–7.44 (m, 2H), 7.52 (d, J=4.0 Hz, 1H), 7.62 (d, J=4.0 Hz, 1H)

PREPARATION EXAMPLE 77

5-Acetylthiophene-2-sulfonic acid cyclopropyl-[2-(4-fluorophenyl)ethyl]-amide

To a suspension of aluminum lithium hydride (0.86 g) in tetrahydrofuran (46 mL) was slowly added dropwise N-cyclopropyl-2-(4-fluorophenyl)acetamide (the compound of Preparation Example 22) (2.17 g) on an iceth. After steirring at room temperature for 8.5 hours, water (0.85 mL), an aqueous solution of 5N sodium hydroxide (0.85 mL) and water (2.5 mL) were poured sequentially, and the solution was stirred at room temperature for 15 hours. The resulting insoluble matter was removed by filtration, the residue that was obtained upon removing the solvent by evaporation was purified by silica gel column chromatography (dichloromethane/methanol), and a crude purifcation product (424 mg) of cyclopropyl-[2-(4-fluorophenyl)ethyl]amine (pale yellow solids) was obtained. From 5-bromothiophene-2-sulfonyl chloride (243 mg) and the above-mentioned amine (354 mg), the title compound (85 mg) was obtained as a colorless oily matter in two steps, which were the same as Preparation Example 41 and Preparation Example 67.

$^1$H-NMR (CDCl$_3$) δ: 0.63–0.84 (m, 4H), 2.10–2.23 (m, 1H), 2.59 (s, 3H), 2.92 (t, J=8.0 Hz, 2H), 3.40 (t, J=8.0 Hz, 2H), 6.85–7.20 (m, 4H), 7.52–7.63 (m, 2H)

PREPARATION EXAMPLE 78

2,5-Dichlorothiophene-3-sulfonic acid [2-(4-fluorophenyl)-ethyl]-methyl-amide

From 2,5-dichlorothiophene-3-sulfonyl chloride (755 mg) and [2-(4-fluorophenyl)ethyl]methylamine (the compound of Preparation Example 14) (510 mg), the title compound (1.14 g) was obtained as a colorless oily matter, in the same way as Preparation Example 41.

$^1$H-NMR (CDCl$_3$) δ: 2.80–2.97 (m, 2H), 2.87 (s, 3H), 3.35–3.48 (m, 2H), 6.92–7.05 (m, 2H), 7.01 (s, 1H), 7.10–7.22 (m, 2H)

PREPARATION EXAMPLE 79

5-Chlorothiophene-3-sulfonic acid [2-(4-fluorophenyl)ethyl]-methyl-amide

To a solution of 2,5-dichlorothiophene-3-sulfonic acid [2-(4-fluorophenyl)ethyl]-methyl-amide (1.14 g) in tetrahydrofuran (10 mL) was added dropwise a solution of 1.59M n-butyl lithium-hexane (2.3 mL) on an ice bath. After stirring for 30 minutes, an aqueous solution of saturated ammonium chloride was poured. After diluting with water, the solution was extracted with ethyl acetate. After the organic layer was washed with saturated sodium chloride water, and was dried with anhydrous sodium sulfate. The residue that was obtained upon removing the solvent by evaporation was purified by silica gel column chromatography (hexane/ethyl acetate), and the title compound (pale yellow oily substance) (939 mg) was obtained (contains impurities).

$^1$H-NMR (CDCl$_3$) δ: 2.77 (s, 3H), 2.81–2.97 (m, 2H), 3.27 (t, J=8.0 Hz, 2H), 6.90–7.07 (m, 3H), 7.09–7.20 (m, 2H), 7.65 (d, J=1.6 Hz, 1H)

PREPARATION EXAMPLE 80

5-Acetylthiophene-3-sulfonic acid [2-(4-fluorophenyl)ethyl]-methyl-amide

A solution of 5-chlorothiophene-3-sulfonic acid [2-(4-fluorophenyl)ethyl]-methyl-amide (345 mg), (1-ethoxyvinyl)-tributyltin (448 mg), cesium fluoride (346 mg), tris-hydroxymethyl-aminomethanedibenzylidene acetone-dipalladium(16 mg) and trit-butylphosphine (1.3 mg) in 1,4-dioxane (4 ml) was heated at 100° C. for 4 hours. After the reaction solution was cooled to room temperature, the solution was diluted with ethyl acetate, the resulting insoluble matter was removed by filtration, and washed with ethyl acetate. The filtrate was evaporated in vacuo and crude enol ether was obtained. Enol ether was dissolved in tetrahydrofuran (3 mL)-1N hydrochloric acid (3 mL), and the solution was stirred at room temperature for 30 minutes. After the solution was diluted with water, the solution was extracted with ethyl acetate, and washed with saturated sodium chloride water. After drying with anhydrous sodium sulfate, the residue that was obtained upon removing the solvent by evaporation was purified by silica gel column chromatography (hexane/ethyl acetate), and the title compound (154 mg) was obtained as a yellow oily substance.

$^1$H-NMR (CDCl$_3$) δ: 2.57 (s, 3H), 2.80 (s, 3H), 2.82–2.98 (m, 2H), 3.29 (t, J=8.0 Hz, 2H), 6.90–7.22 (m, 4H), 7.72 (t, J=0.8 Hz, 1H), 8.07 (t, J=0.8 Hz, 1H)

PREPARATION EXAMPLE 81

2,5-Dichlorothiophene-3-sulfonic acid methyl-amide

From 2,5-dichlorothiophene-3-sulfonyl chloride (3.3 g), the title compound (3.3 g) was obtained as a colorless oily matter, in the same way as Preparation Example 69.

$^1$H-NMR (CDCl$_3$) δ: 2.76 (d, J=5.2 Hz, 3H), 4.56–4.71 (m, 1H), 7.14 (s, 1H)

PREPARATION EXAMPLE 82

5-Chlorothiophene-3-sulfonic acid methyl-amide

From 2,5-dichlorothiophene-3-sulfonic acid-methyl-amide (3.3 g), the title compound (2.58 g) was obtained as a colorless oily matter, in the same way as Preparation Example 79. However, 2.2 equivalents of n-butyl lithium was used.

$^1$H-NMR (CDCl$_3$) δ: 2.73 (d, J=5.6 Hz, 3H), 4.30–4.50 (m, 1H), 7.16 (d, J=2.0 Hz, 1H), 7.74 (d, J=2.0 Hz, 1H)

PREPARATION EXAMPLE 83

5-Chlorothiophene-3-sulfonic acid [2-(4-fluorophenyl)-2-hydroxyethyl]-methyl-amide From 5-chlorothiophene-3-sulfonic acid-methyl-amide (2.58 g), the title compound (1.33 g) was obtained as a colorless oily matter in two steps, which were the same as Preparation Example 70 and Preparation Example 71.

$^1$H-NMR (CDCl$_3$) δ: 2.72 (d, J=2.8 Hz, 1H), 2.85 (s, 3H), 3.11 (dd, J=14.0 and 3.6 Hz, 1H), 3.27 (dd, J=14.0 and 8.4 Hz), 4.89–5.02 (m, 1H), 6.97–7.12 (m, 3H), 7.36 (dd, J=8.8 and 5.6 Hz, 2H), 7.70 (d, J=1.6 Hz, 1H)

PREPARATION EXAMPLE 84

5-Acetylthiophene-3-sulfonic acid [2-(4-fluorophenyl)-2-hydroxyethyl]-methyl-amide From 5-chlorothiophene-3-sulfonic acid [2-(4-fluorophenyl)-2-hydroxyethyl]-methyl-amide (150 mg), the title compound (58 mg) was obtained as a colorless oily matter, in the same way as Preparation Example 80.

$^1$H-NMR (CDCl$_3$) δ: 2.57 (s, 3H), 2.69 (d, J=2.4 Hz, 1H), 2.87 (s, 3H), 3.14 (dd, J=14.0 and 3.6 Hz, 1H), 3.31 (dd, J=14.0 and 8.4 Hz, 1H), 4.90–5.02 (m, 1H), 6.99–7.13 (m, 2H), 7.30–7.46 (m, 2H), 7.78 (d, J=1.2 Hz, 1H), 8.13 (d, J=1.2 Hz, 1H)

PREPARATION EXAMPLE 85

5-Vinylthiophene-3-sulfonic acid [2-(4-fluorophenyl)ethyl]-methyl-amide

A solution of 5-chlorothiophene-3-sulfonic acid [2-(4-fluorophenyl)ethyl]amide (739 mg), vinyltributyltin (772 mg), cesium fluoride (740 mg), and bis(trit-butylphosphine)palladium (34 mg) in 1,4-dioxane (9 mL) was heated at 100° C. for 16 hours. After the reaction solution was cooled to room temperature, this solution was diluted with ethyl acetate, the resulting insoluble matter was removed by Celite filtration, and washed with ethyl. The residue resulting from the removal of the solvent by evaporation was purified by silica gel column chromatography (hexane/ethyl acetate), and the title compound (328 mg) was obtained as a yellow oily substance.

$^1$H-NMR (CDCl$_3$) δ: 2.77 (s, 3H), 2.85 (t, J=8.0 Hz, 2H), 3.26 (t, J=8.0 Hz, 2H), 5.29 (d, J=10.8 Hz, 1H), 5.63 (d, J=17.2 Hz, 1H), 6.72 (dd, J=17.2 and 10.8 Hz, 1H), 6.92–7.02 (m, 2H), 7.04 (s, 1H), 7.09–7.20 (m, 2H), 7.69 (s, 1H)

PREPARATION EXAMPLE 86

5-Formylthiophene-3-sulfonic acid [2-(4-fluorophenyl)ethyl]-methyl-amide

To a solution of 5-vinylthiophene-3-sulfonic acid[2-(4-fluorophenyl)ethyl]-methyl-amide (328 mg) in dichloromethane (2 mL) was added sodium meta periodate (863 mg) and ruthenium trichloride monohydrate (5 mg) at room temperature. After stirring for 2 hours, this solution was diluted with water and ethyl acetate, and Celite filtration was carried out. The organic layer was separated, after drying with anhydrous sodium sulfate, the residue that was obtained upon removing the solvent by evaporation were purified by silica gel column chromatography (hexane/ethyl acetate) and the title compound (138 mg) was obtained as a yellow oily substance.

$^1$H-NMR (CDCl$_3$) δ: 2.82 (s, 3H), 2.89 (t, J=8.0 Hz, 2H), 3.32 (t, J=8.0 Hz, 2H), 7.00 (t, J=8.4 Hz, 2H), 7.16 (dd, J=8.4 and 5.6 Hz, 2H), 7.80 (s, 1H), 8.18 (s, 1H), 9.90 (s, 1H)

PREPARATION EXAMPLE 87

5-(1-Hydroxy-2-methylpropyl)thiophene-3-sulfonic acid [2-(4-fluorophenyl)ethyl]-methyl-amide To a solution of 5-formylthiophene-3-sulfonic acid [2-(4-fluorophenyl)ethyl]-methyl-amide (138 mg) in tetrahydrofuran (2 mL) was added dropwise a solution (0.25 mL) of 2.0M isopropyl magnesium bromide-tetrahydrofuran on an ice bath. After stirring for 1 hour, an aqueous solution of saturated ammonium chloride was added, and the solution was extracted with ethyl acetate. After drying the organic layer with anhydrous sodium sulfate, the residue that was obtained upon removing the solvent by evaporation was purified by silica gel column chromatography (hexane/ethyl acetate) and the title compound (57 mg) was obtained as a yellow oily substance.

$^1$H-NMR (CDCl$_3$) δ: 0.90 (d, J=6.8 Hz, 3H), 0.99 (d, J=6.8 Hz, 3H), 2.11 (d, J=4.4 Hz, 1H), 2.75 (s, 3H), 2.79–2.93 (m, 2H), 3.15–3.34 (m, 2H), 4.59–4.72 (m, 1H), 6.98 (t, J=8.4 Hz, 2H), 7.05 (s, 1H), 7.15 (dd, J=8.4 and 5.6 Hz, 2H), 7.79 (s, 1H)

PREPARATION EXAMPLE 88

5-Isobutyrylthiophene-3-sulfonic acid[2-(4-fluorophenyl)ethyl]-methyl-amide

To a solution of 5-(1-hydroxy-2-methylpropyl)thiophene-3-sulfonic acid [2-(4-fluorophenyl)ethyl]-methyl-amide in dichloromethane (2 mL) was added 4 Å molecular sieves (60 mg), N-methyl morpholin-N-oxide (27 mg) and tetrapropyl ammonium ruthenium tetroxide; (n-Pr)$_4$NRuO$_4$ (5 mg). After stirring at room temperature for 1.5 hours, the reaction solution was directly adsorbed onto silica gel, purification by silica gel column chromatography (hexane/ethyl acetate) was carried out, and the title compound (30 mg) was obtained as a yellow oily substance.

$^1$H-NMR (CDCl$_3$) δ: 1.60 (d, J=6.4 Hz, 6H), 2.78 (s, 3H), 2.87 (t, J=8.0 Hz, 2H), 3.20–3.43 (m, 3H), 6.99 (t, J=8.4 Hz, 2H), 7.17 (dd, J=8.4 and 5.6 Hz, 2H), 7.75 (d, J=1.2 Hz, 1H), 8.06 (d, J=1.2 Hz, 1H)

PREPARATION EXAMPLE 89

5-Chlorothiophene-3-sulfonic acid[2-(4-fluorophenyl)-2-methoxymethoxyethyl]-methyl-amide To a solution of 5-chlorothiophene-3-sulfonic acid [2-(4-fluorophenyl)-2-hydroxyethyl]-methyl-amide (the compound of Preparation Example 83) (1.33 g) in dichloromethane (7 mL) was added dropwise diisopropylethylamine (1.2 mL) and 0.34 mL of chloromethyl methyl ether (0.34 mL) on an ice bath. Sodium iodide (25 mg) was added, and the solution was stirred at room temperature for 4 hours at room temperature. In addition, diisopropylethylamine (1.2 mL) and chloromethyl methyl ether (0.34 mL) were added to this solution, and the solution was further stirred for 17 hours. After the solution was diluted with ethyl acetate, and was washed with water and saturated sodium chloride water. After drying the organic layer with anhydrous sodium sulfate, the residue that was obtained upon removing the solvent by evaporation was purified by silica gel column chromatography (hexane/ethyl acetate), and the title compound (646 mg) was obtained as a colorless solid. Recovery of raw materials was 557 mg.

$^1$H-NMR (CDCl$_3$) δ: 2.88 (s, 3H), 3.22 (dd, J=14.4 and 4.4 Hz, 1H), 3.28 (dd, J=14.4 and 8.4 Hz), 3.35 (s, 3H), 4.53 (d, J=17.2 Hz, 1H), 4.54 (d, J=17.2 Hz, 1H), 4.85 (dd, J=8.4 and 4.4 Hz, 1H), 7.00–7.14 (m, 3H), 7.23–7.40 (m, 2H), 7.66 (d, J=1.2 Hz, 1H)

PREPARATION EXAMPLE 90

5-Formylthiophene-3-sulfonic acid[2-(4-fluorophenyl)-2-methoxymethoxyethyl]-methyl-amide From 5-chlorothiophene-3-sulfonic acid [2-(4-fluorophenyl)-2-methoxymethoxyethyl]-methyl-amide (646 mg), two steps were carried out, which were the same as Preparation Example 85 and Preparation Example 86, and the title compound (243 mg) was obtained as a yellow oily substance.

$^1$H-NMR (CDCl$_3$) δ: 2.91 (s, 3H), 3.25 (dd, J=14.4 and 4.4 Hz, 1H), 3.34 (dd, J=14.4 and 8.4 Hz, 1H), 3.35 (s, 3H), 4.52 (d, J=17.2 Hz, 1H), 4.54 (d, J=17.2 Hz, 1H), 4.88 (dd, J=8.4 and 4.4 Hz, 1H), 7.06 (t, J=8.4 Hz, 2H), 7.32 (dd, J=8.4 and 5.2 Hz, 2H), 7.86 (d, J=1.2 Hz, 1H), 8.20 (d, J=1.2 Hz, 1H), 9.91 (s, 1H)

PREPARATION EXAMPLE 91

5-Isobutyrylthiophene-3-sulfonic acid[2-(4-fluorophenyl)-2-hydroxyethyl]-methyl-amide The compound that was obtained from 5-formylthiophene-3-sulfonic acid [2-(4-fluorophenyl)-2-methoxymethoxyethyl]-methyl-amide (128 mg) by carrying out two steps, which were the same as Preparation Example 87 and Preparation Example 88, was heated at 60° C. for 2 hours in a mixed solvent of tetrahydrofuran (2 mL) and 5N hydrochloric acid (1 mL). After the reaction solution was cooled to room temperature, the solution was diluted with water and extracted with ethyl acetate, then washed with saturated sodium chloride water. After drying with anhydrous sodium sulfate, the solvent was removed by evaporation, and the title compound was obtained. This was used in the following reaction without purification.

$^1$H-NMR (CDCl$_3$) δ: 1.27 (d, J=6.8 Hz, 6H), 2.69 (d, J=2.8 Hz, 1H), 2.84 (s, 3H), 3.14 (dd, J=14.4 and 3.6 Hz, 1H), 3.34 (dd, J=114.4 and 7.2 Hz, 1H), 3.65–3.77 (m, 1H), 4.89–5.06 (m, 1H), 6.95–7.13 (m, 2H), 7.23–7.48 (m, 2H), 7.80 (d, J=1.2 Hz, 1H), 8.12 (d, J=1.2 Hz, 1H)

PREPARATION EXAMPLE 92

5-(2-Bromo acetyl)thiophene-3-sulfonic acid [2-(4-fluorophenyl)ethyl]-methyl-amide From 5-acetylthiophene-3-sulfonic acid [2-(4-fluorophenyl)ethyl]-methyl-amide (the compound of Preparation Example 80) (310 mg), the title compound (286 mg) was obtained as a yellow oily substance, in the same way as Preparation Example 64.

$^1$H-NMR (CDCl$_3$) δ: 2.80 (s, 3H), 2.83–2.93 (m, 2H), 3.20–3.35 (m, 2H), 4.54 (s, 2H), 6.90–7.30 (m, 4H), 7.84 (s, 1H), 8.14 (s, 1H)

PREPARATION EXAMPLE 93

5-(2-Dimethylamino acetyl)thiophene-3-sulfonic acid [2-(4-fluorophenyl)ethyl]-methyl-amide To a solution (0.6 mL) of 2.0M dimethylamine-tetrahydrofuran diluted with tetrahydrofuran (2 mL), was added dropwise 5-(2-bromoacetyl)thiophene-3-sulfonic acid [2-(4-fluorophenyl)ethyl]-methyl-amide (46 mg) in tetrahydrofuran (1 mL) at room temperature. An aqueous solution of saturated sodium bicarbonate was added, and the solution was extracted with ethyl acetate. After the organic layer was washed with saturated sodium chloride water and dried with anhydrous sodium sulfate, the residuals that were obtained upon removing the solvent by evaporation were purified by silica gel column chromatography (dichloromethane/methanol), and the title compound (16 mg) was obtained as a yellow oily substance.

$^1$H-NMR (CDCl$_3$) δ: 2.37 (s, 6H), 2.80 (s, 3H), 2.88 (t, J=8.0 Hz, 2H), 3.29 (t, J=8.0 Hz, 2H), 3.54 (s, 2H), 7.00 (t, J=8.0 Hz, 2H), 7.17 (dd, J=8.0 and 5.6 Hz, 2H), 8.00 (d, J=0.8 Hz, 1H), 8.05 (d, J=0.8 Hz, 1H)

PREPARATION EXAMPLE 94

5-(2-Acetoxy acetyl)thiophene-3-sulfonic acid [2-(4-fluorophenyl)ethyl]-methyl-amide From 5-(2-bromo acetyl)thiophene-3-sulfonic acid [2-(4-fluorophenyl)ethyl]-methyl-amide (the compound of Preparation Example 92) (286 mg), the title compound (234 mg) was obtained as a yellow oily substance, in the same way as Preparation Example 65.

$^1$H-NMR (CDCl$_3$) δ: 2.11 (s, 3H), 2.69 (s, 3H), 2.71–2.84 (m, 2H), 3.10–3.26 (m, 2H), 5.06 (s, 2H), 6.78–6.94 (m, 2H), 6.98–7.10 (m, 2H), 7.67 (d, J=1.2 Hz, 1H), 8.02 (d, J=0.8 Hz, 1H)

PREPARATION EXAMPLE 95

3-{[2-(4-Fluorophenyl)-2-hydroxy-ethyl]-methyl-sulfamoyl}-thiophene-2-carboxylic acid methyl ester To a solution of 1-(4-fluorophenyl)-2-methylamino-ethanol (8.4 g) and triethylamine (7 mL) in tetrahydrofuran (80 mL) was added 3-chloro sulfonyl-thiophene-2-carboxylic acid methyl ester (10 g) on an ice bath over 20 minutes. The solution was brought back to room temperature and stirred for 1 hour. Ethyl acetate was added to the reaction solution, the resulting salt was removed by filtration, and solvent was evaporated at reduced pressure. The residue was purified by NH-silica gel column chromatography (hexane/ethyl acetate), and a pale yellow oily substance (15.6 g) was obtained.

$^1$H-NMR (CDCl$_3$) δ: 2.98 (s, 3H), 3.08 (d, J=3.2 Hz, 1H), 3.37 (dd, J=14.4 and 3.2 Hz, 1H), 3.55 (dd, J=14.4 and 7.2 Hz, 1H), 3.91 (s, 3H), 4.92–5.01 (m, 1H), 7.00–7.11 (m, 2H), 7.33–7.43 (m, 2H), 7.47–7.51 (m, 2H)

PREPARATION EXAMPLE 96

(3-{[2-(4-Fluorophenyl)-2-hydroxy-ethyl]-methyl-sulfamoyl}-thiophene-2-yl)-carbamic acid t-butyl ester To a mixture solution of 3-{[2-(4-fluorophenyl)-2-hydroxy-ethyl]-methyl-sulfamoyl}-thiophene-2-c arboxylic acid methylester (15 g) in tetrahydrofuran (30 mL) and methanol (30 mL) was added an aqueous solution (25 mL) of 2N sodium hydroxide. After stirring at room temperature for 1 hour, the solution was neutralized with 2N hydrochloric acid, and was extracted with ethyl acetate. After drying the organic layer with anhydrous magnesium sulfate, the solvent was removed by evaporation and a solid (15.2 g) was obtained. t-Butyl alcohol (210 mL), diphenylphosphoryl azide (11 g) and triethylamine (5.6 mL) were added to this solid (12 g). After stirring for 2 hours while heating at 90° C. to 100° C., the reaction solution was evaporated in vacuo, and the residuals were purified by NH silica gel (hexane/ethyl acetate). The solid that solidified from diethyl ether was filtered and collected, and the title compound (9.6 g) was obtained as a colorless solid.

$^1$H-NMR (CDCl$_3$) δ: 1.53 (s, 9H), 2.70 (d, J=2.8 Hz, 1H), 2.82 (s, 3H), 3.13 (dd, J=14.4, 3.6 Hz, 1H), 3.29 (dd, J=14.4, 8.8 Hz, 1H), 3.89–4.95 (m, 1H), 6.78 (dd, J=6.0, 0.8 Hz, 1H), 6.90 (d, J=6.0, Hz, 1H), 7.01–7.08 (m, 2H), 7.32–7.38 (m, 2H), 9.14 (brs, 1H)

PREPARATION EXAMPLE 97

(5-Bromo-3-{[2-(4-fluorophenyl)-2-hydroxy-ethyl]-methyl-sulfamoyl)-thiophene-2-yl)-carbamic acid t-butyl ester To a solution of (3-{[2-(4-fluorophenyl)-2-hydroxy-ethyl]-methyl-sulfamoyl}-thiophene-2-yl) carbamic acid t-butyl ester (the compound of Preparation Example 96) (6 g) in N,N-dimethylformamide (50 mL) was added N-bromosuccinimide (2.6 g) in small amounts on an ice bath. After stirring at room temperature for 1 hour, water was added, the solution was extracted with ethyl acetate. After the organic layer was washed with water, an aqueous solution of sodium bicarbonate and saturated sodium chloride water, and was dried with anhydrous magnesium sulfate. The extract was purified by passing through a column of NH silica gel, and the title compound (6.6 g) was obtained as a colorless candy-like substance.

$^1$H-NMR (CDCl$_3$) δ: 1.52 (s, 9H), 2.63 (d, J=3.2 Hz, 1H), 2.84 (s, 3H), 3.18 (dd, J=14.4, 3.6 Hz, 1H), 3.32 (dd, J=14.4, 8.8 Hz, 1H), 4.90–4.95 (m, 1H), 6.84 (s, 1H), 7.01–7.09 (m, 2H), 7.32–7.38 (m, 2H), 9.16 (brs, 1H)

PREPARATION EXAMPLE 98

(5-Acetyl-3-{[2-(4-fluorophenyl)-2-hydroxy-ethyl]-methyl-sulfamoyl}-thiophene-2-yl)-carbamic acid t-butyl ester (5-Bromo-3-{[2-(4-fluorophenyl)-2-hydroxy-ethyl]-methyl-sulfamoyl}-thiophene-2-yl)carbamic acid tert-butyl ester (the compound of Preparation Example 97) (5.5 g), tributyl(1-ethoxyvinyl)tin (6.7 g), cesium fluoride (5.3 g) and tetrakis(triphenylphosphine)palladium (0.73 g) were stirred in 1,4-dioxane (50 mL) at 100° C. for 2 hours. After ethyl acetate was added and insoluble matter was removed by filtration, 2N hydrochloric acid was added, and the solution was stirred for 10 minutes. After washing the organic layer with water, an aqueous solution of sodium bicarbonate and saturated sodium chloride water, and was dried with anhydrous magnesium sulfate. The residue resulting from the removal of the solvent by evaporation was purified by silica gel column chromatography (hexane/ethyl acetate), and the title compound (3.2 g9 was obtained as a colorless solid.

$^1$H-NMR (CDCl$_3$) δ: 1.53 (s, 9H), 2.47 (s, 3H), 2.56 (d, J=2.8 Hz, 1H), 2.85 (s, 3H), 3.21 (dd, J=14.4, 3.6 Hz, 1H), 3.37 (dd, J=14.4, 8.8 Hz, 1H), 4.92–4.97 (m, 1H), 7.03–7.09 (m, 2H), 7.32–7.38 (m, 2H), 7.52 (s, J=5.6, 1H), 9.34 (brs, 1H)

PREPARATION EXAMPLE 99

5-Acetyl-2-amino-thiophene-3-sulfonic acid [2-(4-fluorophenyl)-2-hydroxy-ethyl]-methyl-amide (5-Acetyl-3-{[2-(4-fluorophenyl)-2-hydroxy-ethyl]-methyl-sulfamo yl}-thiophene-2-yl)carbamic acid t-butyl ester (1.3 g) was added to trifluoroacetic acid (10 mL). After stirred for 10 minutes at room temperature, water was added to the residue that was evaporated in vacuo, and the pH of saturated sodium bicarbonate was adjusted to 11. The solution was extracted with ethyl acetate, and the organic layer was washed with saturated sodium chloride water, whereafter this solution was dried with anhydrous magnesium sulfate. The solid obtained by passing through a short column of NH-silica gel and evaporating the solvent at reduced pressure was washed with ethyl acetate, and the title compound (713 mg) was obtained as an ocher solid.

PREPARATION EXAMPLE 100

5-Acetyl-2-methylamino-thiophene-3-sulfonic acid [2-(4-fluorophenyl)-2-hydroxy-ethyl]-methyl-amide a)(5-Bromo-3-{[2-(4-fluorophenyl)-2-hydroxy-ethyl]-methyl-sulfamoyl}-thiophene-2-yl)-methyl-carbamic acid t-butyl ester To a solution of (5-bromo-3-{[2-(4-fluorophenyl)-2-hydroxy-ethyl]-methyl-sulfamoyl}-thiophene-2-yl)-carbamic acid t-butyl ester (the compound of Preparation Example 97) (1 g) and potassium carbonate (278 mg) in N,N-dimethylformamide was added methyl iodide (0.75 mL). After stirred for 2 hours, ethyl acetate was added, and insoluble matter was removed by filtration. The residue resulting form evaporating the filtrate in vacuo was purified by silica gel column chromatography (hexane/ethyl acetate), and a colorless oily matter (958 mg) was obtained.

$^1$H-NMR (CDCl$_3$) δ: 1.40 (s, 9H), 2.94 (s, 3H), 3.18–3.24 (m, 1H), 3.21 (s, 3H), 3.32–3.42 (br, 1H), 4.78–4.89 (br, 1H), 6.99–7.06 (m, 2H), 7.11 (s, 1H), 7.30–7.36 (m, 2H)

b) (5-Acetyl-3-([2-(4-fluorophenyl)-2-hydroxy-ethyl]-methyl-sulfamoyl}-thiophene-2-yl)-methyl-carbamic acid t-butyl ester From (5-bromo-3-{[2-(4-fluorophenyl)-2-hydroxy-ethyl]-methyl-sulfamoyl}-thiophene-2-yl)-methyl-carbamic acid t-butyl ester (946 mg) and tributyl-(1-ethoxy-vinyl)tin (1.31 g), a colorless amorphous matter (600 mg) was obtained, in the same way as Preparation Example 98.

$^1$H-NMR (CDCl$_3$) δ: 1.40 (s, 9H), 2.54 (s, 3H), 2.97 (s, 3H), 3.21–3.27 (m, 1H), 3.26 (s, 3H), 3.33–3.47 (br, 1H), 4.82–4.90 (br, 1H), 6.99–7.07 (m, 2H), 7.30–7.36 (m, 2H), 7.73 (s, 1H)

c) Title Compound (5-Acetyl-3-{[2-(4-fluorophenyl)-2-hydroxy-ethyl]-methyl-sulfamoyl}-thiophene-2-yl)-methyl-carbamic acid t-butyl ester (600 mg) was treated with trifluoroacetic acid, and the title compound (438 mg) was obtained as a colorless solid, in the same way as Preparation Example 98.

$^1$H-NMR (CDCl$_3$) δ: 2.41 (s, 3H), 2.74 (d, J=3.2 Hz, 1H), 2.82 (s, 3H), 3.01 (d, J=4.8 Hz, 3H), 3.16 (dd, J=14.2, 3.4 Hz, 1H), 3.38 (dd, J=14.2, 8.6 Hz, 1H), 4.89–4.95 (m, 1H), 7.04–7.10 (m, 2H), 7.34–7.39 (m, 2H), 7.47 (s, 1H)

PREPARATION EXAMPLE 101

N-(5-Acetyl-3-{[2-(4-fluorophenyl)-2-hydroxyethyl]-methyl-sulfamoyl}-thiophene-2-yl)-propionic acid amide To a solution of 5-acetyl-2-amino-thiophene-3-sulfonic acid [2-(4-fluorophenyl)-2-hydroxy-ethyl]-methyl-amide (the compound of Preparation Example 99) (150 mg) and triethylamine (557 μL) in tetrahydrofuran was added propionic acid chloride (195 μL) in small amounts. After stirring at room temperature for 2 hours, triethylamine (557 μL) and propionic acid chloride (195 μL) were further added, and the solution was stirred for 30 minutes. Water was added to the reaction solution, the solution was extracted with ethyl acetate, and the organic layer was dried with anhydrous magnesium sulfate. The residue resulting from the removal of the solvent by evaporation was purified by silica gel column chromatography (hexane/ethyl acetate), and the title compound (75 mg) was obtained as a colorless solid.

$^1$H-NMR (CDCl$_3$) δ: 1.28 (t, J=7.6 Hz, 3H), 2.49 (s, 3H), 2.54 (d, J=2.8 Hz, 1H), 2.55 (q, J=7.6 Hz, 2H), 2.86 (s, 3H), 3.22 (dd, J=14.4, 3.6 Hz, 1H), 3.40 (dd, J=14.4, 8.8 Hz, 1H), 4.91–4.97 (m, 1H), 7.03–7.11 (m, 2H), 7.33–7.38 (m, 2H), 7.56 (s, 1H), 10.25 (brs, 1H)

PREPARATION EXAMPLE 102

N-(5-Acetyl-3-{[2-(4-fluorophenyl)-2-hydroxyethyl]-methyl-sulfamoyl}-thiophene-2-yl)-4-fluorobenzamide To a solution of 5-acetyl-2-amino-thiophene-3-sulfonic acid [2-(4-fluorophenyl)-2-hydroxy-ethyl]-methyl-amide (the compound of Preparation Example 99) (120 mg) in ethyl acetate-tetrahydrofuran (4:1) (30 mL) was added an aqueous solution (10 mL) of 2N sodium hydroxide. After stirring vigorously at room temperature, 4-fluorobenzylchloride (51 mg) was added. After 30 minutes, an aqueous solution (10 mL) of 2N sodium hydroxide, then 4-fluorobenzoyl-chloride (100 mg) were added, and the solution was stirred for 30 minutes. In addition, an aqueous solution (10 mL) of 2N sodium hydroxide, then 4-fluorobenzoyl-chloride (100 mg) were added. After stirring for 30 minutes, extraction was carried out by adding ethyl acetate, and the organic layer was dried with anhydrous magnesium sulfate. Purification was carried out by purification with silica gel column chromatography (hexane/ethyl acetate), and the title compound (59 mg) was obtained as yellow solids.

$^1$H-NMR (CDCl$_3$) δ: 2.51 (d, J=3.2 Hz, 1H), 2.52 (s, 3H), 2.91 (s, 3H), 3.27 (dd, J=14.4, 3.6 Hz, 1H), 3.43 (dd, J=14.4, 8.4 Hz, 1H), 4.40–4.99 (m, 1H), 6.99–7.07 (m, 2H), 7.21–7.27 (m, 2H), 7.29–7.36 (m, 2H), 7.61 (s, 1H), 7.96–8.02 (m, 2H), 11.14 (brs, 1H)

PREPARATION EXAMPLE 103

Acetic acid 2-(5-t-butoxycarbonyl imino-4-{[2-(4-fluorophenyl)-2-t-butyldimethylsilvioxyethyl]-methyl-sulfamoyl}thiophene-2-yl)-2-oxoethyl ester From (5-acetyl-3-{[2-(4-fluorophenyl)-2-hydroxyethyl]methylsulfamoyl}-thiophene-2-yl) carbamic acid t-butyl ester (the compound of Preparation Example 97) (200 mg), two steps were carried out, which were the same as Preparation Example 92 and Preparation Example 94, and the title compound (106 mg) was obtained as a brown oily substance. Note that in the first step, 3 equivalents of an excess t-butyldimethylsilyltrifluoromethane sulfonate were used, and a protection of hydroxyl groups was carried out simultaneously.

$^1$H-NMR (CDCl$_3$) δ: −0.10 (s, 3H), 0.10 (s, 3H), 0.89 (s, 9H), 1.55 (s, 9H), 2.19 (s, 3H), 2.78 (s, 3H), 3.08–3.20 (m, 2H), 4.86–4.95 (m, 1H), 5.08 (s, 2H), 7.04 (t, J=8.4 Hz, 2H), 7.32 (dd, J=8.4 and 5.2 Hz, 2H), 7.52 (s, 1H), 9.37 (br s, 1H)

PREPARATION EXAMPLE 104

(3-{[2-(4-Fluorophenyl)ethyl]methylsulfamoyl}-5-isobutyryl-thiophene-2-yl) carbamic acid t-butyl ester From (5-bromo-3-{[2-(4-fluorophenyl)ethyl]methylsulfamoyl}thiophene-2-yl)-carbamic acid t-butyl ester (the compound of Preparation Example 98) (980 mg), 4 steps were carried out, which were the same as Preparation Example 85, 86, 87 and 88, and the title compound (123 mg) was obtained as an orange oily substance. However, in the step that was the same as Preparation Example 85, (tetrakistriphenylphosphine)palladium was used as the palladium catalyst.

$^1$H-NMR (CDCl$_3$) δ: 1.20 (d, J=6.8 Hz, 6H), 1.54 (s, 9H), 2.78 (s, 3H), 2.86 (t, J=7.2 Hz, 2H), 3.13–3.29 (m, 1H), 3.34 (t, J=7.2 Hz, 2H), 6.99 (t, J=8.4 Hz, 2H), 7.14 (dd, J=8.4 and 5.2 Hz, 2H), 7.49 (s, 1H), 9.29 (br s, 1H)

PREPARATION EXAMPLE 105

3-{[2-(4-Fluorophenyl)-2-methoxymethoxyethyl]methylsulfamoyl}-thiophene-2-carboxylic acid methyl ester From 3-{[2-(4-fluorophenyl)-2-hydroxyethyl]methylsulfamoyl}thiophene-2-carboxylic acid methyl ester (the compound of Preparation Example 95) (5.1 g), the title compound (4.91 g) was obtained as a pale yellow oily substance, in the same way as Preparation Example 89.

$^1$H-NMR (CDCl$_3$) δ: 2.99 (s, 3H), 3.36 (s, 3H), 3.47–3.57 (m, 2H), 3.88 (s, 3H), 4.49–4.59 (m, 2H), 4.86–4.93 (m, 1H), 7.00–7.08 (m, 2H), 7.28–7.37 (m, 2H), 7.41–7.49 (m, 2H)

PREPARATION EXAMPLE 106

(3-{[2-(4-fluorophenyl)-2-methoxymethoxyethyl]methylsulfamoyl}-thiophene-2-yl)carbamic acid t-butyl ester From 3-{[2-(4-fluorophenyl)-2-methoxymethoxyethyl]methylsulfamoyl}-thiophene-2-carboxylic acid methylester (4.91 g), the title compound (5.36 g) was obtained as a colorless oily matter, in the same way as Preparation Example 96.

$^1$H-NMR (CDCl$_3$) δ: 1.52 (s, 9H), 2.84 (s, 3H), 3.22 (dd, J=14.4 and 4.4 Hz, 1H), 3.33 (dd, J=14.4 and 8.4 Hz, 1H), 3.34 (s, 3H), 4.49–4.57 (m, 2H), 4.84 (dd, J=8.4 and 4.4 Hz, 1H), 6.77 (d, J=5.6 Hz, 1H), 6.89 (d, J=5.6 Hz, 1H), 6.99–7.12 (m, 2H), 7.23–7.34 (m, 2H), 9.16 (br s, 1H)

PREPARATION EXAMPLE 107

(3-{[2-(4-fluorophenyl)-2-methoxymethoxyethyl] methylsulfamoyl}-5-formylthiophene-2-yl)carbamic acid t-butyl ester From (3-{[2-(4-fluorophenyl)-2-methoxymethoxyethyl] methylsulfamoyl}-thiophene-2-yl)carbamic acid t-butyl ester (5.36 mg), the same bromine group introduction as Preparation Example 97 and the same vinyl group introduction and oxidative cleavage reaction as Preparation Example 85 and 86 were carried out, and the title compound (1.34 g) was obtained as a brown oily substance. Note that in the step that was the same as Preparation Example 85, (tetrakistriphenylphosphine)palladium was used as the palladium catalyst.

$^1$H-NMR (CDCl$_3$) δ: 1.52 (s, 9H), 2.89 (s, 3H), 3.29 (dd, J=14.4 and 4.4 Hz, 1H), 3.32 (s, 3H), 3.42 (dd, J=14.4 and 8.4 Hz, 1H), 4.47–4.57 (m, 2H), 4.86 (dd, J=8.4 and 4.4 Hz, 1H), 7.06 (t, J=8.4 Hz, 2H), 7.31 (dd, J=8.4 and 5.6 Hz, 2H), 7.56 (s, 1H), 9.37 (br s, 1H), 9.74 (s, 1H)

PREPARATION EXAMPLE 108

(3-{[2-(4-Fluorophenyl)-2-methoxymethoxyethyl] methylsulfamoyl}-5-isobutyrylthiophene-2-yl)carbamic acid t-butyl ester Using (3-{[2-(4-fluorophenyl)-2-methoxymethoxyethyl] methylsulfamoyl}-5-formylthiophene-2-yl)carbamic acid t-butyl ester (200 mg), isopropyl group was introduced in the same way as Preparation Example 87, and a crude alcohol was obtained. Dess-Martin reagent (204 mg) was added to a solution of this compound in dichloromethane (2 mL). After stirring for 1 hour, an aqueous solution of saturated sodium bicarbonate and an aqueous solution of sodium thiosulfate were added, and the solution was extracted with ethyl acetate. After washing with saturated sodium chloride water, the solution was dried with anhydrous sodium sulfate. The solution was filtered through a small amount of silica gel, and the title compound (180 mg) was obtained as an orange oily substance.

$^1$H-NMR (CDCl$_3$) δ: 1.20 (d, J=7.2 Hz, 6H), 1.54 (s, 9H), 2.87 (s, 3H), 3.20–3.30 (m, 2H), 3.33 (s, 3H), 3.41 (dd, J=14.4 and 8.4 Hz, 1H), 4.45–4.60 (m, 2H), 4.85 (dd, J=8.4 and 4.4 Hz, 1H), 7.05 (t, J=8.8 Hz, 2H), 7.30 (dd, J=8.8 and 5.6 Hz, 2H), 7.53 (s, 1H), 9.30 (br s, 1H)

PREPARATION EXAMPLE 109

(3-{[2-(4-Fluorophenyl)-2-methoxymethoxyethyl] methylsulfamoyl}-5-phenyl acetylthiophene-2-yl) carbamic acid t-butyl ester From (3-{[2-(4-fluorophenyl)-2-methoxymethoxyethyl] methylsulfamoyl}-5-formylthiophene-2-yl)carbamic acid t-butyl ester (160 mg) and 0.35 mL of a solution (0.35 mL) of 2.0M benzyl magnesium chloride-tetrahydrofuran, [3-{[2-(4-fluorophenyl)-2-methoxymethoxyethyl]methylsulfamoyl}-5-(1-hydroxy-2-phenylethyl)thiophene-2-yl]carbamic acid t-butyl ester was obtained, in the same way as Preparation Example 87. Thereafter, oxidation reaction was carried out, which was the same as Preparation Example 108, and the title compound (47 mg) was obtained as an orange oily substance.

$^1$H-NMR (CDCl$_3$) δ: 1.53 (s, 9H), 2.81 (s, 3H), 3.17 (dd, J=14.4 and 4.0 Hz, 1H), 3.29 (s, 3H), 3.31–3.42 (m, 1H), 4.07 (s, 2H), 4.42–4.59 (m, 2H), 4.82 (dd, J=8.4 and 4.0 Hz, 1H), 7.06 (t, J=8.8 Hz, 2H), 7.12–7.40 (m, 7H), 7.52 (s, 1H), 9.28 (brs, 1H)

PREPARATION EXAMPLE 110

(3-{[2-(4-Fluorophenyl)-ethyl]-methyl-sulfamoyl}-thiophene-2-yl)-carbamic acid t-butyl ester a) 3-[2-(4-Fluorophenyl)-ethylsulfamoyl]-thiophene-2-carboxylic acid methyl ester To a solution of 74-fluorophenethylamine (7.3 g) in pyridine (200 mL) was added 3-chloro sulfonyl-thiophene-2-carboxylic acid methyl ester (12 g) was added on an ice bath over 20 minutes. After stirring on the ice bath for 1 hour, and at room temperature for 30 minutes, the solvent was evaporated at reduced pressure. The residue was dissolved in ethyl acetate, and the organic layer was washed with 1N hydrochloric acid, water, sodium bicarbonate water, water, saturated sodium chloride water, in this order. After the organic layer was dried with anhydrous magnesium sulfate, the solvent was removed by evaporation and a colorless solid (11.4 g) was obtained.

$^1$H-NMR (CDCl$_3$) δ: 2.77 (t, 7.2 Hz, 2H), 3.25 (dt, J=7.2, 7.2 Hz, 2H), 3.93 (s, 3H), 6.19–6.35 (m, 1H), 6.89–6.96 (m, 2H), 6.99–7.05 (m, 2H), 7.52 (d, J=5.2 Hz, 1H), 7.56 (d, J=5.2 Hz, 1H)

b) 3-{[2-(4-Fluorophenyl)-ethyl]-methyl-sulfamoyl}-thiophene-2-carboxylic acid methyl ester In the presence of potassium carbonate (2.58 g), 3-[2-(4-fluorophenyl)-ethylsulfamoyl]-thiophene-2-carboxylic acid methylester (3.2 g) was reacted with methyl iodide (0.69 mL), and an oily substance (3.38 g) was obtained, in the same way as Preparation Example 52.

$^1$H-NMR (CDCl$_3$) δ: 2.84–2.90 (m, 2H), 2.93 (s, 3H), 3.47–3.52 (m, 2H), 3.89 (s, 3H), 6.91–6.98 (m, 2H), 7.10–7.16 (m, 2H), 7.41 (d, J=5.2 Hz, 1H), 7.44 (d, J=5.2 Hz, 1H)

c) Title Compound

From 3-{[2-(4-fluorophenyl)-ethyl]-methyl-sulfamoyl}-thiophene-2-carboxylic acid methylester (1 g), the title compound (1 g) was obtained as an oily substance, in the same way as Preparation Example 96.

$^1$H-NMR (CDCl$_3$) δ: 1.53 (s, 9H), 2.76 (s, 3H), 2.80–2.86 (m, 2H), 3.26–3.32 (m, 2H), 6.76 (dd, J=5.6, 0.8 Hz, 1H), 6.86 (d, J=5.6 Hz, 1H), 6.94–7.00 (m, 2H), 7.10–7.15 (m, 2H), 9.14 (brs, 1H)

PREPARATION EXAMPLE 111

(5-Acetyl-3-{[2-(4-fluorophenyl)-ethyl]-methyl-sulfamoyl}-thiophene-2-yl)carbamic acid t-butyl ester a)(5-Bromo-3-{([2-(4-fluorophenyl)-ethyl]-methyl-sulfamoyl}-thiophene-2-yl) carbamic acid t-butyl ester From (3-{[2-(4-fluorophenyl)-ethyl]-methyl-sulfamoyl}-thiophene-2-yl)-carbamic acid tert-butyl ester (the compound of Preparation Example 110) (395 mg), a colorless candy-like substance (397 mg) was obtained, in the same way as Preparation Example 97.

$^1$H-NMR (CDCl$_3$) δ: 1.52 (s, 9H), 2.77 (s, 3H), 2.80–2.88 (m, 2H), 3.28–3.35 (m, 2H), 6.76 (s, J=5.6, 1H), 6.95–7.40 (m, 2H), 7.11–7.16 (m, 2H), 9.14 (brs, 1H)

b) Title Compound

From (5-bromo-3-{[2-(4-fluorophenyl)-ethyl]-methyl-sulfamoyl}-thiophene-2-yl) carbamic acid t-butyl ester (395 mg), a yellow solid (180 mg) were obtained, in the same way as Preparation Example 98.

$^1$H-NMR (CDCl$_3$) δ: 1.54 (s, 9H), 2.46 (s, 3H), 2.79 (s, 3H), 2.83–2.89 (m, 2H), 3.31–3.36 (m, 2H), 6.95–7.02 (m, 2H), 7.11–7.17 (m, 2H), 7.43 (s, J=5.6, 1H), 9.28 (brs, 1H)

PREPARATION EXAMPLE 112

5-Acetyl-2-amino-thiophene-3-sulfonic acid [2-(4-fluorophenyl)-ethyl]-methyl-amide From (5-acetyl-3-{[2-(4-fluorophenyl)-ethyl]-methyl-sulfamoyl}-thiophene-2-yl) carbamic acid t-butyl ester (180 mg), 88 mg of the title compound (88 mg) was obtained as a colorless solid, in the same way as Preparation Example 99.

$^1$H-NMR (CDCl$_3$) δ: 2.40 (s, 3H), 2.79 (s, 3H), 2.83–2.89 (m, 2H), 3.29–3.35 (m, 2H), 5.89 (brs, 2H), 6.95–7.02 (m, 2H), 7.11–7.17 (m, 2H), 7.30 (s, J=5.6, 1H),

PREPARATION EXAMPLE 113

(5-[1-(t-Butyldimethylsiloxy)vinyl]-3-{[2-(4-fluorophenyl)ethyl]-methylsulfamoyl}thiophene-2-yl) carbamic acid t-butyl ester To a solution of (5-acetyl-3-{[2-(4-fluorophenyl)ethyl] methylsulfamoyl}thiophene-2-yl)-carbamic acid t-butyl ester (the compound of Preparation Example 111) (946 mg) in dichloromethane (8 mL) was added triethylamine (0.58 mL) and 0.71 mL of t-butyldimethylsilyltrifluoromethane sulfonate (0.71 mL) on an ice bath. After stirring for 30 minutes, an aqueous solution of saturated sodium bicarbonate was added, and the solution was extracted with ethyl acetate. After drying the organic layer with anhydrous sodium sulfate, the residue that was obtained upon removal of the solvent by evaporation was purified by silica gel column chromatography (hexane/ethyl acetate) and, the title compound (985 mg) was obtained as a colorless oily matter.

$^1$H-NMR (CDCl$_3$) δ: 0.18 (s, 6H), 0.94 (s, 9H), 1.55 (s, 9H), 2.75 (s, 3H), 2.83 (t, J=7.6 Hz, 2H), 3.27 (t, J=7.6 Hz, 2H), 4.27 (d, J=2.4 Hz, 1H), 4.64 (d, J=2.4 Hz, 1H), 6.91 (s, 1H), 6.97 (t, J=8.8 Hz, 2H), 7.13 (dd, J=8.8 and 5.2 Hz, 2H), 9.11 (br s, 1H)

PREPARATION EXAMPLE 114

(4-Cyano-3-{[2-(4-fluorophenyl)ethyl]methylsulfamoyl}-7-oxo-4,5,6,7-tetrahydrobenzo[b]thiophene-2-yl)carbamic acid t-butyl ester To a solution of (5-[1-(t-butyldimethylsiloxy)vinyl]-3-{[2-(4-fluorophenyl)ethyl]methyl-sulfamoyl}-thiophene-2-yl)carbamic acid t-butyl ester (the compound of Preparation Example 113) (235 mg) and acrylonitrile (4 lpL) in xylene (1 mL) was irradiated with a 200 W microwave. After reacting at 100° C. to 150° C. for 30 minutes, the reaction solution was purified by silica gel column chromatography (hexane/ethyl acetate) and (4-cyano-3-{[2-(4-fluorophenyl) ethyl]methylsulfamoyl}-7-t-butyl-dimethylsiloxy-4,5,6,7-tetrahydrobenzo[b]thiophene-2-yl)carbamic acid t-butyl ester (54 mg) was obtained as a mixture. In addition, the same reaction was carried out from the starting materials (293 mg), and the mixture (45 mg) was obtained.

To a solution of the mixture (99 mg) in tetrahydrofuran (2 mL) was added dropwise a solution (0.2 mL) of 1.0M tetrabutylammonium fluoride in tetrahydrofuran on an ice bath. After stirring for 10 minutes, the solution was diluted with water, and the solution was extracted with ethyl acetate, and washed with saturated sodium chloride water. After drying the organic layer with anhydrous sodium sulfate, the residuals that were obtained upon removal of the solvent by evaporation were purified by silica gel column chromatography (hexane/ethyl acetate), (4-cyano-3-{[2-(4-fluorophenyl)ethyl]methylsulfamoyl}-7-hydroxy-4,5,6,7-tetrahydrobenzo[b]thiophene-2-yl)carbamic acid t-butyl ester (35 mg) was obtained as a mixture.

Next, the above-mentioned crude alcohol (35 mg) was oxidized by the same method as Preparation Example, and the title compound (15 mg) was obtained as a colorless oily matter.

$^1$H-NMR (CDCl$_3$) δ: 1.57 (s, 9H), 2.35–3.08 (m, 6H), 2.85 (s, 3H), 3.23–3.40 (m, 1H), 3.64–3.77 (m, 1H), 4.32–4.41 (m, 1H), 7.00 (t, J=8.4 Hz, 2H), 7.18 (dd, J=8.4 and 5.2 Hz, 2H), 9.69 (br s, 1H)

PREPARATION EXAMPLE 115

7-Oxo-4,5,6,7-tetrahydrobenzo[b]thiophene-3-carboxylic acid ethyl amide

To a solution of 7-oxo-4,5,6,7-tetrahydrobenzo[b] thiophene-3-carboxylic acid (the compound of Preparation Example 4) (98 mg) in tetrahydrofuran (2 mL) was added 0.11 mL of triethylamine (0.11 mL) and ethyl chlorocarbonate (58 μL) on an ice bath. After stirring for 30 minutes, a solution (1 mL) of 2M ethylamine-tetrahydrofuran was further added dropwise and the solution was stirred for 20 minutes. After the solution was extracted with water, then was extracted with ethyl acetate, and washed with saturated sodium chloride water. After the organic layer was dried with anhydrous sodium sulfate, the solvent was removed by evaporation and the title compound (100 mg) was obtained as a reddish-brown solid.

$^1$H-NMR (CDCl$_3$) δ: 1.26 (t, J=7.2 Hz, 3H), 2.12–2.25 (m, 2H), 2.53–2.68 (m, 2H), 3.03–3.17 (m, 2H), 3.38–3.52 (m, 2H), 5.83 (br s, 1H), 7.86 (s, 1H)

PREPARATION EXAMPLE 116

7-Oxo-4,5,6,7-tetrahydrobenzo[b]thiophene-3-carboxylic acid ethyl-methyl-amide

To a solution of 7-oxo-4,5,6,7-tetrahydrobenzo[b] thiophene-3-carboxylic acid (the compound of Preparation Example 4) (106 mg) in dichloromethane (2 mL) was added one drop of N,N-dimethylformamide. After oxalyl chloride (100 μL) was further added dropwise and the solution was stirred for 25 minutes. After removing the solvent by evaporation, the residual solvent was removed by azeotropic evaporation with toluene, and crude acidic chloride was obtained. Thereafter, this chloride was dissolved in pyridine (1 mL), ethyl methylamine (93 μL) was added dropwise, and the solution was stirred for 1 hour. After pyridine was evaporated at reduced pressure, the solution was diluted with ethyl acetate, and washed with 1N hydrochloric acid and saturated sodium chloride water. The crude product obtained after the organic layer was dried with anhydrous sodium sulfate and the solvent was removed by evaporation was dissolved in ethyl acetate, passed through a silica gel column, and the title compound (92 mg) was obtained as an orange oily substance.

$^1$H-NMR (CDCl$_3$) δ: 1.05–1.42 (m, 3H), 2.13–2.23 (m, 2H), 2.58–2.70 (m, 2H), 2.80–2.90 (m, 2H), 2.90–3.20 (m, 3H), 3.22–3.71 (m, 2H), 7.60 (s, 1H)

PREPARATION EXAMPLE 117

3-(4-Fluorophenyl)-2-[(7-oxo-4,5,6,7-tetrahydrobenzo[b]thiophene-3-carbonyl)amino]propionic acid From 7-oxo-4,5,6,7-tetrahydrobenzo[b]thiophene-3-carboxylic acid (the compound of Preparation Example 4) (105 mg) and DL-4-fluorophenylalanine, the title compound (190 mg) was obtained as a viscous yellow oily substance, in the same way as Preparation Example 116.

$^1$H-NMR (CDCl$_3$) δ: 2.18–2.30 (m, 2H), 2.45–2.71 (m, 2H), 2.83–3.11 (m, 2H), 3.22 (dd, J=14.4 and 6.0 Hz, 1H), 3.36 (dd, J=14.4 and 5.6 Hz, 1H), 4.92–5.11 (m, 1H), 6.32 (d, J=6.8 Hz, 1H), 7.01 (t, J=8.4 Hz, 2H), 7.17 (dd, J=8.4 and 5.2 Hz, 1H), 7.88 (s, 1H)

PREPARATION EXAMPLE 118

5-Bromo-thiophene-3-carboxylic acid [2-(4-fluorophenyl)-ethyl]-amide a) 5-Bromo-thiophene-3-carboxylic acid To a solution of thiophene-3-carboxylic acid (18.2 g) in N,N-dimethylformamide (250 mL) was added N-bromosuccinimide (27.8 g) in small amounts on an ice bath. After stirring at room temperature overnight, the reaction solution was poured into water (1.5 L), and the resulting solid was collected by filtration and washed with water. After dissolving in ethyl acetate, and dried with anhydrous magnesium sulfate, the drying agent was removed by filtration, and evaporation in vacuo was carried out. The solid that was generated by dissolving the residue in ethyl acetate, and adding hexane were collected by filtration, and the crude product (16 g) of 5-bromo-thiophene-3-carboxylic acid was obtained as a colorless solid.

$^1$H-NMR (CDCl$_3$) δ: 7.50 (d, J=1.6 Hz, 1H), 8.09 (d, J=1.6 Hz, 1H)

b) Title Compound

To a solution of 5-bromo-thiophene-3-carboxylic acid (5 g) and [2-(4-fluorophenyl)-ethyl]methyl-amine (the compound of Preparation Example 14) (3.7 g) in dichloromethane (150 mL) was added 1-Ethyl-3-(3-dimethylamino propyl)-carbodiimide.hydrochloride (5.1 g) was added. After stirring for 1.5 hours, the residue resulting from evaporation of the reaction solution in vacuo was purified by silica gel column chromatography (hexane/ethyl acetate), and the title compound (6 g) was obtained as a colorless oily matter.

$^1$H-NMR (CDCl$_3$) δ: 2.72–3.18 (m, 5H), 3.48–3.78 (m, 2H), 6.68–7.43 (m, 6H)

PREPARATION EXAMPLE 119

5-Acetyl-thiophene-3-carboxylic acid [2-(4-fluorophenyl)-ethyl]-amide

From 5-bromo-thiophene-3-carboxylic acid [2-(4-fluorophenyl)-ethyl]-amide (the compound of Preparation Example 118) (3.5 g), the title compound (2.25 g) was obtained as a colorless oily matter, in the same way as Preparation Example 98.

$^1$H-NMR (CDCl$_3$) δ: 2.44–2.60 (m, 3H), 2.74–3.22 (m, 5H), 3.55–3.78 (m, 2H), 6.88–7.80 (m, 6H)

PREPARATION EXAMPLE 120

4-Acetyl-thiophene-2-carboxylic acid [2-(4-fluorophenyl)-ethyl]-methyl-amide a) 4-Bromo-thiophene-2-carboxylic acid [2-(4-fluorophenyl)-ethyl]-methyl-amide From 4-bromo-thiophene-2-carboxylic acid and 1.47 g of [2-(4-fluorophenyl)-ethyl]-methyl-amine (the compound of Preparation Example 14) (1.98 g), a colorless solid (2.53 g) was obtained, in the same way as Preparation Example 118-b).

$^1$H-NMR (CDCl$_3$) δ: 2.87–2.95 (m, 2H), 3.11 (s, 3H), 3.66–3.74 (m, 2H), 6.93–7.02 (m, 2H 7.03–7.22 (br, 3H), 7.32 (brs, 1H)

b) 4-Acetyl-thiophene-2-carboxylic acid [2-(4-fluorophenyl)-ethyl]-methyl-amide

From 4-bromo-thiophene-2-carboxylic acid [2-(4-fluorophenyl)-ethyl]-methyl-amide (1.5 g), the title compound (974 mg) was obtained as a colorless oily product, in the same way as Preparation Example 98.

$^1$H-NMR (CDCl$_3$) δ: 2.52 (s, 3H), 2.93 (t, J=7.6 Hz, 2H), 3.15 (s, 3H), 3.73 (t, J=7.6 Hz, 2H), 6.94–7.02 (m, 2H), 7.05–7.24 (br, 2H), 7.63 (brs, 1H), 8.07 (s, 1H)

PREPARATION EXAMPLE 121

5-Acetyl-thiophene-2-carboxylic acid [2-(4-fluorophenyl)-ethyl]-methyl-amide a) 5-Bromo-thiophene-2-carboxylic acid [2-(4-fluorophenyl)-ethyl]-methyl-amide From 5-bromo-thiophene-2-carboxylic acid (1.0 g) and [2-(4-fluorophenyl)-ethyl]-methyl-amine (the compound of Preparation Example 14) (740 mg), a colorless solid (1.39 g) was obtained, in the same way as Preparation Example 118-b).

$^1$H-NMR (CDCl$_3$) δ: 2.91 (t, J=7.4 Hz, 2H), 3.10 (s, 3H), 3.70 (t, J=7.4 Hz, 2H), 6.94–7.03 (m, 4H), 7.10–7.20 (br, 2H)

b) 5-Acetyl-thiophene-2-carboxylic acid [2-(4-fluorophenyl)-ethyl]-methyl-amide

From 5-bromo-thiophene-2-carboxylic acid[2-(4-fluorophenyl)-ethyl]-methyl-amide (1.0 g), the title compound (555 mg) was obtained as a colorless solid, in the same way as Preparation Example 98.

MS m/e (ESI) 305.09 (MNa$^+$)

PREPARATION EXAMPLE 122

[[(Aminooxy)carbonyl](methyl)amino]methane-hydrochloride a) t-Butyl[(dimethylamino)carbonyl]oxycarbamate To a suspension of sodium hydride (865 mg) in dimethylformamide (12 mL) and tetrahydrofuran (15 mL) was added t-butyl-N-hydroxycarbamate (2.5 g) on an ice bath. After stirring for 30 minutes, dimethylcarbamoyl chloride (2.32 g) was added and was stirred for 1 hour. Water was added to the reaction solution, and the solution was extracted with ethyl acetate. The solid that was obtained by drying the organic layer and removing the solvent by evaporation was washed with hexane, and a colorless solid (3.18 g) were obtained.

$^1$H-NMR (DMSO-$d_6$) δ: 1.40 (s, 9H), 2.83–2.90 (br, 6H), 10.3 (br, 1H)

b) Title Compound

To a solution of t-butyl[(dimethylamino)carbonyl]oxycarbamate (3.04 g) in ethyl acetate (5 mL) was added a solution (18 mL) of 4N hydrochloric acid/ethyl acetate at room temperature. After stirring for 2 hours, the solid that precipitated was collected by filtration, and the title compound (1.85 g) was obtained as a colorless solid.

MS m/e (ESI) 104.97 (MH$^+$)

EXAMPLE 1

(7Z)-7-Hydroxyimino-4,5,6,7-tetrahydro-benzo[b] thiophene-3-sulfonic acid[2-(4-fluorophenyl)-2-hydroxyethyl]-methyl-amide To a solution of 7-oxo-4,5,6,7-tetrahydro-benzo[b] thiophene-3-sulfonic acid [2-(4-fluorophenyl)-2-hydroxyethyl]-methyl-amide (the compound of Preparation Example 48) (150 mg) in tetrahydrofuran (3 mL) and ethanol (3 mL) was added an aqueous solution (2.5 mL) of hydroxyamine hydrochloride (112 mg) and sodium acetate (133 mg), and the mixture was stirred at 70–80° C. for 3 hours. The organic solvent was removed by evaporation, water and ethyl acetate were added for separation/extraction. The organic layer was dried with anhydrous magnesium sulfate, the solvent was evaporated, and the residue was purified by silica gel column chromatography (hexane/ethyl acetate; ethyl acetate 10–40%). Among the 2 spots detected by TLC (the solvent system; hexane-ethyl acetate=1:1), the polar fractions (low Rf value on TLC) were collected, and the title compound (116 mg) was obtained as a colorless solid.

$^1$H-NMR (DMSO-$d_6$) δ: 1.82–1.92 (m, 2H), 2.48–2.57 (m, 2H), 2.78–2.85 (m, 2H), 2.80 (s, 3H), 3.18–3.24 (m, 2H), 4.70–4.77 (m, 1H), 5.64 (d, J=4.0 Hz, 1H), 7.10–7.18 (m, 2H), 7.30–7.38 (m, 2H), 8.30 (s, 1H), 11.70 (s, 1H)

EXAMPLE 2

(7E)-7-Hydroxyimino-4,5,6,7-tetrahydro-benzo[b] thiophene-3-sulfonic acid[2-(4-fluorophenyl)-2-hydroxyethyl]-methyl-amide Among the reaction product from Example 1, those fractions from the fractionation by silica gel column chromatography (ethyl acetate/hexane) that are low polarity elution fractions (demonstrating high Rf value on TLC) were collected, and the title compound (29 mg) was obtained as a colorless solid.

$^1$H-NMR (DMSO-$d_6$) δ: 1.72–1.82 (m, 2H), 2.56–2.64 (m, 2H), 2.66–2.73 (m, 2H), 2.77 (s, 3H), 3.13–3.19 (m, 2H), 4.68–4.75 (m, 1H), 5.62 (d, J=4.80 Hz, 1H), 7.08–7.18 (m, 2H), 7.28–7.36 (m, 2H), 8.08 (s, 1H), 11.17 (s, 1H)

EXAMPLE 3

(7Z)-7-Hydroxyimino-4,5,6,7-tetrahydro-benzo[b] thiophene-3-sulfonic acid[2-(4-fluorophenyl)-ethyl]-methyl-amide Prepared from 7-oxo-4,5,6,7-tetrahydro-benzo[b] thiophene-3-sulfonic acid [2-(4-fluorophenyl)-ethyl]-methyl-amide (the compound of Preparation Example 41) (400 mg) by an analogous method to Example 1, a compound demonstrating a low Rf value by TLC (system=hexane:ethyl acetate=2:1) was isolated through silica gel column chromatography (hexane/ethyl acetate; ethyl acetate 5–35%). The title compound (300 mg) was obtained as a colorless solid.

$^1$H-NMR (DMSO-$d_6$) δ: 1.81–1.89 (m, 2H), 2.48–2.56 (m, 2H), 2.75–2.84 (m, 7H), 3.27–3.34 (m, 2H), 7.06–7.11 (m, 2H), 7.21–7.26 (m, 2H), 8.32 (s, 1H), 11.72 (s, 1H)

EXAMPLE 4

(7E)-7-Hydroxyimino-4,5,6,7-tetrahydro-benzo[b] thiophene-3-sulfonic acid[2-(4-fluorophenyl)-ethyl]-methyl-amide From the reaction product of Example 3, the (E) isomer was isolated in the same way as Example 2, and the title compound (70 mg) was obtained as a colorless solid.

$^1$H-NMR (DMSO-$d_6$) δ: 1.75–1.83 (m, 2H), 2.59–2.65 (m, 2H), 2.66–2.73 (m, 2H), 2.77 (s, 3H), 3.77–2.83 (m, 2H), 3.25–3.32 (m, 2H), 7.06–7.12 (m, 2H), 7.21–7.26 (m, 2H), 8.13 (s, 1H), 11.20 (s, 1H)

EXAMPLE 5

(7Z)-7-Hydroxyimino-4,5,6,7-tetrahydro-benzo[b] thiophene-3-sulfonic acid[2-(4-fluoro-2-nitro-Phenyl)-ethyl]-methyl-amide From 7-oxo-4,5,6,7-tetrahydro-benzo[b]thiophene-3-sulfonic acid[2-(4-fluoro-2-nitro-phenyl)-ethyl]-methyl-amide (the compound of Preparation Example 42) (68 mg), the title compound (27 mg) was obtained as a colorless solid, in the same way as Example 1.

$^1$H-NMR (DMSO-$d_6$) δ: 1.82–1.92 (m, 2H), 2.48–2.57 (m, 2H), 2.78–2.85 (m, 2H), 2.81 (s, 3H), 3.07 (t, J=7.0 Hz, 2H), 3.38 (t, J=7.0 Hz, 2H), 7.57–7.62 (m, 2H), 7.88–7.94 (m, 1H), 8.29 (s, 1H), 11.72 (s, 1H)

EXAMPLE 6

(7Z)-7-Hydroxyimino-4,5,6,7-tetrahydro-benzo[b] thiophene-3-sulfonic acid[2-(4-fluoro-3-nitro-phenyl)-ethyl]-methyl-amide From 7-oxo-4,5,6,7-tetrahydro-benzo[b]thiophene-3-sulfonic acid[2-(4-fluoro-3-nitro-phenyl)-ethyl]-methyl-amide (the compound of Preparation Example 43) (108 mg), the title compound (74 mg) was obtained as a colorless amorphous substance, in the same way as Example 1.

$^1$H-NMR (DMSO-d$_6$) δ: 1.78–1.87 (m, 2H), 2.46–2.54 (m, 2H), 2.73–2.80 (m, 2H), 2.77 (s, 3H), 2.91 (t, J=7.0 Hz, 2H), 3.35 (t, J=7.2 Hz, 2H), 7.48 (dd, J=8.4, 11.2 Hz, 1H), 7.63–7.68 (m, 1H), 8.03 (dd, J=2.2, 7.4 Hz, 1H), 8.29 (s, 1H), 11.70 (s, 1H)

EXAMPLE 7

(7Z)-7-Hydroxyimino-4,5,6,7-tetrahydro-benzo[b]thiophene-3-sulfonic acid methyl-(2-pyridine-3-yl-ethyl)-amide From 7-oxo-4,5,6,7-tetrahydro-benzo[b]thiophene-3-sulfonic acid methyl-(2-pyridine-3-yl-ethyl)-amide (the compound of Preparation Example 44) (72 mg), the title compound (32 mg) was obtained as a colorless amorphous substance, in the same way as Example 1.

$^1$H-NMR (DMSO-d$_6$) δ: 1.80–1.90 (m, 2H), 2.48–2.56 (m, 2H), 2.76–2.88 (m, 4H), 2.78 (s, 3H), 3.30–3.38 (m, 2H), 7.26–7.31 (m, 1H), 7.60–7.65 (m, 1H), 8.33 (s, 1H), 8.39–8.45 (m, 2H), 11.72 (s, 1H)

EXAMPLE 8

(7E)-7-Hydroxyimino-4,5,6,7-tetrahydro-benzo[b]thiophene-3-sulfonic acid methyl-(2-pyridine-3-yl-ethyl)-amide From the reaction product of Example 7, the (E) isomer was isolated in the same way as Example 2, and the title compound (10 mg) was obtained as a colorless amorphous substance.

$^1$H-NMR (DMSO-d$_6$) δ: 1.75–1.84 (m, 2H), 2.59–2.65 (m, 2H), 2.67–2.73 (m, 2H), 2.78 (s, 3H), 2.80–2.88 (m, 2H), 3.28–3.38 (m, 2H), 7.27–7.32 (m, 1H), 7.61–7.66 (m, 1H), 8.13 (s, 1H), 8.39–8.45 (m, 2H), 11.21 (s, 1H)

EXAMPLE 9

(7Z)-7-Hydroxyimino-4,5,6,7-tetrahydro-benzo[b]thiophene-3-sulfonic acid methyl-(2-pyridine-4-yl-ethyl)-amide From 7-oxo-4,5,6,7-tetrahydro-benzo[b]thiophene-3-sulfonic acid methyl-(2-pyridine-4-yl-ethyl)-amide (the compound of Preparation Example 45) (100 mg), the title compound (40 mg) was obtained as a colorless solid, in the same way as Example 1.

$^1$H-NMR (DMSO-d$_6$) δ: 1.77–1.86 (m, 2H), 2.46–2.54 (m, 2H), 2.73–2.78 (m, 2H), 2.75 (s, 3H), 2.78–2.85 (m, 2H), 3.30–3.40 (m, 2H), 7.19–7.23 (m, 2H), 8.31 (s, 1H), 8.40–8.43 (m, 2H), 11.72 (s, 1H)

EXAMPLE 10

(7E)-7-Hydroxyimino-4,5,6,7-tetrahydro-benzo[b]thiophene-3-sulfonic acid methyl-(2-pyridine-4-yl-ethyl)-amide From the reaction product of Example 9, the (E) isomer was isolated in the same way as Example 2, and the title compound (15 mg) was obtained as a colorless solid.

$^1$H-NMR (DMSO-d$_6$) δ: 1.73–1.82 (m, 2H), 2.59–2.65 (m, 2H), 2.66–2.71 (m, 2H), 2.77 (s, 3H), 2.81–2.88 (m, 2H), 3.57–3.63 (m, 2H), 7.22–7.26 (m, 2H), 8.14 (s, 1H), 8.43–8.46 (m, 2H), 11.21 (s, 1H)

EXAMPLE 11

(7Z)-3-{[4-(4-Fluorophenyl)piperazine-1-yl]sulfonyl]-5,6-dihydro-1-benzothiophene-7 (4H)-one oxime From 3-[4-(4-fluorophenyl)-piperazine-1-sulfonyl]5,6-dihydro-4H-benzo[b]-thiophene-7-one (the compound of Preparation Example 46) (148 mg), the title compound (35 mg) was obtained as a colorless solid, in the same way as Example 1.

$^1$H-NMR (DMSO-d$_6$) δ: 1.87–1.96 (m, 2H), 2.54–2.61 (m, 2H), 2.94–3.00 (m, 2H), 3.14 (br, 8H), 6.92–6.98 (m 2H), 7.02–7.09 (m, 2H), 8.39 (s, 1H), 11.77 (s, 1H)

EXAMPLE 12

(7Z)-3-[(4-Hydroxy-4-phenyl-piperidine-1-yl)sulfonyl]-5,6-dihydro-1-benzothiophene-7 (4H)-one oxime From 3-(4-hydroxy-4-phenyl-piperidine-1-sulfonyl)-5,6-dihydro-4H-benzo[b]thiophene-7-one (the compound of Preparation Example 47) (72 mg), the title compound (25 mg) was obtained as a colorless solid, in the same way as Example 1.

$^1$H-NMR (DMSO-d$_6$) δ: 1.87–2.02 (m, 4H), 2.55–2.62 (m, 2H), 2.76–2.89 (m, 2H), 2.94–3.00 (m, 2H), 3.28 (m, 2H), 3.52–3.60 (m, 2H), 5.03 (s, 1H), 7.18–7.24 (m, 1H), 7.27–7.33 (m 2H), 7.43–7.46 (m, 2H), 8.37 (s, 1H), 11.75 (s, 1H)

EXAMPLE 13

(7Z)-N-[(2S)-2-(4-Fluorophenyl)-2-hydroxyethyl]-7-(hydroxyimino)-N-methyl-4,5,6,7-tetrahydro-1-benzothiophene-3-sulfonamide To a solution of N-[(2S)-2-(4-fluorophenyl)-2-hydroxyethyl]-N-methyl-7-oxo-4,5,6,7-tetrahydro-1-benzothiophene-3-sulfonamide (the compound of Preparation Example 49) (370 mg) in ethanol (4 mL) and water (2 mL) was added hydroxylamine.hydrochloride (100 mg) and sodium acetate (118 mg). After heating at 50° C. for 4 hours, the reaction solution was cooled to room temperature, the solution was dilued with water and extracted with ethyl acetate, and then was washed with saturated sodium chloride water. The crude product that was obtained after drying the solution with anhydrous sodium sulfate and removing the solvent by evaporation was purified by silica gel column chromatography (ethyl acetate/hexane; ethyl acetate 10–40%), fraction that was eluted with a solvent of higher polarity (the fractions that demonstrated low Rf values) was collected, and the title compound (280 mg) was obtained as a colorless solid. The NMR data of the present compound were consistent with those described in Example 1

EXAMPLE 14

(7Z)-N-[(2R)-2-(4-Fluorophenyl)-2-hydroxyethyl]-7-(hydroxyimino)-N-methyl-4,5,6,7-tetrahydro-1-benzothiophene-3-sulfonamide From N-[(2R)-2-(4-fluorophenyl)-2-hydroxyethyl]-N-methyl-7-oxo-4,5,6,7-tetrahydro-1-benzothiophene-3-sulfonamide (the compound of Preparation Example 50) (350 mg), the title compound (260 mg) was obtained as a colorless solid, in the same way as Example 1. The NMR data of the present compound were consistent with those described in Example 1

EXAMPLE 15

(7Z)-7-Hydroxyimino-4,5,6,7-tetrahydro-benzo[b]
thiophene-3-sulfonic acid[2-(2,4-difluorophenyl)-2-
hydroxyethyl]-amide From 7-oxo-4,5,6,7-tetrahydro-benzo[b]thiophene-3-sulfonic acid[2-(2,4-difluorophenyl)-2-hydroxyethyl]-amide (the compound of Preparation Example 51) (90 mg), the title compound (52 mg) was obtained as a colorless solid, in the same way as Example 1,
$^1$H-NMR (DMSO-$d_6$) δ: 1.80–1.88 (m, 2H), 2.47–2.54 (m, 2H), 2.80–2.86 (m, 2H), 2.95 (dd, J=13.2, 7.0 Hz, 1H), 3.02 (dd, J=13.2, 5.4 Hz, $_1$H), 4.69–4.75 (m, 1H), 5.60 (br, 1H), 6.97–7.03 (m, 1H), 7.60–7.12 (m, 1H), 7.36–7.43 (m, 1H), 7.84 (br, 1H), 8.16 (s, 1H), 11.61 (s, 1H)

EXAMPLE 16

(7E)-7-Hydroxyimino-4,5,6,7-tetrahydro-benzo[b]
thiophene-3-sulfonic acid[2-(2,4-difluorophenyl)-2-
hydroxyethyl]-amide From the reaction product of Example 15, the (E) isomer was isolated in the same way as Example 2, and the title compound (29 mg) was obtained as a colorless solid.
$^1$H-NMR (DMSO-$d_6$) δ: 1.74–1.82 (m, 2H), 2.46–2.51 (m, 2H), 2.57–2.63 (m, 2H), 2.69–2.75 (m, 2H), 2.97 (dd, J=13.6, 7.0 Hz, 1H), 3.03 (dd, J=13.6, 5.2 Hz, 1H), 4.70–4.76 (m, 1H), 5.61 (br, 1H), 6.98–7.04 (m, 1H), 7.60–7.13 (m, 1H), 7.37–7.44 (m, 1H), 7.83 (br, 1H), 7.95 (s, 1H), 11.13 (s, 1H)

EXAMPLE 17

(7Z)-7-Hydroxyimino-4,5,6,7-tetrahydro-benzo[b]
thiophene-3-sulfonic acid[2-(2,4-difluorophenyl)-2-
hydroxyethyl]-methyl-amide From 7-oxo-4,5,6,7-tetrahydro-benzo[b]thiophene-3-sulfonic acid[2-(2,4-difluorophenyl)-2-hydroxyethyl]-methyl-amide (the compound of Preparation Example 52) (109 mg), the title compound (135 mg) was obtained as a colorless solid, in the same way as Example 1,
$^1$H-NMR (DMSO-$d_6$) δ: 1.81–1.88 (m, 2H), 2.48–2.54 (m, 2H), 2.77–2.84 (m, 5H), 3.20 (dd, J=13.6, 7.6 Hz, 1H), 3.26–3.33 (m, 1H), 4.93–5.00 (m, 1H), 5.75 (d, J=4.8 Hz, 1H), 7.02–7.08 (m, 1H), 7.11–7.17 (m, 1H), 7.46–7.53 (m, 1H), 8.26 (s, 1H), 11.68 (s, 1H)

EXAMPLE 18

(7E)-7-Hydroxyimino-4,5,6,7-tetrahydro-benzo[b]
thiophene-3-sulfonic acid[2-(2,4-difluorophenyl)-2-
hydroxyethyl]-methyl-amide From the reaction product of Example 17, the (E) isomer was isolated in the same way as Example 2, and the title compound (45 mg) was obtained as a colorless solid. δ: 1.75–1.83 (m, 2H), 2.57–2.63 (m, 2H), 2.67–2.73 (m, 2H), 2.82 (s, 3H), 3.18 (dd, J=13.6, 7.2 Hz, 1H), 3.24–3.30 (m, 1H), 4.94–5.00 (m, 1H), 5.76 (d, J=4.8 Hz, 1H), 7.03–7.09 (m, 1H), 7.11–7.18 (m, 1H), 7.46–7.54 (m, 1H), 8.07 (s, 1H), 11.17 (s, 1H)

EXAMPLE 19

(7Z)-7-Hydroxyimino-4,5,6,7-tetrahydro-benzo[b]
thiophene-3-sulfonic acid [2-hydroxy-2-(4-pyrrolidine-1-yl-phenyl)-ethyl]-methyl-amide From 7-oxo-4,5,6,7-tetrahydro-benzo[b]thiophene-3-sulfonic acid[2-hydroxy-2-(4-pyrrolidine-1-yl-phenyl)-ethyl]-methyl-amide (the compound of Preparation Example 53) (35 mg), the title compound (13 mg) was obtained as a colorless amorphous substance, in the same way as Example 1.
$^1$H-NMR (DMSO-$d_6$) δ: 1.79–1.87 (m, 2H), 1.90–1.96 (m, 4H), 2.70–2.83 (m, 2H), 2.77 (s, 3H), 3.13–3.23 (m, 6H), 3.28–3.34 (m, 2H), 4.52–4.58 (m, 1H), 5.27 (d, J=4.4 Hz, 1H), 6.43 (d, J=8.4 Hz, 2H), 7.04 (d, J=8.4 Hz, 2H), 8.26 (s, 1H), 11.67 (s, 1H)

EXAMPLE 20

(7Z)-7-Hydroxyimino-4,5,6,7-tetrahydro-benzo[b]
thiophene-3-sulfonic acid[3-(4-chlorophenoxy)-2-
hydroxy-propyl]-methyl-amide From 7-oxo-4,5,6,7-tetrahydro-benzo[b]thiophene-3-sulfonic acid[3-(4-chloro-phenoxy)-2-hydroxy-propyl]-methyl-amide (the compound of Preparation Example 54) (41 mg), the title compound (27 mg) was obtained as a colorless amorphous substance, in the same way as Example 1.
$^1$H-NMR (DMSO-$d_6$) δ: 1.83–1.92 (m, 2H), 2.50–2.57 (m, 2H), 2.86 (s, 3H), 2.91 (t, J=6.2 Hz, 2H), 3.11 (dd, J=6.8, 14.0 Hz, 1H), 3.27 (dd, J=5.0, 13.8 Hz, 1H), 3.80–3.93 (m, 2H), 3.94–4.02 (m, 1H), 5.34 (d, J=5.2 Hz, 1H), 6.89–6.94 (m, 2H), 7.28–7.33 (m, 2H), 8.32 (s, 1H), 11.71 (s, 1H)

EXAMPLE 21

(7Z)-7-Hydroxyimino-4,5,6,7-tetrahydro-benzo[b]
thiophene-3-sulfonic acid (2-hydroxy-2-pyridine-4-
yl-ethyl)-methyl-amide From 7-oxo-4,5,6,7-tetrahydro-benzo[b]thiophene-3-sulfonic acid (2-hydroxy-pyridine-4-yl-ethyl)-methyl-amide (the compound of Preparation Example 55) (202 mg), the title compound (140 mg) was obtained as a colorless solid, through silica gel column chromatography (ethyl acetate/methanol 0–10%) purification, in the same way as Example 1.
$^1$H-NMR (DMSO-$d_6$) δ: 1.80–1.88 (m, 2H), 2.47–2.54 (m, 2H), 2.77–2.83 (m, 5H), 3.23 (d, J=6.4 Hz, 2H), 4.72–4.78 (m, 1H), 5.81 (d, J=4.4 Hz, 1H), 7.29–7.32 (m, 2H), 8.30 (s, 1H), 8.47–8.50 (m, 2H), 11.69 (s, 1H)

EXAMPLE 22

(7E)-7-Hydroxyimino-4,5,6,7-tetrahydro-benzo[b]
thiophene-3-sulfonic acid (2-hydroxy-2-pyridine-4-
vi-ethyl)-methyl-amide From the reaction product of Example 21, the (E) isomer was isolated in the same way as Example 2, and the title compound (33 mg) was obtained as a colorless solid.
$^1$H-NMR (DMSO-$d_6$) δ: 1.74–1.83 (m, 2H), 2.58–2.63 (m, 2H), 2.67–2.73 (m, 2H), 2.80 (s, 1H), 3.21 (d, J=6.0 Hz, 2H), 4.72–4.79 (m, 1H), 5.82 (d, J=4.8 Hz, 1H), 7.31 (d, J=5.0 Hz, 2H), 8.11 (s, 1H), 8.49 (d, J=5.0 Hz, 2H), 11.17 (s, 1H)

EXAMPLE 23

(7Z)-N-{1-(4-Fluorophenyl)-2-[(7-hydroxyimino-4,5,6,7-tetrahydrobe nzo[b]-thiophene-3-sulfonyl)methylamino]ethyl}acetamide To a solution of 7-oxo-4,5,6,7-tetrahydrobenzo[b]thiophene-3-sulfonic acid [2-amino-2-(4-fluorophenyl)ethyl]-methyl-amide (the compound of Preparation Example 57) (35 mg) in tetrahydrofuran (2 mL) was added dropwise triethylamine (39 µL) and acetyl chloride (10 µL). After stirring for 30 minutes, water was added and the solution was extracted with ethyl acetate, the solvent was removed by evaporation, and a crude product of an N-acetyl compound was obtained. From this crude product, the title compound (23 mg) was obtained as a pink solid, in the same way as Example 1.

$^1$H-NMR (DMSO-$d_6$) δ: 1.71–1.90 (m, 2H), 1.82 (s, 3H), 2.28–3.64 (m, 6H), 2.73 (s, 3H), 5.08 (dd, J=16.0 and 7.2 Hz, 1H), 7.12 (t, J=8.8 Hz, 2H), 7.35 (dd, J=8.8 and 5.6 Hz, 2H), 8.27 (s, 1H), 8.32 (d, J=8.8 Hz, 1H), 11.70 (s, 1H)

EXAMPLE 24

(7Z)-7-Hydroxyimino-4,5,6,7-tetrahydrobenzo[b]thiophene-3-sulfonic acid[(2-(4-fluorophenyl)-2-methane sulfonylamino-ethyl)]-methyl-amide From 7-oxo-4,5,6,7-tetrahydrobenzo[b]thiophene-3-sulfonic acid [2-amino-2-(4-fluorophenyl)ethyl]-methyl-amide (the compound of Preparation Example 57) (35 mg) and methanesulfonyl chloride (llpL), the title compound (18 mg) was obtained as a pink solid, in the same way as Example 23.

$^1$H-NMR (DMSO-$d_6$) δ: 1.74–1.89 (m, 2H), 2.42–3.54 (m, 6H), 2.64 (s, 3H), 2.75 (s, 3H), 4.45–4.63 (m, 1H), 7.16 (t, J=8.8 Hz, 2H), 7.40 (dd, J=8.8 and 5.6 Hz, 2H), 7.43–7.97 (m, 1H), 8.28 (s, 1H), 11.69 (s, 1H)

EXAMPLE 25

7-Hydroxyimino-4,5,6,7-tetrahydrobenzo[b]thiophene-3-sulfonic acid [(2-(4-fluorophenyl)-2-ureide ethyl)]-methyl-amide To a solution of 7-oxo-4,5,6,7-tetrahydrobenzo[b]thiophene-3-sulfonic acid [2-amino-2-(4-fluorophenyl)ethyl]-methyl-amide (the compound of Preparation Example 57) (54 mg) in N,N-dimethylformamide (1 mL) was added dropwise pyridine (29 µL) and phenyl chloroformate (22 µL). After stirring for 12 hours, 29% aqueous ammonia was added, and was extracted with ethyl acetate. The solution was washed with water and saturated sodium chloride water. The residue resulting from the removal of the solvent by evaporation was purified by silica gel column chromatography (dichloromethane/methanol), and the corresponding urea (30 mg) was obtained.

From the above-mentioned urea (30 mg), the title compound (pink solids) (9 mg) was obtained as a mixture where (E):(Z)=4:1, in the same way as Example 1.

$^1$H-NMR (DMSO-$d_6$) δ: 1.70–1.90 (m, 2H), 2.40–3.50 (m, 6H), 2.73 (s, 3H), 4.76–4.94 (m, 1H), 5.56 (s, 2H), 6.50 (d, J=8.8 Hz, 1H), 7.00–7.43 (m, 4H), 8.08 and 8.28[each s, 1H (1:4)], 11.18 and 11.69[each s, 1H (1:4)]

EXAMPLE 26

(7Z)-2-Amino-7-hydroxyimino-4,5,6,7-tetrahydrobenzo[b]-thiophene-3-sulfonic acid [2-(4-fluorophenyl)-2-hydroxyethyl]-methyl-amide From 2-amino-7-oxo-4,5,6,7-tetrahydro-benzo[b]thiophene-3-sulfonic acid [2-(4-fluorophenyl)-2-hydroxyethyl]-methyl-amide (the compound of Preparation Example 59) (143 mg), the title compound (70 mg) was obtained as a colorless solid, in the same way as Example 1.

$^1$H-NMR (DMSO-$d_6$) δ: 1.67–1.75 (m, 2H), 2.32–2.37 (m, 2H), 2.48–2.53 (m, 2H), 2.70 (s, 3H), 3.10–3.15 (m, 2H), 4.63–4.69 (m, 1H), 5.55 (d, J=4.4 Hz, 1H), 7.07–7.13 (m, 4H), 7.27–7.32 (m, 2H), 10.84 (s, 1H)

EXAMPLE 27

(7E)-2-Amino-7-hydroxyimino-4,5,6,7-tetrahydrobenzo[b]-thiophene-3-sulfonic acid [2-(4-fluorophenyl)-2-hydroxyethyl]-methyl-amide From the reaction product of Example 26, the (E) isomer was isolated in the same way as Example 2, and the title compound (40 mg) was obtained as a colorless solid.

$^1$H-NMR (DMSO-$d_6$) δ: 1.63–1.72 (m, 2H), 2.38–2.45 (m, 2H), 2.46–2.53 (m, 2H), 2.70 (s, 3H), 3.11 (d, J=6.4 Hz, 2H), 4.64–4.71 (m, 1H), 5.55 (d, J=4.4 Hz, 1H), 7.07–7.13 (m, 2H), 7.17 (brs, 2H), 7.28–7.33 (m, 2H), 10.58 (s, 1H)

EXAMPLE 28

(7Z)-7-Hydroxyimino-2-methoxy-4,5,6,7-tetrahydro-benzo[b]-thiophene-3-sulfonic acid [2-(4-fluorophenyl)-2-hydroxyethyl]-methyl-amide From 2-methoxy-7-oxo-4,5,6,7-tetrahydro-benzo[b]thiophene-3-sulfonic acid [2-(4-fluorophenyl)-2-hydroxyethyl]-methyl-amide (the compound of Preparation Example 60) (55 mg), the title compound (20 mg) was obtained as a colorless amorphous substance, in the same way as Example 1.

$^1$H-NMR (DMSO-$d_6$) δ: 1.77–1.85 (m, 2H), 2.42–2.48 (m, 2H), 2.71 (s, 3H), 2.76–2.81 (m, 2H), 3.18 (d, J=6.8 Hz, 2H), 4.00 (s, 3H), 4.66–4.73 (m, 1H), 5.57 (d, J=4.4 Hz, 1H), 7.10–7.16 (m, 2H), 7.30–7.35 (m, 2H), 11.39 (s, 1H)

EXAMPLE 29

(7E)-2-Methoxy-7-hydroxyimino-4,5,6,7-tetrahydro-benzo[b]-thiophene-3-sulfonic acid [2-(4-fluorophenyl)-2-hydroxyethyl]-methyl-amide From the reaction products of Example 28, the (E) isomer was isolated in the same way as Example 2, and the title compound (40 mg) was obtained as a colorless amorphous substance.

$^1$H-NMR (DMSO-$d_6$) δ: 1.72–1.80 (m, 2H), 2.53–2.59 (m, 2H), 2.65–2.70 (m, 2H), 2.72 (s, 3H), 3.16 (d, J=6.4 Hz, 2H), 3.98 (s, 3H), 4.67–4.73 (m, 1H), 5.57 (d, J=4.4 Hz, 1H), 7.10–7.16 (m, 2H), 7.30–7.36 (m, 2H), 10.86 (s, 1H)

EXAMPLE 30

(7Z)-7-Hydroxyimino-2-morpholin-4-yl-4,5,6,7-tetrahydro-benzo[b]-thiophene-3-sulfonic acid [2-(4-fluorophenyl)-2-hydroxyethyl]-methyl-amide From 2-morpholin-4-yl-7-oxo-4,5,6,7-tetrahydro-benzo[b]thiophene-3-sulfonic acid[2-(4-fluorophenyl)-2-hydroxyethyl]-methyl-amide (the compound of Preparation Example 61) (80 mg), the title compound (41 mg) was obtained as a colorless amorphous substance, in the same way as Example 1.

$^1$H-NMR (DMSO-$d_6$) δ: 1.76–1.85 (m, 2H), 2.42–2.48 (m, 2H), 2.71 (s, 3H), 2.77–2.83 (m, 2H), 2.93–3.04 (m, 4H), 3.19 (dd, J=14.0, 8.0 Hz, 1H), 3.27–3.34 (m, 1H), 3.53–3.63 (m, 4H), 4.66–4.72 (m, 1H), 5.56 (d, J=4.4 Hz, 1H), 7.10–7.16 (m, 2H), 7.30–7.35 (m, 2H), 11.46 (s, 1H)

EXAMPLE 31

(7Z)-7-Hydroxyimino-6-methyl-4,5,6,7-tetrahydrobenzo[b]-thiophene-3-sulfonic acid[(2-(4-fluorophenyl)ethyl)]-methyl-amide From 6-methyl-7-oxo-4,5,6,7-tetrahydrobenzo[b]thiophene-3-sulfonic acid [2-(4-fluorophenyl)ethyl]-methyl-amide (the compound of Preparation Example 62) (152 mg), the title compound (87 mg) was obtained as a orange solid, in the same way as Example 1.

$^1$H-NMR (DMSO-$d_6$) δ: 1.14 (d, J=6.8 Hz, 3H), 1.56–3.60 (m, 9H), 2.74 (s, 3H), 6.90–7.34 (m, 4H), 8.30 (s, 1H), 8.35 (s, 1H), 11.82 (s, 1H)

EXAMPLE 32

(7Z)-7-Hydroxyimino-6-methyl-4,5,6,7-tetrahydrobenzo[b]-thiophene-3-sulfonic acid[(2-(4-fluorophenyl)-2-hydroxyethyl)]-methyl-amide From 6-methyl-7-oxo-4,5,6,7-tetrahydrobenzo[b]thiophene-3-sulfonic acid [2-(4-fluorophenyl)-2-hydroxyethyl]-methyl-amide (the compound of Preparation Example 63) (155 mg), the title compound (a orange solid) (109 mg) was obtained, in the same way as Example 1.

$^1$H-NMR (DMSO-$d_6$) δ: 1.10–1.27 (m, 3H), 1.60–3.46 (m, 7H), 2.78 (s, 3H), 4.61–4.83 (m, 1H), 5.61 (d, J=4.4 Hz, 1H), 6.90–7.45 (m, 4H), 8.28 (s, 1H), 8.35 (s, 1H), 11.81 (s, 1H)

EXAMPLE 33

(7Z)-6-Hydroxy-7-hydroxyimino-4,5,6,7-tetrahydrobenzo[b]-thiophene-3-sulfonic acid[(2-(4-fluorophenyl)ethyl)]-methyl-amide To a solution of 6-acetoxy-7-oxo-4,5,6,7-tetrahydrobenzo[b]thiophene-3-sulfonic acid [2-(4-fluorophenyl)ethyl]-methyl-amide (the compound of Preparation Example 65) (200 mg) in pyridine (2 mL) was added hydroxylamine.hydrochloride (61 mg). After stirring at room temperature for 2.5 hours, two products were observed by TLC. After the solution was diluted with ethyl acetate, the solution was washed with water and saturated sodium chloride water. The crude products obtained after drying with anhydrous sodium sulfate, removing the solvent by evaporation were purified by silica gel column chromatography (ethyl acetate/hexane), the fraction that was eluted by a solvent with a higher polarity (the fractions that demonstrated low Rf values) were collected, and (7Z)-6-acetoxy-7-hydroxyimino-4,5,6,7-tetrahydrobenzo[b]thiophene-3-sulfonic acid[2-(4-fluorophenyl)ethyl]-methyl-amide was obtained. Thereafter, to methanol (1 mL) was added excess potassium carbonate. The solution was stirred at room temperature for 1 hour. Water was added, the solution was extracted with ethyl acetate, and the organic layer was dried with anhydrous magnesium sulfate. The residue resulting from the removal of the solvent by evaporation was purified by LC-MS, and the title compound (0.9 mg) was obtained as a colorless solid.

$^1$H-NMR (CDCl$_3$) δ: 1.40–3.20 (m, 7H), 2.83 (s, 3H), 3.29–3.50 (m, 2H), 4.55–4.74 (m, 1H), 6.98 (t, J=8.4 Hz, 2H), 7.05–7.21 (m, 2H), 8.13 (s, 1H) MS m/e (ESI) 399.02 (MH$^+$)

EXAMPLE 34

(7Z)-2-Amino-4-cyano-7-hydroxyimino-4,5,6,7-tetrahydrobenzo[b]-thiophene-3-sulfonic acid[(2-(4-fluorophenyl)ethyl)]-methyl-amide To a solution of (4-cyano-3-{[2-(4-fluorophenyl)ethyl]methylsulfamoyl}-7-oxo-4,5,6,7-tetrahydrobenzo[b]thiophene-2-yl)carbamic acid t-butyl ester (the compound of Preparation Example 114) (15 mg) in pyridine was added an excess hydroxylamine.hydrochloride. After stirring at room temperature for 13 hours, 2N hydrochloric acid was added, and the solution was extracted with ethyl acetate. The solution was washed with water and saturated sodium chloride water. The solvent was removed by evaporation, and the N-Boc protected compound (15 mg) of the title compound was obtained.

The above-mentioned protected compound (15 mg) was dissolved in trifluoroacetic acid (0.5 mL). After allowing to stand for 1 hour, the solvent was removed by evaporation, purification by silica gel column chromatography (hexane/ethyl acetate) was carried out, and the title compound (8.5 mg) was obtained as a gray solid.

$^1$H-NMR (DMSO-$d_6$) δ: 1.80–3.44 (m, 8H), 2.71 (s, 3H), 4.16 (br, 1H), 7.08 (t, J=8.8 Hz, 2H), 7.24 (dd, J=8.8 and 5.6 Hz, 2H), 7.28 (s, 2H), 11.40 (s, 1H)

MS m/e (ESI) 423.31 (MH$^+$)

EXAMPLE 35

5-[(1Z)-Hydroxyimino-ethyl)thiophene-2-sulfonic acid [2-(4-fluorophenyl)ethyl]amide From 5-acetylthiophene-2-sulfonic acid [2-(4-fluorophenyl)-ethyl]amide (the compound of Preparation Example 67) (706 mg), the same reaction as Example 1 was carried out. After the reaction solution was cooled to room temperature, the solid that precipitated was filtered, washed with ethanol-water 1:1, and the title compound (115 mg) was obtained as a gray solid.

$^1$H-NMR (DMSO-$d_6$) δ: 2.26 (s, 3H), 2.63–2.79 (m, 2H), 2.96–3.09 (m, 2H), 6.90–7.30 (m, 4H), 7.45 (d, J=4.0 Hz, 1H), 7.51 (d, J=4.0 Hz, 1H), 7.83–8.02 (m, 1H), 12.24 (brs, 1H)

EXAMPLE 36

5-[(1E)-Hydroxyimino-ethyl]thiophene-2-sulfonic acid [2-(4-fluorophenyl)ethyl]amide The solid that was generated by cooling the mother liquor of Example 35 to ice-cold temperatures was collected, and the (E) isomer (178 mg) was obtained as a yellow solid.

$^1$H-NMR (DMSO-$d_6$) δ: 2.14 (s, 3H), 2.62–2.80 (m, 2H), 2.93–3.12 (m, 2H), 6.80–7.28 (m, 4H), 7.32 (d, J=3.6 Hz, 1H), 7.45 (d, J=3.6 Hz, 1H), 7.80–8.10 (m, 1H), 11.57 (s, 1H)

EXAMPLE 37

5-[(1Z)-Hydroxyimino-ethyl]thiophene-2-sulfonic acid [2-(4-fluorophenyl)ethyl]-methyl-amide From 5-acetylthiophene-2-sulfonic acid [2-(4-fluorophenyl)-ethyl]-methyl-amide (the compound of Preparation Example 68) (257 mg), the title compound (77 mg) was obtained as a pale yellow solid (solidified from diethyl ether-hexane), in the same way as Example 1.

$^1$H-NMR (DMSO-$d_6$) δ: 2.27 (s, 3H), 2.70 (s, 3H), 2.74–2.90 (m, 2H), 3.09–3.23 (m, 2H), 6.85–7.42 (m, 4H), 7.53 (d, J=4.0 Hz, 1H), 7.62 (d, J=4.0 Hz, 1H), 12.33 (brs, 1H)

EXAMPLE 38

5-[(1E)-Hydroxyimino-ethyl]thiophene-2-sulfonic acid [2-(4-fluorophenyl)ethyl]-methyl-amide Among the product obtained in the reaction of Example 37, the (E) isomer was isolated in the same way as Example 2, and the title compound (66 mg) was obtained as a colorless solid (solidified from ethyl acetate).

$^1$H-NMR (DMSO-$d_6$) δ: 2.15 (s, 3H), 2.71 (s, 3H), 2.75–2.86 (m, 2H), 3.12–3.22 (m, 2H), 6.90–7.17 (m, 4H), 7.41 (d, J=4.0 Hz, 1H), 7.55 (d, J=4.0 Hz, 1H), 11.61 (s, 1H)

EXAMPLE 39

5-[(1Z)-Hydroxyimino-ethyl]thiophene-2-sulfonic acid [2-(4-fluorophenyl)-2-hydroxyethyl]-methyl-amide From 5-acetylthiophene-2-sulfonic acid [2-(4-fluorophenyl)-2-hydroxyethyl]-methyl-amide (the compound of Preparation Example 72) (210 mg), the title compound (88 mg) was obtained as a pale yellow solid (solidified from diethyl ether-hexane), in the same way as Example 1.

$^1$H-NMR (DMSO-$d_6$) δ: 2.25 (s, 3H), 2.70 (s, 3H), 2.93–3.15 (m, 2H), 4.65–4.82 (m, 2H), 5.63 (d, J=4.8 Hz, 1H), 7.13 (t, J=8.8 Hz, 2H), 7.35 (dd, J=8.8 and 5.6 Hz, 2H), 7.51 (d, J=4.0 Hz, 1H), 7.59 (d, J=4.0 Hz, 1H), 12.30 (s, 1H)

EXAMPLE 40

5-[(1E)-Hydroxyimino-ethyl)thiophene-2-sulfonic acid [2-(4-fluorophenyl)-2-hydroxyethyl]-methyl-amide Among the reaction product of Example 39, the (E) isomer was isolated in the same way as Example 2, and the title compound (49 mg) was obtained as a colorless solid (solidified from ethyl acetate-hexane).

$^1$H-NMR (DMSO-$d_6$) δ: 2.14 (s, 3H), 2.72 (s, 3H), 2.98–3.14 (m, 2H), 4.63–4.84 (m, 2H), 5.64 (d, J=4.4 Hz, 1H), 7.13 (t, J=8.8 Hz, 2H), 7.35 (dd, J=8.8 and 6.0 Hz, 2H), 7.38 (d, J=4.0 Hz, 1H), 7.52 (d, J=4.0 Hz, 1H), 11.59 (s, 1H)

EXAMPLE 41

5-[(1Z)-Hydroxyimino ethyl)thiophene-2-sulfonic acid [2-(4-fluorophenyl)-2-methoxyethyl]-methyl-amide From 5-acetylthiophene-2-sulfonic acid [2-(4-fluorophenyl)-2-methoxyethyl]-methyl-amide (the compound of Preparation Example 74) (86 mg), the title compound (15 mg) was obtained as a colorless solid (solidified from diethyl ether-hexane), in the same way as Preparation Example 1.

$^1$H-NMR (DMSO-$d_6$) δ: 2.26 (s, 3H), 2.73 (s, 3H), 3.08 (s, 3H), 3.00–3.25 (m, 2H), 4.37–4.48 (m, 1H), 7.19 (t, J=8.8 Hz, 2H), 7.34 (dd, J=8.8 and 5.6 Hz, 2H), 7.51 (d, J=4.0 Hz, 1H), 7.61 (d, J=4.0 Hz, 1H), 12.31 (brs, 1H)

EXAMPLE 42

5-[(1Z)-Hydroxyimino-ethyl]thiophene-2-sulfonic acid [2-fluoro-2-(4-fluorophenyl)ethyl]-methyl-amide From 5-acetylthiophene-2-sulfonic acid [2-fluoro-2-(4-fluorophenyl)ethyl]-methyl-amide (the compound of Preparation Example 76) (116 mg), the title compound (25 mg) was obtained as a colorless solid (solidified from diethyl ether-hexane), in the same way as Example 1.

$^1$H-NMR (DMSO-$d_6$) δ: 2.27 (s, 3H), 2.80 (s, 3H), 3.18–3.65 (m, 2H), 5.60–6.00 (m, 1H), 7.24 (t, J=8.8 Hz, 2H), 7.47 (dd, J=8.8 and 5.6 Hz, 2H), 7.54 (d, J=4.4 Hz, 1H), 7.68 (d, J=4.4 Hz, 1H), 12.35 (brs, 1H)

EXAMPLE 43

5-[(1Z)-Hydroxyimino-ethyl)thiophene-2-sulfonic acid cyclopropyl-[2-(4-fluorophenyl)ethyl]amide From 5-acetylthiophene-2-sulfonic acid cyclopropyl[2-(4-fluorophenyl)ethyl]-methyl-amide (the compound of Preparation Example 77) (85 mg), the title compound (20 mg) was obtained as a colorless solid, in the same way as Example 1. The NMR showed a mixture of rotamers.

$^1$H-NMR (DMSO-$d_6$) δ: 0.56–0.78 (m, 4H), 2.06–2.20 (m, 1H), 2.27 and 2.29[each s, 3H (1:1)], 2.74–2.90 (m, 2H), 6.95–7.36 (m, 4H), 7.50 and 7.55[each d, each J=4.4 Hz, 1H (1:1)], 7.61 and 7.69[each d, each J=4.4 Hz, 1H (1:1)], 12.28 and 12.34[each s, 1H (1:1)]

EXAMPLE 44

5-[(1Z)-Hydroxyimino-ethyl]thiophene-3-sulfonic acid [2-(4-fluorophenyl)-2-hydroxyethyl]-methyl-amide From 5-acetylthiophene-3-sulfonic acid [2-(4-fluorophenyl)-2-hydroxyethyl]-methyl-amide (the compound of Preparation Example 80) (154 mg), the title compound (33 mg) was obtained as a pale yellow solid (solidified from diethyl ether-hexane), in the same way as Example 1.

$^1$H-NMR (DMSO-$d_6$) δ: 2.25 (s, 3H), 2.69 (s, 3H), 2.72–2.84 (m, 2H), 3.11–3.23 (m, 2H), 6.90–7.40 (m, 4H), 7.57 (d, J=1.6 Hz, 1H), 8.33 (d, J=1.6 Hz, 1H), 12.03 (brs, 1H)

EXAMPLE 45

5-[(1E)-Hydroxyimino-ethyl]thiophene-3-sulfonic acid [2-(4-fluorophenyl)-ethyl]-methyl-amide From the reaction product of Example 44, the (E) isomer was isolated in the same way as Example 2, and the title compound (44 mg) was obtained as a slightly yellow solid (solidified from diethyl ether-hexane).

$^1$H-NMR (DMSO-$d_6$) δ: 2.15 (s, 3H), 2.70 (s, 3H), 2.73–2.90 (m, 2H), 3.06–3.24 (m, 2H), 6.90–7.37 (m, 4H), 7.46 (d, J=1.6 Hz, 1H), 8.11 (d, J=1.6 Hz, 1H), 11.45 (s, 1H)

EXAMPLE 46

5-[(1Z)-Hydroxyimino-ethyl]thiophene-3-sulfonic acid [2-(4-fluorophenyl)-2-hydroxyethyl]-methyl-amide From 5-acetylthiophene-3-sulfonic acid [2-(4-fluorophenyl)-2-hydroxyethyl]-methyl-amide (the compound of Preparation Example 84) (58 mg), the title compound (6 mg) was obtained as a pale yellow solid, in the same way as Example 1.

$^1$H-NMR (DMSO-$d_6$) δ: 2.25 (s, 3H), 2.72 (s, 3H), 3.00–3.60 (m, 2H), 4.67–4.81 (m, 1H), 5.60 (d, J=4.8 Hz, 1H), 7.00–7.49 (m, 4H), 7.57 (d, J=1.6 Hz, 1H), 8.32 (d, J=1.6 Hz, 1H), 12.01 (br s, 1H)

EXAMPLE 47

5-(1-Hydroxyimino-2-methylpropyl)thiophene-3-sulfonic acid [2-(4-fluorophenyl)-ethyl]-methyl-amide To a mixture solution of 5-isobutyrylthiophene-3-sulfonic acid [2-(4-fluorophenyl)-ethyl]-methyl-amide (the compound of Preparation Example 88) (30 mg) in ethanol (2 mL) and water (1 mL) was added hydroxylamine.hydrochloride (11 mg) and sodium acetate (13 mg). After heating and refluxing for 12 hours, the reaction solution was cooled to room temperature. The solution was diluted with water and extracted with ethyl acetate. This solution was washed with saturated sodium chloride water. The crude product that was obtained after drying with anhydrous sodium sulfate and removing the solvent by evaporation was purified by silica gel column chromatography (ethyl acetate/hexane), the title compound (a pale yellow viscous oily substance) (29 mg) was obtained as a mixture where (E):(Z)=1:1.

$^1$H-NMR (DMSO-$d_6$) δ: 1.17 and 1.22[each d, each J=7.2 Hz, 6H (1:1)], 2.68 and 2.70[each s, 3H (1:1)], 2.62–3.42 (m, 5H), 6.95–7.35 (m, 4H), 7.40 and 7.62[each s, 1H (1:1)], 8.12 and 8.33 [each s, 1H (1:1)], 11.45 and 12.13[each s, 1H (1:1)]

EXAMPLE 48

5-(1-Hydroxyimino-2-methylpropyl)thiophene-3-sulfonic acid [2-(4-fluorophenyl)-2-hydroxyethyl]-methyl-amide From 5-isobutyrylthiophene-3-sulfonic acid [2-(4-fluorophenyl)-2-hydroxyethyl]-methyl-amide (the compound of Preparation Example 91), the title compound (E: Z=1:1.7) (45 mg) was obtained as a pale yellow viscous oily substance, in the same way as Example 47.

$^1$H-NMR (DMSO-$d_6$) δ: 1.15 and 1.21[each d, each J=6.8 Hz, 6H (1.7:1)], 2.69 and 2.70[each s, 3H (1.7:1)], 2.96–3.60 (m, 3H), 4.15–4.33 (m, 1H), 5.52–5.70 (m, 1H), 6.97–7.70 (m, 5H), 8.08 and 8.29[each d, each J=1.6 Hz, 1H (1:1.7)], 11.44 and 12.11[s and brs, 1H (1:1.7)]

EXAMPLE 49

5-[1-Hydroxyimino-(2-dimethylamino)ethyl]thiophene-3-sulfonic acid[2-(4-fluorophenyl)ethyl]-methyl-amide From 5-(2-dimethylamino acetyl)thiophene-3-sulfonic acid [2-(4-fluorophenyl)ethyl]-methyl-amide (the compound of Preparation Example 93) (16 mg), the title compound (a pale yellow viscous oily substance) (6 mg) was obtained as a mixture where (E):(Z)=1:2, in the same way as Example 47.

$^1$H-NMR (DMSO-$d_6$) δ: 2.12 and 2.14[each s, 6H (2:1)], 2.70 (s, 3H), 2.62–2.85 (m, 2H), 3.04–3.23 (m, 2H), 3.36 and 3.51[each s, 2H (2:1)], 7.00–7.35 (m, 4H), 7.57 and 7.87[each s, 1H (1:2)], 8.11 and 8.31[each s, 1H (1:2)], 11.70 and 12.29[each s, 1H (1:2)]

EXAMPLE 50

5-[(1Z)-Hydroxyimino-2-acetoxyethyl]thiophene-3-sulfonic acid [2-(4-fluorophenyl)ethyl]-methyl-amide A solution of 5-(2-acetoxy acetyl)thiophene-3-sulfonic acid [2-(4-fluorophenyl)-ethyl]-methyl-amide (the compound of Preparation Example 94) (234 mg) in pyridine (2 mL) was added hydroxylamine.hydrochloride (61 mg). After stirring at room temperature for 2.5 hours, the solution was diluted with ethyl acetate, and washed with water and saturated sodium chloride water. The crude product that was obtained after drying with anhydrous sodium sulfate and removing the solvent by evaporation was purified by silica gel column chromatography (ethyl acetate/hexane), the fraction that was eluted by a solvent with a higher polarity (the fractions that demonstrate lower Rf values by TLC) was collected, and the title compound (57 mg) was obtained as a colorless solid.

$^1$H-NMR (DMSO-$d_6$) δ: 1.93 (s, 3H), 2.70 (s, 3H), 2.60–2.91 (m, 2H), 3.06–3.27 (m, 2H), 5.08 (s, 2H), 6.94–7.34 (m, 4H), 7.64 (s, 1H), 8.39 (s, 1H), 12.77 (s, 1H)

EXAMPLE 51

5-[(1Z)-Hydroxyimino-2-hydroxyethyl]thiophene-3-sulfonic acid [2-(4-fluorophenyl)ethyl]-methyl-amide To a solution of 5-(1-hydroxyimino-2-acetoxyethyl) thiophene-3-sulfonic acid [2-(4-fluorophenyl)ethyl]-methyl-amide (Example 50) (55 mg) in methanol (1 mL) was added an excess potassium carbonate (50 mg). After stirring at room temperature for 1 hour, the solution was diluted with water and extracted with ethyl acetate. The solution was washed with saturated sodium chloride water. After drying with anhydrous sodium sulfate, filtration was carried out using a small amount of silica gel (200 mg), and the title compound (41 mg) was obtained as a pale yellow viscous oily substance.

$^1$H-NMR (DMSO-$d_6$) δ: 2.71 (s, 3H), 2.63–2.86 (m, 2H), 3.08–3.25 (m, 2H), 4.43 (d, J=5.6 Hz, 2H), 5.42 (t, J=5.6 Hz,

1H), 7.10 (t, J=8.4 Hz, 2H), 7.26 (dd, J=8.4 and 6.0 Hz, 2H), 7.79 (s, 1H), 8.35 (s, 1H), 12.28 (s, 1H)

EXAMPLE 52

2-Amino-5-[(1Z)-hydroxyimino-ethyl]-thiophene-3-sulfonic acid [2-(4-fluorophenyl)-2-hydroxyethyl]-methyl-amide From 5-acetyl-2-amino-thiophene-3-sulfonic acid [2-(4-fluorophenyl)-2-hydroxyethyl]-methyl-amide (the compound of Preparation Example 99) (100 mg), and the title compound (22 mg) was obtained as a colorless amorphous substance, in the same way as Example 1.

$^1$H-NMR (DMSO-$d_6$) δ: 2.08 (s, 3H), 2.70 (s, 3H), 3.03–3.17 (m, 2H), 4.70–4.78 (m, 1H), 5.59 (d, J=4.4 Hz, 1H), 6.97 (s, 2H), 6.98 (s, 1H), 7.11–7.19 (m, 2H), 7.35–7.43 (m, 2H), 11.23 (s, 1H)

EXAMPLE 53

2-Amino-5-[(1E)-hydroxyimino-ethyl]-thiophene-3-sulfonic acid [2-(4-fluorophenyl)-2-hydroxyethyl]-methyl-amide From the reaction product of Example 52, the (E) isomer was isolated in the same way as Example 2, and the title compound (74 mg) was obtained as a colorless amorphous matter.

$^1$H-NMR (DMSO-$d_6$) δ: 2.02 (s, 3H), 2.70 (s, 3H), 3.05–3.17 (m, 2H), 4.72–4.79 (m, 1H), 5.59 (d, J=4.4 Hz, 1H), 6.84 (s, 1H), 7.01 (s, 2H), 7.11–7.17 (m, 2H), 7.35–7.43 (m, 2H), 10.92 (s, 1H)

EXAMPLE 54

[3-{[2-(4-Fluorophenyl)-2-hydroxyethyl]-methyl-sulfamoyl}-5-[(1Z)-hydroxyimino-ethyl]-thiophene-2-yl]-carbamic acid t-butyl ester From (5-acetyl-3-{[2-(4-fluorophenyl)-2-hydroxyethyl]-methyl-sulfamoyl}-5-thiophene-2-yl)-carbamic acid t-butyl ester (the compound of Preparation Example 98) (800 mg), the title compound (320 mg) was obtained as a colorless solid, in the same way as Example 1.

$^1$H-NMR (DMSO-$d_6$) δ: 1.46 (s, 9H), 2.17 (s, 3H), 2.73 (s, 3H), 3.13 (dd, J=13.6, 4.8 Hz, 1H), 3.25 (dd, J=13.6, 8.0 Hz, 1H), 4.70–4.78 (m, 1H), 5.58 (d, J=4.4 Hz, 1H), 7.10–7.18 (m, 2H), 7.28 (s, 1H), 7.33–7.39 (m, 2H), 9.16 (s, 1H) 11.77 (s, 1H)

EXAMPLE 55

[3-{[2-(4-Fluorophenyl)-2-hydroxyethyl]-methyl-sulfamoyl}-5-[(1E)-hydroxyimino-ethyl]-thiophene-2-yl]-carbamic acid t-butyl ester From the reaction product of Example 54, the (E) isomer was isolated in the same way as Example 2, and the title compound (450 mg) was obtained as a colorless solid.

$^1$H-NMR (DMSO-$d_6$) δ: 1.46 (s, 9H), 2.08 (s, 3H), 2.74 (s, 3H), 3.15 (dd, J=13.6, 4.8 Hz, 1H), 3.24 (dd, J=14.0, 8.0 Hz, 1H), 4.70–4.76 (m, 1H), 5.67 (d, J=4.4 Hz, 1H), 7.10–7.17 (m, 3H), 7.32–7.39 (m, 2H), 9.16 (s, 1H) 11.24 (s, 1H)

EXAMPLE 56

5-[(1E)-Hydroxyimino-ethyl)-2-methylamino-thiophene-3-sulfonic acid[2-(4-fluorophenyl)-2-hydroxyethyl]-methyl-amide From 5-acetyl-2-methylamino-thiophene-3-sulfonic acid [2-(4-fluorophenyl)-2-hydroxyethyl]-methyl-amide (the compound of Preparation Example 100) (60 mg), the title compound (24 mg) was obtained as a colorless solid, in the same way as Example 1, $^1$H-NMR (DMSO-$d_6$) δ: 2.04 (s, 3H), 2.70 (s, 3H), 2.84 (d, J=4.8 Hz, 3H), 3.09–3.15 (m, 2H), 4.70–4.78 (m, 1H), 5.62 (d, J=4.4 Hz, 1H), 6.97 (s, 1H), 7.06–7.19 (m, 3H), 7.35–7.42 (m, 2H), 10.89 (s, 1H)

EXAMPLE 57

5-[(1E)-Hydroxyimino-ethyl)-2-methylamino-thiophene-3-sulfonic acid[2-(4-fluorophenyl)-2-hydroxyethyl]-methyl-amide From the reaction product of Example 56, the (E) isomer was isolated in the same way as Example 2, and the title compound (16 mg) was obtained as a colorless amorphous substance.

$^1$H-NMR (DMSO-$d_6$) δ: 2.10 (s, 3H), 2.69 (s, 3H), 2.85 (d, J=5.2 Hz, 3H), 3.08–3.16 (m, 2H), 4.71–4.79 (m, 1H), 5.64 (d, J=4.0 Hz, 1H), 7.04–7.19 (m, 3H), 7.36–7.42 (m, 2H), 7.72 (s, 1H), 11.29 (s, 1H)

EXAMPLE 58

N-[3-{[2-(4-Fluorophenyl)-2-hydroxyethyl]-methyl-sulfamoyl}-5-[(1Z)-hydroxyimino-ethyl]-thiophene-2-yl]-propionic acid amide From N-(5-acetyl-3-{[2-(4-fluorophenyl)-2-hydroxyethyl]-methyl-sulfamoyl}-thiophene-2-yl)-propionic acid amide (the compound of Preparation Example 101) (72 mg), the title compound (22 mg) was obtained as a colorless solid, in the same way as Example 1.

$^1$H-NMR (DMSO-$d_6$) δ: 1.07 (t, J=7.6 Hz, 3H), 2.19 (s, 3H), 2.53 (q, J=7.6 Hz, 2H), 2.73 (s, 3H), 3.12 (dd, J=13.6, 4.8 Hz, 1H), 3.28 (dd, J=13.6, 8.0 Hz, 1H), 4.74 (ddd, J=8.0, 4.4, 4.0 Hz, 1H), 5.72 (d, J=4.4 Hz, 1H), 7.11–7.18 (m, 2H), 7.32 (s, 1H), 7.33–7.39 (m, 2H), 10.06 (s, 1H) 11.76 (s, 1H)

EXAMPLE 59

4-Fluoro-N-[3-{[2-(4-fluorophenyl)-2-hydroxyethyl]-methyl-sulfamoyl}-5-[(1Z)-hydroxyimino-ethyl]-thiophene-2-yl]benzamide From N-(5-acetyl-3-{[2-(4-fluorophenyl)-2-hydroxyethyl]-methyl-sulfamoyl}-thiophene-2-yl)-4-fluoro-benzamide (the compound of Preparation Example 102) (56 mg), the title compound (15 mg) was obtained as a colorless solid, in the same way as Example 1.

$^1$H-NMR (DMSO-$d_6$) δ: 2.22 (s, 3H), 2.79 (s, 3H), 3.17 (dd, J=14.0, 4.8 Hz, 1H), 3.26–3.34 (m, 1H), 4.70–4.77 (m, 1H), 5.65 (d, J=4.4 Hz, 1H), 7.05–7.12 (m, 2H), 7.29–7.36 (m, 3H), 7.41 (s, 1H), 7.44–7.51 (m, 2H), 7.90–7.96 (m, 2H), 10.86 (s, 1H) 11.89 (s, 1H)

EXAMPLE 60

2-Amino-5-[(1Z)-hydroxyimino-ethyl]-thiophene-3-sulfonic acid [2-(4-fluorophenyl)-ethyl]-methyl-amide From 5-acetyl-2-amino-thiophene-3-sulfonic acid [2-(4-fluorophenyl)-ethyl]-methyl-amide (the compound of Preparation Example 112) (84 mg), the title compound (27 mg) was obtained as a colorless solid, in the same way as Example 1.

$^1$H-NMR (DMSO-d$_6$) δ: 2.09 (s, 3H), 2.70 (s, 3H), 2.74–2.80 (m, 2H), 3.17–3.23 (m, 2H), 6.95–6.99 (m, 2H), 7.00 (s, 1H), 7.06–7.14 (m, 2H), 7.25–7.31 (m, 2H), 11.24 (s, 1H)

EXAMPLE 61

2-Amino-5-[(1E)-hydroxyimino-ethyl]-thiophene-3-sulfonic acid [2-(4-fluorophenyl)-ethyl]-methyl-amide From the reaction product of Example 60, the (E) isomer was isolated in the same way as Example 2, and the title compound (46 mg) was obtained as a colorless solid.

$^1$H-NMR (DMSO-d$_6$) δ: 2.02 (s, 3H), 2.70 (s, 3H), 2.75–2.81 (m, 2H), 3.18–3.23 (m, 1H), 6.87 (s, 1H), 6.99–7.04 (m, 2H), 7.07–7.13 (m, 2H), 7.25–7.31 (m, 2H), 10.92 (s, 1H)

EXAMPLE 62

2-Amino-5-[2-hydroxy-(1Z)-hydroxyimino-ethyl] thiophene-3-sulfonic acid[2-(4-fluorophenyl)-2-hydroxyethyl]-methyl-amide From acetic acid 2-(5-t-butoxycarbonyl-imino-4-{[2-(4-fluorophenyl)-2-t-butyldimethylsilyloxyethyl]methylsulfamoyl}-thiophene-2-yl)-2-oxoethylester (the compound of Preparation Example 103) (106 mg), the title compound (20 mg) was obtained as a brown solid, in the same way as the step that removes the protection group by trifluoroacetic acid in the later stage of Example 50, Example 51 and Example 34.

$^1$H-NMR (DMSO-d$_6$) δ: 2.68 (s, 3H), 2.98–3.17 (m, 2H), 4.26 (d, J=6.0 Hz, 2H), 4.69–4.79 (m, 1H), 5.23 (t, J=6.0 Hz, 1H), 5.60 (d, J=4.4 Hz, 1H), 6.97 (br s, 2H), 7.14 (t, J=8.8 Hz, 2H), 7.24 (s, 1H), 7.38 (dd, J=8.8 and 5.6 Hz, 2H), 11.45 (s, 1H)

EXAMPLE 63

2-Amino-5-[(1Z)-hydroxyimino-2-methylpropyl] thiophene-3-sulfonic acid[2-(4-fluorophenyl)ethyl]-methyl-amide From (3-{[2-(4-fluorophenyl)ethyl]methylsulfamoyl}-5-isobutyrylthiophen-2-yl)carbamic acid t-butyl ester (the compound of Preparation Example 104), the title compound (73 mg) was obtained as a pearl-grey solid, in the same way as Example 1, followed by the step that removes the protection group in the later stage of Example 34.

$^1$H-NMR (DMSO-d$_6$) δ: 1.11 (d, J=6.8 Hz, 6H), 2.67 (s, 3H), 2.75 (t, J=7.2 Hz, 2H), 2.96–3.08 (m, 1H), 3.17 (t, J=7.2 Hz, 2H), 6.76–7.00 (m, 2H), 7.02 (s, 1H), 7.08 (t, J=8.8 Hz, 2H), 7.25 (dd, J=8.8 and 5.6 Hz, 2H), 11.35 (br s, 1H)

MS m/e (ESI) 400.1 (MH$^+$)

EXAMPLE 64

2-Amino-5-(1-hydroxyimino-2-methylpropyl) thiophene-3-sulfonic acid[2-(4-fluorophenyl)-2-hydroxyethyl]-methyl-amide To a solution of (3-{[2-(4-fluorophenyl)-2-methoxymethoxyethyl]methylsulfamoyl}-5-isobutyryl-thiophene-2-yl)carbamic acid t-butyl ester (the compound of Preparation Example 108) (180 mg) in pyridine (1 mL) was added hydroxylamine.hydrochloride (46 mg). After stirring at 50° C. for 4.5 hours, the solution was diluted with ethyl acetate, and was washed with 5N hydrochloric acid, water and saturated sodium chloride water. The crude product that was obtained after drying with anhydrous sodium sulfate and removing the solvent by evaporation was purified by silica gel column chromatography (ethyl acetate/hexane), and oxime (137 mg) was obtained. Subsequently, a mixed solvent of tetrahydrofuran (1 mL) and 5N hydrochloric acid (1 mL) was treated by heat at 50° C. for 6 hours. After neutralizing with an aqueous solution (1 mL) of 5N sodium hydroxide and an aqueous solution of saturated sodium bicarbonate, the solution was extracted with ethyl acetate. The organic layer was dried with anhydrous sodium sulfate. The residue that was obtained upon removing the solvent by evaporation was purified by silica gel column chromatography (ethyl acetate/hexane), a ketone compound (38 mg) was obtained. In addition, the same oxime formation reaction as described above was carried out, and the title compound (22 mg), which was a mixture where (E):(Z)=1:3, was obtained as a pale yellow solid.

$^1$H-NMR (DMSO-d$_6$) δ: 1.02 and 1.11[each d, each J=6.8 Hz, 6H (1:3)], 2.20–3.50 (m, 3H), 2.67 and 2.71[each s, 3H (3:1)], 4.62–4.82 (m, 1H), 5.50–5.66 (m, 1H), 6.75–7.70 (m, 7H), 10.87 and 11.34[each s, 1H (1:3)]

EXAMPLE 65

2-Amino-5-[(1Z)-hydroxyimino-2-phenylethyl] thiophene-3-sulfonic acid[2-(4-fluorophenyl)-2-hydroxyethyl]-methyl-amide From (3-{[2-(4-fluorophenyl)-2-methoxymethoxyethyl]methylsulfamoyl}-5-phenyl acetylthiophene-2-yl)carbamic acid t-butyl ester (the compound of Preparation Example 109) (47 mg), the same oximation reaction as Example 64 was carried out, and the corresponding oxime compound (46 mg) was obtained. Thereafter, this compound was dissolved in trifluoroacetic acid (0.5 mL), and allowed to stand at room temperature for 10 minutes. The crude product that was obtained by removing the solvent by evaporation was purified by silica gel column chromatography (ethyl acetate/hexane). The title compound (10 mg) was obtained as an orange solid by solidification from diethyl ether-hexane.

$^1$H-NMR (DMSO-d$_6$) δ: 2.27–3.60 (m, 5H), 3.81 (s, 2H), 4.60–4.80 (m, 1H), 5.54 (d, J=2.8 Hz, 1H), 6.82–7.51 (m, 12H), 11.49 (s, 1H)

EXAMPLE 66

(7Z)-7-({[(3-Ethyl anilino)carbonyl]oxo}imino)-3-{[[2-(4-fluorophenyl)-2-hydroxyethyl](methyl) amino]sulfonyl}-4,5,6,7-tetrahydro-1-benzothiophene To a solution of (7Z)-7-hydroxyimino-4,5,6,7-tetrahydrobenzo[b]thiophene-3-sulfonic acid[2-(4-fluorophenyl)-2- hydroxyethyl]-methyl-amide (the compound of Example 1) (50 mg) and triethylamine (17 μL) in toluene (0.5 mL) was added a solution (0.5 mL) of 1-ethyl-3-isocyanate-benzene (18 μL) in toluene on an ice bath. After stirring for 30 minutes, the solvent was evaporated at reduced pressure, purification by silica gel column chromatography (dichloromethane/methanol; methanol 0–1%) was carried out, and the title compound (47 mg) was obtained as a colorless amorphous substance.

$^1$H-NMR (CD$_3$OD) δ: 1.24 (t, J=7.6 Hz, 3H), 1.99–2.08 (m, 2H), 2.64 (dd, J=7.6 Hz, 15.2 Hz, 2H), 2.73–2.79 (m, 2H), 2.89 (s, 3H), 2.94–3.01 (m, 2H), 3.32–3.37 (m, 2H), 4.81–4.87 (m, 1H), 6.95–6.99 (m, 1H), 7.01–7.08 (m, 2H), 7.21–7.27 (m, 1H), 7.33–7.42 (m, 4H), 8.41 (s, 1H)

From (7Z)-7-hydroxyimino-4,5,6,7-tetrahydro-benzo[b]thiophene-3-sulfonic acid[2-(4-fluorophenyl)-2-hydroxyethyl]-methyl-amide (the compound of Example 1) and isocyanate derivatives, the compounds described from Example 67 to Example 85 were synthesized, in the same way as Example 66.

EXAMPLE 67

(7Z)-3-{[[2-(4-Fluorophenyl)-2-hydroxyethyl](methyl)amino]-sulfonyl}-7-{[(2-toluidyl carbonyl)oxy]imino}-4,5,6,7-tetrahydro-1-benzothiophene From the compound (50 mg) of Example 1 and 1-isocyanate-2-methyl-benzene (15 μL), the title compound (30 mg) was obtained as a colorless solid.

$^1$H-NMR (CD$_3$OD) δ: 1.99–2.08 (m, 2H), 2.32 (s, 3H), 2.72–2.78 (m, 2H), 2.89 (s, 3H), 2.94–3.00 (m, 2H), 3.32–3.38 (m, 2H), 4.80–4.90 (m, 1H), 7.01–7.08 (m, 2H), 7.13–7.29 (m, 3H), 7.32–7.38 (m, 2H), 7.41–7.46 (m, 1H), 8.40 (brs, 1H)

EXAMPLE 68

(7Z)-3-{[[2-(4-Fluorophenyl)-2-hydroxyethyl](methyl)amino]-sulfonyl}-7-{[(3-toluidyl carbonyl)oxy]imino}-4,5,6,7-tetrahydro-1-benzothiophene From the compound (50 mg) of Example 1 and 1-isocyanate-3-methyl-benzene (16 μL), the title compound (55 mg) was obtained as a colorless amorphous substance.

$^1$H-NMR (CD$_3$OD) δ: 1.98–2.08 (m, 2H), 2.34 (s, 3H), 2.71–2.78 (m, 2H), 2.89 (s, 3H), 2.95–3.00 (m, 2H), 3.32–3.38 (m, 2H), 4.80–4.90 (m, 1H), 6.91–6.96 (m, 1H), 7.00–7.08 (m, 2H), 7.17–7.24 (m, 1H), 7.32–7.39 (m, 4H), 8.40 (s, 1H)

EXAMPLE 69

(7Z)-3-{[[2-(4-Fluorophenyl)-2-hydroxyethyl](methyl)amino]-sulfonyl}-7-{[(4-toluidyl carbonyl)oxy]imino}-4,5,6,7-tetrahydro-1-benzothiophene From the compound (60 mg) of Example 1 and 1-isocyanate-4-methyl-benzene (23 μL), the title compound (66 mg) was obtained as a colorless amorphous matter.

$^1$H-NMR (DMSO-d$_6$) δ: 1.89–1.98 (m, 2H), 2.24 (s, 3H), 2.65–2.73 (m, 2H), 2.81 (s, 3H), 2.83–2.90 (m, 2H), 3.16–3.25 (m, 2H), 4.70–4.76 (m, 1H), 5.63 (d, J=4.4 Hz, 1H), 7.09–7.17 (m, 4H), 7.30–7.37 (m, 2H), 7.39–7.45 (m, 2H), 8.59 (s, 1H), 9.71 (s, 1H)

EXAMPLE 70

(7Z)-3-{[[2-(4-Fluorophenyl)-2-hydroxyethyl](methyl)amino]-sulfonyl}-7-({[(2-methoxyanilino)carbonyl]oxy}imino)-4,5,6,7-tetrahydro-1-benzothiophene From the compound (60 mg) of Example 1 and 1-isocyanate-2-methoxy-benzene (24 μL), the title compound (41 mg) was obtained as a colorless solid.

$^1$H-NMR (DMSO-d$_6$) δ: 1.90–2.02 (br, 2H), 2.64–2.75 (br, 2H), 2.82 (s, 3H), 2.84–2.93 (br, 2H), 3.16–3.28 (br, 2H), 3.85 (s, 3H), 4.70–4.78 (m, $_1$H), 5.64 (d, J=4.0 Hz, 1H), 6.90–7.01 (m, 1H), 7.04–7.18 (m, 4H), 7.29–7.38 (m, 2H), 7.76–7.83 (m, 1H), 8.58 (s, 1H), 9.01 (s, 1H)

EXAMPLE 71

(7Z)-3-{[[2-(4-Fluorophenyl)-2-hydroxyethyl](methyl)amino]-sulfonyl}-7-({[(3-methoxyanilino)carbonyl]oxy}imino)-4,5,6,7-tetrahydro-1-benzothiophene From the compound (60 mg) of Example 1 and 1-isocyanate-3-methoxy-benzene (24 μL), the title compound (67 mg) was obtained as a colorless amorphous matter.

$^1$H-NMR (DMSO-d$_6$) δ: 1.90–2.00 (m, 2H), 2.66–2.73 (m, 2H), 2.82 (s, 3H), 2.84–2.90 (m, 2H), 3.20–3.25 (m, 2H), 3.72 (s, 3H), 4.70–4.76 (m, 1H), 5.63 (d, J=4.4 Hz, $_1$H), 6.62–6.67 (m, 1H), 7.09–7.25 (m, 5H), 7.30–7.36 (m, 2H), 8.60 (s, 1H), 9.82 (s, 1H)

EXAMPLE 72

(7Z)-3-{[[2-(4-Fluorophenyl)-2-hydroxyethyl](methyl)amino]-sulfonyl}-7-({[(4-methoxyanilino)carbonyl]oxy}imino)-4,5,6,7-tetrahydro-1-benzothiophene From the compound (120 mg) of Example 1 and 46 μL of 1-isocyanate-4-methoxy-benzene (46 μL), the title compound (128 mg) was obtained as a colorless amorphous matter.

$^1$H-NMR (CD$_3$OD) δ: 2.00–2.08 (m, 2H), 2.73–2.79 (m, 2H), 2.90 (s, 3H), 2.95–3.00 (m, 2H), 3.33–3.38 (m, 2H), 3.79 (s, 3H), 4.82–4.87 (m, 1H), 6.88–6.74 (m, 2H), 7.01–7.08 (m, 2H), 7.32–7.39 (m, 2H), 7.40–7.46 (m, 2H), 8.40 (s, 1H)

EXAMPLE 73

(7Z)-7-({[(4-Ethoxyanilino)carbonyl]oxo}imino)-3-{[[2-(4-fluoro-phenyl)-2-hydroxyethyl](methyl)amino]sulfonyl}-4,5,6,7-tetrahydro-1-benzothiophene From the compound (60 mg) of Example 1 and 1-ethoxy-4-isocyanate-benzene (27 μL), the title compound (66 mg) was obtained as a colorless amorphous matter.

$^1$H-NMR (DMSO-d$_6$) δ: 1.13 (t, J=7.0 Hz, 3H), 1.92–2.01 (m, 2H), 2.67–2.74 (m, 2H), 2.83 (s, 3H), 2.86–2.93 (m, 2H), 3.19–3.28 (m, 2H), 3.99 (dd, J=6.9 Hz, 14.0 Hz, 2H), 4.72–4.78 (m, 1H), 5.65 (d, J=4.4 Hz, 1H), 6.88–6.93 (m, 2H), 7.12–7.18 (m, 2H), 7.32–7.38 (m, 2H), 7.41–7.46 (m, 2H), 8.60 (s, 1H), 9.64 (s, 1H)

EXAMPLE 74

(7Z)-7-({[(2-Fluoroanilino)carbonyl]oxo}imino)-3-{[[2-(4-fluoro-phenyl)-2-hydroxyethyl](methyl)amino]sulfonyl}-4,5,6,7-tetrahydro-1-benzothiophene From the compound (50 mg) of Example 1 and 1-fluoro-2-isocyanate-benzene (16 μL), the title compound (50 mg) was obtained as a colorless solid.

$^1$H-NMR (CD$_3$OD) δ: 2.02–2.13 (m, 2H), 2.75–2.81 (m, 2H), 2.92 (s, 3H), 2.97–3.03 (m, 2H), 3.33–3.38 (m, 2H), 4.86–4.91 (m, 1H), 7.00–7.06 (m, 2H), 7.11–7.21 (m, 3H), 7.31–7.37 (m, 2H), 7.97–8.06 (m, 1H), 8.31 (s, 1H)

EXAMPLE 75

(7Z)-7-({[(4-Fluoroanilino)carbonyl]oxo}imino)-3-{[[2-(4-fluoro-Phenyl)-2-hydroxyethyl](methyl)amino]sulfonyl}-4,5,6,7-tetrahydro-1-benzothiophene From the compound (120 mg) of Example 1 and 4-fluoro-4-isocyanate-benzene (34 μL), the title compound (102 mg) was obtained as a colorless amorphous matter.

$^1$H-NMR (CD$_3$OD) δ: 2.01–2.08 (m, 2H), 2.54–2.79 (m, 2H), 2.90 (s, 3H), 2.95–3.00 (m, 2H), 3.33–3.38 (m, 2H), 4.84–4.88 (m, 1H), 7.01–7.12 (m, 4H), 7.32–7.39 (m, 3H), 7.52–7.58 (m, 2H), 8.41 (s, 1H)

EXAMPLE 76

(7Z)-7-({[(3-Cyanoanilino)carbonyl]oxo}imino)-3-{[[2-(4-fluoro-Phenyl)-2-hydroxyethyl](methyl)amino]sulfonyl}-4,5,6,7-tetrahydro-1-benzothiophene From the compound (50 mg) of Example 1 and 3-isocyanate-benzo nitrile (18 mg), the title compound (63 mg) was obtained as a colorless amorphous matter.

$^1$H-NMR (CD$_3$OD) δ: 2.00–2.09 (m, 2H), 2.74–2.80 (m, 2H), 2.90 (s, 3H), 2.95–3.01 (m, 2H), 3.33–3.38 (m, 2H), 4.81–4.92 (m, 1H), 7.00–7.10 (m, 1H), 7.32–7.39 (m, 2H), 7.41–7.60 (m, 2H), 7.84–7.88 (m, 1H), 7.98–8.01 (m, 1H), 8.43 (s, 1H)

EXAMPLE 77

(7Z)-7-({[(4-Cyanoanilino)carbonyl]oxo}imino)-3-{[[2-(4-fluoro-phenyl)-2-hydroxyethyl](methyl)amino]sulfonyl}-4,5,6,7-tetrahydro-1-benzothiophene From the compound (50 mg) of Example 1 and 4-isocyanate-benzo nitrile (18 mg), a colorless solid of the title compound (24 mg) was obtained.

$^1$H-NMR (CD$_3$OD) δ: 2.03–2.12 (m, 2H), 2.76–2.82 (m, 2H), 2.91 (s, 3H), 2.96–3.02 (m, 2H), 3.31–3.38 (m, 2H), 4.85–4.91 (m, 1H), 6.99–7.06 (m, 2H), 7.31–7.37 (m, 2H), 7.63–7.68 (m, 2H), 7.75–7.78 (m, 2H), 8.33 (s, 1H)

EXAMPLE 78

(7Z)-7-({[(2,4-Dimethylanilino)carbonyl]oxo}imino)-3-{[[2-(4-fluoro-phenyl)-2-hydroxyethyl](methyl)amino]sulfonyl}-4,5,6,7-tetrahydro-1-benzothiophene From the compound (50 mg) of Example 1 and 1-isocyanate-2,4-dimethyl-benzene (17 μL), the title compound (68 mg) was obtained as a colorless solid.

$^1$H-NMR (CD$_3$OD) δ: 2.01–2.11 (m, 2H), 2.29 (s, 3H), 2.31 (s, 3H), 2.73–2.79 (m, 2H), 2.91 (s, 3H), 2.93–3.02 (m, 2H), 3.30–3.42 (m, 2H), 4.84–4.90 (t, J=6.4 Hz, 1H), 6.97–7.07 (m, 4H), 7.31–7.40 (m, 3H), 8.32 (brs, 1H)

EXAMPLE 79

(7Z)-7-({[(3,4-Dimethoxyanilino)carbonyl]oxo}imino)-3-{[[2-(4-fluorophenyl)-2-hydroxyethyl](methyl)amino]sulfonyl}-4,5,6,7-tetrahydro-1-benzothiophene From the compound (50 mg) of Example 1 and 4-isocyanate-1,2-dimethoxy-benzene (18 μL), the title compound (33 mg) was obtained as a colorless amorphous substance.

$^1$H-NMR (CD$_3$OD) δ: 1.98–2.07 (m, 2H), 2.72–2.78 (m, 2H), 2.89 (s, 3H), 2.94–3.00 (m, 2H), 3.28–3.37 (m, 2H), 3.81 (s, 3H), 3.83 (s, 3H), 4.80–4.88 (m, 1H), 6.92 (d, J=8.8 Hz, 1H), 7.01–7.10 (m, 3H), 7.24 (d, J=2.4 Hz, 1H), 7.32–7.38 (m, 2H), 8.40 (s, 1H)

EXAMPLE 80

(7Z)-7-({[(2,4-Dimethoxyanilino)carbonyl]oxo}imino)-3-{[[2-(4-fluorophenyl)-2-hydroxyethyl](methyl)amino]sulfonyl}-4,5,6,7-tetrahydro-1-benzothiophene From the compound (50 mg) of Example 1 and 1-isocyanate-2,4-dimethoxy-benzene (22 mg), the title compound (50 mg) was obtained as a colorless amorphous matter.

$^1$H-NMR (CD$_3$OD) δ: 1.99–2.08 (m, 2H), 2.71–2.77 (m, 2H), 2.89 (s, 3H), 2.94–3.00 (m, 2H), 3.32–3.38 (m, 2H), 3.79 (s, 3H), 3.88 (s, 3H), 4.82–4.88 (m, 1H), 6.51 (dd, J=2.6 Hz, 9.0 Hz, 1H), 6.61 (d, J=2.4 Hz, 1H), 6.99–7.09 (m, 2H), 7.32–7.38 (m, 2H), 7.64–7.78 (br, 1H), 8.40 (brs, 1H)

EXAMPLE 81

(7Z)-3-{[[2-(4-Fluorophenyl)-2-hydroxyethyl](methyl)amino]-sulfonyl}-7-[({[3,4-(methylenedioxy)anilino]carbonyl}oxy)imino]-4,5,6,7-tetrahydro-1-benzothiophene From the compound (50 mg) of Example 1 and 5-isocyanate-benzo[1,3]dioxol (20 mg), the title compound (46 mg) was obtained as a colorless amorphous matter.

$^1$H-NMR (CD$_3$OD) δ: 1.99–2.08 (m, 2H), 2.71–2.78 (m, 2H), 2.90 (s, 3H), 2.94–3.00 (m, 2H), 3.28–3.38 (m, 2H), 4.82–4.89 (m, 1H), 5.94 (s, 2H), 6.78 (d, J=8.4 Hz, 1H), 6.93 (dd, J=2.0 Hz, 8.4 Hz, 1H), 7.00–7.09 (m, 2H), 7.15 (d, J=1.6 Hz, 1H), 7.32–7.38 (m, 2H), 8.40 (s, 1H)

EXAMPLE 82

(7Z)-7-({[(Cyclohexylamino)carbonyl]oxo}imino)-
3-{[[2-(4-fluoro-1phenyl)-2-hydroxyethyl](methyl)
amino]sulfonyl}-4,5,6,7-tetrahydro-1-ben-
zothiophene From the compound (30 mg) of Example 1 and isocyanate-cyclohexane (28 μL), the title compound (31 mg) was obtained as a colorless oily matter.

$^1$H-NMR (CD$_3$OD) δ: 1.16–1.46 (m, 6H), 1.62–2.06 (m, 6H), 2.68–2.74 (m, 2H), 2.89 (s, 3H), 2.92–2.98 (m, 2H), 3.32–3.37 (m, 2H), 3.44–3.60 (br, 1H), 4.82–4.89 (m, 1H), 7.00–7.07 (m, 2H), 7.32–7.37 (m, 2H), 8.38 (s, 1H)

EXAMPLE 83

(7z)-7-({[(Ethylamino)carbonyl]oxo}imino)-3-{[[2-(4-fluorophenyl)-2-hydroxyethyl](methyl)amino]
sulfonyl}-4,5,6,7-tetrahydro-1-benzothiophene From the compound (50 mg) of Example 1 and isocyanate-ethane (71 mg), the title compound (45 mg) was obtained as a colorless amorphous substance.

$^1$H-NMR (DMSO-d$_6$) δ: 1.08 (t, J=7.2 Hz, 3H), 1.89–1.98 (m, 2H), 2.62–2.69 (m, 2H), 2.82 (s, 3H), 2.83–2.90 (m, 2H), 3.10–3.18 (m, 2H), 3.21–3.26 (m, 2H), 4.70–4.78 (m, 1H), 5.64 (d, J=4.4 Hz, 1H), 7.10–7.18 (m, 2H), 7.31–7.38 (m, 2H), 7.58 (t, J=5.6 Hz, 1H), 8.55 (s, 1H)

EXAMPLE 84

(7Z)-3-{[[2-(4-Fluorophenyl)-2-hydroxyethyl](methyl)amino]-sulfonyl}-7-({[(isopropylamino)carbonyl]oxy}imino)-4,5,6,7-tetrahydro-1-benzothiophene From the compound (50 mg) of Example 1 and 2-isocyanate-propane (85 mg), the title compound (45 mg) was obtained as a colorless amorphous substance.

$^1$H-NMR (DMSO-d$_6$) δ: 1.13 (d, J=6.4 Hz, 6H), 1.87–1.97 (m, 2H), 2.61–2.67 (m, 2H), 2.80 (s, 3H), 2.82–2.87 (m, 2H), 3.18–3.24 (m, 2H), 3.66–3.79 (m, 1H), 4.68–4.76 (m, 1H), 5.62 (d, J=4.4 Hz, 1H), 7.08–7.15 (m, 2H), 7.28–7.36 (m, 3H), 8.52 (s, 1H)

EXAMPLE 85

(7Z)-7-({[(Benzylamino)carbonyl]oxo}imino)-3-
{[[2-(4-fluoro-phenyl)-2-hydroxyethyl](methyl)
amino]sulfonyl}-4,5,6,7-tetrahydro-1-ben-
zothiophene From the compound (50 mg) of Example 1 and isocyanate methyl-benzene (41 mg), the title compound (63 mg) was obtained as a colorless amorphous substance.

$^1$H-NMR (DMSO-d$_6$) δ: 1.89–1.99 (m, 2H), 2.63–2.69 (m, 2H), 2.82 (s, 3H), 2.84–2.90 (m, 2H), 3.21–3.26 (m, 2H), 4.28–4.34 (m, 2H), 4.71–4.78 (m, 1H), 5.64 (d, J=4.4 Hz, 1H), 7.10–7.18 (m, 2H), 7.22–7.28 (m, 1H), 7.28–7.39 (m, 6H), 8.18 (t, J=6.0 Hz, 1H), 8.57 (s, 1H)

EXAMPLE 86

(7Z)-7-({[(Dimethylamino)carbonyl]oxy}imino)-3-
{[[2-(4-fluoro-phenyl)-2-hydroxyethyl](methyl)
amino]sulfonyl}-4,5,6,7-tetrahydro-1-ben-
zothiophene 7-Oxo-4,5,6,7-tetrahydro-benzo[b]thiophene-3-sulfonic acid [2-(4-fluorophenyl)-2-hydroxyethyl]-methyl-amide (the compound of Preparation Example 48) (60 mg) and [[(aminooxy)carbonyl](methyl)amino]methane hydrochloride (the compound of Preparation Example 122) (24 mg) were stirred in acetic acid at 50° C. for 3 hours. The residue resulting from the removal of the solvent by evaporation was purified by silica gel column chromatography (hexane/ethyl acetate). Among the two spots that were identifeid by developing the reaction solution by TLC (solvent system was hexane:ethyl acetate=1:3), the fraction of the compound with a high polarity (low Rf value) was collected, and the title compound (9 mg) was obtained as a colorless amorphous substance.

$^1$H-NMR (DMSO-d$_6$) δ: 1.92 (m, 2H), 2.64 (m, 2H), 2.81 (s, 3H), 2.85 (m, 2H), 2.9 (brs, 3H), 3.1 (brs, 3H), 3.2 (m, 2H), 4.7 (m, 1H), 5.63 (d, J=4.8 Hz, 1H), 7.12 (m, 2H), 7.33 (m, 2H), 8.50 (s, 1H)

EXAMPLE 87

(7Z)-7-{[(Aminocarbonyl)oxy]imino}-3-{[[2-(4-
fluorophenyl)-2-hydroxyethyl](methyl)amino]sulfo-
nyl}-4,5,6,7-tetrahydro-1-benzothiophene a)(7Z)-7-({[(Trimethylsilylamino)carbonyl]
oxy}imino)-3-({[2-(4-fluorophenyl)-2-hydroxyethyl]
(methyl)amino]sulfonyl)-4,5,6,7-tetrahydro-1-ben-
zothiophene To a solution of the compound (1.0 g) of Example 1 in toluene (10 mL) was added triethylamine (1.75 mL) and trimethylsilyl isocyanate. After stirring at room temperature for 2 hours, the solution was diluted with ethyl acetate, and the resulting insoluble matter was extracted, the crude product that were obtained by removing the solvent by evaporation was purified by NH-silica gel column chromatography (ethyl acetate/hexane), and a pale yellow oily substance (1.0 g) was obtained.

$^1$H-NMR (CDCl$_3$) δ: 0.06 (s, 9H), 1.88–2.08 (m, 2H), 2.52–2.69 (m, 2H), 2.84 (s, 3H), 2.87–3.03 (m, 2H), 3.17 (dd, J=14.4 and 8.0 Hz, 1H), 3.31 (dd, J=14.4 and 4.4 Hz, 1H), 4.93 (dd, J=8.0 and 4.4 Hz, 1H), 7.02 (t, J=8.8 Hz, 2H), 7.31 (dd, J=8.8 and 5.6 Hz, 2H), 8.05 (s, 1H)

b) Title Compound

To a solution of the above-mentioned compound (1.0 g) in tetrahydrofuran (6 mL) was added dropwise a mixture of a solution (2.3 mL) of 1.0M tetrabutylammonium fluoride-tetrahydrofuran and acetic acid (0.13 mL). After stirring at room temperature for 30 minutes, the crude product that was obtained by removing the solvent by evaporation was purified by silica gel column chromatography (ethyl acetate/hexane and dichloromethane/methanol), and the title compound (827 mg) was obtained as a pale yellow solid.

¹H-NMR (CDCl₃) δ: 1.91–2.08 (m, 2H), 2.55–2.66 (m, 2H), 2.79 (brs, 1H), 2.91 (s, 3H), 2.93–3.04 (m, 2H), 3.23 (dd, J=14.4 and 3.6 Hz, 1H), 3.36 (dd, J=14.4 and 8.4 Hz, 1H), 4.89–5.00 (m, 1H), 7.05 (t, J=8.8 Hz, 2H), 7.35 (dd, J=8.8 and 5.2 Hz, 2H), 8.11 (s, 1H)

EXAMPLE 88

(7Z)-7-{[(2,2-Dimethylpropanoyl)oxy]imino}-N-[2-(4-fluorophenyl)-2-hydroxyethyl]-N-methyl-4,5,6,7-tetrahydro-1-benzothiophene-3-sulfonamide To a solution of the compound (30 mg) of Example 1 and triethylamine (18 μL) in dichloromethane (10 mL) was added dropwise pivaloyl chloride (13 mg) in dichloromethane (1 mL) on an ice bath. After stirring for 30 minutes, the solvent was removed at reduced pressure, the residue was purified by silica gel column chromatography (hexane/ethyl acetate), and the title compound (35 mg) was obtained as a colorless amorphous substance.

¹H-NMR (DMSO-d₆) δ: 1.90–1.99 (m, 2H), 2.64–2.70 (m, 2H), 2.83 (s, 3H), 2.84–2.90 (m, 2H), 3.21–3.26 (m, 2H), 4.71–4.78 (m, 1H), 5.65 (d, J=4.4 Hz, 1H), 7.00–7.17 (m, 2H), 7.32–7.38 (m, 2H), 8.59 (s, 1H)

EXAMPLE 89

(7E)-7-({[(Dimethylamino)carbonyl]oxy}imino)-3-{[[2-(4-fluoro-phenyl)-2-hydroxyethyl](methyl)amino]sulfonyl}-4,5,6,7-tetrahydro-1-benzothiophene The fraction of the compound that demonstrated a lower polarity (high Rf value) by TLC in the reaction of Example 86 was collected, and the title compound (29 mg) was obtained as a colorless amorphous substance.

¹H-NMR (DMSO-d₆) δ: 1.86 (m, 2H), 2.7 (m, 4H), 2.80 (s, 3H), 2.88 (brs, 3H), 2.90 (brs, 3H), 3.2 (m, 2H), 4.7 (m, 1H), 5.63 (d, J=4.4 Hz, 1H), 7.13 (m, 2H), 7.33 (m, 2H), 8.28 (s, 1H)

EXAMPLE 90

4-{2-[{[(7Z)-7-({[(Ethylamino)carbonyl]oxy}imino)-4,5,6,7-tetrahydro-1-benzothien-3-yl]sulfonyl}(methyl)amino]-1-hydroxyethyl}pyridine From (E)-7-hydroxyimino-4,5,6,7-tetrahydro-benzo[b]thiophene-3-sulfonic acid (2-hydroxy-2-pyridine-4-yl-ethyl)-methyl-amide (Example 21 compound) (30 mg) and isocyanate-ethane (50 μL), the title compound (31 mg) was obtained as a colorless solid, in the same way as Example 66.

¹H-NMR (DMSO-d₆) δ: 1.08 (t, J=7.2 Hz, 3H), 1.88–1.98 (m, 2H), 2.52–2.68 (m, 2H), 2.83–2.90 (m, 5H), 3.09–3.18 (m, 2H), 3.25–3.30 (m, 2H), 4.74–4.82 (m, 1H), 5.23 (d, J=4.4 Hz, 1H), 7.30–7.34 (m, 2H), 7.58 (t, J=5.6 Hz, 1H), 8.47–8.51 (m, 2H), 8.55 (s, 1H)

From the reaction between 2-amino-5-[(1 Z)-hydroxyimino-ethyl]-thiophene-3-sulfonic acid [2-(4-fluorophenyl)-2-hydroxyethyl]-methyl-amide (the compound of Example 52) and isocyanate derivatives, the compounds described below in Example 91 to Example 94 were obtained, in the same way as Example 66.

EXAMPLE 91

2-Amino-5-((1Z)-N-{[(cyclohexylamino)carbonyl]oxy}ethane imidoyl)-3-{[[2-(4-fluorophenyl)-2-hydroxyethyl](methyl)amino]-sulfonyl}thiophene From the compound (80 mg) of Example 52 and isocyanate-cyclohexane (50 μL), the title compound (50 mg) was obtained as a colorless solid.

¹H-NMR (DMSO-d₆) δ: 1.07–1.34 (m, 5H), 1.52–1.84 (m, 5H), 2.20 (s, 3H), 2.72 (s, 3H), 3.06–3.20 (m, 2H), 3.28–3.40 (m, 1H), 4.72–4.78 (m, 1H), 5.60 (d, J=4.4 Hz, 1H), 7.09–7.19 (m, 4H), 7.26–7.42 (m, 4H)

EXAMPLE 92

2-Amino-5-((1Z)-N-{[(4-fluoro anilino)carbonyl]oxy}ethane imidoyl)-3-{[[2-(4-fluorophenyl)-2-hydroxyethyl](methyl)amino]-sulfonyl}thiophene From the compound (40 mg) of Example 52 and 1-fluoro-4-isocyanate-benzene (28 mg), the title compound (40 mg) was obtained as a colorless amorphous matter.

¹H-NMR (DMSO-d₆) δ: 2.31 (s, 3H), 2.73 (s, 3H), 3.07–3.22 (m, 2H), 4.73–4.79 (m, 1H), 5.63 (d, J=4.4 Hz, 1H), 7.12–7.21 (m, 4H), 7.34 (s, 1H), 7.37–7.43 (m, 3H), 7.53–7.58 (m, 2H), 9.80 (s, 1H)

EXAMPLE 93

2-Amino-5-((1Z)-N-{[(2,4-difluoro anilino)carbonyl]oxy}ethane imidoyl)-3-{[[2-(4-fluorophenyl)-2-hydroxyethyl](methyl)amino]-sulfonyl}thiophene From the compound (40 mg) of Example 52 and 2,4-difluoro-1-isocyanate-benzene (32 mg), the title compound (39 mg) was obtained as a colorless solid.

¹H-NMR (DMSO-d₆) δ: 2.31 (s, 3H), 2.73 (s, 3H), 3.07–3.22 (m, 2H), 4.73–4.79 (m, 1H), 5.63 (d, J=4.4 Hz, 1H), 7.07–7.19 (m, 3H), 7.32–7.45 (m, 4H), 7.54–7.62 (m, 1H), 9.40 (s, 1H)

EXAMPLE 94

2-Amino-5-((1Z)-N-{[(ethylamino)carbonyl]oxy}ethane imidoyl)-3-{[[2-(4-fluorophenyl)-2-hydroxyethyl](methyl)amino]-sulfonyl}thiophene From the compound (52 mg) of Example 52 and isocyanate-ethane (15 mg), the title compound (14 mg) was obtained as a colorless solid.

¹H-NMR (DMSO-d₆) δ: 1.07 (t, J=7.2 Hz, 3H), 2.25 (s, 3H), 2.72 (s, 3H), 3.06–3.22 (m, 4H), 4.72–4.78 (m, 1H), 5.62 (d, J=4.4 Hz, 1H), 7.12–7.19 (m, 2H), 7.28 (s, 1H), 7.33–7.42 (m, 2H), 7.43–7.48 (m, 1H)

EXAMPLE 95

2-Amino-5-((1E)-N-{[(cyclohexylamino)carbonyl]oxy}ethane imidoyl)-3-{[[2-(4-fluorophenyl)-2-hydroxyethyl](methyl)amino]-sulfonyl}thiophene From 2-amino-5-[(1E)-hydroxyimino-ethyl]-thiophene-3-sulfonic acid[2-(4-fluorophenyl)-2-hydroxyethyl]-methyl-amide (the compound of Example 53) (120 mg) and isocyanate-cyclohexane (80 μL), the title compound (69 mg) was obtained as a colorless amorphous matter, in the same way as Example 66.

$^1$H-NMR (DMSO-d$_6$) δ: 1.03–1.38 (m, 5H), 1.52–1.84 (m, 5H), 2.25 (s, 3H), 2.72 (s, 3H), 3.06–3.22 (m, 2H), 3.28–3.42 (m, $_1$H), 4.72–4.79 (m, 1H), 5.62 (d, J=4.4 Hz, 1H), 7.11–7.19 (m, 3H), 7.28 (s, 1H), 7.33–7.43 (m, 4H)

EXAMPLE 96

5-(1-Hydroxyimino-ethyl)-thiophene-3-carboxylic acid [2-(4-fluorophenyl)-ethyl]-methyl-amide From 5-acetyl-thiophene-3-carboxylic acid [2-(4-fluorophenyl)-ethyl]-methyl-amide (the compound of Preparation Example 119) (80 mg), the same reaction as Example 1 was carried out, and the title compound (75 mg) was obtained as an (E), (Z) mixture of oxime compounds (colorless film).

MS m/e (ESI) 342.89 (MNa$^+$)

EXAMPLE 97

4-(1-Hydroxyimino-ethyl)-thiophene-2-carboxylic acid [2-(4-fluorophenyl)-ethyl]-methyl-amide From 4-acetyl-thiophene-2-carboxylic acid [2-(4-fluorophenyl)-ethyl]-methyl-amide (the compound of Preparation Example 120) (80 mg), the same reaction as Example 1 was carried out, and the title compound (82 mg) was obtained as an (E), (Z) mixture of oxime compounds (oily substance).

$^1$H-NMR (CDCl$_3$) δ: 2.22 (s, 3H), 2.91 (t, J=7.2 Hz, 2H), 3.10 (s, 3H), 3.70 (t, J=7.4 Hz, 2H), 6.95 (t, J=8.4 Hz, 2H), 7.14 (br, 2H), 7.50 (s, 1H), 7.57 (s, 1H)

EXAMPLE 98

5-(1-Hydroxyimino-ethyl)-thiophene-2-carboxylic acid [2-(4-fluorophenyl)-ethyl]-methyl-amide From 5-acetyl-thiophene-2-carboxylic acid [2-(4-fluorophenyl)-ethyl]-methyl-amide (the compound of Preparation Example 121) (80 mg), the same reaction as Example 1 was carried out, and the title compound (80 mg) was obtained as an (E), (Z) mixture of oxime compounds (oily substance).

MS m/e (ESI) 342.89 (MNa$^+$)

EXAMPLE 99

(7Z)-7-Hydroxyimino-4,5,6,7-tetrahydrobenzo[b]thiophene-3-carboxylic acid ethyl amide A solution of 7-oxo-4,5,6,7-tetrahydrobenzo[b]thiophene-3-carboxylic acid ethyl amide (the compound of Preparation Example 115) (96 mg) in ethanol (2 mL) and water (1 mL) was added hydroxylamine.hydrochloride (39 mg) and 46 mg of sodium acetate (46 mg). After heating at 50° C. for 4.5 hours, the reaction solution was cooled to room temperature, the solid that precipitated was collected by filtration, and the title compound (36 mg) was obtained as a colorless solid.

$^1$H-NMR (CDCl$_3$-DMSO-d$_6$) δ: 1.07 (t, J=7.2 Hz, 3H), 1.73–1.88 (m, 2H), 2.41–2.55 (m, 2H), 2.84–2.96 (m, 2H), 3.18–3.31 (m, 2H), 6.73–6.88 (m, 1H), 7.66 (s, 1H), 10.70 (s, 1H)

EXAMPLE 100

(7Z)-7-Hydroxyimino-4,5,6,7-tetrahydrobenzo[b]thiophene-3-carboxylic acid ethyl-methyl-amide From 7-oxo-4,5,6,7-tetrahydrobenzo[b]thiophene-3-carboxylic acid ethyl-methyl-amide (the compound of Preparation Example 116) (92 mg), the same reaction as Example 99 was carried out. Purification by silica gel column chromatography (dichloromethane/methanol), then solidification in t-butylmethyl ether-hexane was carried out, and the title compound (42 mg) was obtained as a yellow solid.

$^1$H-NMR (CDCl$_3$) δ: 1.02–1.35 (m, 2H), 1.91–2.07 (m, 2H), 2.57–2.72 (m, 2H), 2.73–2.84 (m, 2H), 2.86–3.18 (m, 3H), 3.20–3.70 (m, 1H), 7.46 (s, 1H)

Synthesis for Example 101-Example 140 was by the method described below.

To a solution of 7-oxo-4,5,6,7-tetrahydrobenzo[b]thiophene-3-carboxylic acid (the compound of Preparation Example 4) (180 mg) in dichloromethane (4 ml) was added two drops of N,N-dimethylformamide, oxalyl chloride (160 μL) was added dropwise, and the solution was stirred at room temperature for 30 minutes. The solvent was removed by evaporation, and the corresponding acid chloride was obtained. This acid chloride was reacted with an amine by method α or method β to prepare an amide.

<method α> The above-mentioned acid chloride was dissolved in pyridine (6 mL), among which one milliliter was stirred with an amine (2 equivalents) for 1 hour. After removing the solvent by evaporation, the solution was diluted with 1N hydrochloric acid or water, extracted with ethyl acetate, and the organic layer was evaporated in vacuo.

<method β> The above-mentioned acid chloride was dissolved in tetrahydrofuran (6 mL), of which one milliliter was added dropwise to a mixed solvent of an aqueous solution (1 mL) of unsaturated sodium bicarbonate and tetrahydrofuran (1 mL) containing an amine (2 equivalents). After stirring for 30 minutes to 1 hour, the solution was diluted with water, extracted with ethyl acetate, and the organic layer was evaporated by vacuo.

Ethanol (1 mL), water (0.5 mL), hydroxylamine hydrochloride (15 mg) and sodium acetate (18 mg) were added to the amide compound that was obtained by <method α> or <method β>. The solution was heated at 50° C. overnight. In the following Examples, when there is no particular description of the purification procedure, target compound was obtained by collecting the solid that was generated upon cooling the reaction solution to room temperature by filtration.

EXAMPLE 101

(7Z)-7-Hydroxyimino-4,5,6,7-tetrahydrobenzo[b]thiophene-3-carboxylic acid (4-fluorophenyl)amide 4-Fluorophenethylamine was used for the amine to carry out the reaction according to <method α>. After purification with LC-MS, the title compound (2.3 mg) was obtained as a colorless solid.

$^1$H-NMR (CDCl$_3$-DMSO-d$_6$) δ: 1.80–1.90 (m, 2H), 2.40–2.55 (m, 2H), 2.93–3.00 (m, 2H), 6.88 (t, J=8.4 Hz, 2H), 7.56 (dd, J=8.8 and 4.8 Hz, 1H), 7.92 (s, 1H), 9.32 (s, 1H), 10.76 (s, 1H)

EXAMPLE 102

(7Z)-7-Hydroxyimino-4,5,6,7-tetrahydrobenzo[b]
thiophene-3-carboxylic acid 4-fluoro benzyl amide 4-Fluorobenzylamine was used for the amine to carry out the reaction according to <method α>. The title compound (16 mg) was obtained as a slightly yellow solid.

$^1$H-NMR (CDCl$_3$-DMSO-d$_6$) δ: 1.80–1.95 (m, 2H), 2.49–2.59 (m, 2H), 2.94–3.05 (m, 2H), 4.46 (d, J=6.0 Hz, 2H), 6.93 (t, J=8.4 Hz, 2H), 7.02–7.14 (m, 1H), 7.18–7.32 (m, 2H), 7.76 (s, 1H), 10.48 (s, 1H)

EXAMPLE 103

(7Z)-7-Hydroxyimino-4,5,6,7-tetrahydrobenzo[b]
thiophene-3-carboxylic acid[2-(4-fluorophenyl)
ethyl]amide 4-Fluorophenethylamine was used as the amine to carry out the reaction according to <method α>. The title compound (15 mg) was obtained as a slightly yellow solid.

$^1$H-NMR (CDCl$_3$-DMSO-d$_6$) δ: 1.79–1.90 (m, 2H), 2.45–2.54 (m, 2H), 2.79 (t, J=7.2 Hz, 2H), 2.89 (t, J=6.0 Hz, 2H), 3.44–3.54 (m, 2H), 6.62–6.76 (m, 1H), 6.88 (t, J=8.4 Hz, 2H), 7.09 (dd, J=8.4 and 5.2 Hz, 2H), 7.60 (s, 1H), 10.61 (s, 1H)

EXAMPLE 104

(7Z)-7-Hydroxyimino-4,5,6,7-tetrahydrobenzo[b]
thiophene-3-carboxylic acid [(2-(3-fluorophenyl)
ethyl)]amide 3-Fluorophenethylamine was used as the amine to carry out the reaction according to <method β>. The title compound (20 mg) was obtained as a pale yellow solid.

$^1$H-NMR (DMSO-d$_6$) δ: 1.75–1.90 (m, 2H), 2.35–2.60 (m, 2H), 2.74–2.93 (m, 4H), 3.38–3.52 (m, 2H), 6.94–7.16 (m, 3H), 7.26–7.40 (m, 1H), 7.96 (s, 1H), 8.21–8.38 (m, 1H), 11.39 (s, 1H)

EXAMPLE 105

(7Z)-7-Hydroxyimino-4,5,6,7-tetrahydrobenzo[b]
thiophene-3-carboxylic acid cyclopentyl amide Cyclopentylamine was used as the amine to carry out the reaction according to <method α>. The title compound (10 mg) was obtained as a slightly yellow solid.

$^1$H-NMR (CDCl$_3$-DMSO-d$_6$) δ: 1.30–1.97 (m, 10H), 2.38–2.53 (m, 2H), 2.90 (t, J=6.4 Hz, 2H), 4.21–4.24 (m, 1H), 6.43–6.58 (m, 1H), 7.64 (s, 1H), 10.66 (s, 1H)

EXAMPLE 106

(7Z)-7-Hydroxyimino-4,5,6,7-tetrahydrobenzo[b]
thiophene-3-carboxylic acid n-pentyl amide n-Pentylamine was used as the amine to carry out the reaction according to <method α>. The title compound (9 mg) was obtained as a slightly yellow solid.

$^1$H-NMR (CDCl$_3$-DMSO-d$_6$) δ: 0.79 (t, J=7.2 Hz, 3H), 1.16–1.30 (m, 4H), 1.39–1.54 (m, 2H), 1.75–1.93 (m, 2H), 2.44–2.56 (m, 2H), 2.92 (t, J=6.4 Hz, 2H), 3.16–3.30 (m, 2H), 6.52–6.68 (m, 1H), 7.66 (s, 1H), 10.63 (s, 1H)

EXAMPLE 107

(7Z)-7-Hydroxyimino-4,5,6,7-tetrahydrobenzo[b]
thiophene-3-carboxylic acid (2-dimethylamino
ethyl)amide-trifluoroacetate N,N-Dimethylethylenediamine was used as the amine to carry out the reaction according to <method α>. A purification by LC-MS was carried out, and the title compound (10.5 mg) was obtained as a colorless oily matter.

MS m/e (ESI) 282.25 (MH$^+$)

EXAMPLE 108

(7Z)-7-Hydroxyimino-4,5,6,7-tetrahydrobenzo[b]
thiophene-3-carboxylic acid (3-dimethylamino propyl)-amide-trifluoroacetate 3-(Dimethylamino)propylamine was used as the amine to carry out the reaction according to <method α>. A purification by LC-MS was carried out, and the title compound (6.4 mg) was obtained as a colorless oily matter.

MS m/e (ESI) 296.31 (MH$^+$)

EXAMPLE 109

(7Z)-7-Hydroxyimino-4,5,6,7-tetrahydrobenzo[b]
thiophene-3-carboxylic acid Phenethyl amide Phenethylamine was used as the amine to carry out the reaction according to <method α>. The title compound (14 mg) was obtained as a colorless solid.

$^1$H-NMR (CDCl$_3$) δ: 1.92–2.04 (m, 2H), 2.56–2.66 (m, 2H), 2.89–3.02 (m, 4H), 3.64–3.74 (m, 2H), 5.77–5.89 (m, 1H), 7.19–7.38 (m, 5H), 7.63 (s, 1H)

EXAMPLE 110

(7Z)-7-Hydroxyimino-4,5,6,7-tetrahydrobenzo[b]
thiophene-3-carboxylic acid methylphenethyl amide N-Methylphenethylamine was used as the amine to carry out the reaction according to <method α>. Silica gel column chromatography (hexane/ethyl acetate) was carried out, and the title compound (16 mg) was obtained as a yellow solid.

$^1$H-NMR spectra broadened due to the presence of rotamers.

MS m/e (ESI) 329.17 (MH$^+$)

EXAMPLE 111

(7Z)-7-Hydroxyimino-4,5,6,7-tetrahydrobenzo[b]
thiophene-3-carboxylic acid (3-phenyl propyl)amide 3-Phenyl propylamine was used as the amine to carry out the reaction according to <method α>. The title compound (11 mg) was obtained as a pale yellow solid.

$^1$H-NMR (CDCl$_3$) δ: 1.90–2.06 (m, 4H), 2.58–2.66 (m, 2H), 2.69–2.79 (m, 2H), 2.98–3.08 (m, 2H), 3.41–3.52 (m, 2H), 5.70–5.84 (m, 1H), 7.16–7.34 (m, 5H), 7.57 (s, 1H)

EXAMPLE 112

(7Z)-7-Hydroxyimino-4,5,6,7-tetrahydrobenzo[b]
thiophene-3-carboxylic acid (4-phenyl butyl)amide 4-Phenyl butylamine was used as the amine to carry out the reaction according to <method α>, and the title compound (19 mg) was obtained as a colorless solid.

$^1$H-NMR (CDCl$_3$) δ: 1.45–1.78 (m, 4H), 1.94–2.06 (m, 2H), 2.59–2.72 (m, 2H), 3.00–3.08 (m, 2H), 3.38–3.48 (m, 2H), 5.74–5.87 (m, 1H), 7.14–7.33 (m, 5H), 7.71 (s, 1H)

EXAMPLE 113

(7Z)-3-(3,4-Dihydro-1H-isoquinoline-2-carbonyl)-5,
6-dihydro-4H-benzo[b]thiophene-7-one oxime 1,2,3,4-Tetrahydroisoquinoline was used as the amine to carry out the reaction according to <method α>. A purification by silica gel column chromatography (hexane/ethyl acetate) was carried out, and the title compound (11 mg) was obtained as a yellow solid.

$^1$H-NMR (CDCl$_3$) δ: 1.88–2.12 (m, 2H), 2.57–3.09 (m, 6H), 3.50–4.10 (m, 2H), 4.40–5.04 (m, 2H), 7.10–7.31 (m, 4H), 7.54 (s, 1H)

EXAMPLE 114

(7Z)-3-(4-phenylpiperidine-1-carbonyl)-5,6-dihydro-
4H-benzo[b]-thiophene-7-one oxime 4-Phenyl piperidine was used as the amine to carry out the reaction according to <method α>. A purification by silica gel column chromatography (hexane/ethyl acetate) was carried out, and the title compound (11 mg) was obtained as a pale yellow solid.

$^1$H-NMR (CDCl$_3$) δ: 1.35–2.08 (m, 6H), 2.60–2.70 (m, 2H), 2.72–5.00 (m, 7H), 7.18–7.36 (m, 5H), 7.51 (s, 1H)

EXAMPLE 115

7-Hydroxyimino-4,5,6,7-tetrahydrobenzo[b]
thiophene-3-carboxylic acid indo-2-yl amide Indo-2-ylamine.hydrochloride was used as the amine to carry out the reaction according to <method β>. The title compound (35 mg) was obtained as a yellow solid (mixture where (Z):(E)=3:1).

$^1$H-NMR (DMSO-d$_6$) δ: 1.86–3.40 (m, 10H), 4.54–4.69 (m, 1H), 7.05–7.27 (m, 4H), 7.86 and 8.06 (each s, 1H (1:3)), 8.45 and 8.60 (each d, each J=7.2 Hz, 1H (3:1)), 10.95 and 11.39 (each s, 1H (1:3))

EXAMPLE 116

(7Z)-7-Hydroxyimino-4,5,6,7-tetrahydrobenzo[b]
thiophene-3-carboxylic acid (1.2,3,4-tetrahydro
naphthalene-1-ylmethyl)amide C-(1,2,3,4-tetrahydro naphthalene-1-yl)methylamine oxalate was used as the amine to carry out the reaction according to <method β>. The title compound (27 mg) was obtained as a pale yellow solid.

$^1$H-NMR (DMSO-d$_6$) δ: 1.57–3.49 (m, 15H), 6.94–7.27 (m, 4H), 8.07 (s, 1H), 8.35–8.50 (m, 1H), 11.40 (s, 1H)

EXAMPLE 117

(7Z)-7-Hydroxyimino-4,5,6,7-tetrahydrobenzo[b]
thiophene-3-carboxylic acid trans-(2-phenyl cyclo-
propyl)amide Trans-2-phenyl cyclopropylamine.hydrochloride was used as the amine to carry out the reaction according to <method >. The title compound (27 mg) was obtained as a colorless solid.

$^1$H-NMR (DMSO-d$_6$) δ: 1.11–1.35 (m, 2H), 1.74–1.92 (m, 2H), 1.97–2.10 (m, 2H), 2.41–2.57 (m, 2H), 2.86–3.05 (m, 3H), 7.08–7.32 (m, 5H), 8.06 (s, 1H), 8.48 (d, J=3.6 Hz, 1H), 11.41 (s, 1H)

EXAMPLE 118

(7Z)-7-Hydroxyimino-4,5,6,7-tetrahydrobenzo[b]
thiophene-3-carboxylic acid[2-(2-chlorophenyl)
ethyl]amide 2-Chlorophenethylamine was used as the amine to carry out the reaction according to <method α>. The title compound (20 mg) was obtained as a pale yellow solid.

$^1$H-NMR (DMSO-d$_6$) δ: 1.74–1.93 (m, 2H), 2.40–2.62 (m, 2H), 2.80–3.05 (m, 4H), 3.37–3.53 (m, 2H), 7.00–7.54 (m, 4H), 7.97 (s, 1H), 8.23–8.43 (m, 1H), 11.39 (s, 1H)

EXAMPLE 119

(7Z)-7-Hydroxyimino-4,5,6,7-tetrahydrobenzo[b]
thiophene-3-carboxylic acid[2-(3-chlorophenyl)
ethyl]amide 3-Chlorophenethylamine was used as the amine to carry out the reaction according to <method α>. The title compound (20 mg) was obtained as a pale yellow solid.

$^1$H-NMR (DMSO-d$_6$) δ: 1.75–1.89 (m, 2H), 2.44–2.57 (m, 2H), 2.76–2.91 (m, 4H), 3.24–3.50 (m, 2H), 7.13–7.40 (m, 4H), 7.95 (s, 1H), 8.22–8.33 (m, 1H), 11.39 (s, 1H)

EXAMPLE 120

(7Z)-7-Hydroxyimino-4,5,6,7-tetrahydrobenzo[b]
thiophene-3-carboxylic acid[2-(4-chlorophenyl)
ethyl]amide 4-Chlorophenethylamine was used as the amine to carry out the reaction according to <method α>. The title compound (24 mg) was obtained as a pale yellow solid (80% purity).

$^1$H-NMR (DMSO-d$_6$) δ: 1.71–1.90 (m, 2H), 2.43–2.63 (m, 2H), 2.71–2.91 (m, 4H), 3.15–3.51 (m, 2H), 7.16–7.42 (m, 4H), 7.96 (s, 1H), 8.20–8.35 (m, 1H), 11.39 (s, 1H)

EXAMPLE 121

(7Z)-7-Hydroxyimino-4,5,6,7-tetrahydrobenzo[b]
thiophene-3-carboxylic acid[2-(2-methoxyphenyl)
ethyl]amide 2-Methoxyphenethylamine was used as the amine to carry out the reaction according to <method α>. The title compound (20 mg) was obtained as a yellow solid (90% purity).

$^1$H-NMR (DMSO-d$_6$) δ: 1.73–1.89 (m, 2H), 2.42–2.56 (m, 2H), 2.73–2.83 (m, 2H), 2.86–2.93 (m, 2H), 3.26–3.43

(m, 2H), 3.77 (s, 3H), 6.85 (t, J=7.2 Hz, 1H), 6.94 (d, J=8.0 Hz, 1H), 7.09–7.23 (m, 2H), 7.97 (s, 1H), 8.19–8.32 (m, 1H), 11.38 (s, 1H)

EXAMPLE 122

(7Z)-7-Hydroxyimino-4,5,6,7-tetrahydrobenzo[b]thiophene-3-carboxylic acid[2-(3-methoxyphenyl)ethyl]amide 3-Methoxyphenethylamine was used as the amine to carry out the reaction according to <method α>. The title compound (7 mg) was obtained as a colorless solid.

$^1$H-NMR (DMSO-$d_6$) δ: 1.76–1.91 (m, 2H), 2.43–2.60 (m, 2H), 2.73–2.97 (m, 4H), 3.22–3.50 (m, 2H), 3.70 (s, 3H), 6.68–6.86 (m, 3H), 7.19 (t, J=8.0 Hz, 1H), 7.97 (s, 1H), 8.21–8.46 (m, 1H), 11.39 (s, 1H)

EXAMPLE 123

(7Z)-7-Hydroxyimino-4,5,6,7-tetrahydrobenzo[b]thiophene-3-carboxylic acid[2-(4-methoxyphenyl)ethyl]amide 4-Methoxyphenethylamine was used as the amine to carry out the reaction according to <method α>. The title compound (17 mg) was obtained as a colorless solid.

$^1$H-NMR (DMSO-$d_6$) δ: 1.76–1.93 (m, 2H), 2.43–2.61 (m, 2H), 2.77–2.80 (m, 2H), 2.83–2.95 (m, 2H), 3.21–3.45 (m, 2H), 3.70 (s, 3H), 6.84 (d, J=8.4 Hz, 2H), 7.13 (d, J=8.4 Hz, 2H), 7.97 (s, 1H), 8.19–8.43 (m, 1H), 11.39 (s, 1H)

EXAMPLE 124

(7Z)-7-Hydroxyimino-4,5,6,7-tetrahydrobenzo[b]thiophene-3-carboxylic acid[2-(4-fluorophenyl)ethyl]-methyl-amide

[2-(4-Fluorophenyl)ethyl]methylamine.hydrochloride (the compound of Preparation Example 14) was used as the amine to carry out the reaction according to <method α>. A purification by silica gel column chromatography (hexane/ethyl acetate) was carried out, and the title compound (12 mg9 was obtained as a pale yellow solid (mixture of rotamers identified by NMR).

$^1$H-NMR (DMSO-$d_6$) δ: 1.77–1.88 (m, 2H), 2.24–3.72 (m, 11H), 6.90–7.38 (m, 4H), 7.45 (s, 0.5H), 7.64 (s, 0.5H), 11.39 (s, 1H)

MS m/e (ESI) 347.36 (MH$^+$)

EXAMPLE 125

(7Z)-7-Hydroxyimino-4,5,6,7-tetrahydrobenzo[b]thiophene-3-carboxylic acid cyanomethyl-[2-(4-fluorophenyl)ethyl]amide

[2-(4-Fluorophenyl)ethylamino] acetonitrile (the compound of Preparation Example 21) was used as the amine to carry out the reaction according to <method β>. A purification by silica gel column chromatography (hexane/ethyl acetate) was carried out, and the title compound (13.2 g) was obtained as a pale yellow solid.

$^1$H-NMR (DMSO-$d_6$) δ: 1.80–3.73 (m, 10H), 4.38–4.68 (m, 2H), 6.80–7.30 (m, 4H), 8.02 (s, 1H), 11.47 (s, 1H)

MS m/e (ESI) 372.37 (MH$^+$)

EXAMPLE 126

(7Z)-7-Hydroxyimino-4,5,6,7-tetrahydrobenzo[b]thiophene-3-carboxylic acid[2-(4-fluorophenyl)ethyl]isopropylamide

[2-(4-Fluorophenyl)-ethyl] isopropylamine (the compound of Preparation Example 22) was used as the amine to carry out the reaction according to <method β>. A purification by silica gel column chromatography (hexane/ethyl acetate) was carried out, and the title compound (10.7 mg) was obtained as a colorless solid.

$^1$H-NMR (DMSO-$d_6$) δ: 0.90–3.80 (m, 17H), 6.80–7.40 (m, 4H), 7.67 (s, 1H), 11.41 (s, 1H)

MS m/e (ESI) 375.42 (MH$^+$)

EXAMPLE 127

(7Z)-7-Hydroxyimino-4,5,6,7-tetrahydrobenzo[b]thiophene-3-carboxylic acid (2-pyridine-2-yl-ethyl)amide 2-Pyridine-2-yl-ethylamine was used as the amine to carry out the reaction according to <method β>. The title compound (2 mg) was obtained as a pale yellow solid.

$^1$H-NMR (DMSO-$d_6$) δ: 1.74–1.89 (m, 2H), 2.37–2.57 (m, 2H), 2.80–3.02 (m, 4H), 3.48–3.60 (m, 2H), 7.20 (dd, J=7.6 and 4.4 Hz, 1H), 7.26 (d, J=7.6 Hz, 1H), 7.68 (ddd, J=7.6, 7.6 and 2.0 Hz, 1H), 7.97 (s, 1H), 8.22–8.45 (m, 1H), 8.58 (br d, J=4.4 Hz), 11.38 (s, 1H)

EXAMPLE 128

(7Z)-7-Hydroxyimino-4,5,6,7-tetrahydrobenzo[b]thiophene-3-carboxylic acid (2-pyridine-3-yl-ethyl)amide 2-Pyridine-3-yl-ethylamine was used as the amine to carry out the reaction according to <method β>. The title compound (7 mg) was obtained as a pale yellow solid.

$^1$H-NMR (DMSO-$d_6$) δ: 1.73–1.89 (m, 2H), 2.40–2.57 (m, 2H), 2.77–2.90 (m, 4H), 3.38–3.50 (m, 2H), 7.29 (dd, J=7.6 and 4.8 Hz, 1H), 7.64 (d, J=7.6 Hz, 1H), 7.95 (s, 1H), 8.24–8.45 (m, 1H), 8.39 (dd, J=4.8 and 1.6 Hz, 1H), 8.42 (d, J=1.6 Hz), 11.38 (s, 1H)

EXAMPLE 129

(7Z)-3-(2-benzylpyrrolidine-1-carbonyl)-5,6-dihydro-benzo[b]-thiophene-7-one oxime 2-Benzyl pyrrolidine was used as the amine to carry out the reaction according to <method α>. A purification by silica gel column chromatography (hexane/ethyl acetate) was carried out, followed by solidification in diethyl ether-hexane, and the title compound (17 mg) was obtained as a pale yellow solid.

$^1$H-NMR (DMSO-$d_6$) δ: 1.50–3.60 (m, 14H), 4.20–4.37 (m, 1H), 6.70–7.45 (m, 5H), 7.80 (s, 1H), 11.39 (s, 1H)

MS m/e (ESI) (MH$^+$) 355.2

EXAMPLE 130

(7Z)-7-Hydroxyimino-4,5,6,7-tetrahydrobenzo[b]thiophene-3-carboxylic acid[2-(4-fluorophenyl)ethyl]-2-propynyl-amide

[2-(4-Fluorophenyl)ethyl]-2-propynylamine was used as the amine to carry out the reaction according to <method α>.

A purification by silica gel column chromatography (hexane/ethyl acetate) was carried out, and the title compound (21 mg) was obtained as a pale yellow solid.

$^1$H-NMR (DMSO-$d_6$) δ: 1.67–4.40 (m, 13H), 6.85–7.80 (m, 5H), 11.43 (s, 1H)

MS m/e (ESI) (MH$^+$) 371.2

EXAMPLE 131

(7Z)-7-Hydroxyimino-4,5,6,7-tetrahydrobenzo[b]thiophene-3-carboxylic acid cyclopropyl-[2-(4-fluorophenyl)ethyl]amide Cyclopropyl-[2-(4-fluorophenyl)-ethyl]amine, whcich was obtained by reducing N-cyclopropyl-2-(4-fluorophenyl)acetamide (the compound of Preparation Example 23) with aluminum lithium hydride, was used as the amine to carry out the reaction according to <method α>. A purification by silica gel column chromatography (hexane/ethyl acetate) was carried out, and the title compound (7 mg) was obtained as a reddish-brown solid.

$^1$H-NMR (DMSO-$d_6$) δ: 0.18–0.73 (m, 4H), 1.10–3.86 (m, 11H), 6.94–7.75 (m, 5H), 11.36 (s, 1H)

MS m/e (ESI) 373.1 (MH$^+$)

EXAMPLE 132

(7Z)-3-(3-Phenylpyrrolidine-1-carbonyl)-5,6-dihydro-benzo[b]-thiophene-7-one oxime 3-Phenyl pyrrolidine was used as the amine to carry out the reaction according to <method α>. A purification by silica gel column chromatography (hexane/ethyl acetate) and a further solidification in diethyl ether-hexane were carried out, and the title compound (5 mg) was obtained as a colorless solid.

$^1$H-NMR (DMSO-$d_6$) δ: 1.73–3.98 (m, 13H), 7.10–7.40 (m, 5H), 7.89 (s, 1H) 11.38 (s, 1H) MS m/e (ESI) (MH$^+$) 341.2

EXAMPLE 133

(7Z)-7-Hydroxyimino-4,5,6,7-tetrahydrobenzo[b]thiophene-3-carboxylic acid[2-(4-fluoro-3-methoxyphenyl)ethyl]amide 2-(4-Fluoro-3-methoxyphenyl)ethylamine.hydrochloride (the compound of Preparation Example 25) was used as the amine to carry out the reaction according to <method β>. The title compound (24 mg) was obtained as a pale yellow solid.

$^1$H-NMR (DMSO-$d_6$) δ: 1.71–1.91 (m, 2H), 2.20–2.70 (m, 2H), 2.72–2.92 (m, 4H), 3.10–3.62 (m, 2H), 3.78 (s, 3H), 6.69–6.82 (m, 1H), 7.00 (dd, J=8.4 and 2.0 Hz, 1H), 7.08 (dd, J=12.0 and 8.4 Hz, 1H), 7.97 (s, 1H), 8.16–8.33 (m, 1H), 11.39 (s, 1H)

EXAMPLE 134

(7Z)-7-Hydroxyimino-4,5,6,7-tetrahydrobenzo[b]thiophene-3-carboxylic acid[2-(4-fluoro-3-methoxyphenyl)ethyl]-methyl-amide

[2-(4-Fluoro-3-methoxyphenyl)ethyl]methylamine.hydrochloride (the compound of Preparation Example 27) was used as the amine to carry out the reaction according to <method α>. A purification by silica gel column chromatography (hexane/ethyl acetate) was carried out, and the title compound (36 mg) was obtained as a yellow solid.

$^1$H-NMR (DMSO-$d_6$) δ: 1.62–1.90 (m, 2H), 2.17–3.93 (m, 14H), 6.45–7.72 (m, 4H), 11.38 (s, 1H)

MS m/e (ESI) 377.2 (MH$^+$)

EXAMPLE 135

(7Z)-7-Hydroxyimino-4,5,6,7-tetrahydrobenzo[b]thiophene-3-carboxylic acid[2-(3-phenoxyphenyl)ethyl]amide 2-(3-Phenoxyphenyl)ethylamine.hydrochloride (the compound of Preparation Example 29) was used as the amine to carry out the reaction according to <method β>. The title compound (14 mg) was obtained as a colorless solid.

$^1$H-NMR (DMSO-$d_6$) δ: 1.72–1.88 (m, 2H), 2.35–2.62 (m, 2H), 2.72–2.92 (m, 4H), 3.35–3.50 (m, 2H), 6.82 (dd, J=8.0 and 2.4 Hz, 1H), 6.86 (s, 1H), 6.95 (d, J=8.0 Hz, 1H), 7.01 (d, J=8.0 Hz, 1H), 7.09 (t, J=8.0 Hz, 1H), 7.23–7.42 (m, 3H), 7.92 (s, 1H), 8.20–8.33 (m, 1H), 11.39 (s, 1H)

EXAMPLE 136

(7Z)-7-Hydroxyimino-4,5,6,7-tetrahydrobenzo[b]thiophene-3-carboxylic acid[2-(3-phenoxyphenyl)ethyl]-methyl-amide

[2-(3-Phenoxyphenyl)ethyl]methylamine.hydrochloride (the compound of Preparation Example 30) was used as the amine to carry out the reaction according to <method β>. A purification by silica gel column chromatography (hexane/ethyl acetate) was carried out, and, solidified from diethyl ether-hexane, the title compound (21 mg) was obtained as a pale yellow solid.

$^1$H-NMR (DMSO-$d_6$) δ: 1.65–1.88 (m, 2H), 2.26–3.80 (m, 11H), 6.60–7.68 (m, 10H), 11.40 (s, 1H) MS m/e (ESI) 421.4 (MH$^+$)

EXAMPLE 137

(7Z)-7-Hydroxyimino-4,5,6,7-tetrahydrobenzo[b]thiophene-3-carboxylic acid[1-(4-fluorophenyl)-cyclopropylmethyl]amide 1-(4-Fluorobenzyl)-cyclopropylamine (the compound of Preparation Example 31) was used as the amine to carry out the reaction according to <method α>. The title compound (16 mg) was obtained as a pale yellow solid.

$^1$H-NMR (DMSO-$d_6$) δ: 0.61–0.84 (m, 4H), 1.71–1.90 (m, 2H), 2.35–2.56 (m, 2H), 2.80–2.98 (m, 4H), 7.00–7.33 (m, 4H), 7.83 (s, 1H), 8.22 (s, 1H), 11.36 (s, 1H)

EXAMPLE 138

(7Z)-3-(3-Methyl-3-phenylpyrrolidine-1-carbonyl)-5,6-dihydro-benzo[b]thiophene-7-one oxime 3-Methyl-3-phenyl-pyrrolidine, which was synthesized by reducing 3-methyl-3-phenyl pyrrolidine-2,5-dione with aluminum lithium hydride, was used as the amine to carry out the reaction according to <method α>. A purification by silica gel column chromatography (hexane/ethyl acetate) was carried out, and, the title compound (7 mg) was obtained as a colorless solid.

$^1$H-NMR (DMSO-$d_6$) δ: 1.18–3.04 (m, 15H), 7.00–7.45 (m, 5H), 7.75–7.95 (m, 1H), 11.39 (s, 1H)

MS m/e (ESI) 355.5 (MH$^+$)

EXAMPLE 139

(7Z)-7-Hydroxyimino-4,5,6,7-tetrahydrobenzo[b]thiophene-3-carboxylic acid (2-thiophene-2-yl-ethyl)amide (2-Thiophene-2-yl-ethyl)-amine was used as the amine to carry out the reaction according to <method α>. The title compound (13 mg) was obtained as a pale yellow solid.

$^1$H-NMR (DMSO-d$_6$) δ: 1.73–1.95 (m, 2H), 2.20–2.75 (m, 2H), 2.80–3.08 (m, 4H), 3.08–3.68 (m, 2H), 6.77–7.02 (m, 2H), 7.32 (dd, J=5.2 and 0.8 Hz, 1H), 8.00 (s, 1H), 8.25–8.45 (m, 1H), 11.49 (s, 1H)

EXAMPLE 140

7-Hydroxyimino-4,5,6,7-tetrahydrobenzo[b]thiophene-3-carboxylic acid methyl-(2-thiophene-2-yl-ethyl)amide Methyl-(2-thiophene-2-yl-ethyl)amine.hydrochloride was used as the amine to carry out the reaction according to <method β>. The title compound (a yellow solid) (28 mg) was obtained as a mixture where (Z):(E)=2.5:1.

$^1$H-NMR (DMSO-d$_6$) δ: 1.64–3.83 (m, 13H), 6.60–7.77 (m, 4H), 10.95 and 11.39[each s, 1H (1:2.5)]

EXAMPLE 141

3-(4-Fluorophenyl)-2-[(7-hydroxyimino-4,5,6,7-tetrahydrobenzo[b]-thiophene-3-carbonyl)-amino]propionic acid From 3-(4-fluorophenyl)-2-[(7-oxo-4,5,6,7-tetrahydrobenzo[b]thiophene-3-carbonyl)-amino]propionic acid (the compound of Preparation Example 117) (22 mg), the title compound (colorless solid) (15 mg) was obtained as mixture of oxime where (Z):(E)=2:1, in the same way as Example 99. Purification was carried out by silica gel column chromatography (dichloromethane/methanol).

$^1$H-NMR (DMSO-d$_6$) δ: 1.63–3.59 (m, 8H), 4.20–4.35 (m, 1H), 6.80–7.40 (m, 4H), 7.57–8.08 (m, 1H), 7.94 and 8.28[each s, 1H (2:1)], 10.95 and 11.40[each s, 1H (1:2)]

EXAMPLE 142

7-Hydroxyimino-4,5,6,7-tetrahydrobenzo[b]thiophene-3-carboxylic acid[1-carbamoyl-2-(4-fluorophenyl)ethyl]amide To a solution of 3-(4-fluorophenyl)-2-[(7-oxo-4,5,6,7-tetrahydrobenzo[b]thiophene-3-carbonyl)-amino]propionic acid (the compound of Preparation Example 117) (43 mg) in tetrahydrofuran (1 mL) was added dropwise triethylamine (50 μL) and ethyl chlorocarbonate (17 μL). After stirring for 30 minutes, 29% aqueous ammonia (1 mL) was added. After adding an aqueous solution of saturated sodium bicarbonate and extracting with a mixed solvent of ethyl acetate-tetrahydrofuran, the solution was washed with an aqueous solution of saturated sodium bicarbonate and saturated sodium chloride water. The residue that was obtained after drying with anhydrous sodium sulfate and removing the solvent by evaporation was treated in such a manner that the same reaction was carried out as Example 99 and purified by LC-MS, and the title compound (6 mg) was obtained.

MS m/e (ESI) 355.5 (MH$^+$)

Test Examples

The inhibitory activity on STAT6 activation of the compound according to present invention was evaluated according to the following test.

1) Construction of the STAT6 Reporter Gene

The oligonucleotide of SEQ ID: 1 resuting from three STAT6 binding regions of the human immunoglobulin germline ε gene promoter linked togeter, and the complementary strand thereof were mixed, and after thermal denaturation and annealing, the 5' and the 3' ends were respectively cut with the restriction enzymes Kpn I (TaKaRa Shuzo Code No. 1068A) and Xba I (TaKaRa ShuzoCode No. 1093A), and the resulting fragment was cloned into the Kpn I/Xba I site of the pUG-BGH-PLAP vector (described in Molecular Pharmacology, 49: 860–873 1996). In addition, the TK promoter region of the herpesvirus for inducing general transcription factors was cloned into the Xba I/Hind III (TaKaRa ShuzoCode No. 1060A) site of the pUG-BGH-PLAP vector. Then, to collect a stable expression cell strain, the neomycin resistance gene, that is a PGK-neo expression cassette, was incorporated into the Sal I (TaKaRa Shuzo, Code No. 1080A) site of this vector. Cloning of the TK promoter and the PGK-neo expression cassette was carried out according to Molecular Pharmacology, 49: 860–873 1996.

(SEQ ID: 1)
5'-AGC<u>GGTACC</u>TCGACTTCCCAAGAACAGAATCGACTTCCCAAGAAC AGAAT

CGACTTCCCAAGAACAGAA<u>TCTAGA</u>GCT-3'

The underlined portions are the Kpn I restriction site and the Xba I restriction site, respectively.

2) Construction of the STAT6 Expression Vector

Using the oligonucleotide of SEQ ID: 2 containing the initiation codon of the STAT6 gene and the oligonucleotide of SEQ ID: 3 containing the stop codon, Total RNA was prepared from human peripheral blood cells with the RNeasy Mini kit (OIAGEN, Code No. 74104). Thereafter, a reverse transcription reaction was carried out with the Takara RNA LA PCR kit (TaKaRa Shuzo, Code No. RR012A) to prepare cDNA, and using the primers of SEQ ID: 2 and 3, a PCR reaction was carried out, to amplify the STAT6 gene.

(SEQ ID: 2)
5'-CG<u>GAATTC</u>ATGTCTCTGTGGGTCTGGTCTCCA-3'

The underlined portion is the EcoR I restriction site.

(SEQ ID: 3)
5'-CCG<u>CTCGAG</u>TCACCAACTGGGGTTGGCCCTTAGG-3'

The underlined portion is the Xho I restriction site.

PCR product was digested with EcoR I (TaKaRa Shuzo, Code No. 1040A) and Xho I (TaKaRa Shuzo, 1094A), thereafter, the digested fragment was isolated on an agarose gel. The isolated fragment was incorporated into the vector fragment derived from the EcoR I/Xho I digestion of the pcDNA3.1 (+) (invtrogen, Code No. U790-20) vector.

3) Transformation and Preparation of a Stable Expression Cell Strain

In a Falcon 6-well plate for tissue culture (Becton Dickinson, Code No. 35-3046), 3.0×10$^5$ of 293 cells derived from human embryo kidney (American Type Culture Collection) were distributed and cultured overnight. The STAT6 reporter gene (1.5 µg), the STAT6 gene (1.5 µg) that were prepared and lipofectamine (GIBCO BRL, Code No. 18324-012) (20 µL) were mixed in OPTI-MEM culture medium (GIBCO BRL, Code No. 31985-070) (0.3 mL), and allowed to stand at room temperature for 20 minutes. Thereafter, the OPTI-MEM culture medium (1.2 mL) was further added, OPTI-MEM culture medium not containing fetal calf serum was added to washed cells, which were cultured for 2 hours. A culture medium (1.5 mL) containing fetal calf serum was added, and the cells were cultured for 19 more hours. The culture was continued by exchanging the culture medium and adding Geneticin (SIGMA, Code No. G-5013) so as to obtain 1 mg/mL, and cells with drug tolerance were selected. The selected drug tolerant cells were suspended in a culture medium containing 1 mg/mL of Geneticin, and distributed in a 96-well microplate (Becton Dickinson, Code No. 35-3072) so as to obtain 0.5 cells/well to carrry out cloning, and the clones expressing alkaline phosphatase in response to IL-4 were collected.

4) STAT6 Activation Inhibition Test

Cells stably expressing the STAT6 gene and the STAT6 reporter gene, and expressing alkaline phosphatase in response to IL-4 were distributed in a 96-well microplate (Becton Dickinson, Code No. 35-3072) so as to obtain 5000 cells/180 µL/well, and cultured overnight. The next day, after adding the compound (10 mM) according to the present application (dissolved in dimethylsulfoxide, diluted with the culture medium so that the concentration in dimethylsulfoxide was less than 0.1% for use) and the human recombinant IL-4 (CALBIOCHEM, Code No. 407635) (1 ng/mL) to obtain 200 µL/well and culturing for 16 hours cultivation subsequent, the supernatant was recovered, and the solution that was recovered was treated at 65° C. for 10 minutes. Thereafter, carbonate buffer (16 mM NaHCO$_3$, 12 mM Na$_2$CO$_3$, 0.8 mM MgSO$_4$) (100 µL) was introduced in each well of a black plate for fluorescence measurement (Dai Nippon Pharmaceuticals, Code No. TS-1001), and the conditioned medium (10 µL) that was treated by heat was added. In addition, Lumistein (Genome Science Laboratories Co., LTD., Code No. R02-ES) (50 µL) was added to each well, and let to stand at room temperature for 1 hour. Note that the alkaline phosphatase activity was measured with MicroLumat ((EG&G BERTHOLD).

In the absence of the compound according to the present invention, the inhibition rate (%) on the alkaline phosphatase activity induced by IL-4 stimulation is regarded as 100%, and the inhibition rate of the compounds according to the present invention were calculated according to the following formula in order to determine the concentration of the compounds according to the present invention that gives 50% suppression of the alkaline phosphatase activity induced by IL-4 ($IC_{50}$).

Inhibition rate (%)=(E−B)/(C−B)×100 wherein
E: alkaline phosphatase activity induced by IL-4 stimulation in the presence of the compound according to the present invention
C: alkaline phosphatase activity induced by IL-4 stimulation in the absence of the compound according to the present invention
B: alkaline phosphatase activity induced without stimulation in the absence of the compound according to the present invention The concentrations of the compounds according to the present application that give 50% suppression of the alkaline phosphatase activity induced by IL-4 ($IC_{50}$) are given in Table 1.

TABLE 1

| Example No. | $IC_{50}$ (nM) |
| --- | --- |
| 1 | 1.13 |
| 2 | 0.22 |
| 3 | 0.6 |
| 5 | 21 |
| 6 | 4.9 |
| 7 | 4.8 |
| 9 | 0.82 |
| 13 | 0.36 |
| 14 | 30 |
| 17 | 15.4 |
| 21 | 5.6 |
| 23 | 9.5 |
| 25 | 13 |
| 26 | 2.6 |
| 27 | 11 |
| 31 | 4.3 |
| 32 | 10.1 |
| 33 | 11 |
| 37 | 30 |
| 44 | 0.63 |
| 47 | 12 |
| 48 | 30 |
| 52 | 7.9 |
| 60 | 1.6 |
| 61 | 66.7 |
| 63 | 40 |
| 64 | 40 |
| 66 | 16 |
| 73 | 0.9 |
| 83 | 34 |
| 87 | 0.5 |
| 88 | 0.42 |
| 110 | 0.32 |
| 124 | 0.15 |

As shown above, the compound according to the present invention has an inhibiory actiion on IL-4 signal transduction, at the same time, has an excellent Inhibitory activity on STAT6 activation. Therefore, it is useful against allergic diseases such as atopic dermatitis.

The entire disclosure of Japanese Patent Application No. 2004-25077 filed on Feb. 2, 2004, including specification, claims and summary are incorporated herein by reference in its entirety.

We claim:

1. A compound represented by the following general formula (I-a')

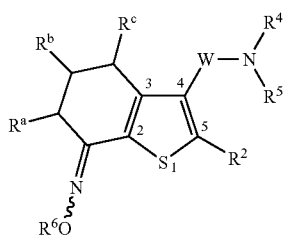

wherein, $R^2$ represents a hydrogen atom, a $C_{1-6}$ alkyl group that may have a substituent selected from substituent group a or a substituent selected from substituent group α;

$R^4$ and $R^5$ independently represent a hydrogen atom, a $C_{1-6}$ alkyl group that may have a substituent selected from substituent group α, a $C_{2-4}$ alkenyl group that may have a substituent selected from substituent group α, a $C_{2-6}$ alkynyl group that may have a substituent selected from substituent group α, a $C_{3-8}$ cycloalkyl group that may have a substituent selected horn substituent group γ, a 3 to 8-membered heterocyclyl group that may have a substituent selected from substituent group γ, a $C_{6-10}$ aryl group that may have a substituent selected from substituent group γ or a 5 to 10-membered heteroaryl group that may have a sub stituent selected from substituent group γ;

$R^6$ represents a hydrogen atom, —$CONR^{7a}R^{7b}$ (wherein, $R^{7a}$ and $R^{7b}$ represent independently a hydrogen atom, a $C_{1-6}$ alkyl group that may have a substituent selected from substituent group α, a $C_{3-8}$ cycloalkyl group that may have a substituent selected from substituent group α or a $C_{6-10}$ aryl group that may have a substituera selected from substituent group γ) or —$COR^{7c}$ (wherein, $R^{7c}$ represents a hydrogen a $C_{1-6}$ alkyl group that may have a substituent selected from substituent group α);

$R^a$, $R^b$ and $R^c$ independently represent a hydrogen atom, a $C_{1-6}$ alkyl group that may have a substituent selected from substituent group a or a substituent selected from substituent group α;

W represents —$SO_2$ or —CO—;

the substituent group a: halogen atoms, hydroxyl groups, mercapto groups, amino groups that may have a substituent selected from substituent group β, nitro groups, cyano groups, formyl groups, carboxyl groups, earbamoyl groups that may have a substituent selected from substituent group β, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ aticoxycarbonyl groups, $C_{1-6}$ alkylsulfinyl groups, $C_{1-6}$ alkylsulfonyl groups, $C_{3-8}$ cycloalkyl groups that may have a substituent selected from substituent group γ, $C_{3-8}$ cycloalkyloxy groups that may have a substituent selected from substituent group γ, $C_{3-8}$ cycloalkythio groups that may have a substituent selected from substituent group γ, 3 to 8-membered beterocyclyl groups that may have a substituent selected from substituent group γ, 3 to 8-membered heterocyclyloxy groups that may have a substituent selected from substituent group γ, 3 to 8-membered heteroeyelylthio groups that may have a substituent selected from substituent group γ, $C_{6-10}$ aryl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxyl groups that may have a substituerit selected from substituent group γ, aryloxycarbonyl groups that may have a substituent selected from substituent group γ, 5 to 10-membered heteroaryl groups that may have a substituent selected from substituent group γ, 5 to 10-membered heteroaryloxy groups that may have a substituent selected from substituent group γ, 5 to 10-membered heteroarylthio groups that may have a substituent selected from substituent group γ, 5 to 10-membered heteroarylcarbonyl groups that may have a substituent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group β: halogen atoms, formyl groups, carboxyl groups, carbamoyl groups, $C_{1-6}$ alkyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{1-6}$ alicylsulfonyl groups, $C_{3-8}$ cycloalkyl groups that may have a substiment selected from substituent group γ, $C_{3-8}$ cycloalkyloxy groups that may have a substituent selected from substituent group γ, $C_{3-8}$ cycloalkythia groups that may have a substituent selected from substituent group γ, 3 to 8-membered heterocyclyl groups that may have a substituent selected from substituent group γ, 3 to 8-merubered heterocyclyloxy groups that may have a substituent selected from substituent group γ, 3 to 8-merubered heterocyclyithia groups that may have a substituerit selected from substituent group γ, $C_{6-10}$ aryl groups that may have a substituent selected from substituent group γ, $C_{6-10}$ aryl $C_{1-6}$ alkyl groups that may have a substituent selected from substituent group γ, $C_{6-10}$ aryloxy groups that may have a substituent selected from substituent group γ, $C_{6-10}$ arylthio groups that may have a substituent selected from substituent group γ, $C_{6-10}$ arylcarbonyl groups that may have a substituent selected from substituent group γ, $C_{6-10}$ arylcarbonyloxy groups that may have a substituent selected from substituerit group γ, $C_{6-10}$ aryloxycarbonyl groups that may have a substituent selected from substituent group γ, 5 to 10-membered heteroaryl groups that may have a substituent selected from substituont group γ, 5 to 10-membered heteroaryloxy groups that may have a substituent selected from substituent group γ, 5 to 10-membered heteroarylthio groups that may have a substituent selected from substituent group γ, 5 to 10-membered heleroarylcarbonyl groups that may have a substiruent selected from substituent group γ, 5 to 10-membered heteroarylcarbonyloxy groups that may have a substituent selected from substituent group γ and 5 to 10-membered heteroaryloxycarbonyl groups that may have a substituent selected from substituent group γ;

the substituent group γ: halogen atoms, hydroxyl groups, mercapto groups, amino groups, nitro groups, cyano groups, formyl groups, carboxyl groups, carbamoyl groups, $C_{1-6}$ alkoxy groups, $C_{1-6}$ alkylthio groups, $C_{2-7}$ alkylcarbonyl groups, $C_{2-7}$ alkylcarbonyloxy groups, $C_{2-7}$ alkoxycarbonyl groups, $C_{1-6}$ alkylsulfinyl groups, $C_{3-6}$ alkylsulfonyl groups, $C_{3-8}$ cycloalkyl groups, $C_{3-8}$ cycloalkyloxy groups, $C_{3-8}$ cycloalkyhio groups, 3 to 8-membered heterocyclyl groups, 3 to 8-membered heterocyclyloxy groups, 3 to 8-membered heterocyclylthio groups, $C_{6-10}$ aryl groups, $C_{6-10}$ aryl $C_{1-6}$ alkyl groups, $C_{6-10}$ aryloxy groups, $C_{6-10}$ arylthio groups, $C_{6-10}$ arylcarbonyl groups, $C_{6-10}$ arylcarbonyloxy groups, $C_{6-10}$ aryloxycarbonyl groups, 5 to 10-membered heteroaryl groups, 5 to 10-membered heteroaryloxy groups, 5 to 10-membered heteroarylthio groups, 5 to 10-membered heteroarylcarbonyl groups, 5 to 10-membered heteroarylcarbonyloxy groups and 5 to 10-membered heteroaryloxycarbonyl groups;

or a salt thereof, or a hydrate thereof.

2. The compound or the salt thereof, or the hydrate thereof according to claim 1, wherein $R^2$ represents a hydrogen atom, a halogen atom, a hydroxyl group, a mercapto group, an amino group that may have 1 or 2 substituents selected from substituent group β, a nitro group, a cyano group, a formyl group, a carboxyl group, a carbamoyl group, a $C_{1-6}$ alkyl group that may have 1 to 3 substituents selected from substituent group α, a $C_{1-6}$ alkoxy group or a 3 to 8-membered heterocyclyl group that may have 1 to 3 substituents selected from substituent group γ.

3. The compound or the salt thereof, or the hydrate thereof according to claim 1, wherein $R^2$ represents a hydrogen atom, an amino group that may have 1 or 2 substituents selected from substituent group β, a $C_{1-6}$ alkyl group that may have 1 to 3 substituents selected from substituent group α, a $C_{1-6}$ alkoxy group, a 3 to 8-membered heterocyclyl group that may have 1 to 3 substituents selected from substituent group γ.

4. The compound or the salt thereof, or the hydrate thereof according to claim 1, wherein $R^2$ represents a hydrogen atom, an amino group that may have 1 or 2 substituents selected from substituent group β or a $C_{1-6}$ alkcoxy group.

5. The compound or the salt thereof, or the hydrate thereof according to claim 1, wherein $R^2$ represents a hydrogen atom, an amino group or a methoxy group.

6. The compound or the salt thereof, or the hydrate thereof according to claim 1, wherein $R^4$ and $R^5$ independently represent a hydrogen atom, a $C_{1-6}$ alkyl group that may have 1 to 3 substituents selected from substituent group α, a $C_{2-6}$ alkynyl group that may have 1 to 3 substituents selected from substituent group α or a $C_{3-8}$ cycloalkyl group that may have 1 to 3 substituents selected from substituent group γ.

7. The compound or the salt thereof, or the hydrate thereof according to claim 1 wherein $R^4$ represents a $C_{1-6}$ alkyl group that may have 1 or 2 substituents selected from substituent group α.

8. The compound or the salt thereot or the hydrate thereof according td claim 1,
wherein $R^4$ is represented by a formula of —$(CH_2)_m$—$CH(R^{4a})R^{4b}$, and
wherein, $R^{4a}$ represents a $C_{6-10}$ aryl group that may have a substiruent selected from substituent group γ or a 5 to 10-membered heteroaryl group that may have a substituent selected from substituent group γ, $R^{4d}$ represents a hydrogen atom or a substituent selected from substituent group α, and m stands for 0, 1, 2, 3, 4 or 5.

9. The compound or the salt thereof, or the hydrate thereof according to claim 8, wherein $R^{4a}$ represents a phenyl group that may have 1 to 3 substituents selected from substituent group γ, a pyridyl group that may have 1 to 3 substituents selected from sabstituent group γ or a thienyl group that may have 1 to 3 substituents selected from substituent group γ.

10. The compound or the salt thereof, or the hydrate thereof according to claim 8, wherein $R^{4a}$ represents a phenyl group that may have 1 to 3 substituents selected from the group consisting of a halogen atom, a hydroxyl group, a mercapto group, an amino group, a nitro group, a cyano group, a formyl group, a carboxyl group, a carbamoyl group, a $C_{1-6}$ alkyl group, a $C_{1-6}$ alkoxy group and a $C_{1-6}$ alkylthio group (hereinafter referred to as "substituent group γ"), a pyridyl group that may have 1 to 3 substituents selected from substituent group γ1 or a thienyl group that may have 1 to 3 substituents selected from substituent group γ1.

11. The compound or the salt thereof, or the hydrate thereof according to claim 8, wherein $R^{4a}$ represents a phenyl group that may have 1 to 3 substituents selected from the group consisting of a halogen atom, a hydroxyl group, a mercapto group, an amino group, a nitro group, a cyano group, a formyl group, a carboxyl group, a carbamoyl group, a $C_{1-6}$ alkyl group, a $C_{1-6}$ alkoxy group and a $C_{1-6}$ alkylthio group.

12. The compound or the salt thereof, or the hydrate thereof according to claim 8, wherein $R^{4a}$ represents a phenyl group that may have 1 to 3 halogen atoms, nitro groups or $C_{1-6}$ alkoxy groups.

13. The compound or the salt thereot or the hydrate thereof according to claim 8, wherein $R^{4a}$ represents a phenyl group that may have 1 to 3 fluorine atoms, nitro groups or methoxy groups.

14. The compound or the salt thereof, or the hydrate thereof according to claim 8, wherein $R^{4a}$ represents a 4-fluorophenyl group.

15. The compound or the salt thereof, or the hydrate thereof according to claim 8, wherein $R^{4b}$ represents a hydrogen atom, a halogen atom, a hydroxyl group, an amino group that may have 1 or 2 substituents selected from substituent group β, a carboxyl group, a carbamoyl group that may have 1 or 2 substituents selected from substituent group β, a $C_{1-6}$ alkoxy group or a $C_{2-7}$ alkylcarbonyloxy group.

16. The compound or the salt thereof, or the hydrate thereof according to claim 8, wherein $R^{4b}$ represents a hydrogen atom, a fluorine atom, a hydroxyl group, a methylcarbonylanino group, a methylsulfonylamino group, a carbamoylamino group, a carboxyl group, a carbamoyl group, a methoxy group or an ethylcarbonyloxy group.

17. The compound or the salt thereof, or the hydrate thereof according to claim 8, wherein $R^{4h}$ represents a hydrogen atom or a hydroxyl group.

18. The compound or the salt thereof, or the hydrate thereof according to claim 8, wherein m stands for 0, 1 or 2.

19. The compound or the salt thereof, or the hydrate thereof according to claim 8, wherein m stands for 1.

20. The compound or the salt thereof, or the hydrate thereof according to claim 8, wherein $R^5$ represents a hydrogen atom, a $C_{1-6}$ alkyl group that may have 1 to 3 substituents selected from substituent group α, a $C_{2-6}$ alkynyl group that may have 1 to 3 substituents selected from substituent group α or a $C_{3-8}$ cycloalkyl group that may have 1 to 3 substituents selected from substituent group γ.

21. The compound or the salt thereof, or the hydrate thereof according to claim 8, wherein $R^5$ represents a hydrogen atom, a cyanomethyl group, a carbamoylmethyl group, an isopropyl group, a propyn-1-yl group, a cyclopropyl group.

22. The compound or the salt thereof, or the hydrate thereof according to claim 8, wherein $R^5$ represents a hydrogen atom or a methyl group.

23. The compound or the salt thereof, or the hydrate thereof according to claim 8, wherein $R^6$ represents a hydrogen atom, —$CONR^{7a}R^{7b}$ (wherein, $R^{7a}$ and $R^{7b}$ independently represent a hydrogen atom, a $C_{1-6}$ alkyl group, a $C_{3-8}$ cycloalkyl group or a $C_{6-10}$ aryl group that may have a substituent selected from a halogen atom, a cyano group, a $C_{1-6}$ alkyl group or a $C_{1-6}$ alkoxy group) or —$COR^{7c}$ (wherein, $R^{7c}$ represents a $C_{1-6}$ alkyl group).

24. The compound or the salt thereof, or the hydrate thereof according to claim 8, wherein $R^6$ represents a hydrogen atom, a pivaloyl group, a carbamoyl group, a dimethylaminocarbonyl group, an ethylaminocarbonyl group, a propylaminocarbonyl group, an isopropylaminocarbonyl group, a t-butylaminoearbonyl group, a cyclohexylaminocarbonyl group, a benzyl aminocarbonyl group, a fluorophenylaminocarbonyl group, an ethyiphenylaninocarbonyl group, a methoxyphenylarninocarbonyl group, an ethoxyphenylaminocarbonyl group, a cyanophenylaminocarbonyl group, a tolylaminocarbonyl group or a rnethylenedioxyphenylaminocarbonyi group.

25. The compound or the salt thereof, or the hydrate thereof according to claim 8, wherein $R^6$ represents a hydrogen atom, a pivaloyl group, a carbarnoyl group, a dimethylaminocarbonyl group, an ethylaminocarbonyl group, an isopropylaminocarbonyl group, a cyclohexylaminocarbonyl group, an ethyiphenylaminocarbonyl group or a methoxyphenylandnocarbonyl group.

26. The compound or the salt thereof, or the hydrate thereof according to claim 1, wherein $R^a$, $R^b$ and $R^c$ independently represent a hydrogen atom, a halogen atom, a hydroxyl group, a mercapto group, an amino group that may have 1 or 2 substituents selected from substituent group β, a nitro group, a cyano group, a carboxyl group, a carbamoyl group, a $C_{1-6}$ alkyl group that may have 1 to 3 substituents selected from substituent group α or a $C_{1-6}$ alkoxy group.

27. The compound or the salt thereof, or the hydrate thereof according to claim 1, wherein $R^u$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group.

28. The compound or the salt thereof, or the hydrate thereof according to claim 1, wherein $R^a$ represents a hydrogen atom, a hydroxyl group, a cyano group or a methyl group.

29. The compound or the salt thereof, or the hydrate thereof according to claim 1, wherein $R^a$ represents a hydrogen atom.

30. The compound or the salt thereof, or thc hydrate thereof according to claim 1, wherein $R^b$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group.

31. The compound or the salt thereof, or the hydrate thereof according to claim 1, wherein $R^b$ represents a hydrogen atom, a hydroxyl group, a cyano group or a methyl group.

32. The compound or the salt thereof, or the hydrate thereof according to claim 1, wherein $R^b$ represents a hydrogen atom.

33. The compound or the salt thereof, or the hydrate thereof according to claim 1, wherein $R^c$ represents a hydrogen atom, a halogen atom, a hydroxyl group, a mercapto group, an amino group, a nitro group, a cyano group, a carboxyl group, a carbamoyl group, a $C_{1-6}$ alkyl group or a $C_{1-6}$ alkoxy group.

34. The compound or the salt thereat or the hydrate thereof according to claim 1, wherein $R^c$ represents a hydrogen atom, a hydroxyl group, a cyano group or a methyl group.

35. The compound or the salt thereof, or the hydrate thereof according to claim 1, wherein $R^c$ represents a hydrogen atom.

36. A compound or a salt thereof, or a hydrate thereof, the compound selected from (7Z)-7-hydroxyimino-4,5,6,7-tetrahydro-benzo[b]thiophene-3-sulfonic acid [2-(4-fluorophenyl)-2-hydroxyethyl]-methyl-amide, (7Z)-7-hydroxyimino-4,5,6,7-tetrahydro-benzo[b]thiophene-3-sulfonic acid[2-(4-fluorophenyl)-ethyl]-methyl-amide, (7Z)-N-[(2S)-2-(4-fluorophenyl)-2-hydroxyethyl]-7-(hydroxyimino)-N-methyl-4,5,6,7-tetrahydro-1-benzothiophene-3-sulfonamide, (7Z)-7-hydroxyimino-4,5,6,7-tetrahydro-benzo[b]thiophene-3-sulfonic acid (2-hydroxy-2-pyridine-4-yl-ethyl)-methyl-amide, (7Z)-7-({[(ethylamino)carbonyl]oxo}imino)-3-{[[2-(4-fluorophenyl)-2-hydroxyethyl](methyl)amino]sulfonyl}-4,5,6,7-tetrahydro-1-benzothiophene, (7Z)-3-{[[2-(4-fluorophenyl)-2-hydroxyethyl](methyl)amino]sulfonyl}-7-({[(isopropylamino)carbonyl]oxy}imino)-4,5,6,7-tetrahydro-1-benzothiophene, (7Z)-7-({[(dimethylamino)carbonyl]oxy}imino)-3-{[[2-(4-fluorophenyl)-2-hydroxyethyl](methyl)amino]sulfonyl}-4,5,6,7-tetrahydro-1-benzothiophene, (7Z)-7-{[(aminocarbonyl)oxy]imino}-3-{[[2-(4-fluorophenyl)-2-hydroxyethyl](methyl)amino]sulfonyl}-4,5,6,7-tetrahydro-1-benzothiophene or (7Z)-7-{[(2,2-dimethylpropanoyl)oxy]imino}-N-[2-(4-fluorophenyl)-2-hydroxyethyl]-N-methyl-4,5,6,7-tetrahydro-1-benzothiophene-3-sulfonamide.

37. A pharmaceutical composition comprising the compound or a salt thereof, or a hydrate thereof according to claim 1 and a pharmaceutically acceptable Oxcipient.

38. A method of treating an allergic disease in a human, wherein the method comprises:

administrating to a subject in need thereof a pharmacologically effective amount of the compound or the salt thereof, or the hydrate thereof according to claim 1, wherein the allersic disease is selected from the group consisting of: atopic dermatitis, allergic coryza, bronchial asthma, hypersensitive pneumoniac or pulmonary aspergillosis.

* * * * *

SEQUENCE LISTING

<160> NUMBER OF SEQ ID NOS: 3

<210> SEQ ID NO 1
<211> LENGTH: 78
<212> TYPE: DNA

```
<213> ORGANISM: Artificial Sequence
<220> FEATURE:
<223> OTHER INFORMATION: Description of Artificial Sequence: Synthetic
      oligonucleotide primer

<400> SEQUENCE: 1
agcggtacct cgacttccca agaacagaat cgacttccca agaacagaat cgacttccca      60
agaacagaat ctagagct                                                    78

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 2
cggaattcat gtctctgtgg ggtctggtct cca                                   33

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 3
ccgctcgagt caccaactgg ggttggccct tagg                                  34
```